(12) United States Patent
Akoulitchev et al.

(10) Patent No.: US 11,802,305 B2
(45) Date of Patent: Oct. 31, 2023

(54) DETECTION PROCESSES USING SITES OF CHROMOSOME INTERACTION

(71) Applicant: Oxford Biodynamics PLC, Oxford (GB)

(72) Inventors: Alexandre Akoulitchev, Oxford (GB); Ewan Hunter, Oxford (GB); Aroul Ramadass, Oxford (GB)

(73) Assignee: Oxford Biodynamics PLC, Oxford (GB)

( * ) Notice: Subject to any disclaimer, the term of this patent is extended or adjusted under 35 U.S.C. 154(b) by 291 days.

(21) Appl. No.: 15/738,469

(22) PCT Filed: Jun. 24, 2016

(86) PCT No.: PCT/GB2016/051910
§ 371 (c)(1),
(2) Date: Dec. 20, 2017

(87) PCT Pub. No.: WO2016/207661
PCT Pub. Date: Dec. 29, 2016

(65) Prior Publication Data
US 2018/0274015 A1 Sep. 27, 2018

(30) Foreign Application Priority Data

Jun. 24, 2015 (GB) ...................................... 1511079
Jun. 24, 2015 (GB) ...................................... 1511080
Nov. 5, 2015 (GB) ...................................... 1519555

(51) Int. Cl.
| | |
|---|---|
| *C12Q 1/6827* | (2018.01) |
| *C12Q 1/6883* | (2018.01) |
| *C12Q 1/6886* | (2018.01) |
| *G16H 50/70* | (2018.01) |
| *G16B 40/00* | (2019.01) |

(52) U.S. Cl.
CPC ......... *C12Q 1/6827* (2013.01); *C12Q 1/6883* (2013.01); *C12Q 1/6886* (2013.01); *G16B 40/00* (2019.02); *G16H 50/70* (2018.01); *C12Q 2521/501* (2013.01); *C12Q 2523/101* (2013.01); *C12Q 2537/159* (2013.01); *C12Q 2600/106* (2013.01)

(58) Field of Classification Search
None
See application file for complete search history.

(56) References Cited

U.S. PATENT DOCUMENTS

| | | | |
|---|---|---|---|
| 10,508,303 B2 | 12/2019 | Ren et al. | |
| 2007/0238094 A1* | 10/2007 | Chaussabel | C12Q 1/6883 435/5 |
| 2010/0075861 A1 | 3/2010 | De et al. | |
| 2010/0130373 A1 | 5/2010 | Dekker et al. | |
| 2019/0071715 A1 | 3/2019 | Ramadass et al. | |

FOREIGN PATENT DOCUMENTS

| | | |
|---|---|---|
| WO | 2005/118873 A2 | 12/2005 |
| WO | 2007/093819 A2 | 8/2007 |
| WO | 2008/084405 A2 | 7/2008 |
| WO | 2009/147386 A1 | 12/2009 |
| WO | 2012/159025 A2 | 11/2012 |
| WO | 2015/077414 A1 | 5/2015 |

OTHER PUBLICATIONS

"Amyotrophic Lateral Sclerosis (ALS) patients could benefit from a new tool being developed by Oxford Biodynamics partly funded by the UK government," Press Release From Oxford BioDynamics of Dec. 16, 2014.
"Biotechnology firm Oxford BioDynamics earns Technology Innovation Award for biomarker discovery platform EpiSwitch™," Press Release From Oxford BioDynamics of Oct. 22, 2015.
Press Release of Jun. 2, 2016: Oxford BioDynamics picks Malaysia to conduct a biomarker discovery programme for diabetes and pre-diabetes.
Press Releases from Oxford BioDynamics from Aug. 10, 2009 to Apr. 25, 2016.
Tests look at the development of type 2 diabetes to predict the progress of the condition; The Diabetes Research & Wellness Foundation, Apr. 21, 2016.
Babu, D., et al., "3D Genome Organization in Health And Disease: Emerging Opportunities In Cancer Translational Medicine", Nucleus 6:5, Sep./Oct. 2015, 382-393.
Biotechnology firm Oxford BioDynamics expands its biomarker discovery programme for ALS diagnosis; International Pharmaceutical Industry (IPI); Jan. 15, 2016. http:<<www.ipimediaworld.com/biotechnology-firm-oxford-biodynamics-expands-its-biomarker-discovery-programme-for-als-diagnosis/>>.
"New Frontiers in Epigenetics: Genomic Biomarkers with EpiSwitchTM Technology", OBD presentation at SingHealth, National Cancer Centre, Singapore (NCCS), Jan. 23, 2012, 1-7.
Akoulitchev, A. "Clinical evaluation of EpiSwitch OBD-27, a Breast Cancer Screening Tool, based on Epigenetics Concept on Japanese population", Chinese language Abstract O-065. Annual Meeting of Japanese Association of Breast Cancer Screening, Okinawa, Nov. 30, 2012.
Akoulitchev, A. et al., "Clinical evaluation of EpiSwitch OBD-27, a Breast Cancer Screening Tool, based on Epigenetics Concept on Japanese population", English translation of D68 [Abstract O-065. Annual Meeting of Japanese Association of Breast Cancer Screening, Okinawa, Nov. 30, 2012.
Akoulitchev, A. "Epigenetics and New Approaches in Molecular Diagnosis", CMR Seminar Announcement poster at SingHealth, Jan. 23, 2012.

(Continued)

*Primary Examiner* — Katherine D Salmon
(74) *Attorney, Agent, or Firm* — Elmore Patent Law Group, P.C.; Joseph C. Zucchero; Carolyn S. Elmore

(57) ABSTRACT

A process for analysing epigenetically active regions of the genome.

1 Claim, 18 Drawing Sheets
Specification includes a Sequence Listing.

(56) References Cited

OTHER PUBLICATIONS

Hughes, E. "Oxford BioDynamics expands biomarker discovery programme for ALS", EPM Magazine; Jan. 28, 2016. <<https://www.epmmagazine.com/news/oxford-biodynamics-expands-biomarker-discovery-programme-for/ >>.

Jeznach, M. et al., "Breast cancer: development of early non-invasive diagnostics to reduce disease mortality and psychological outcomes", Psychoonkologia, vol. 2, 2013, 35-49.

Jeznach, M. "Systemic Epigenetic Biomarkers for ALS Improve Early Diagnosis, Treatment and Trials", International Pharmaceutical Industry Magazine, vol. 8 Issue 1, Spring 2016.

Pchejetski, D. et al., "Validation of a New Epigenetic-Based Prognostic Blood Test to Predict Prostate Cancer Aggressiveness", Annals of Oncology, 24 (Supplement 9): ix31-ix65, 2013.

Campus Internal Grant Report (Academics year 2010-11). Journal of Saitama Medical University, 2012, vol. 39, No. 1, p. 4-8, Abstract only.

Goodyear, C., et al., "Epigenetic Chromosome Conformations Predict MTX Responsiveness in Early Rheumatoid Arthritis Patients". Presentation made at ACR/ARHP Annual Meeting (Nov. 6-11, 2015 in San Francisco, CA), publicly disclosed earlier on Mar. 31, 2014 at 'The Scottish Early Rheumatoid Arthritis (SERA) Meeting' in Perth, Scotland.

Bastonini, E., et al., "Chromatin barcodes as biomarkers for melanoma," Pigment Cell Melanoma Res., 27: 788-800 (2014).

Alshaker, H., et al., "Development of a new epigenetic-based blood test to stratify prostate cancer patients according to risk groups," International Journal of Molecular Medicine, 34 (Suppl S9) (2014).

Sun, J., et al., "A Novel Suppressive Long Noncoding RNA within the IGF1R Gene Locus Is Imprinted in Acute Myelocytic Leukemia," Blood, 124(21): p. 3592 (2014). Retrieved from the internet May 21, 2020. <<https://ashpublications.org/blood/article/124/21/3592/97498/A-Novel-Suppressive-Long-Noncoding-RNA-within-the?searchresult=1>>.

Oxford BioDynamics Website (2013-2014) http://web.archive.org/web/20131209081232/http://oxfordbiodynamics.com/applications/predictive-biomarkers.

Kubiak, M., et al., "Can chromatin conformation technologies bring light into human molecular pathology?" Acta Biochimica Polonica, 62(3): 483-489 (2015).

Mukhopadhyay, S., et al., "Formation of distinct chromatin conformation signatures epigenetically regulate macrophage activation," Intl. Immunopharmacol., 18: 7-11 (2013).

Cheng, J. X., et al., "Disease-Associated Chromatin Conformation and Therapeutic Implications In Leukemia," Blood, 122(21): 4892 (2013).

Jakub, J. W., et al., "A pilot study of chromosomal aberrations and epigenetic changes in peripheral blood samples to identify patients with melanoma," Melanoma Research, 25: 406-411 (2015).

Carini, et al., "Epigenetic Chromosome Conformations Predict MTX Responsiveness in Early Rheumatoid Arthritis Patients", Annual Meeting of the American-College-of-Rheumatology (ACR) and Association-of-Rheumatology-Health; San Francisco, CA, USA; 2015, vol. 67, Suppl. 10. Retrieved from the Internet: URL:http://acrabstracts.org/abstract/epigenetic-chromosome-conformations-predict-mtx-responsiveness-in-early-rheumatoid-arthritis-patients/ [retrieved on Sep. 8, 2016].

Jakub, J. W., et al., "Diagnostic Value of Epigenetic Chromatin Conformation Changes Identified in Peripheral Blood To Differentiate Early Stage Melanoma From Healthy Volunteers and Other Cutaneous Malignancies," WSA 2013 Annual Scientific Session, 2013.

Crutchley, J., et al., "Chromatin conformation signatures: ideal human disease biomarkers?", Biomarkers in Medicine, vol. 4, No. 4, Aug. 1, 2010 (Aug. 1, 2010), pp. 611-629.

Byers, R. J., et al., "Subtractive hybridization: Genetic takeaways and the search for meaning", International Review of Experimental Pathology, Blackwell Scientific, Oxford, GB, vol. 81, No. 6, pp. 391-404 (2000).

Ranganathan, P., et al., "Will pharmacogenetics allow better prediction of methotrexate toxicity and efficacy in patients with rheumatoid arthritis?" Annals of the Rheumatic Diseases, British Medical Association, GB, vol. 62, No. 1, Jan. 1, 2003 (Jan. 1, 2003), pp. 4-9.

Plant, D., et al., "Genetic and epigenetic predictors of responsiveness to treatment in RA," Nature Reviews, Rheumatology, vol. 10, No. 6, Jun. 1, 2014 (Jun. 1, 2014).

Wessels, J., et al., "A clinical pharmacogenetic model to predict the efficacy of methotrexate monotherapy in recent-onset rheumatoid arthritis", Arthritis & Rheumatism, vol. 56, No. 6, Jun. 1, 2007 (Jun. 1, 2007), pp. 1765-1775.

Martin, P., et al., "Capture Hi-C reveals novel candidate genes and complex long-range interactions with related autoimmune risk loci", Nature Communications, vol. 6(10069), www.nature.com/naturecommunications, Nov. 30, 2015 (Nov. 30, 2015).

Verlaan, D. J., et al., "Allele-Specific Chromatin Remodeling in the ZPBP2/GSDMB/ORMDL3 Locus Associated with the Risk of Asthma and Autoimmune Disease," The American Journal of Human Genetics, 85, 377-393 (2009).

Shulha, H. P., et al., "Human-Specific Histone Methylation Signatures at Transcription Start Sites in Prefrontal Neurons", PLoS Biol 10(11): e1001427.

McCord, R., et al., "Chromatin signatures of DLBCL subtypes" [abstract] in: Proceedings of the 105th Annual Meeting of the American Association for Cancer Research; Apr. 5-9, 2014; San Diego, CA. Philadelphia (PA): AACR; Cancer Research 2014;74(19 Suppl):Abstract 462. doi:10.1158/1538-7445.AM2014-462 [retrieved Aug. 20, 2018] <URL: http://cancerres.aacrjournals.org/content/74/19_Supplement/462.

Wikipedia, "Chromosoma conformation capture" as at Apr. 28, 2014 [retrieved Aug. 20, 2018] <URL: https://en.wikipedia.org/w/index.php?title=Chromosome_conformation_capture&oldid=606170436.

Wang, S., et al., "Disease mechanisms in rheumatology—tools and pathways: defining functional genetic variants in autoimmune diseases", Arthritis and Rheumatology, 67(1): 1-10 (2015).

Xu, Z., et al., "Mapping of long-range INS promoter interactions reveals a role for calcium-activated chloride channel ANO1 in insulin secretion", PNAS, 111(47): 16760-16765 (2014).

Dekker, J., et al., "Capturing chromosome conformation", Science, 295: 1306-1311 (2002).

Mitchell, R. M., "A CSF biomarker panel for identification of patients with amyotrophic lateral sclerosis", Neurology, 72(1): 14-19, (2009). Epub Nov. 5, 2008.

Mitchell, R. M., "Plasma biomarkers associated with ALS and their relationship to iron homeostasis", Muscle Nerve, 42: 95-103 (2010).

Woollacott, I. O. C., et al., "The C9ORF72 expansion mutation: gene structure, phenotypic and diagnostic issues", Acta Neuropathol., 127(3): 319-332 (2014).

Salter, M., et al., "Initial Identification of a Blood-Based Chromosome Conformation Signature for Aiding in the Diagnosis of Amyotrophic Lateral Sclerosis.", EBioMedicine, 33: 169-184 (2018). doi: 10.1016/j.ebiom.2018.06.015. Epub Jun. 23, 2018.

Goodyear, C., et al., "Epigenetic Chromosome Conformations Predict MTX Responsiveness in Early Rheumatoid Arthritis Patients". Presentation made at ACR/ARHP Annual Meeting (Nov. 6-11, 2015 in San Francisco, CA).

Liao, K. P., et al., "Environmental influences on risk for rheumatoid arthritis," Curr. Opin. Rheumatol., 21: 279-283 (2009).

Bottini, N., et al., "Epigenetics in rheumatoid arthritis: a primer for rheumatologists," Curr. Rheumatol. Rep., 15, 372 (2013).

McInnes, I. B., et al., "The pathogenesis of rheumatoid arthritis," N. Engl. J. Med., 365(23): 2205-2219 (2011).

Liu, Y., et al., "Epigenome-wide association data implicate DNA methylation as an intermediary of genetic risk in rheumatoid arthritis," Nat. Biotechnol., 31(2): 142-147 (2013).

Nakano, K., et al., "DNA methylome signature in rheumatoid arthritis," Ann. Rheum. Dis., 72(1): 110-117 (2013).

De La Rica, L., et al., "Identification of novel markers in rheumatoid arthritis through integrated analysis of DNA methylation and microRNA expression," J. Autoimmun., 41: 6-16 (2013).

(56) References Cited

OTHER PUBLICATIONS

Viatte, S., et al., Genetics and epigenetics of rheumatoid arthritis, Nat. Rev. Rheumatol., 9(3): 141-153 (2013).
Hider, S. L., et al., "Can clinical factors at presentation be used to predict outcome of treatment with methotrexate in patients with early inflammatory polyarthritis?" Ann. Rheum. Dis., 68: 57-62 (2009).
Farragher, T. M., et al., "Early treatment with, and time receiving, first disease-modifying antirheumatic drug predicts long-term function in patients with inflammatory polyarthritis," Ann. Rheum. Dis., 69: 689-695 (2010).
Bakker, M. F., et al., "Early clinical response to treatment predicts 5-year outcome in RA patients: follow-up results from the CAMERA study," Ann. Rheum. Dis., 70: 1099-1103 (2011).
Barrera, P., et al., "Drug survival, efficacy and toxicity of monotherapy with a fully human anti-tumour necrosis factor-α antibody compared with methotrexate in long-standing rheumatoid arthritis," Rheumatology, 41: 430-439 (2002).
Deng, W., et al., "Do chromatin loops provide epigenetic gene expression states?" Curr. Opin. Genet. Dev., 20(5): 548-54 (2010).
Kadauke, S., et al, "Chromatin loops in gene regulation," Biochim Biophys Acta., 1789(1): 17-25 (2009).
Christova, R., et al., "P-STAT1 mediates higher-order chromatin remodelling of the human MHC in response to IFNγ," J. Cell Sci., 120(18): 3262-3270 (2007).
Watanabe, T., et al., "Higher-Order Chromatin Regulation and Differential Gene Expression in the Human Tumour Necrosis Factor/Lymphotoxin Locus in Hepatocellular Carcinoma Cells," Mol. Cell. Biol., 32: 1529-1541 (2012).
Harismendy, O., et al., "9p21 DNA variants associated with coronary artery disease impair interferon-γ signalling response," Nature, 470(11): 264-268 (2011).
Rau, R., et al., "Benefit and risk of methotrexate treatment in rheumatoid arthritis," Clin. Exp. Rheumatol., 22: S83-S94 (2004).
Kosaka, N., et al., "Unraveling the Mystery of Cancer by Secretory micro RNA: Horizontal microRNA Transfer between Living Cells," Front. in Genet., 2: 97 (2011).
Rozen, S., et al., "Primer3 on the WWW for general users and for biologist programmers," Methods Mol Biol., 132: 365-386 (2000).
Hunter, E., et al., U.S. Appl. No. 15/738,476, filed May 23, 2018.
Youdell, M., et al., "Development of Novel ALS Treatment on the Basis of Mechanisms of Cellular Chronological Life Span Control," Poster at the 12th annual Northeast ALS Consortium (NEALS); Oct. 7, 2013. Exhibit A—document providing enlarged sections of poster.
Williams, M. T., et al., "Fcg Receptor Targeting Reduces Bone Disease in a Pre-clinical Model of Multiple Myeloma," 57th American Society of Hematology Meeting in Orlando; Dec. 9, 2015. Exhibit B—document providing enlarged sections of poster.
Hunter, E., et al., Development of Epigenetic Profiling of ALS Patients with Chromosome Conformation Biomarkers Offers Novel Signatures for Non-invasive Diagnostic and Prognostic Stratifications; Annual 2015 ALS Consortium Conference in Tampa, Florida; Nov. 6, 2015. Exhibit C—document providing enlarged sections of presentation.
Brites, N. and Vaz, A.R., "Microglia centered pathogenesis in ALS: insights in cell interconnectivity," Frontiers in Cellular Neuroscience, 8(Article 117): 1-24 (2014).
Fontana, L., et al., "Extending Healthy Life Span—From Yeast to Humans," Science, 328: (5976), 321-326 (2010).
Figueroa-Romero, C. et al., "Identification of Epigenetically Altered Genes in Sporadic Amyotrophic Lateral Sclerosis", PLOS One, vol. 7, No. 12, e52672, Dec. 2012.
Cobb, J. et al., "Genome-Wide Data Reveal Novel Genes for Methotrexate Response in a Large Cohort of Juvenile Idiopathic Arthritis Cases", The Pharmacogenomics Journal, vol. 14, Apr. 8, 2014, 356-364.
Fullwood, M. et al., "An Oestrogen-Receptor-α-Bound Human Chromatin Interactome", Nature, vol. 462, Nov. 5, 2009, 58-64.
Imakaev, M. et al., "Iterative Correction of Hi-C Data Reveals Hallmarks of Chromosome Organization", Nature Methods, vol. 9, No. 10, Oct. 2012, 999-1003.
Lajoie, B. et al., "The Hitchhiker's Guide to Hi-C Analysis: Practical Guidelines", Methods, vol. 72, 2015, 65-75.
Li, G. et al., "Extensive Promoter-Centered Chromatin Interactions Provide a Topological Basis for Transcription Regulation", Cell, vol. 148, Jan. 20, 2012, 84-98.
Sandhu, K. et al., "Large-Scale Functional Organization of Long-Range Chromatin Interaction Networks", Cell Rep., vol. 2, No. 5, Nov. 29, 2012, 1207-1219.

\* cited by examiner

DETECTION PROCESSES USING SITES OF CHROMOSOME INTERACTION

RELATED APPLICATIONS

This application is a US National stage entry of International Application No. PCT/GB2016/051910, which designated the United States and was filed on Jun. 24, 2016, published in English.

This application claims priority under 35 U.S.C. § 119 or 365 to GB Application No. 1511080.2, filed Jun. 24, 2015, GB Application No. 1511079.4, filed Jun. 24, 2015 and GB Application No. 1519555.5, filed Nov. 5, 2015. The entire teachings of the above applications are incorporated herein by reference.

FIELD OF THE INVENTION

The invention relates to detecting chromosome interactions at epigenetically active regions of the genome.

BACKGROUND OF THE INVENTION

Chromosome interactions are increasingly seen as important in the regulation of the genome and as relevant to disease causes.

SUMMARY OF THE INVENTION

The inventors have identified regions of the genome where chromosomal interactions are relevant to disease. These key regions play important roles in body and cell processes. The regions identified by the inventors together with the new methods provided by the invention allow typing of individuals into subgroups with different characteristics based on the chromosome state at the region. The inventors view disease-associated chromosome interactions as having a key role in defining many different disease and non-disease characteristics between subgroups.

The invention provides a method of determining the epigenetic chromosome interactions which are relevant to a companion epigenetic test that distinguishes between subgroups, comprising contacting a first set of nucleic acids from the subgroups with a second set of nucleic acids representing an index population of chromosome interactions, and allowing complementary sequences to hybridise, wherein the nucleic acids in the first and second sets of nucleic acids represent a ligated product comprising sequences from both of the chromosome regions that have come together in the epigenetic chromosome interaction, and wherein the pattern of hybridisation between the first and second set of nucleic acids allows a determination of which epigenetic chromosome interactions are specific to subgroups in the population, wherein the subgroups differ in a characteristic relevant to a companion epigenetic test, and wherein optionally the chromosomes interactions are present in a defined disease-associated region of the genome.

The invention also provides a method for carrying out a companion epigenetic test which determines which subgroup a person is in, which method comprises:

(a) typing a locus which has been identified by the above method as having an epigenetic interaction characteristic to the subgroup, and/or (b) typing a chromosome interaction which has been identified by the above method as being relevant to, or associated with, a characteristic of the subgroup, and/or (c) detecting the presence or absence of at least 5 epigenetic chromosome interactions, preferably at at least 5 different loci, which are characteristic for:

(i) responding to a specific treatment and/or prophylaxis (in particular to a specific pharmaceutical treatment and/or prophylaxis), and/or (ii) predisposition to a specific condition, and/or (iii) the presence of residual disease which may lead to relapse, and/or (iv) responsiveness to an environmental change, and/or (v) response to a genetic change, and/or (vi) a change or a difference in the state of the metabolic system, the immune system, the endocrine system, the digestive system, integumentary system, the skeletal system, the muscular system, the lymphatic system, the respiratory system, the nervous system, or the reproductive system; wherein optionally the method is carried out to select an individual for a medical or non-medical treatment relevant to the characteristic that defines the subgroups, wherein said treatment is optionally unrelated to the disease that the region is associated with.

In a preferred embodiment the invention provides a method for detecting chromosome states which represent different subgroups in a population comprising determining whether a chromosome interaction is present or absent within a defined disease-associated region of the genome, wherein said disease is of the metabolic system, the immune system, the endocrine system, the digestive system, integumentary system, the skeletal system, the muscular system, the lymphatic system, the respiratory system, the nervous system or the reproductive system, and wherein said chromosome interaction is optionally identified by a method of determining which chromosomal interactions are relevant to a chromosome state corresponding to different subgroups of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to a particular subgroup in a population for a particular chromosome state.

DETAILED DESCRIPTION OF THE INVENTION

Figure 1:
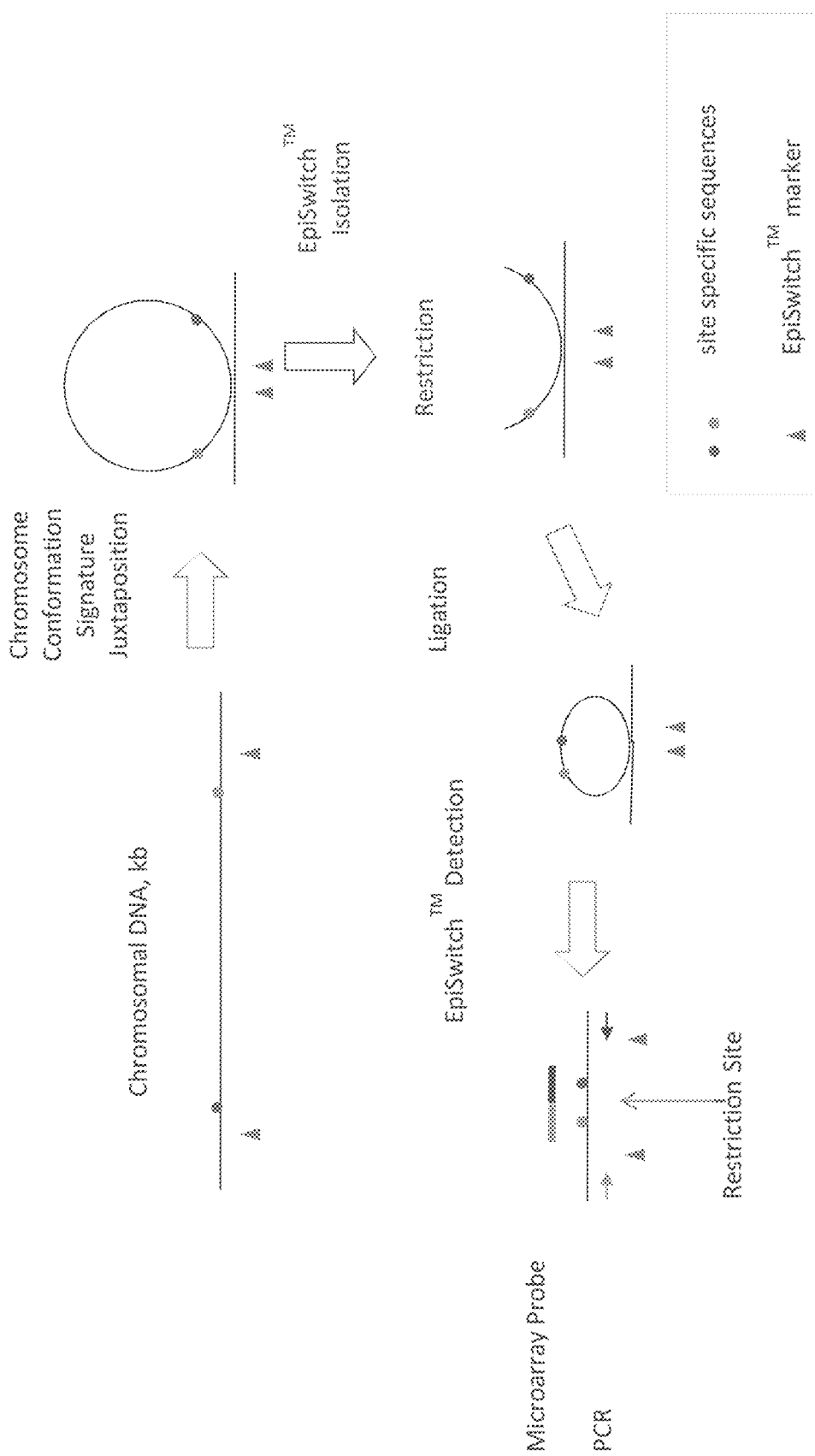
FIG. 1 is a Schematic diagram of the 3C extraction method. 3C means chromatin conformation capture, or chromosome conformation capture.
Figure 2:
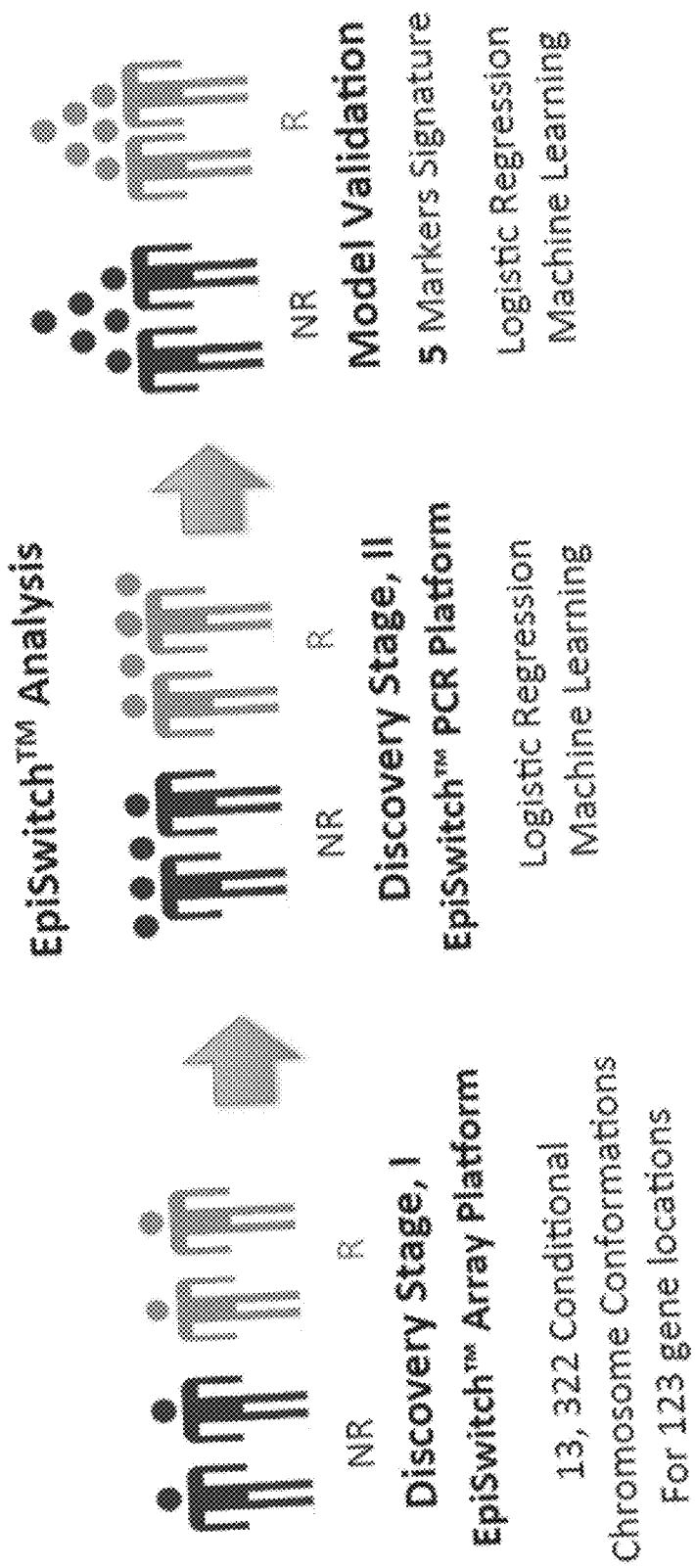
FIG. 2 is a Scheme illustrating EpiSwitch™ Analysis, and the Design for Discovery and Validation of Epigenetic Stratifying Biomarker Signatures [patients who are responders (R) or non-responders (NR) to a particular drug treatment for a particular disease/condition]. Epigenetic stratification is based on conditional chromosome confirmations screened and monitored by EpiSwitch™ Array and PCR (polymerase chain reaction) platforms. Disease specific epigenetic nature of the identified biomarkers can be confirmed by stratification against healthy controls (HC). Validation can be performed on further patients and further HC.

The invention has several different aspects, including inter alia:
- a method for identifying chromosome interactions relevant to different subgroups of the population;
- a method which selects a subgroup with particular characteristics, and/or a method of identifying the subgroup of an individual;
- a method of determining the effect of a drug (e.g. a pharmaceutical therapeutic agent), comprising detecting the change in epigenetic chromosome interactions caused by the drug; and/or
- a method of determining the effects of a genetic modification at one locus on the chromosome interactions at other loci; and/or
- a nucleic acid which may be in the form of a library with other nucleic acids.

Disease-Associated Regions

The invention concerns typing of chromosome interactions at disease-associated or epigenetically active regions. In such regions chromosome interactions will occur which affect an aspect of disease, such as in any of the disease conditions mentioned herein. The chromosome interactions may affect susceptibility to disease, responsiveness to therapy or likelihood of relapse. Specific chromosome interactions, genes and regions are disclosed in the tables herein with reference to a specific disease characteristic. In one embodiment those chromosome interactions, or chromosome interactions in those genes and regions, may be typed to detect characteristics that are different to the disease characteristic which is given herein for that table, such as a non-disease characteristic or a characteristic in a different disease, or a different aspect of the same disease.

The chromosome interaction which is typed may or may not be one which occurs between a gene (including coding sequence) and its regulatory region, such as a promoter. The chromosome interaction which is typed mayor may not be one which is inherited, for example an inherited imprinted characteristic of a gene region.

Epigenetic Interactions

As used herein, the term 'epigenetic' interactions typically refers to interactions between distal regions of a locus on a chromosome, said interactions being dynamic and altering, forming or breaking depending upon the status of the region of the chromosome.

In particular methods of the invention chromosome interactions are detected by first generating a ligated nucleic acid that comprises sequence from both regions of the chromosomes that are part of the interactions. In such methods the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a characteristic (such as a disease condition) will normally occur early in a biological process, for example compared to other epigenetic markers such as methylation or changes to binding of histone proteins. Thus the method of the invention is able to detect early stages of a biological process. This allows early intervention (for example treatment) which may as a consequence be more effective. Furthermore there is little variation in the relevant chromosome interactions between individuals within the same subgroup. Detecting chromosome interactions is highly informative with up to 50 different possible interactions per gene, and so methods of the invention can interrogate 500,000 different interactions.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions.

The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNP's within and/or outside of the genes, gene fusions and/or deletions of intergenic DNA, microRNA, and non-coding RNA. For example, it is known that roughly 20% of SNPs are in non-coding regions, and therefore the method as described is also informative in non-coding situation. In one embodiment the regions of the chromosome which come together to form the interaction are less than 5 kb, 3 kb, 1 kb, 500 base pairs or 200 base pairs apart on the same chromosome.

The chromosome interaction which is detected is preferably within any of the genes mentioned in the Tables herein. However it may also be upstream or downstream of the genes, for example up to 50,000, up to 30,000, up to 20,000, up to 10,000 or up to 5000 bases upstream or downstream from the gene or from the coding sequence.

Types of Clinical Situation

The aim of the present invention is to permit detection of chromosome interactions relevant to a characteristic that defines subgroups in the population. For example, this technology allows stratification based on biomarkers for specific phenotypes (e.g. relating to medical conditions), i.e. by recognising a particular chromosome confirmation signature and/or a change in that particular signature.

The methods of the invention may be used in the context of specific characteristics relating to disease, such as responsiveness to treatments, identification of the most effective therapy/drug, monitoring the course of disease, identifying predisposition to disease, identifying the presence of residual disease and/or the likelihood of relapse. Therefore the methods may or may not be used for diagnosis of the presence of a specific condition. The methods of the invention can be used to type loci where the mechanisms of disease are unknown, unclear or complex. Detection of chromosome interactions provides an efficient way of following changes at the different levels of regulation, some of which are complex. For example in some cases around 37,000 non-coding RNAs can be activated by a single impulse.

Subgroups and Personalised Treatment

As used herein, a "subgroup" preferably refers to a population subgroup (a subgroup in a population), more preferably a subgroup in the population of a particular animal such as a particular eukaryote, or mammal (e.g. human, non-human, non-human primate, or rodent e.g. mouse or rat) or a particular nematode worm (e.g. *C. elegans*). Most preferably, a "subgroup" refers to a subgroup in the human population.

The invention includes detecting and treating particular subgroups in a population. Within such subgroups the characteristics discussed herein (such as responsiveness to treatment) will be present or absent.

Epigenetic interaction differences on a chromosome are, generally speaking, structural differences which exist at a genomic level. The inventors have discovered that these differ between subsets (for example two or at least two subsets) in a given population. Identifying these differences will allow physicians to categorize their patients as a part of one subset of the population as described in the method. The invention therefore provides physicians with a method of personalizing medicine for the patient based on their epigenetic chromosome interactions, and provide an alternative more effective treatment regime.

In another embodiment, threshold levels for determining to what extent a subject is defined as one subgroup and not the other of the population are applied. In one embodiment wherein the subgroups comprise responders versus non-responders of a therapy for the treatment of a particular disease, said threshold may be measured by change in DAS28 score. In one embodiment a score above 1.2 units indicates a subject falls into the responder subgroup, whilst a score below 1.2 units indicates a subject is defined as a non-responder. Typically a subgroup will be at least 10%, 30%, 50% or 80% of the general population.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a method of the invention may comprise a step of generating ligated nucleic acids (e.g. DNA) by:
(i) in vitro crosslinking of epigenetic chromosomal interactions present at the chromosomal locus;
(ii) optionally isolating the cross-linked DNA from said chromosomal locus;
(iii) subjecting said cross-linked DNA to cutting, for example by restriction digestion with an enzyme that cuts it at least once (in particular an enzyme that cuts at least once within said chromosomal locus);
(iv) ligating said cross-linked cleaved DNA ends (in particular to form DNA loops); and
(v) identifying the presence of said ligated DNA and/or said DNA loops, in particular using techniques such as PCR (polymerase chain reaction), to identify the presence of a specific chromosomal interaction.

PCR (polymerase chain reaction) may be used to detect or identify the ligated nucleic acid, for example the size of the PCR product produced may be indicative of the specific chromosome interaction which is present, and may therefore be used to identify the status of the locus. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is Taq I polymerase.

Embodiments Such as EpiSwitch™ Technology

The EpiSwitch™ Technology relates to the use of microarray EpiSwitch™ marker data in the detection of epigenetic chromosome conformation signatures specific for phenotypes. The present inventors describe herein how the EpiSwitch™ Array Platform has been used for discovery of chromosome signature pool of biomarkers specific for particular disadvantageous phenotype subgroups versus healthy controls. The inventors also provide examples of validated use and translation of chromosome conformation signatures from microarray into PCR platform with examples of several markers specific between subgroups from the cohorts tested on the array.

Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 to 6 hours.

Samples and Sample Treatment

The sample will contain DNA from the individual. It will normally contain cells. In one embodiment a sample is obtained by minimally invasive means, and may for example be blood. DNA may be extracted and cut up with a standard restriction enzyme. This can pre-determine which chromosome conformations are retained and will be detected with the EpiSwitch™ platforms. In one embodiment wherein the sample is a blood sample previously obtained from the patient, the described method is advantageous because the procedure is minimally invasive. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic Acids of the Invention

The invention provides nucleic acids. These may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids comprise sequence from any of the genes mentioned in any of the tables, in particular where the nucleic acid is used in an embodiment relevant to the condition relevant for that table. Preferred nucleic acids comprise the specific probe sequences mentioned in any of the tables for specific conditions; or fragments and/or homologues of such sequences. Preferably the nucleic acids are DNA. It is understood that where a specific sequence is provided the invention may use the complementary sequence as required in the particular embodiment.

The Second Set of Nucleic Acids-the 'Index' Sequences

The second set of nucleic acid sequences has the function of being a set of index sequences, and is essentially a set of nucleic acid sequences which are suitable for identifying subgroup specific sequence. They can represents the 'background' chromosomal interactions and might be selected in some way or be unselected. They are in general a subset of all possible chromosomal interactions.

The second set of nucleic acids may be derived by any suitable method. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which modify, regulate or in any way mediate a disease state/phenotype in population. The second set of nucleic acids may represent chromosome interactions that affect a disease state in a species, for example comprising nucleic acids sequences which encode cytokines, kinases, or regulators associated with any disease state, predisposition to a disease or a disease phenotype. The second set of nucleic acids typically comprises sequences representing epigenetic interactions relevant and not relevant to the characteristic that defines the subgroup.

In one particular embodiment the second set of nucleic acids derive at least partially from naturally occurring sequences in a population, and are typically obtained by in silico methods. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All, or at least 90% or at least 50%, of these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are normally from individuals known to be in two or more distinct subgroups defined by presence or absence of a characteristic relevant to a companion diagnostic, such as any such characteristic mentioned herein. The first nucleic acids may have any of the characteristics and properties of the second set of nucleic acids mentioned herein. The first set of nucleic acids is normally derived from a sample from the individuals which has undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Library of Nucleic Acids

The invention provides a library of nucleic acids which comprises at least 200, at least 500, at least 1000, at least 5000 or at least 10000 different nucleic acids of the invention, such as 'second' nucleic acids. The invention provides a particular library of nucleic acids which typically comprises at least 200 different nucleic acids. The library may be in the form of nucleic acids bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a method of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Selecting a Subgroup with Particular System Characteristics

The invention provides a method which comprises detecting the presence or absence of chromosome interactions, typically 5 to 20 or 5 to 500 such interactions, preferably 20 to 300 or 50 to 100 interactions, in order to determine the presence or absence of a characteristic in an individual. Preferably the chromosome interactions are those in any of the genes mentioned herein. In one embodiment the chromosome interactions which are typed are those represented by the nucleic acids in any one or more of the relevant Tables disclosed herein, for example when the method is for the purpose of determining the presence or absence of characteristics defined in those tables.

Specific Conditions

The method of the invention can be used to detect the presence of any of the specific conditions or characteristics mentioned herein, and preferably is used to detect:
responsiveness to IFN-B (IFN-beta) treatment in multiple sclerosis patients (in particular in humans), and/or
predisposition to relapsing-remitting multiple sclerosis (in particular in humans), and/or
likelihood of primary progressive multiple sclerosis (in particular in humans), and/or
predisposition to amyotrophic lateral sclerosis (ALS) disease state (in particular in humans), and/or,
predisposition to fast progressing amyotrophic lateral sclerosis (ALS) disease state (in particular in humans), and/or predisposition to aggressive type 2 diabetes disease state (in particular in humans), and/or
predisposition to type 2 diabetes disease state (in particular in humans), and/or
predisposition to a pre-type 2 diabetes state (in particular in humans), and/or
predisposition to type 1 diabetes disease state (in particular in humans), and/or
predisposition to systemic lupus erythematosus (SLE) disease state (in particular in humans), and/or
predisposition to ulcerative colitis disease state (in particular in humans), and/or
likelihood of relapse of colorectal cancer for ulcerative colitis patients (in particular in humans), and/or
likelihood of malignant peripheral nerve sheath tumours for neurofibromatosis patients (in particular in humans), and/or likelihood of developing prostate cancer and/or aggressive prostate cancer (in particular in humans), and/or
likelihood of developing and/or predisposition to a neurodegenerative disease or condition, preferably a dementia such as Alzheimer's disease, mild cognitive impairment, vascular dementia, dementia with Lewy bodies, frontotemporal dementia, or more preferably Alzheimer's disease, most preferably beta-amyloid aggregate induced Alzheimer's disease; in particular in a human; and/or
comparison between dementia patients (preferably Alzheimer's disease patients, more preferably Alzheimer's disease patients with beta-amyloid aggregates) and cognitively-impaired patients without Alzheimer's disease, in particular with respect to memory and/or cognition; and/or
responsiveness to methotrexate in rheumatoid arthritis patients; and/or
responsiveness to therapy for acute myeloid leukaemia; and/or
likelihood of relapse in melanoma; and/or
responsiveness to anti-PD-1 treatment in melanoma.

In one embodiment the method of the invention detects responsiveness to immunotherapy, such as antibody therapy. Preferably the responsiveness to antibody therapy of cancer is detected, for example in immunotherapy using anti-PD-1 or anti-PD-L1 or a combined anti-PD-1/anti-PD-L1 therapy. Preferably the cancer is melanoma, breast cancer, prostate cancer, acute myeloid leukaemia (AML), diffuse large B-cell lymphoma (DLBCL), pancreatic cancer, thyroid cancer, nasal cancer, liver cancer or lung cancer. In such embodiments detection of chromosome interactions in STAT5B and/or IL15 are preferred, such as described in the Examples. The work in the Examples is consistent with the fact that response to immunotherapy is a feature of the immune system epigenetic set up rather than cancer identity. ['Anti-PD-1' is an antibody or antibody derivative or fragment that binds specifically to PD-1 (programmed cell death protein 1). 'Anti-PD-Li' is an antibody or antibody derivative or fragment that binds specifically to PD-Li protein which is a ligand of PD-1.]

In one embodiment responsiveness to therapy, preferably anti-PD1 therapy, is detected in any of the following cancers, preferably of the stage or class which is indicated and/or preferably with other indicated characteristics such as viral infection.

DLBCL_ABC: Diffuse large B-cell lymphoma subtype activated B-cells
DLBCL_GBC: Diffuse large B-cell lymphoma subtype germinal center B-cells
HCC: hepatocellular carcinoma
HCC_HEPB: hepatocellular carcinoma with hepatitis B virus
HCC_HEPC: hepatocellular carcinoma with hepatitis C virus
HEPB+R: Hepatitis B in remission
Pca_Class3: Prostate cancer stage 3
Pca_Class2: Prostate cancer stage 2
Pca_Class1: Prostate cancer stage 1
BrCa_Stg4: Breast cancer stage 4
BrCa_Stg3B: Breast cancer stage 3B
BrCa_Stg2A: Breast cancer stage 2A
BrCa_Stg2B: Breast cancer stage 2B
BrCa_Stg1A: Breast cancer stage 1A
BrCa_Stg1: Breast cancer stage 1

Preferably, the presence or absence of any of the chromosome interactions within any of the relevant genes mentioned in the tables are detected. For example in at least 1, 3, 10, 20, 50 of the genes mentioned in any one of the tables. Preferably the presence or absence of chromosome interactions represented by the probes sequences in the tables is determined in the method. These numbers of genes or chromosome interactions can be used in any of the different embodiments mentioned herein.

The Individual that is Tested

The individual to be tested may or may not have any symptoms of any disease condition or characteristic mentioned herein. The individual may be at risk of any such condition or characteristic. The individual may have recovered or be in the process of recovering from the condition or characteristic. The individual is preferably a mammal, such as a primate, human, non-human mammal or rodent. The individual may be male or female. The individual may be 30 years old or older. The individual may be 29 years old or younger.

Embodiments Concerning Genetic Modifications

In certain embodiments the methods of the invention can be carried out to detect chromosome interactions relevant to or impacted by a genetic modification, i.e. the subgroups may differ in respect to the genetic modification. Clearly the modification might be of entire (non-human) organisms or parts of organisms, such as cells. The first set of nucleic acids may be from at least two subgroups, one of which has a defined genetic modification and one which does not have the genetic modification, and the method may determine which chromosomal interactions are relevant to, and/or affected by, the genetic modification. The modification may be achieved by any suitable means, including CRISPR technology. The invention includes a method of determining whether a genetic modification to the sequence at a first locus of a genome affects other loci of the genome comprising detecting chromosome signatures at one or more other loci after the genetic modification is made, wherein preferably the genetic modification changes system characteristics, wherein said system is preferably the metabolic system, the immune system, the endocrine system, the digestive system, integumentary system, the skeletal system, the muscular system, the lymphatic system, the respiratory system, the nervous system, or the reproductive system. Said detecting chromosome signatures optionally comprises detecting the presence or absence of 5 or more (e.g. 5) different chromosomal Interactions, preferably at 5 or more (e.g. 5) different loci, preferably as defined in any of the Tables. Preferably the chromosomal signatures or Interactions are identified by any suitable method mentioned herein.

In one embodiment the genetic modification is achieved by a method comprising introducing into a cell (a) two or more RNA-guided endonucleases or nucleic acid encoding two or more RNA-guided endonucleases and (b) two or more guiding RNAs or DNA encoding two or more guiding RNAs, wherein each guiding RNA guides one of the RNA-guided endonucleases to a targeted site in the chromosomal sequence and the RNA-guided endonuclease cleaves at least one strand of the chromosomal sequence at the targeted site.

In another embodiment the modification is achieved by a method of altering expression of at least one gene product comprising introducing into a eukaryotic cell containing and expressing a DNA molecule having a target sequence and encoding the gene product an engineered, non-naturally occurring Clustered Regularly Interspaced Short Palindromic Repeats (CRISPR)—CRISPR associated (Cas) (CRISPR-Cas) system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a Type-II Cas9 protein, wherein components (a) and (b) are located on same or different vectors of the system, whereby the guide RNA targets the target sequence and the Cas9 protein cleaves the DNA molecule, whereby expression of the at least one gene product is altered; and, wherein the Cas9 protein and the guide RNA do not naturally occur together, wherein preferably each RNA-guided endonuclease is derived from a Cas9 protein and comprises at least two nuclease domains, and optionally wherein one of the nuclease domains of each of the two RNA-guided endonucleases is modified such that each RNA-guided endonuclease cleaves one strand of a double-stranded sequence, and wherein the two RNA-guided endonucleases together introduce a double-stranded break in the chromosomal sequence that is repaired by a DNA repair method such that the chromosomal sequence is modified.

Typically the modification comprised a deletion, insertion or substitution of at least 5, 20, 50, 100 or 1000 bases, preferably up 10,000 or 1,000,000 bases.

The modification may be at any of the loci mentioned herein, for example in any of the regions or genes mentioned in any of the tables. The chromosomal interactions which are detected at other (non-modified) loci may also be in any of the loci mentioned herein, for example in any of the regions or genes mentioned in any of the tables.

Embodiments relating to genetic modifications many be performed on any organism, including eukaryotes, chordates, mammals, plants, agricultural animals and plants, and non-human organisms.

Preferred Gene Regions, Loci, Genes and Chromosome Interactions

For all aspects of the invention preferred gene regions, loci, genes and chromosome interactions are mentioned in the tables, for example in tables 1-18, 22, 24, 26, 27, 39-41, 43-46, 48-49 and 52. Typically the methods of the invention chromosome interactions are detected from at least 1, 3, 10, 20, 30 or 50 of the relevant genes listed in the tables. Preferably the presence or absence of at least 1, 3, 10, 20, 30 or 50 of the relevant specific chromosome interactions represented by the probe sequences in any one of the tables herein is detected. Preferably the presence or absence of at least 1, 3, 10, 20, 30 or 50 of the relevant specific chromosome interactions represented by the primer sequences in any of the tables, for example 44, 45, 47 or 52, are detected.

The region may be upstream or downstream of any of the genes mentioned herein, for example 50 kb upstream or 20 kb downstream, for example from the coding sequence.

In one embodiment the locus (including the gene and/or place where the chromosome interaction is detected) may comprise a CTCF binding site. This is any sequence capable of binding transcription repressor CTCF. That sequence may consist of or comprise the sequence CCCTC which may be present in 1, 2 or 3 copies at the locus. The CTCF binding site sequence may comprise the sequence CCGCGNGG-NGGCAG (in IUPAC notation). The CTCF binding site may be within at least 100, 500, 1000 or 4000 bases of the chromosome interaction or within any of the chromosome regions shown in the tables herein.

In one embodiment the chromosome interactions which are detected are present at any of the positions or in any of the regions (including the 4 kb region) shown in the tables. In the case where ligated products are detected in the method then sequence shown in any of the probe sequences in any of the tables may be detected. Thus typically sequence from both regions of the probe (i.e. from both sites of the chromosome interaction) could be detected. In preferred embodiments probes are used in the method which comprise or consist of the same or complementary sequence to a probe shown in any table. In some embodiments probes are used which comprise sequence which is homologous to any of the probe sequences shown in the tables.

In one embodiment for each condition the presence or absence of at least 1, 3, 5, 10, 20 of the relevant specific chromosome interactions represented by the top range of p-values or adjusted p-values shown in Table 51 are detected. In another embodiment for each condition the presence or absence of at least 1, 3, 5, 10, 20, 30 or 50 of the relevant specific chromosome interactions represented by the mid range of p-values or adjusted p-values shown in Table 51 are detected. In yet another embodiment for each condition the presence or absence of at least 1, 3, 5, 10, 20, 30 or 50 of the relevant specific chromosome interactions represented by the bottom range of p-values or adjusted p-values shown in Table 51 are detected. In another embodiment for each condition the presence or absence of at least 1, 2, 3, 5 or 10 of the relevant specific chromosome interactions from each of the top, mid and bottom ranges of p-values or adjusted p-values shown in Table 51 are detected, i.e. at least 3, 6, 9, 18 or 30 in total.

Particular combinations of chromosome interactions can be detected (i.e. determining the presence of absence of), which typically represent all of the interactions disclosed in a table herein or a selection from a table. As mentioned herein particular numbers of interactions can be selected from individual tables. In one embodiment at least 10%, 20%, 30%, 50%, 70% or 90% of the interactions disclosed in any table, or disclosed in relation to any condition, are detected. In another embodiment at least 10%, 20%, 30%, 50%, 70%, 90% or 100% of the interactions disclosed as being 'common' to more than one condition in any of the lists in the Examples are detected.

The interactions which are detected may correspond to presence or absence of a particular characteristic, for example as defined herein, such as in any table herein. If a combination of interactions are detected then they may all correspond with presence of the characteristic or they may all correspond to absence of the characteristic. In one embodiment the combination of interactions which is detected corresponds to at least 2, 5 or 10 interactions which relate to presence of the characteristic and at least 2, 5 or 10 other interactions that relate to absence of the characteristic.

The probe shown in table 52 may be part of or combined with any of the selections mentioned herein, particularly for conditions relating to cancer, and responsiveness to therapy, such as anti-PD1 therapy.

Tables Provided Herein

The tables herein either show probe (Episwitch™ marker) data or gene data representing chromosome interactions present in a condition (the first mentioned group) and absent in a control group, typically but not necessarily healthy individuals (the second mentioned group). The probe sequences show sequence which can be used to detect a ligated product generated from both sites of gene regions that have come together in chromosome interactions, i.e. the probe will comprise sequence which is complementary to sequence in the ligated product. The first two sets of Start-End positions show probe positions, and the second two sets of Start-End positions show the relevant 4 kb region. The following information is provided in the probe data table:

HyperG_Stats: p-value for the probability of finding that number of significant EpiSwitch™ markers in the locus based on the parameters of hypergeometric enrichment Probe Count Total: Total number of EpiSwitch™ Conformations tested at the locus Probe Count Sig: Number of EpiSwitch™ Conformations found to be statistical significant at the locus FDR HyperG: Multi-test (False Discovery Rate) corrected hypergeometric p-value Percent Sig: Percentage of significant EpiSwitch™ markers relative the number of markers tested at the locus log FC: logarithm base 2 of Epigenetic Ratio (FC)

AveExpr: average log 2-expression for the probe over all arrays and channels

T: moderated t-statistic p-value: raw p-value adj. p-value: adjusted p-value or q-value B-B-statistic (lods or B) is the log-odds that that gene is differentially expressed.

FC-non-log Fold Change

FC_1-non-log Fold Change centred around zero

LS-Binary value this relates to FC_1 values. FC_1 value below −1.1 it is set to −1 and if the FC_1 value is above 1.1 it is set to 1. Between those values the value is 0 The gene table data shows genes where a relevant chromosome interaction has been found to occur. The p-value in the loci table is the same as the HyperG_Stats (p-value for the probability of finding that number of significant EpiSwitch™ markers in the locus based on the parameters of hypergeometric enrichment).

The probes are designed to be 30 bp away from the Taq1 site. In case of PCR, PCR primers are also designed to detect ligated product but their locations from the Taq1 site vary.

Probe locations:
Start 1—30 bases upstream of Taq1 site on fragment 1
End 1—Taq1 restriction site on fragment 1
Start 2—Taq1 restriction site on fragment 2
End 2—30 bases downstream of Taq1 site on fragment 2
4 kb Sequence Location:
Start 1—4000 bases upstream of Taq1 site on fragment 1
End 1—Taq1 restriction site on fragment 1
Start 2—Taq1 restriction site on fragment 2
End 2—4000 bases downstream of Taq1 site on fragment 2

The following information is provided in the tables for each of the top ALS PCR markers:

GLMNET-procedures for fitting the entire lasso or elastic-net regularization. Lambda set to 0.5 (elastic-net)

GLMNET_1-lambda set to 1 (lasso)

FP-Exact Fishers Test P-value

Coef-Logistic Regression Coefficient, if you raise e (eˆX) to power of the coefficient you get the odds ratio for the variable S.E.-Standard Error Wald-Wald Equation Statistic. Wald statistics are part of a Wald test that the maximum likelihood estimate of a model coefficient is equal to 0. The test assumes that the difference between the maximum likelihood estimate and 0 is asymptotically normally distributed Pr(>|Z|)—P-value for the marker within the logistic model. Values below <0.05 are statistically significant and should be used in the logistic model.

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2\times10^5$ cells. The sample may contain up to $5\times10^5$ cells. In one embodiment, the sample will contain $2\times10^5$ to $5.5\times10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs.

In one embodiment, the typical fragment size is from 200 base pairs to 4,000 base pairs, such as 400 to 2,000 or 500 to 1,000 base pairs.

In one embodiment of the EpiSwitch method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Methods and Uses of the Invention

The method of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:
the locus may be any of the loci, regions or genes mentioned herein,
and/or wherein the chromosomal interaction may be any of the chromosome interactions mentioned herein or corresponding to any of the probes disclosed in the tables, and/or
wherein the ligated product may have or comprise (i) sequence which is the same as or homologous to any of the probe sequences disclosed herein; or (ii) sequence which is complementary to (ii).

The method of the invention can be described as a method for detecting chromosome states which represent different subgroups in a population comprising determining whether a chromosome interaction is present or absent within a defined epigenetically active (disease associated) region of the genome, wherein preferably:
the subgroup is defined by presence or absence of a characteristic mentioned herein, and/or
the chromosome state may be at any locus, region or gene mentioned herein; and/or
the chromosome interaction may be any of those mentioned herein or corresponding to any of the probes disclosed herein.

The invention includes detecting chromosome interactions at any locus, gene or regions mentioned herein. The invention includes use of the nucleic acids and probes mentioned herein to detect chromosome interactions, for example use of at least 10, 50, 100 or 500 such nucleic acids or probes to detect chromosome interactions in at least 10, 20, 100 or 500 different loci or genes.

Use of the Method of the Invention to Identify New Treatments

Knowledge of chromosome interactions which are shared between different disease conditions can be used to identify new treatments for conditions. Thus a known therapy for a particular condition which acts on the locus where the shared chromosomal interaction occurs may be used to treat other conditions where the chromosomal interaction is relevant. Thus in one embodiment the invention includes a method of selecting a therapy for treating a first condition comprising determining whether a chromosomal interaction associated with that condition is also associated with a second condition, and selecting a drug that treats the second condition and which acts on the locus where said chromosomal interaction occurs for treating the first condition, wherein optionally:
the chromosomal interaction is as defined in any one of the tables herein, and/or
the chromosomal interaction is identified by a method mentioned herein, and/or
said locus is any region or gene which is mentioned in a table herein, and/or
said first condition and/or said second condition are different conditions mentioned herein.

The Venn diagrams and Examples refer to conditions with genes and chromosome interactions in common. The first and second conditions may be selected from the combinations of conditions which are disclosed in individual Venn diagrams or individual lists in the Examples.

Methods of the Invention which relate to Common Characteristics of Conditions

Analysis of chromosomal interactions relevant to different conditions has shown that some interactions occur in both of them and represent an underlying common characteristic, such as a common mechanism or cause. Such chromosomal interactions can be used as the basis of a 'general' diagnostic test to detect conditions with the same common characteristic. Therefore the invention provides an embodiment in which the method is carried out as a general diagnostic test for a common characteristic of a multiplicity of conditions (such as 2, 3, 4, 5, or more conditions) wherein the presence of a chromosomal interaction is determined which common to more than one condition, wherein optionally the chromosomal interaction is mentioned in more than one table herein for different conditions, and/or the common characteristic is of being an autoimmune disease and/or a neurological condition.

The Venn diagrams and Examples refer to conditions with genes and chromosome interactions in common. They therefore disclose conditions which have underlying common characteristics as shown by common genes and chromosome interactions. In a preferred embodiment at least 1, 3, 5 or 10 chromosome interactions present in the list of common genes or chromosome interactions found to be common in the list are detected.

Homologues Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to % sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG Package provides the BEST-FIT program which can be used to calculate homology and/or % sequence identity (for example used on its default settings) (Devereux et al (1984) Nucleic Acids Research 12, p387-395). The PILEUP and BLAST algorithms can be used to calculate homology and/or % sequence identity and/or line up sequences (such as identifying equivalent or corresponding sequences (typically on their default settings), for example as described in Altschul S. F. (1993) J Mol Evol 36:290-300; Altschul, 5, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased.

Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent SurePrint G3 Custom CGH microarray platform. Detection of binding of first nucleic acids to the array may be performed by a dual colour system.

Therapeutic Agents

Therapeutic agents are mentioned herein. The invention provides such agents for use in preventing or treating the relevant condition. This may comprise administering to an individual in need a therapeutically effective amount of the agent. The invention provides use of the agent in the manufacture of a medicament to prevent or treat the disease. The methods of the invention may be used to select an individual for treatment. The methods of the invention, and in particular the method for carrying out a companion epigenetic test, may include a treatment step where a person identified by the method may then be administered with an agent that prevents or treats the relevant condition.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. The may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention also provides a kit for carrying out any process of the invention, including detection of a chromosomal interaction associated with a particular subgroup. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction. The invention also provides a device that is capable of detecting the relevant chromosome interactions.

The device preferably comprises any specific binding agents, probe or primer pair capable of detecting the chromosome interaction, such as any such agent, probe or primer pair described herein.

Preferred Therapeutic Agents for Use in the Invention for Specific Stated Condition A. Predisposition to Relapsing-Remitting Multiple Sclerosis (RRMS)
  Drugs used to treat the condition:
    Disease modifying therapies (DMT):
    Injectable medications
      Avonex (interferon beta-1a)
      Betaseron (interferon beta-1b)
      Copaxone (glatiramer acetate)
      Extavia (interferon beta-1b)
      Glatopa (glatiramer acetate)
      Plegridy (peginterferon beta-1a)
      Rebif (interferon beta-1a)
    Oral medications
      Aubagio (teriflunomide)
      Gilenya (fingolimod)
      Tecfidera (dimethyl fumarate)
    Infused medications
      Lemtrada (alemtuzumab)
      Novantrone (mitoxantrone)
      Tysabri (natalizumab)
    Managing relapses:
    High-dose intravenous Solu-Medrol®(methylprednisolone)
    High-dose oral Deltasone®(prednisone)
    H.P. Acthar Gel (ACTH)
      Steriods:
    Methylprednisolone B. Likelihood of Primary Progressive Multiple Sclerosis (PPMS)
  Drugs used to treat the condition:
    Steroids
    Immunosuppressive therapies such as total lymphoid radiation, cyclosporine, methotrexate, 2-chlorodeoxyadenosine, cyclophosphamide, mitoxantrone, azathioprine, interferon, steroids, and immune globulin.
    Copaxone
    Ocrelizumab (Genetech).

C. Predisposition to Fast Progressing Amyotrophic Lateral Sclerosis (ALS) Disease State
  Drugs used to treat the condition:
    Riluzole
    Baclofen.

D. Predisposition to Type 2 Diabetes Disease State
  Drugs used to treat the condition:
    Metformin
    Sulphonylureas such as:
      glibenclamide
      gliclazide
      glimepiride
      glipizide
      gliquidone
    Glitazones (thiazolidinediones, TZDs)
    Gliptins (DPP-4 inhibitors) such as:
      Linagliptin
      Saxagliptin
      Sitagliptin
      Vildagliptin
    GLP-1 agonists such as:
      Exenatide
      Liraglutide
    Acarbose
    Nateglinide and Repaglinide
    Insulin treatment.

E. Predisposition to Type 1 Diabetes Disease State
  Drugs used to treat the condition:
    Lantus subcutaneous
    Lantus Solostar subcutaneous
    Levemir subcutaneous
    Novolog Flexpen subcutaneous
    Novolog subcutaneous
    Humalog subcutaneous
    Novolog Mix 70-30 FlexPen subcutaneous
    SymlinPen 60 subcutaneous
    Humalog KwikPen subcutaneous
    SymlinPen 120 subcutaneous
    Novolin R injection
    Toujeo SoloStar subcutaneous
    Apidra subcutaneous
    Humalog Mix 75-25 subcutaneous
    Humulin 70/30 subcutaneous
    Humalog Mix 75-25 KwikPen subcutaneous
    Novolin N subcutaneous
    Humulin R injection
    Novolin 70/30 subcutaneous
    insulin detemir subcutaneous
    Levemir FlexTouch subcutaneous
    Humulin N subcutaneous
    insulin glargine subcutaneous
    Apidra SoloStar subcutaneous
    insulin lispro subcutaneous
    insulin regular human injection
    insulin regular human inhalation
    Humalog Mix 50-50 KwikPen subcutaneous insulin aspart subcutaneous
Novolog Mix 70-30 subcutaneous
Humalog Mix 50-50 subcutaneous
Afrezza inhalation
insulin NPH human recomb subcutaneous
insulin NPH and regular human subcutaneous
insulin aspart protamine-insulin aspart subcutaneous
Humulin 70/30 KwikPen subcutaneous
Humulin N KwikPen subcutaneous
Tresiba FlexTouch U-100 subcutaneous
Tresiba FlexTouch U-200 subcutaneous
insulin lispro protamine and lispro subcutaneous
pramlintide subcutaneous
insulin glulisine subcutaneous
Novolog PenFill subcutaneous
insulin degludec subcutaneous F. Predisposition to Systemic Luous Ervthematosus (SLE) Disease State
  Drugs used to treat the condition:
    Non-steroidal anti-inflammatory drugs (NSAIDS): ibuprofen, naproxen and diclofenac.
    Hydroxychloroquine
    Corticosteriods
    Immunosuppressants: azathioprine, methotrexate, mycophenolate mofetil and cyclophosphamide.
    Rituximab
    Belimumab.
    Corticosteroids: prednisone, cortisone and hydrocortisone
    NSAIDs: indomethacin (Indocin), nabumetone (Relafen), and celecoxib (Celebrex)
    Anti-inflammatories: aspirin and acetaminophen (Tylenol)
    Disease-Modifying Anti-Rheumatic Drugs (DMARDs): hydroxychloroquine (Plagenil), cyclosporine (Gengraf, Neoral, Sandimmune), and azathioprine (Azasan, Imuran).
    Antimalarials: chloroquine (Aralen) and hydroxychloroquine (Plaquenil).
    BLyS-specific Inhibitors or Monoclonal Antibodies (MAbS): Belimumab (Benlysta).
    Immunosuppressive Agents/Immune Modulators: azathioprine (Imuran), methotrexate (Rheumatrex), and cyclophosphamide (Cytoxan).
    Anticoagulants: low-dose aspirin, heparin (Calciparine, Liquaemin), and warfarin (Coumadin).

G. Predisposition to Ulcerative Colitis Disease State
Drugs used to treat the condition:
  Anti-inflammatory drugs: Aminosalicylates-sulfasalazine (Azulfidine), as well as certain 5-aminosalicylates, including mesalamine (Asacol, Lialda, Rowasa, Canasa, others), balsalazide (Colazal) and olsalazine (Dipentum) and Corticosteroids—prednisone and hydrocortisone.
  Immune system supressors: azathioprine (Azasan, Imuran), mercaptopurine (Purinethol, Purixam), cyclosporine (Gengraf, Neoral, Sandimmune), infliximab (Remicade), adalimumab (Humira), golimumab (Simponi) and vedolizumab (Entyvio).
  Other medications to manage specific symptoms of ulcerative colitis:
    Antibiotics
    Anti-diarrheal medication
    Pain relievers
    Iron supplements.

H. Likelihood of Relapse of Colorectal Cancer for Ulcerative Colitis Patients
  Drugs used to treat the condition:
    Aminosalicylates
    UC steroids
    Azathioprine I. Likelihood of Malianant Perioheral Nerve Sheath Tumours for Neurofibromatosis Patients
  Treatment
  Treatments for MPNST include surgery, radiotherapy and chemotherapy.

J. Likelihood of Developing Drostate Cancer and/or Amressive Prostate Cancer
  Drugs used to treat the condition:
    luteinising hormone-releasing hormone (LHRH) agonists
    anti-androgen treatment
    combined LHRH and anti-androgen treatment
    Steroids
    Other medical treatments:
    Abiraterone
    Enzalutamide
    docetaxel(Taxotere®)
    carboplatin or cisplatin chemotherapy K. Alzheimer's disease:
Drugs used to treat the condition:
  Donepezil
  Rivastigmine
  Galantamine
  Memantine

PUBLICATIONS

The contents of all publications mentioned herein are incorporated by reference into the present specification and may be used to further define the features relevant to the invention.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma *. The normalisation of the arrays is done using the normalised within Arrays function in Limma * and this is done to the on chip Agilent positive controls and EpiSwitch™ positive controls. The data is filtered based on the Agilent Flag calls, the Agilent control probes are removed and the technical replicate probes are averaged, in order for them to be analysed using Limma *. The probes are modelled based on their difference between the 2 scenarios being compared and then corrected by using False Discovery Rate. Probes with Coefficient of Variation (CV)<=30% that are <=−1.1 or =>1.1 and pass the p<=0.1 FDR p-value are used for further screening. To reduce the probe set further Multiple Factor Analysis is performed using the FactorMineR package in R.

* Note: LIMMA is Linear Models and Empirical Bayes Processes for Assessing Differential Expression in Microarray Experiments. Limma is a R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

Examples

The invention is illustrated by the following non-limiting Examples.

Example—Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value <=0.1 are selected and then further reduced by their Epigenetic ratio (ER), probes ER have to be <=−1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation.

Genetic locations below p-value of 0.3 or 0.2 are selected. The statistical probes mapping to these genetic locations, with the markers from step 2, form the high value markers for EpiSwitch™ PCR translation.

Array Design and Processing

Array Design

1. Genetic loci are processed using the 511 software (currently v3.2) to:
   a. Pull out the sequence of the genome at these specific genetic loci (gene sequence with 50 kb upstream and 20 kb downstream)
   b. Define the probability that a sequence within this region is involved in CC's
   c. Cut the sequence using a specific RE
   d. Determine which restriction fragments are likely to interact in a certain orientation
   e. Rank the likelihood of different CC's interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent Sure design website for custom CGH array.
7. Use probe group to design Agilent custom CGH array.

Array Processing

1. Process samples using EpiSwitch™ SOP for template production.
2. Clean up with ethanol precipitation by array processing laboratory.
3. Process samples as per Agilent SureTag complete DNA labelling kit—Agilent Oligonucleotide Array-based CGH for Genomic DNA Analysis Enzymatic labelling for Blood, Cells or Tissues
4. Scan using Agilent C Scanner using Agilent feature extraction software.

Indication Examples

Example 1—Amyotrophic Lateral Sclerosis (ALS)

The motor neurone disease Amyotrophic lateral sclerosis (ALS or Lou Gehrig's disease) is a fatal neurodegenerative disease characterised by progressive death of the primary motor neurones in the central nervous system. Symptoms include muscle weakness and muscle wasting, difficulty in swallowing and undertaking everyday tasks. As the disease progresses, the muscles responsible for breathing gradually fail, causing difficulty in breathing, and finally death. ALS has an average prevalence of 2 per 100,000, but is higher in the UK and USA with up to 5 per 100,000. There are estimated to be over 50,000 patients in the USA and 5,000 patients in the UK with the condition. The mortality rate for ALS sufferers is high: the median survival from diagnosis with ALS (i.e. the time when 50% of patients have died) varies in different studies, but in the most reliable (unbiased) population studies it is about 22 months with a range of 18-30 months. With no known cure, treatment of ALS focuses on supportive care. There is only one drug currently approved for treatment, riluzole which provides a modest increase in lifespan for ALS patients but minimal improvement in symptoms. Despite intensive research into the biological basis of ALS, diagnosis and methods of treatment, as well as monitoring of disease progression remains a challenge. Such prognostic tests would greatly benefit ALS sufferers by allowing sub-stratification of patients according to the biological mediators of clinical heterogeneity, potentially allowing a more precise prognosis and care planning by identifying fast and slow progressors. OBD has been discovering EpiSwitch™ markers to stratify ALS vs. healthy controls, and fast progressing ALS vs. slow progressing ALS, to develop and validate diagnostic, prognostic and predictive EpiSwitch™ biomarkers for ALS.

Source: Northeast Amyotrophic Lateral Sclerosis Consortium (NEALS)—USA

See Tables 1a, 1b, 1c and 1d hereinafter for ALS Probes— EpiSwitch™ markers to stratify ALS vs. healthy controls. Table 10 shows the gene data for this indication.

Further work was performed to validate the top ALS array markers and identify primers that could study the interactions. Statistical analysis of the array markers informed shortlist selection for PCR based assay development. From the list of the best stratifying ALS array probes, 99 markers were taken to the PCR stage.

Primers were designed using Integrated DNA Technologies (IDT) software (and Primer3web version 4.0.0 software if required) from markers identified from the microarray. Primer testing was carried out on each primer set; each set was tested on a pooled subset of samples to ensure that appropriate primers could study the potential interactions. Presence of an amplified product from PCR was taken to indicate the presence of a ligated product, indicating that particular chromosome interaction was taking place. If the primer testing was successful then the primer sets were taken through to screening.

The signature set was isolated using a combination of univariate (LIMMA package, R language) and 25 multivariate (GLMNET package, R language) statistics and validated using logistic modelling within WEKA (Machine learning algorithms package). The best 10 stratifying PCR markers were selected for validation on 58 individuals (29×ALS; 29×Healthy controls—HC) using data from the Northeast Amyotrophic Lateral Sclerosis Consortium (NEALS). These were selected based on their Exact Fisher's P-value. A consistently good marker from all 3 tests was the EpiSwitch marker in CD36. The first 9 PCR markers shown in Table 44 stratified between ALS and HC with 90% rank discrimination index. The ALS data was analysed against a small independent cohort of samples provided by Oxford University. Even in a small subset of samples stratification of samples was shown based on the biomarkers. Four markers stratify the subset of 32 (16 ALS, 16 Healthy Control) samples with p-value <0.3. These markers are ALS.21.23_2, DNM3.5.7_8, ALS.61.63_4 and NEALS.101.103_32, in genes EGFR, DNM3, CD36 and GLYCAMI respectively. The Fisher-Exact test, GLMNET and Bayesian Logistic modelling marked CLIC4 as a valuable addition to the four core markers.

Example 2—Diabetes Mellitus (DM) Type ii (T2DM)

Type 2 diabetes (also known as T2DM) is the most common form of diabetes. Diabetes may occur through either, the pancreas not producing enough hormone insulin which regulates blood sugar levels, or the body not being able to effectively use the hormone it produces due to reduced insulin sensitivity. Until recently, T2DM has only been diagnosed in adults, but it is now occurring in children and young adults. According to World Health Organisation (WHO), diabetes reached pandemic levels with 346 million sufferers worldwide and its incidence is predicted to double by 2030. In 2004 alone, approximately 3.4 million people died as a consequence of diabetes and its complications with the majority of deaths occurring in low- and middle-income countries. The incidence of T2DM is increasing due to an ageing population, changes in lifestyle such as lack of exercise and smoking, as well as diet and obesity. T2DM is not insulin dependent and can be controlled by changes in lifestyle such as diet, exercise and further aided with medication. Individuals treated with insulin are at a higher risk of developing severe hypoglycaemia (low blood glucose levels) and thus their medication and blood glucose levels require routine monitoring. Generally, older individuals with established T2DM are at a higher risk of cardiovascular disease (CVD) and other complications and thus usually require more treatment than younger adults with a recently-recognised disease. It has been estimated that seven million people in the UK are affected by pre-diabetic conditions, which increase the risk of progressing to T2DM. Such individuals are characterised by raised blood glucose levels, but are usually asymptomatic and thus may be overlooked for many years having a gradual impact on their health. Inventors develop prognostic stratifications for pre-diabetic state and T2DM. Presented herein are EpiSwitch™ markers to stratify pre-diabetic state (Pre-T2DM) vs. healthy controls, as well as the discovery of EpiSwitch™ markers to stratify T2DM vs. healthy control, and prognostic markers to stratify aggressive T2DM vs. slow T2DM.

Source: Norfolk and Norwich University Hospitals (NNUH), NHS Foundation Trust—Norwich UK See Tables 2a, 2b, 2c and 2d hereinafter for Pre-type 2 diabetes mellitus probes—EpiSwitch™ markers to stratify pre-type 2 diabetes vs. healthy controls. Table 11 shows the gene data.

See also Tables 3a, 3b, 3c, 3d hereinafter for Type 2 diabetes mellitus probes—EpiSwitch™ markers to stratify type 2 diabetes mellitus vs. healthy controls. Table 12 shows the gene data.

Example 3—Diabetes Mellitus Type I (T1DM)

Diabetes mellitus (DM) type 1 (also known as T1DM; formerly insulin-dependent diabetes or Juvenile diabetes) is a form of diabetes that results from the autoimmune destruction of the insulin-producing beta cells in the pancreas. The classical symptoms are polyuria (frequent urination), polydipsia (increased thirst), polyphagia (increased hunger) and weight loss. Although, T1DM accounts for 5% of all diabetes cases, it is one of the most common endocrine and metabolic conditions among children. Its cause is unknown, but it is believed that both genetic factors and environmental triggers are involved. Globally, the number of people with T1DM is unknown, although it is estimated that about 80,000 children develop the disease each year. The development of new cases varies by country and region. The United States and northern Europe fall between 8-17 new cases per 100,000 per year. Treatment of diabetes involves lowering blood glucose and the levels of other known risk factors that damage blood vessels.

Administration of insulin is essential for survival. Insulin therapy must be continued indefinitely and does not usually impair normal daily activities. Untreated, diabetes can cause many serious long-term complications such as heart disease, stroke, kidney failure, foot ulcers and damage to the eyes. Acute complications include diabetic ketoacidosis and coma. OBD's diabetes programme is focused on a development of EpiSwitch™ biomarkers for diagnostic and prognostic stratifications of T1DM.

Presented herein are EpiSwitch™ markers to stratify T1DM versus healthy controls.

Source: Caucasian samples collected by Procurement Company Tissue Solutions based in Glasgow (Samples collected in Russia); NEALS consortium controls (QU.).

See Tables 4a, 4b, 4c and 4d hereinafter for Type 1 diabetes mellitus (T1DM) probes—EpiSwitch™ markers to stratify T1DM vs. healthy controls. Table 13 shows the gene data.

Example 4—Ulcerative Colitis (UC)

Ulcerative colitis (UC), a chronic inflammatory disease of the gastrointestinal tract, is the most common type of inflammatory disease of the bowel, with an incidence of 10 per 100,000 people annually, and a prevalence of 243 per 100,000. Although, UC can occur in people of any age, it is more likely to develop in people between the ages of 15 and 30 and older than 60. The exact cause of ulcerative colitis is unknown. However, it is believed that an overactive intestinal immune system, family history and environmental factors (e.g. emotional stress) may play a role in causing UC.

It is more prevalent in people of Caucasian and Ashkenazi Jewish origin than in other racial and ethnic subgroups. The most common signs and symptoms of this condition are diarrhoea with blood or pus and abdominal discomfort. It can also cause inflammation in joints, spine, skin, eyes, and the liver and its bile ducts. UC diagnosis is carried out through taking family history, physical exam, lab tests and endoscopy of large intestine. This lifelong disease is associated with a significant morbidity, and the potential for social and psychological sequelae particularly if poorly controlled. An estimated 30-60% of people with ulcerative colitis will have at least one relapse per year. About 80% of these are mild to moderate and about 20% are severe. Approximately 25% of people with UC will have one or more episodes of acute severe colitis in their lifetime. Of these, 20% will need a surgical removal of all or part of the colon (colectomy) on their first admission and 40% on their next admission. Although mortality rates have improved steadily over the past 30 years, acute severe colitis still has a mortality rate of up to 2%. Mortality is directly influenced by the timing of interventions, including medical therapy and colectomy.

Ulcerative colitis has a well-documented association with the development of colorectal cancer, with greatest risk in longstanding and extensive disease. Treatment of relapse may depend on the clinical severity, extent of disease and patient's preference and may include the use of aminosalicylates, corticosteroids or immunomodulators. The resulting wide choice of agents and dosing regimens has produced widespread heterogeneity in management across the UK, and emphasises the importance of comprehensive guidelines to help healthcare professionals provide consistent high quality care.

Presented herein are EpiSwitch™ markers to stratify UC versus healthy controls for a development of disease-specific signatures for UC.

Source: Caucasian samples collected by Procurement Company Tissue Solutions based in Glasgow (Samples collected in Russia; NEALS consortium controls (QSA).

See Tables 5a, 5b, 5c and 5d hereinafter for Ulcerative colitis (UC) probes—EpiSwitch™ markers to stratify UC vs. healthy controls. Table 14 shows the gene data.

Example 5—Systemic Lupus Erythematosus (SLE)

Systemic lupus erythematosus (SLE), also known as discoid lupus or disseminated lupus erythematosus, is an autoimmune disease which affects the skin, joints, kidneys, brain, and other organs. Although "lupus" includes a number of different diseases, SLE is the most common type of lupus. SLE is a disease with a wide array of clinical manifestations including rash, photosensitivity, oral ulcers, arthritis, inflammation of the lining surrounding the lungs and heart, kidney problems, seizures and psychosis, and blood cell abnormalities. Symptoms can vary and can change over time and are not disease specific which makes diagnosis difficult. It occurs from infancy to old age, with peak occurrence between ages 15 and 40. The reported prevalence of SLE in the population is 20 to 150 cases per 100,000. In women, prevalence rates vary from 164 (white) to 406 (African American) per 100,000. Due to improved detection of mild disease, the incidence nearly tripled in the last 40 years of the 20th century. Estimated incidence rates are 1 to 25 per 100,000 in North America, South America, Europe and Asia. The exact cause of SLE is not known, but several factors have been associated with the disease. People with lupus often have family members with other autoimmune conditions. There may be environmental triggers like ultraviolet rays, certain medications, a virus, physical or emotional stress, and trauma. There is no cure for SLE and the treatment is to ease the symptoms. These will vary depending on expressed symptoms and may include anti-inflammatory medications, steroids, corticosteroids and anti-malarial drugs. Survival has been improving, suggesting that more or milder cases are being recognised. OBD has been developing prognostic signatures for SLE.

See Tables 6a, 6b, 6c and 6d for SLE probes—EpiSwitch™ markers to stratify SLE vs. healthy controls. Table 15 shows the gene data.

Source: Caucasian samples collected by Procurement Company Tissue Solutions based in Glasgow (Samples collected in USA); NEALS consortium controls.

Example 6—Multiple Sclerosis (MS)

Multiple sclerosis (MS) is an acquired chronic immune-mediated inflammatory condition of the central nervous system (CNS), affecting both the brain and spinal cord. The cause of MS is unknown. It is believed that an abnormal immune response to environmental triggers in people who are genetically predisposed results in immune-mediated acute, and then chronic, inflammation. The initial phase of inflammation is followed by a phase of progressive degeneration of the affected cells in the nervous system. MS is more common among people in Europe, the United States, Canada, New Zealand, and sections of Australia and less common in Asia and the tropics. It affects approximately 100,000 people in the UK. In the US, the number of people with MS is estimated to be about 400,000, with approximately 10,000 new cases diagnosed every year. People with MS typically develop symptoms between the ages 20 and 40, experiencing visual and sensory disturbances, limb weakness, gait problems, and bladder and bowel symptoms. They may initially have partial recovery, but over time develop progressive disability. Although, there is no cure, there are many options for treating and managing MS. They include drug treatments, exercise and physiotherapy, diet and alternative therapies. MS is a potentially highly disabling disorder with considerable personal, social and economic consequences. People with MS live for many years after diagnosis with significant impact on their ability to work, as well as an adverse and often highly debilitating effect on their quality of life and that of their families. OBD's MS programme involves looking at prognostic stratifications between primary progressive and relapsing-remitting MS.

The most common (approx. 90%) pattern of disease is relapsing-remitting MS (MSRR). Most people with this type of MS first experience symptoms in their early 20s. After that, there are periodic attacks (relapses), followed by partial or complete recovery (remissions). The pattern of nerves affected, severity of attacks, degree of recovery, and time between relapses all vary widely from person to person. Eventually, around two-thirds of people with relapsing-remitting MS enter a secondary progressive phase of MS. This occurs when there is a gradual accumulation of disability unrelated to relapses, which become less frequent or stop completely.

Presented herein are EpiSwitch™ monitoring markers to stratify MS patients who are responders to IFN-B treatment versus non-responders; EpiSwitch™ markers to stratify MSRR versus healthy controls and EpiSwitch™ markers to stratify MSRR (relapsing remitting type of MS) versus MSPP (primary progressive type of MS).

Source: Caucasian samples collected by procurement company Tissue Solutions, based in Glasgow (Samples collected in MS-RR: Russia: MS IFN-β R vs NR: USA); NEALS consortium controls (U5) See Tables 7a, b, c and d hereinafter for Relapsing-Remitting Multiple Sclerosis (MSRR) probes-EpiSwitch™ markers to stratify MSRR vs. healthy controls. Table 16 shows the gene data.

See also Tables 8a, 8b, 8c and 8d hereinafter for Multiple Sclerosis (MS) probes—EpiSwitch™ monitoring markers to stratify MS patients who are (B) responders to IFN-β (IFN-beta) treatment vs. (A) non-responders. Table 17 shows the gene data.

Example 7—Neurofibromatosis (NF)

In patients with NF1 mutation transformation into malignant state is difficult to predict, as it is governed by epigenetic context of the patient. In NF2 mutants, prognosis of the disease is very reliable and strongly defined by the genetics itself. Presented herein are EpiSwitch™ markers to stratify Malignant Peripheral Nerve Sheath Tumours (MPNSTs) vs. Benign plexiform showing 329 top probes in enriched data.

Source: Belgium—University of Leuven

See Tables 9a and 9b hereinafter for Neurofibromatosis (NF) probes—EpiSwitch™ markers to stratify Benign plexiform vs. Malignant Peripheral Nerve Sheath Tumours (MPNSTs). Table 18 shows the gene data.

Example 8: A Method of Determining the Chromosome Interactions which are Relevant to a Companion Diagnostic that Distinguishes Between Non-Responders and Responders of Methotrexate for the Treatment of Rheumatoid Arthritis Source: Glasgow Scottish Educational Research Association (SERA) cohort.

Introduction to and Brief Summary of Example 8

Stable epigenetic profiles of individual patients modulate sensitivity of signalling pathways, regulate gene expression, influence the paths of disease development, and can render ineffective the regulatory controls responsible for effective action of the drug and response to treatment. Here we analysed epigenetic profiles of rheumatoid arthritis (RA) patients in order to evaluate its role in defining the non-responders to Methotrexate (MTX) treatment.

Reliable clinical prediction of response to first-line disease modifying anti-rheumatic drugs (DMARDs, usually methotrexate (MTX)) in rheumatoid arthritis is not currently possible. Currently the ability to determine response to first line DMARDs (in particular, methotrexate (MTX)) is dependent on empiric clinical measures after the therapy.

In early rheumatoid arthritis (ERA), it has not been possible to predict response to first line DMARDs (in particular, methotrexate (MTX)) and as such treatment decisions rely primarily on clinical algorithms. The capacity to classify drug naïve patients into those that will not respond to first line DMARDs would be an invaluable tool for patient stratification. Here we report that chromosome conformational signatures (highly informative and stable epigenetic modifications that have not previously been described in RA) in blood leukocytes of early RA patients can predict non-responsiveness to MTX treatment.

Methods:

Peripheral blood mononuclear cells (PBMCs) were obtained from DMARD naïve ERA patients recruited in the Scottish early rheumatoid arthritis (SERA) inception cohort. Inclusion in this study was based on diagnosis of RA (fulfilling the 2010 ACR/EULAR Criteria) with moderate to high disease activity (DAS28 Z 3.2) and subsequent monotherapy with methotrexate (MTX). DAS28=Disease Activity Score of 28 joints. EULAR=The European League Against Rheumatism. ACR=American College of Rheumatology. MTX responsiveness was defined at 6 months using the following criteria: Responders—DAS28 remission (DAS28<2.6) or a good response (DAS28 improvement of >1.2 and DAS28≥3.2). Non-responders—no improvement in DAS28 (50.6). Initial analysis of chromosome conformational signatures (CCS) in 4 MTX responders, 4 MTX non-responders and 4 healthy controls was undertaken using an EpiSwitch™ array containing 13,322 unique probes covering 309 RA-related genetic loci. Differentiating CCS were defined by LIMMA * linear modeling, subsequent binary filtering and cluster analysis. A validation cohort of 30 MTX responders and 30 non-responders were screened for the differentiating CCS using the EpiSwitch™ PCR platform. The differentiating signature was further refined using binary scores and logistical regression modeling, and the accuracy and robustness of the model determined by ROC analysis **.

* Note: LIMMA is Linear Models and Empirical Bayes Methods for Assessing Differential Expression in Microarray Experiments. Limma is a R package for the analysis of gene expression data arising from microarray or RNA-Seq.

** Note: ROC means Receiver Operating Characteristic and refers to ROC curves. An ROC curve is a graphical plot that illustrates the performance of a binary classifier system as its discrimination threshold is varied. The curve is created by plotting the true positive rate against the false positive rate at various threshold settings.

CCS EpiSwitch™ array analysis identified a 30-marker stratifying profile differentiating responder and non-responder ERA patients. Subsequent evaluation of this signature in our validation cohort refined this to a 5-marker CCS signature that was able to discriminate responders and non-responders. Prediction modeling provided a probability score for responders and non-responders, ranging from 0.0098 to 0.99 (0=responder, 1=non-responder). There was a true positive rate of 92% (95% confidence interval [95% CI] 75-99%) for responders and a true negative rate of 93% (95% CI 76-99%) for non-responders. Importantly, ROC analysis to validate this stratification model demonstrated that the signature had a predictive power of sensitivity at 92% for NR to MTX.

We have identified a highly informative systemic epigenetic state in the peripheral blood of DMARD naïve ERA patients that has the power to stratify patients at the time of diagnosis. The capacity to differentiate patients a priori into non-responders, using a blood-based clinical test, would be an invaluable clinical tool; paving the way towards stratified medicine and justifying more aggressive treatment regimes in ERA clinics.

Detailed Version of Example 8

The capacity to differentiate patients a priori into responders (R) and non-responders (NR) would be an invaluable tool for patient stratification leading to earlier introduction of effective treatment. We have used the EpiSwitch™ biomarker discovery platform to identify Chromosome Conformation Signatures (CCS) in blood-derived leukocytes, which are indicative of disease state and MTX responsiveness. Thereby we identified an epigenetic signature contained in the CXCL13, IFNAR1, IL-17A, IL-21R and IL-23 loci that provide the first prognostic molecular signature that enables the stratification of treatment naïve early RA (ERA) patients into MTX R and NR. Importantly, this stratification model had a predictive power of sensitivity at 92% for NR to MTX. This epigenetic RA biomarker signature can distinguish between ERA and healthy controls (HC). This combinatorial, predictive peripheral blood signature can support earlier introduction of more aggressive therapeutics in the clinic, paving the way towards personalized medicine in RA.

RA is a chronic autoimmune disease affecting up to 1% of the global population. Pathogenesis is multifactorial and characterized by primarily immune host gene loci interacting with environmental factors, particularly smoking and other pulmonary stimuli. The exposure of a genetically susceptible individual to such environmental factors suggests an epigenetic context for disease onset and progression. Recent studies of chromatin markers (e.g. methylation status of the genome) provide the first evidence of epigenetic differences associated with RA. However, to date neither genetic associations, nor epigenetic changes, have provided a validated predictive marker for response to a given therapy. Moreover, clinical presentation only weakly predicts the efficacy and toxicity of conventional DMARDs. MTX, the commonest first-choice medication recommended by EULAR (The European League Against Rheumatism) and ACR (American College of Rheumatology) management guidelines, delivers clinically meaningful response rates ranging from 50 to 65% after 6 months of treatment. Such responses, and especially the rather smaller proportion that exhibits high hurdle responses, cannot currently be predicted in an individual patient. This begets a 'trial and error' based approach to therapeutic regimen choice (mono or combinatorial therapeutics). The ability to predict drug responsiveness in an individual patient would be an invaluable clinical tool, given that response to first-line treatment is the most significant predictor of long-term outcome.

Herein we focused on epigenetic profiling of DMARD-naïve, ERA patients from the Scottish Early Rheumatoid Arthritis (SERA) inception cohort in order to ascertain if there is a stable blood-based epigenetic profile that indicates NR to MTX treatment and thus enables a priori identification and stratification of such patients to an alternate therapeutic. The source Epigenetic modulation can strongly influence cellular activation and transcriptional profiles. Conceivably, the mode of action for a drug could be affected by epigenetically modified loci. We have focused on CCS, also known as long-range chromatin interactions, because they reflect highly informative and stable high-order epigenetic status which have significant implications for transcriptional regulation. They also offer significant advantages and early functional links to phenotypic differences, and have been reported as informative biomarkers candidates in oncology and other disease areas.

We used early RA (ERA) patients provided by the Scottish early rheumatoid arthritis (SERA) inception cohort. Demographic, clinical and immunological factors were obtained at diagnosis and 6 months. Inclusion in this study was based on a diagnosis of RA (fulfilling the 2010 ACR/EULAR Criteria) with 5 moderate to high disease activity (DAS28 z 3.2) and subsequent monotherapy with MTX. Responders were defined as patients who upon receiving MTX achieved DAS28 remission (DAS28<2.6) or a good response (DAS28 improvement of >1.2 and DAS28≤53.2) at 6 months. Non-responders were defined as patients who upon receiving MTX had no improvement in DAS28 (50.6) at 6 months. Blood samples for epigenetic analysis were collected at diagnosis. (DAS28=Disease Activity Score of 28 joints.) We used a binary epigenetic biomarker profiling by analysing over 13,322 chromosome conformation signatures (CCS) (13,322 unique probes) across 309 genetic loci functionally linked to RA. CCS, as a highly informative class of epigenetic biomarkers, were read, monitored and evaluated on EpiSwitch™ platform which has been already successfully utilized in blood based stratifications of Mayo Clinic cohort with early melanoma and is currently used for predictive stratification of responses to immunotherapies with PD-1/PD-L1.

Identified epigenetic profiles of naïve RA patients were subject to statistical analysis using GraphPad Prism, WEKA and R Statistical language. By using EpiSwitch™ platform and extended cohort of 90 clinical samples we have identified a pool of over 922 epigenetic lead biomarkers, statistically significant for responders, non-responders, RA patients and healthy controls.

To identify a pre-treatment circulating CCS status in ERA patients, 123 genetic loci (Table 22) associated with RA pathogenesis were selected and annotated with chromosome conformations interactions predicted using the EpiSwitch™ in silico prediction package. The EpiSwitch™ in silico prediction generated 13,322 high-confidence CCS marker candidates (Table 22). These candidates were used to generate a bespoke discovery EpiSwitch™ array to screen peripheral blood mononuclear cells isolated at the time of diagnosis (DMARD-naïve) from 4 MTX responders (R) and 4 MTX NR, all clinically defined after 6 months therapy (Table 23), and 4 healthy controls (HC). To identify the CCS that differentiated R, NR and HC, a LIMMA * linear model of the normalized epigenetic load was employed. A total of 922 statistically significant stratifying markers (significance assessed on the basis of adjusted p value and EpiSwitch™ Ratio) were identified. Of the 922 lead markers, 420 were associated with NR, 210 with R and 159 with HC. Binary filtering and cluster analysis was applied to the EpiSwitch™ markers to assess the significance of CCS identified. A stepwise hierarchical clustering approach (using Manhattan distance measure with complete linkage agglomeration and taking into account R vs NR, HC vs R & HC vs NR) reduced the number 35 of significant markers from 922 to 65 and finally resulted in a 30-marker stratifying profile (Table 3).

* Note: LIMMA is Linear Models and Empirical Bayes Methods for Assessing Differential Expression in Microarray Experiments. Limma is a R package for the analysis of gene expression data arising from microarray or RNA-Seq.

To refine and validate the CCS signature, the 30 identified markers were screened in a second ERA patient cohort of R and NR (Table 25) in a stepwise approach, using the EpiSwitch™ PCR platform. In the first instance, the entire 30 CCS markers were run in 12 ERA patients (6 R and 6 NR). The best differentiating CCS markers were Identified by applying a Chi-squared test for independence with Yate's continuity correction on the binary scores, revealing a 12-marker CCS profile (Table 26). These 12 CCS markers were run on an additional 12 ERA patients (6 R and 6 NR) and the data combined with the previous 12 ERA.

Combining the 24 patient samples (12 R and 12 NR) a logistic regression Model in the WEKA classification platform (using 5-fold cross validation to score the discerning power of each marker) was built and run 10 times by random data re-sampling of the initial data set to generate 10 different start points for model generation. The markers with the highest average scores were selected, thus reducing the profile to the 10 best discerning CCS markers (Table 26). The 10 CCS markers were used to probe a further 36 ERA samples (18 R and 18 NR). Combining all data (30 R and 30 NR), and using the same logistical regression and score calculation analysis, revealed a 5 CCS marker signature (IFNAR1, IL-21R, IL-23, IL-17A and CXCL13) that distinguished MTX R from NR (Table 26). CCS in the CXCL13 and IL-17A loci were associated 20 with non-responders whilst CCS in the IFNAR1, IL-23 and IL-21R loci were associated with responders. This was an intriguing profile given the central role postulated for the IL-17 axis in human autoimmunity.

Importantly, the composition of the stratifying signature identifies the location of chromosomal conformations that potentially control genetic locations of primary importance for determining MTX response. Principal component analysis (PCA) of the binary scores for the classifying 5 EpiSwitch™ CCS markers provided clear separation of ERA patients based on their MTX response. The model provided a prediction probability score for responders and non-responders, ranging from 0.0098 to 0.99 (0=responder, 1=non-responder). The cut-off values were set at 50.30 for responders and 20.70 for non-responders. The score of 50.30 had a true positive rate of 92% (95% confidence interval [95% CI] 75-99%) whilst a score of 20.70 had a true negative response rate of 93%(95% CI 76-99%). The number of observed and predicted patients per response category (R or NR to MTX) is shown in Table A below. With the EpiSwitch™ CCS marker model, 53 patients (88%) were classified as either responder or non-responder.

Table A. Observed and predicted number of R and NR to MTX monotherapy at 6 months using the EpiSwitch™ CCS model

TABLE A

Observed and predicted number of R and NR to MTX monotherapy at 6 months using the EpiSwitch ™ CCS model

| Observed response | Predicted response | | |
|---|---|---|---|
| | Non-responder | Undefined | Responder |
| Non-responder | 25 | 3 | 2 |
| Responder | 2 | 4 | 24 |

Cut off levels were chosen based on the probability of response to MTX of (approximately)>0.70 for NR and <0.3 for R. NR and R were defined as described in the methods.

In order to test the 'accuracy' and 'robustness of performance' of the logistic classifying model that determined the 5 EpiSwitch™ CSS markers, 150 ROC ** curves (with unique start points) were generated by random data re-sampling of the R and NR data. This resulted in the data being split into training (66%, equivalent to 6000 known class samples) and test (34%, equivalent to 3000 unknown class samples) groups; importantly the same split is never seen in the data for cross validation. The average discriminative ability (AUC) of the model was 89.9% (95% CI 87-100%), with an average sensitivity (adjusted for response prevalence) for NR of 92% and an average specificity for R of 84%. To determine the predictive capability of the model, the average model accuracy statistics were adjusted for population R/NR to MTX using Bayes prevalence theorem. Using a 55% MTX response rate, the positive predictive value (PPV) was 90.3% whilst the negative predictive value (NPV) was 86.5%. If the response rate was adjusted to 60%, this decreased the PPV to 87% whilst increasing the NPV to 89%.

As an independent evaluation of the discerning powers of the selected 5 EpiSwitch™ CCS markers, factor analysis of mixed data (FAMD) incorporating 30 HC was performed. This illustrated that the signature not only has the power to differentiate between MTX R and NR but also retains sufficient disease-specific features to differentiate between healthy individuals and RA patients.

Example 8—Table 27C and 27D—Stratifying Between RA-MTX Responders and Non-Responders Table 27C, and continuation Table 27D show inter alia a list of about 54 DNA probes (60mers) and their DNA sequences. These probes represent some of the probes used in Example 9. The probes illustrated in Table 27C and 27D can be used to stratify between RA-MTX responders and RA-MTX non-responders. The shown probes were investigated further by PCR. P Value=Probability value; adj.=adjusted.

Example 8—Conclusion

In conclusion, our study of the epigenetic profile classification of DMARD naïve ERA patients on the basis of prospective clinical assessment for R/NR has identified a consistent epigenetic signature, which discriminates an epigenetic state that is conducive and non-conducive to MTX response. This is to our knowledge, the first example of a stable and selectively differentiating blood based epigenetic biomarker in early RA patients that appears disease related (versus healthy controls) and that can predict non-responsiveness to first-line MTX therapy. This model offers direct and practical benefits with a validated classifier based on 5 conditional CCS and their detection by the industrial ISO-13485 EpiSwitch™ platform, which has the potential to be routinely available in the near future within clinical practice. Importantly, by adopting this predictive signature it should be possible to stratify MTX naïve ERA patients into R and NR cohorts. This offers the potential to accelerate patient progression through the currently approved treatment strategy for ERA seeking earlier use of effective therapeutics, hence leading to a 'personalised' treatment regime. Furthermore, alternative CCS signatures will be present in RA patients (and patients with other autoimmune diseases) that could be used to justify fast-tracked biological treatment regimes in the clinic. This would have far reaching socioeconomic implications, providing more cost effective and robust therapeutic approaches.

Example 8—Material and Methods

RA Patient Population

ERA patients in this study are part of the Scottish early rheumatoid arthritis (SERA) inception cohort. Demographic, clinical and immunological factors were obtained at diagnosis and 6 months. Inclusion in the inception cohort was based on clinical diagnosis of undifferentiated polyarthritis or RA (≥1 swollen joint) at a secondary care rheumatology unit in Scotland. Exclusion criteria were previous or current DMARD/biological therapy and/or established alternative diagnosis (i.e. psoriatic arthritis, reactive arthritis). Inclusion in this study was based on a diagnosis of RA (fulfilled the 2010 ACR/EULAR criteria for RA) with moderate to high disease activity (DAS28≥3.2) and subsequent monotherapy with MTX. [DAS28=Disease Activity Score of 28 joints. EULAR=European League Against Rheumatism. ACR=American College of Rheumatology.] Responders were defined as patients who upon receiving MTX achieved DAS28 remission (DAS28<2.6) or a good response (DAS28 improvement of >1.2 and DAS28≤3.2) at 6 months. Non-responders were defined as patients who upon receiving MTX had no improvement in DAS28 (≤0.6) at 6 months. Blood samples were collected at diagnosis (Baseline) in EDTA tubes and centrifuged to generate a buffy layer containing PBMCs, which was harvested and stored at −80° C.

EpiSwitch™ processing, array and PCR detection. Probe design and locations for EpiSwitch™ assays Pattern recognition methodology was used to analyse human genome data in relation to the transcriptional units in the human genome. The proprietary EpiSwitch™ pattern recognition software provides a probabilistic score that a region is involved in chromatin interaction. Sequences from 123 gene loci were downloaded and processed to generate a list of the 13,322 most probable chromosomal interactions. 60mer probes were designed to interrogate these potential interactions and uploaded as a custom array to the Agilent SureDesign website. Sequence-specific oligonucleotides were designed using Primer3, at the chosen sites for screening potential markers by nested PCR. Oligonucleotides were tested for specificity using oligonucleotide specific BLAST.

Chromatin Conformation Signature Analysis from Patient PBMC's

Template preparation: Chromatin from 50 µl of each PBMC sample was extracted using the EpiSwitch™ assay following the manufacturer's instructions (Oxford BioDynamics Ltd). Briefly, the higher order structures are fixed with formaldehyde, the chromatin extracted, digested with Taq1, dilution and ligation in conditions to maximize intramolecular ligation, and subsequent proteinase K treatment. EpiSwitch™ microarray: EpiSwitch™ microarray hybridization was performed using the custom Agilent 8x60k array using the Agilent system, following the manufacturer's instructions (Agilent). Each array contains 55088 probes spots, representing 13,322 potential chromosomal interactions predicted by the EpiSwitch™ pattern recognition software quadruplicated, plus EpiSwitch™ and Agilent controls. Briefly, 1 µg of EpiSwitch™ template was labelled using the Agilent SureTag labelling kit. Processing of labelled DNA was performed. Array analysis was performed immediately after washing using the Agilent scanner and software. In order to compare all the experiments the data was background corrected and normalized. Since each spot in the array is present in quadruplicate, the median of the four spots of each probe in the array was calculated and its log 2 transformed value was used for further analysis. The coefficient of variation and p-value was calculated for each probe replicate. EpiSwitch™ PCR detection: Oligonucleotides were tested on template to confirm that each primer set was working correctly. To accommodate for technical and replicate variations, each sample was processed four times. All the extracts from these four replicates were pooled and the final nested PCR was performed on each sample. This procedure permitted the detection of limited copy-number templates with higher accuracy. All PCR amplified samples were visualised by electrophoresis in the LabChip' GX from Perkin Elmer, using the LabChip DNA 1K Version2 kit (Perkin Elmer) and internal DNA marker was loaded on the DNA chip according to the manufacturer's protocol using fluorescent dyes. Fluorescence was detected by laser and electropherogram read-outs translated into a simulated band on gel picture using the instrument software. The threshold we set for a band to be deemed positive was 30 fluorescence units and above.

Statistical Methods and Packages.

GraphPad Prism and SPSS were used for all statistical analyses of clinical data. The chi-square test and Fisher's exact test (for categorical variables), the t-test for independent samples (for continuous normally distributed variables), and the Mann-Whitney U test (for continuous variables without normal distribution) were used to identify differences. The level of statistical significance was set at 0.05, and all tests were 2-sided. R (and appropriate packages) were used for evaluation of EpiSwitch™ data. This included Stats package for Chi-square test and GLM (logit), ROCR package for ROC curves from WEKA odds probabilities, gplot & stats package in R for Heatmaps. FactorMiner package was used for PCA and Factor plots. Weka was used for Attribute Reduction, data randomisation and re-sampling, Logistic Model Classifier, AUC calculations and model accuracy calculations.

Example 8A—RA Analysis: MTX Responders Vs Non-Responders: Work Subsequent to Example 8

In Example 1A, a biostatistical hypergeometric analysis was carried out, using the "Statistical Pipeline" method(s) at the beginning of the Examples section in the present specification, to generate further refined DNA probes stratifying between MTX responders vs MTX non-responders, for RA patients on MTX monotherapy.

Results: Table 27A (and continuation part Tables 27B and 27AB) hereinafter discloses Probe and Loci data for RA-MTX—DNA probes stratifying between responders (R) and non-responders (NR). B=B-statistic (lods or B), which is the log-odds that that gene is differentially expressed. FC is the non-log Fold Change. FC_1 is the non-log Fold Change centred around zero. It is seen that Table 27A+27B includes the sequences of 25 refined preferable DNA probes (60mers) for identifying MTX responders (MTX-R), and of 24 refined preferable DNA probes (60mers) for identifying MTX responders (MTX-NR), from the hypergeometric analysis.

Example 9: A Method of Determining the Chromosome Interactions Relevant to a Companion Diagnostic as Pharmacodynamic Biomarker During the Inhibition of LSD1 in the Treatment of AML (Acute Myeloid Leukemia)

Source: Institute of Cancer Research UK.

Pharmacodynamic Biomarkers

Pharmacodynamic (PD) biomarkers are molecular indicators of drug effect on the target in an organism. A PD biomarker can be used to examine the link between drug regimen, target effect, and biological tumour response. Coupling new drug development with focused PD biomarker measurements provides critical data to make informed, early go/no-go decisions, to select rational combinations of targeted agents, and to optimise schedules of combination drug regimens. Use of PD endpoints also enhances the rationality and hypothesis-testing power throughout drug development, from selection of lead compounds in preclinical models to first-in-human trials (National Cancer Institute).

The inventors have discovered that chromosome signatures could be used as pharmacodynamic biomarkers to monitor response to a number of drugs at time points consistent with phenotypic changes observed.

EpiSwitch™ Markers—Ideal Pharmacodynamic Biomarkers

Work on BET (bromodomain and extra-terminal) inhibitors on MV4-11 cell lines has shown that BET inhibition causes the transcriptional repression of key oncogenes BCL2, CDK6, and C-MYC BET inhibitors like LSD1 inhibitors are epigenetic therapies, targeting the acetylated and methylation states of histones. As topological changes at loci precede any regulatory changes, the findings at the MYC locus with EpiSwitch™ show evidence of regulatory change with LSD1 inhibition. MV4-11 cell line harbours translocations that express MLL-AF4 and FLT3-ITD whereasTHP-1 only expresses MLL-AF9.

EpiSwitch™ LSD1 Inhibition Biomarker Study for AML (Acute Myeloid Leukemia)

Epigenetic biomarkers identified by EpiSwitch™ platform are well suited for delineating epigenetic mechanisms of LSD1 demethylase and for stratification of different specificities of LSD1 inhibitors within and between cell lines. This work demonstrates that chromosome conformation signatures could be used as mechanism-linked predictive biomarkers in LSD1 inhibition. A standard LSD1 inhibitor is investigated in this study, tranylcypromine (TCP).

EpiSwitch™ LSD1 Pharmacodynamic Biomarker Discovery

The cells were treated with 1 uM of tranylcypromine (TCP). Two AML (acute myeloid leukemia) cell lines THP-1 and MV4-11 were tested with the above compound. Chromosome signatures identified in the vicinity of MYD88 gene in THP-1 cells are shown in Table 28. Chromosome signatures identified in the vicinity of MYD88 gene in MV4-11 cells are shown in Table 29. Each number combination, points to individual chromosome interaction. The positions across the gene have been created and selected based on restriction sites and other features of detection and primer efficiency and were then analysed for interactions. The result in tables 28 and 29 represent no signature detection. A signature detection is represented with the number 1. Below are the PCR EpiSwitch™ marker results for the MyD88 locus for cell lines THP-1 and MV4-11. FACS analysis was used to sort for the expression of CD11b± cells, as an indicator of differentiation. MyD88 and MYC loci were selected on the basis of previously published studies, as key genetic drivers of treatment changes at 72 hrs.

LSD1 Inhibitor (TCP) Experiments—Discovery Findings

The conformations that change at the later time point (72 hrs) relative to the untreated cells show the most consistency between the 2 cell types. These are the markers above the bold double line shown in the THP-1 data, and highlighted by the shaded cells in the MV4-11 data.

LSD1 inhibition removes a long range interaction with 5' upstream to the ORF of MYD88, changing the regulatory landscape for the locus.

LSD1 Inhibition Analysis Versus Gene Expression Data—Temporal and Structural Correlation of MYC Locus Conformations with Gene Expression (GEX)

MYC is the target gene that drives the AML (acute myeloid leukemia) pathology, but at 72 hrs treatment, the fold change is too small to be significant for a marker. The changes seen in Table 30 at the MYC locus at 72 hrs for GEX data correlates to the conformation changes identified at 72 hrs. The negative GEX change at MYC relative to the untreated cells is in keeping with the requirement to perturb MYC proliferation effect. The change is small also in keeping with the tight control elicited on this locus by numerous signal cascades.

Unlike GEX data above, the EpiSwitch™ biomarkers clearly detect changes in chromosome conformation signatures at 72 hr treatments correspondent with cells differentiation and their death by apoptosis (phenotypic change).

LSD1 Inhibition Analysis versus Gene Expression Data—Temporal and Structural Correlation of MyD88 Locus Conformations with Gene Expression (GEX) The changes seen at MyD88 at 72 hrs for the GEX data correlate to the conformation changes identified at 72 hrs. The GEX change is positive relative to untreated cells, which is in keeping with the differential seen in these AML (acute myeloid leukemia) cells after treatment with the LSD1 inhibitor.

Only 1.5 fold change observed at 72 hr treatment with TCP at MYD88 locus identified both by GEX and EpiSwitch™. This level of change is too affected by noise in microarray gene expression analysis. However, epigenetic changes observed for chromosome signatures are clean to follow a binary format of 0 or 1. The data shows distinct pattern of changes. Both MYC and MYD88 are epigenetic drivers that, as shown in the GEX data, may not present with the strong response in gene expression, but can be identified as key epigenetic changes are visible through chromosome signatures. These two genetic drivers define phenotypic changes required for successful therapy treatment. At 72 hrs cells differentiate and undergo apoptosis. [Tables 31 to 33 also relate to this Example]

Example 10: A Method of Determining the Chromosome Interactions which are Relevant to a Companion Diagnostic for Prognosis of Melanoma Relapse in Treated Patients (PCR Data). Source: Mayo Clinic Metastatic Melanoma Cohort, USA A prognostic biomarker predicts the course or outcome (e.g. end, stabilisation or progression) of disease. This study discovers and validates chromosome signatures that could act as prognostic biomarkers for relapse to identify clear epigenetic chromosome conformation differences in monitored melanoma patients, who undergone surgery treatment, for signs of relapse or recovery, and to validate such biomarkers for potential to be prognostic biomarkers for monitoring relapse of melanoma. Here we want to present our example of validated prognostic use of chromosome conformation signatures in application to confirmed melanoma patients who have undergone treatment by the resection of the original growth in order to identify the candidates who are likely to relapse within 2 years of treatment.

224 melanoma patients were treated with surgery to remove their cancer. They were then observed for a period of two years with blood being drawn for analysis at >100 days after the surgery.

EpiSwitch™ Prognostic Biomarker Discovery

Chromosome signatures of 44 genes associated with melanoma and the rest of the genome for any disease-specific long range interaction by Next Generation Sequencing NGS were tested. Non-biased assessment of chromosome signatures associated with melanoma through deep sequencing provided initial pool of 2500 candidate markers. Further analysis by EpiSwitch™ platform on expanding sets of blood samples from melanoma patients and patients with non-melanoma skin cancers (NMSC) as control, reduced the initial pool of candidate markers to 150. With further expansion on sample numbers it has been reduced to 32, as shown in Table 34.

Prognosis of Relapse

Top 15 markers previously identified for stratification of melanoma from non-melanoma skin cancers comprise TBx2 7/15, TYR 1/9, TYR 13/17, TYR 3/11, TYR 3/23, P16 11/19, P16 7/23, P16 9/29, MITF 35/51, MITF 43/61, MITF 49/55, BRAF 5/11, BRAF 27/31, BRAF 21/31, BRAF 13/21, which were taken from a total of 8 genes: TBx2; TYR; BRAF; MiTF; p16; BRN2; p21; TBx3 3C analysis of melanoma patients' epigenetic profiles revealed 150 chromosome signatures with a potential to be prognostic biomarkers, reduced to three in expanding sets of testing sample cohorts. The three chromosome signatures which show the switches in chromosome conformational signature highly consistent with treatment and 2 year outcome for relapse, and this are the best potential prognostic melanoma markers are: BRAF 5/11, p16-11/19 and TYR 13/17. Finally, three chromosome signatures were carried out to the validation stage as prognostic biomarkers.

Table 35 shows that relapse has been observed within two years after the treatment among the above patients. Through completely non-biased analysis of chromosome signatures these disease-specific three markers remained present and unchanged after treatment in majority of patients who relapsed after treatment. Table 36 provides evidence that chromosome signatures change as a result of treatment to reflect more healthy profile. Through completely non-biased analysis of chromosome signatures the same disease-specific three markers have changed and were absent in majority of patients after treatment, with no signs of relapse for 2 years. Table 37 shows that the same three prognostic biomarkers show a strong tendency to be absent in healthy population. From all melanoma specific biomarkers identified in initial discovery stage, only these three markers carried prognostic value due to their change after treatment, in that they were different from diagnostic markers. Table 38 also relates to this Example.

These results confirm that the three identified chromosome signatures exemplify the evidence for chromosome signatures acting as valid and robust prognostic biomarkers.

Example 11: Predictive/Pharmacodynamic Biomarkers for Drug Response: Anti-PD-1 in Metastatic Melanoma Patients (Array Data)

Melanoma

Malignant melanoma is the least common, but most aggressive form of skin cancer. It occurs in melanocytes, cells responsible for synthesis of the dark pigment melanin. The majority of malignant melanomas are caused by heavy UV exposure from the sun. Most of the new melanoma cases are believed to be linked to behavioural changes towards UV exposure from sunlight and sunbeds. Globally, in 2012, melanoma occurred in 232,000 people and resulted in 55,000 deaths. Incidence rates are highest in Australia and New Zealand. The worldwide incidence has been increasing more rapidly amongst men than any other cancer type and has the second fastest incidence increase amongst women over the last decade. The survival rates are very good for individuals with stage 1 and 2 melanomas. However, only 7-19% of melanoma patients whose cancer has spread to distant lymph nodes or other parts of the body will live for more than 5 years. Currently, the only way to accurately diagnose melanoma is to perform an excision biopsy on the suspicious mole. The treatment includes surgical removal of the tumour. There is no melanoma screening programme in the UK, but educational programmes have been created to raise awareness of risks and symptoms of melanoma. There is a high demand for screening programmes in countries where melanoma incidence is very high e.g. in Australia.

This work concerns biomarkers for diagnosis, prognosis, residual disease monitoring and companion diagnostics for melanoma immunotherapies.

Study Background

The major issue with all immunomodulators currently tested in the treatment of cancers is their low 10 response rates. In the case of late melanoma, for anti-PD-i or anti-PD-Li monoclonal antibodies, the objective response rate is only 30-40%. Such therapy is in strong need of biomarkers predicting responders vs. non-responders. The PD-1 locus is regulated by cytokines epigenetically through resetting of long range chromosome conformation signatures.

OBD Technology

EpiSwitch™ platform technology is ideally suited for stratification of PD-1 epigenetic states prior to and in response to immunotherapy. An EpiSwitch™ array has been designed for analysis of >332 loci implicated in controls and modulation of response to anti-PD-1 treatment in melanoma patients.

Methods

Biomarker identification using EpiSwitch™ array analysis:

1. Chromosome conformations for 332 gene locations determined by EpiSwitch,™ pattern recognition.
2. 14,000 EpiSwitch™ markers on PD1 screening array.

Samples

All patients have been previously treated with chemotherapy and anti-CTLA-4 therapy. Two time points considered pre-treatment (baseline samples) and post-treatment (12 week samples)

Discovery Cohort 4 responders vs. 4 non-responders at baseline 4 responders vs. 4 responders at 12 weeks (Matched)

Hypergeometric Analysis

As the last step of the array data analysis, the hypergeometric analysis was carried out in order to identify regulatory hubs i.e. most densely regulated genes as being potential causative targets and preferred loci for stratification. The data is ranked by the Epigenetic Ratio for R vs R 12W (12W_FC_1), 1 in BL Binary indicates the loop is present in Responders vs Non-Responders, but when Responders baseline are compared to Responders at 12 weeks. The epigenetic ratio indicates that the presence of the loop is more abundant in the 12 week Responder patient samples. This indicates that there has been an expansion of this signature.

SUMMARY

This epigenetic screen of anti-PD1 therapy for potential predictive and pharmacodynamic biomarkers provides a wealth of new regulatory knowledge, consistent with prior biological evidence. The work provides a rich pool of predictive and pharmacodynamic/response EpiSwitch™ markers to use in validation analysis. The results show presence of a defined epigenetic profile permissive for anti-PD-1 therapy. The epigenetic profile permissive for anti-PD1 therapy is present in naïve patients at baseline and is strengthened with treatment over 12 weeks period.

Table 39a. Top Probes—Anti PD1 (Melanoma)—responders

Table 39b. Top Probes—Anti PD1 (Melanoma)—responders—probe sequences

Table 39c. Top Probes—Anti PD1 (Melanoma)—Responders—Loci

Table 39d. Top Probes—Anti PD1 (Melanoma) Non-responders

Table 39e. Top Probes-Anti PD1 (Melanoma) Non-responders

Table 39f. Top Probes—Anti PD1 (Melanoma) Non-responders—probes sequences and loci Table 40a. Anti-PD1: pharmacodynamic response markers Table 40b. Anti-PD1: pharmacodynamic response markers Table 41a. Anti-PD1: pharmacodynamic response markers—No difference in baseline Responders and baseline Non-Responders but show a significant change in 12 week Responder Table 41b. Probe location—Anti-PD1: pharmacodynamic response markers—No difference in baseline Responders and baseline Non-Responders but shows a significant change in 12 week Responders Example 11—Further Information This work concerns EpiSwitch™ as the basis for a diagnostic test to address the issue of poor melanoma diagnosis by general practitioners. 15 lead EpiSwitch™ biomarkers were screened and identified from an initial set of 86 patient samples representing true clinical setting. The biomarkers were then trained and validated in 2 independent patient cohorts: one from Australia (395 patients) and one from the Mayo Clinic (119 patients):

119 independently and retrospectively annotated blood samples

59 Melanoma Samples

60 Controls (20 NMSC, 20 Benign Conditions, 20 Healthy Patients) )

2 Clinic collection in the USA

|  |  | 95% Confidence Interval (CI) |
|---|---|---|
| Sensitivity | 90.0% | 79.9%-95.3% |
| Specificity | 78.3% | 66.4%-86.9% |
| PPV | 88.7% | 77.4%-94.7% |
| NPV | 80.6% | 69.6%-88.3% |

68 EpiSwitch™ Markers identified by statistical processing as predictive biomarkers at baseline for anti-PD-1 therapy. (PD1-R vs NR BL). R is Responder, and NR is Non-Responder.

63 EpiSwitch™ Markers identified by statistical processing as response biomarkers for anti-PD-1 therapy. (PD1 R-BL v R-12W)

10 Markers are both good candidates for predictive and response markers

Fisher-Exact test results: top 8 predictive EpiSwitch™ Array Markers validated with the EpiSwitch™ PCR platform on the independent patient cohort (see Table 42). See Table 43 for the discerning markers from the Fisher-Exact analysis for PCR analysis between Responders at Baseline and Responders at 12 weeks. 1 is Conformation Present. 0 is Conformation Absent/Array: R12_W indicates that the conformation was present in the Responders at 12 weeks. The STAT5B_17_40403935_40406459_40464294_40468456_FR probe was measured in Responder v Non-Responder at Baseline and the conformation is present in the Responder.

In this comparison the marker is in Responders at 12 weeks, this is the case as the concentrating of DNA used to detect the conformation in Responder vs Non Responder is greater than in Responder baseline v Responder at 12 weeks, indicating the Epigenetic Load has increased in the anti-PD-1 responding patients.

Markers STAT5B and IL15 are of particular interest and are involved in key personalised medical and regulatory events responsible for the efficacies response to anti-PD1 therapies (see Tables 46 to 49).

Example 12

Chromosomes Interactions Relevant to Anti-PD1 Responsiveness in Different Cancers Table 50 shows the pattern of chromosome interactions present in responders to anti-PD1 (unless otherwise stated with NR (non-responder)) in individuals with particular cancers. The terminology used in the table is explained below.

DLBCL_ABC: Diffuse large B-cell lymphoma subtype activated B-cells

DLBCL_GBC: Diffuse large B-cell lymphoma subtype germinal centre B-cells

HCC: hepatocellular carcinoma

HCC_HEPB: hepatocellular carcinoma with hepatitis B virus

HCC_HEPC: hepatocellular carcinoma with hepatitis C virus
HEPB+R: Hepatitis B in remission
Pca_Class3: Prostate cancer stage 3
Pca_Class2: Prostate cancer stage 2
Pca_Class1: Prostate cancer stage 1
BrCa_Stg4: Breast cancer stage 4
BrCa_Stg3B: Breast cancer stage 3B
BrCa_Stg2A: Breast cancer stage 2A
BrCa_Stg2B: Breast cancer stage 2B
BrCa_Stg1A: Breast cancer stage 1A
BrCa_Stg1: Breast cancer stage 1
PD_1_R_Melanoma: Melanoma responder
PD_1_NR_Melanoma: Melanoma non responder Example 13

Figure 3:
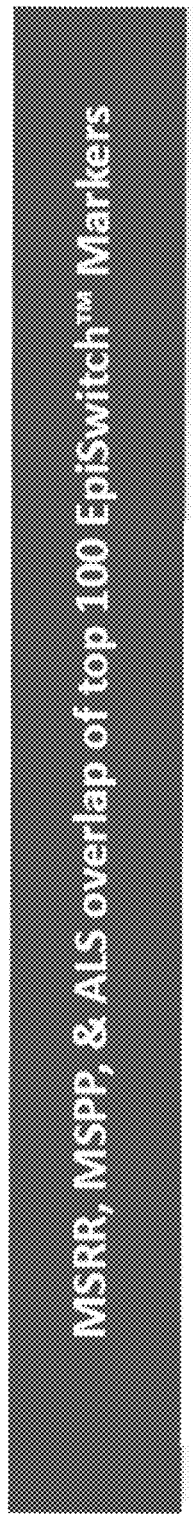
FIGS. 3 to 18 show Venn diagrams for genes and markers common to more than one condition.
Figure 4:
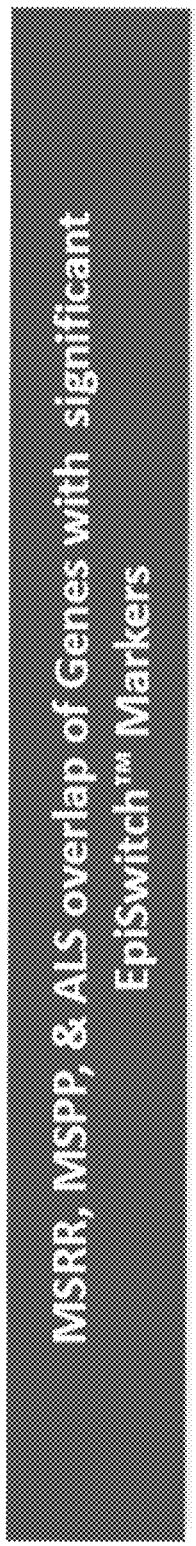
Figure 4:
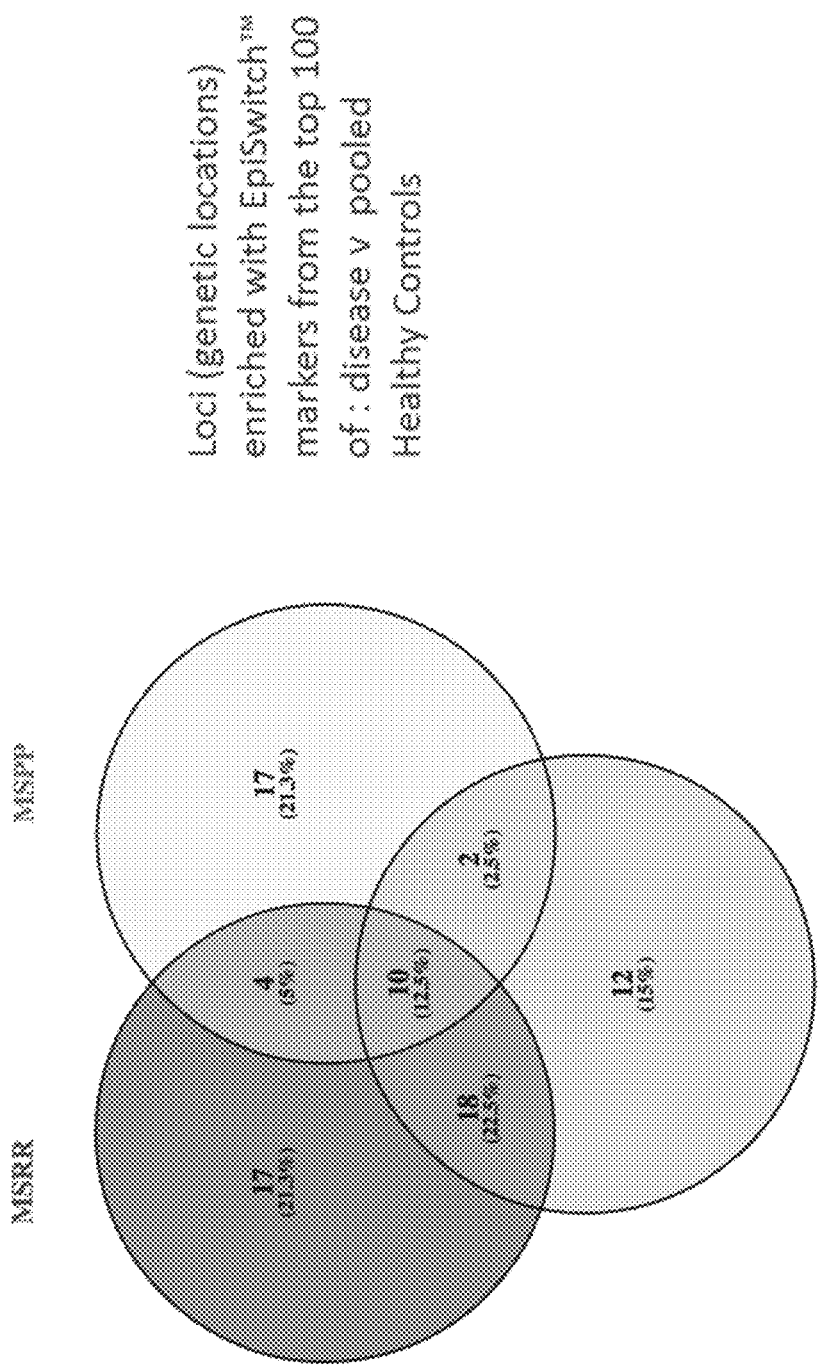
Figure 5:
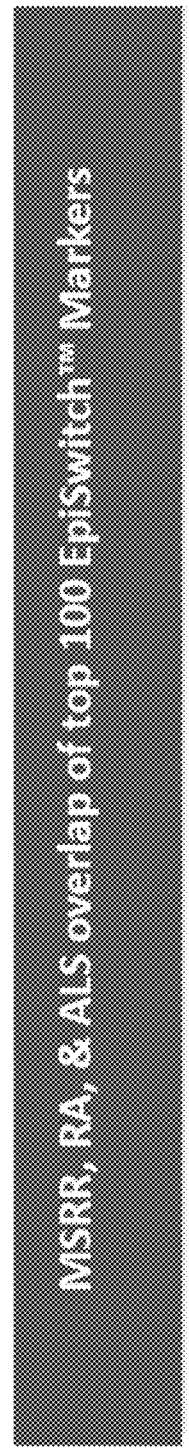
Figure 5:
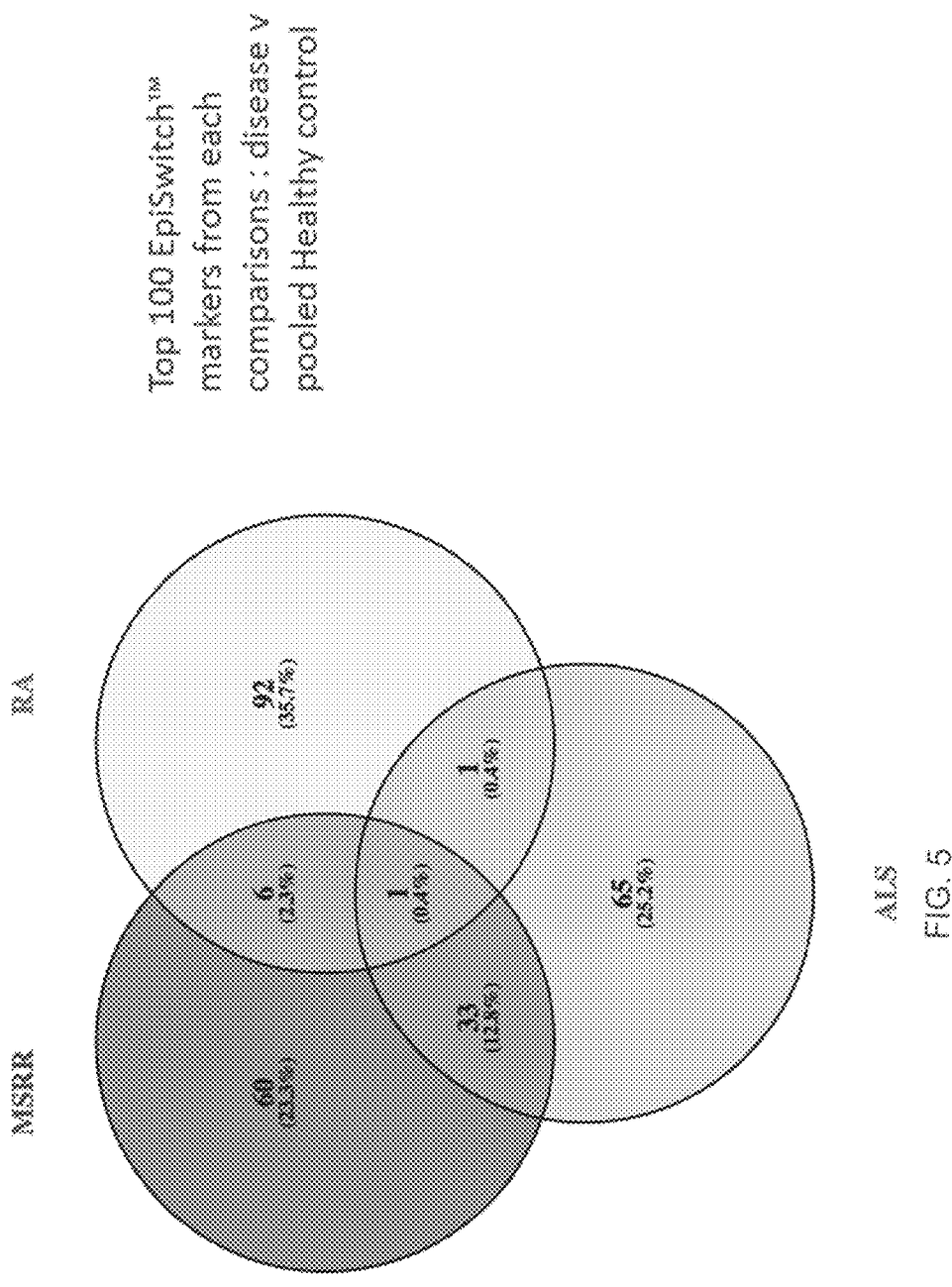
Figure 6:
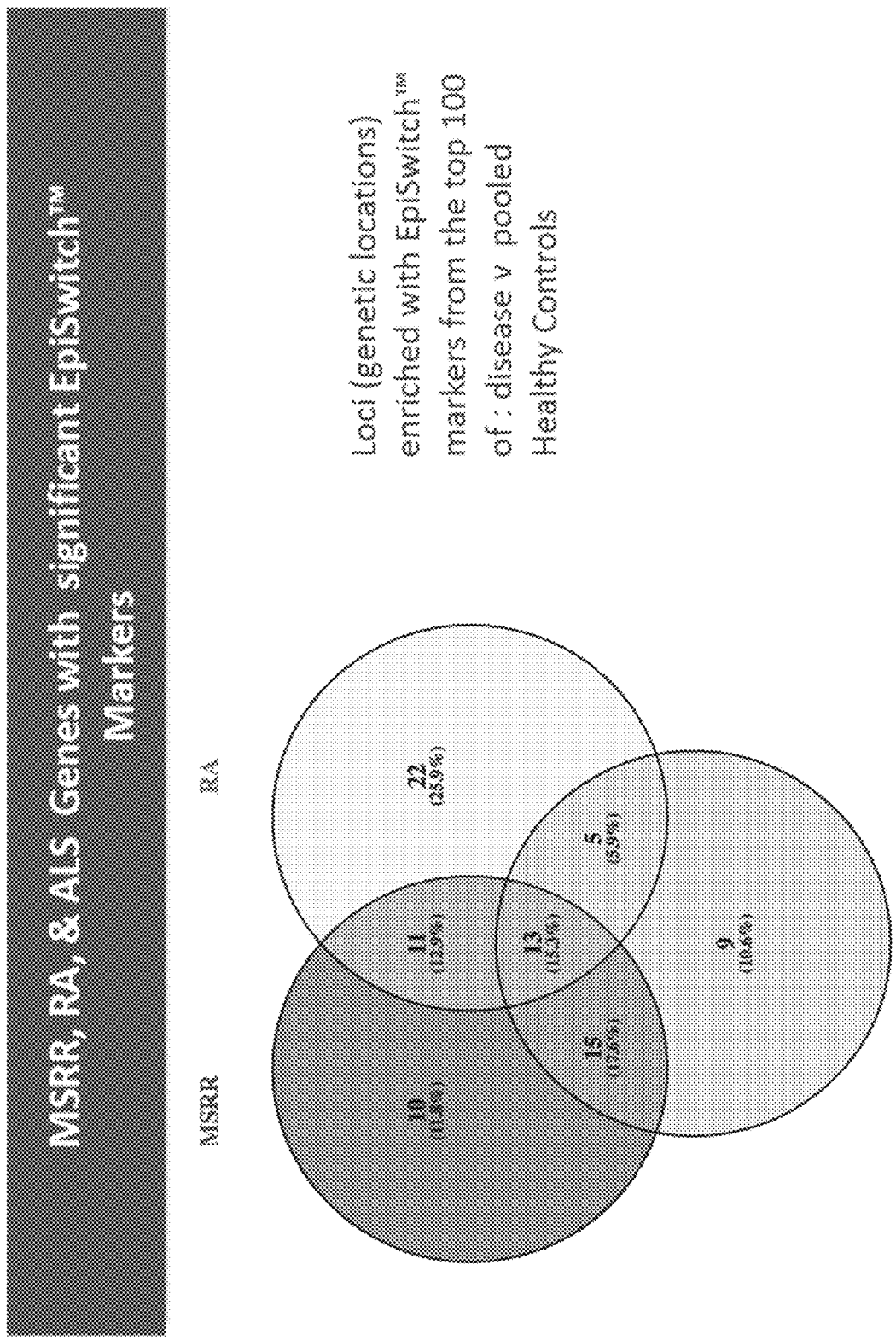
Figure 7:
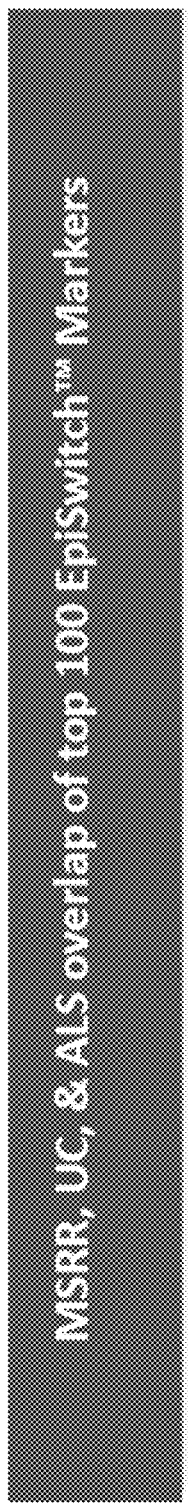
Figure 7:
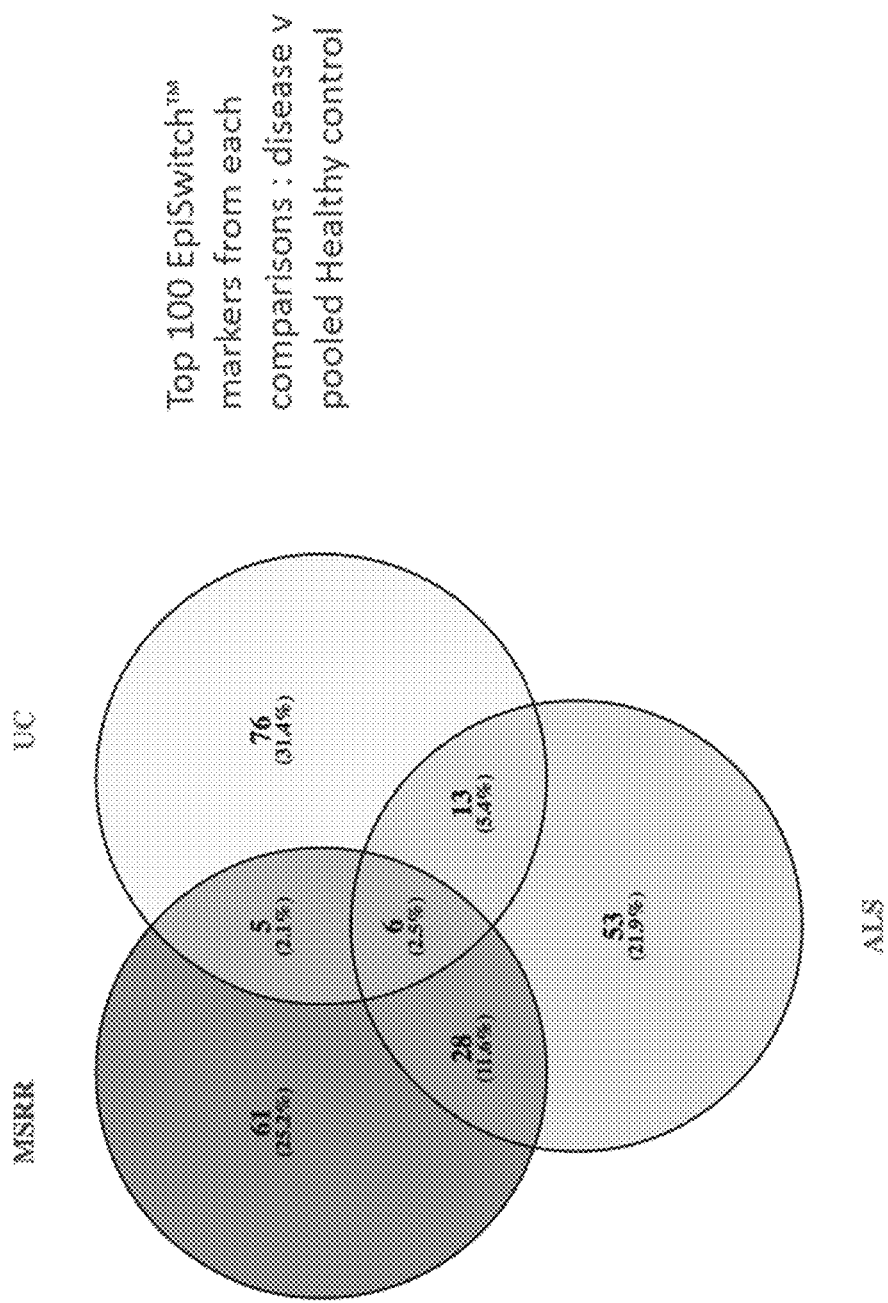
Figure 8:
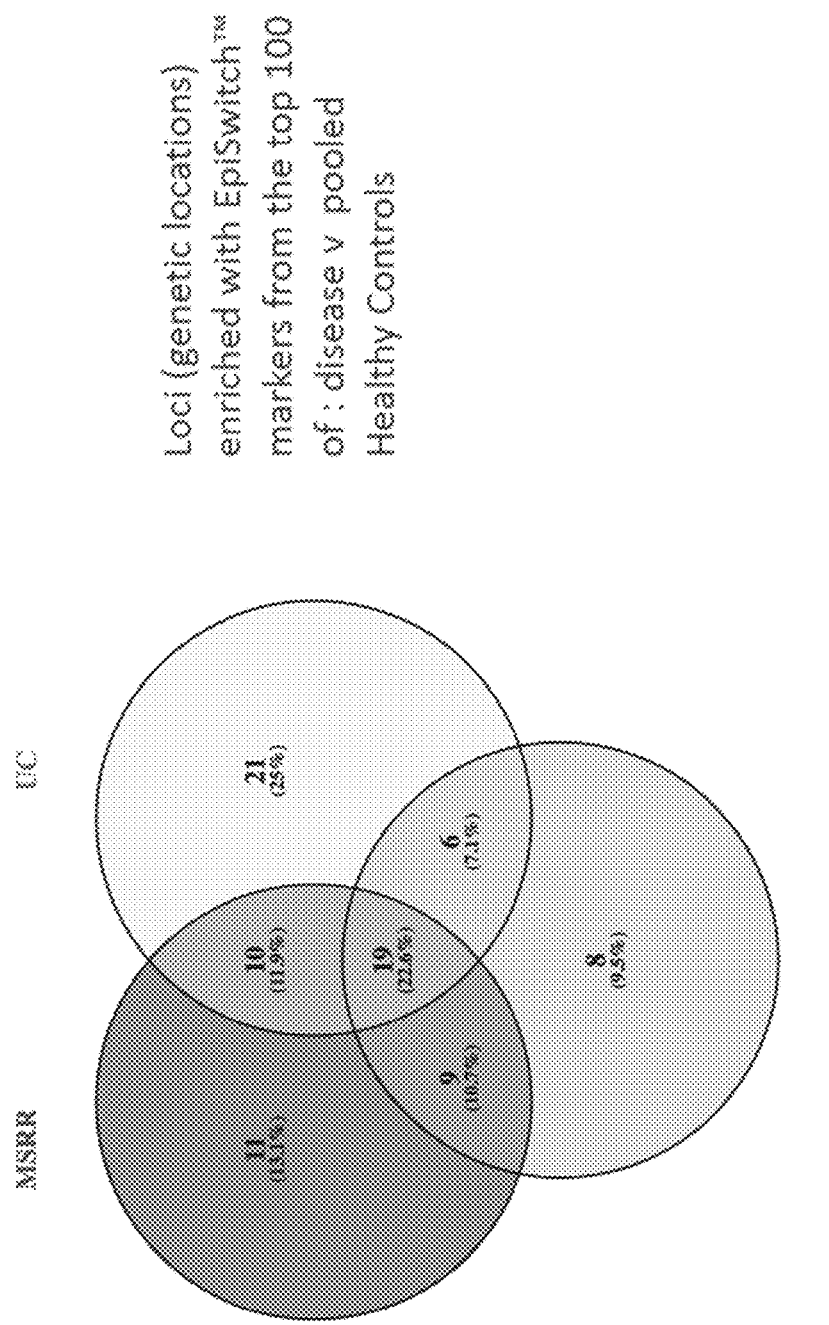
Figure 9:
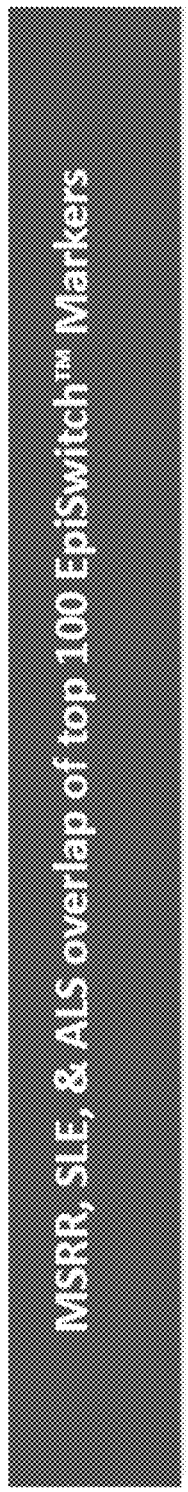
Figure 10:
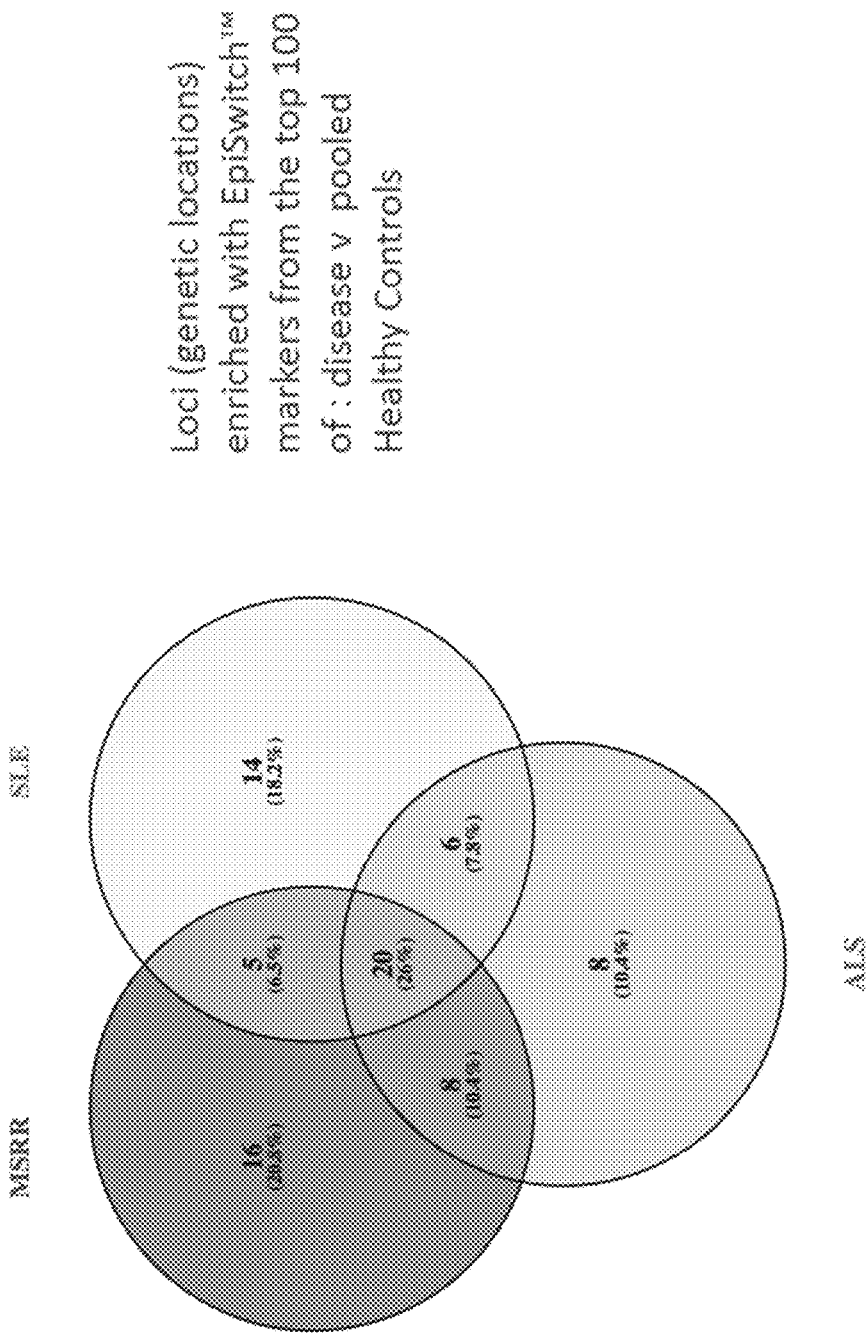
Figure 11:
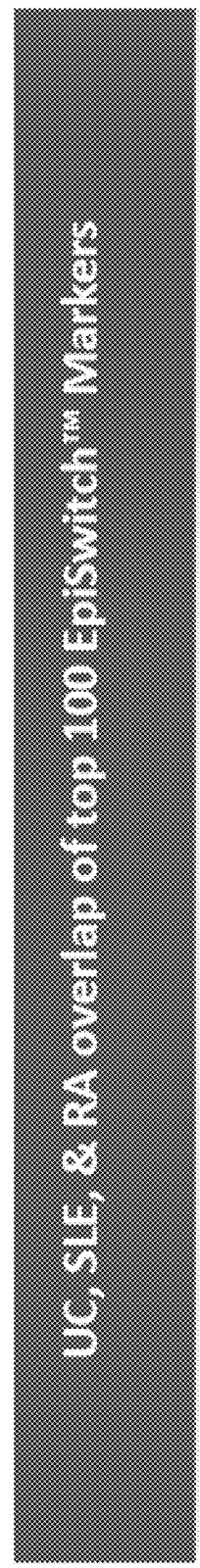
Figure 11:
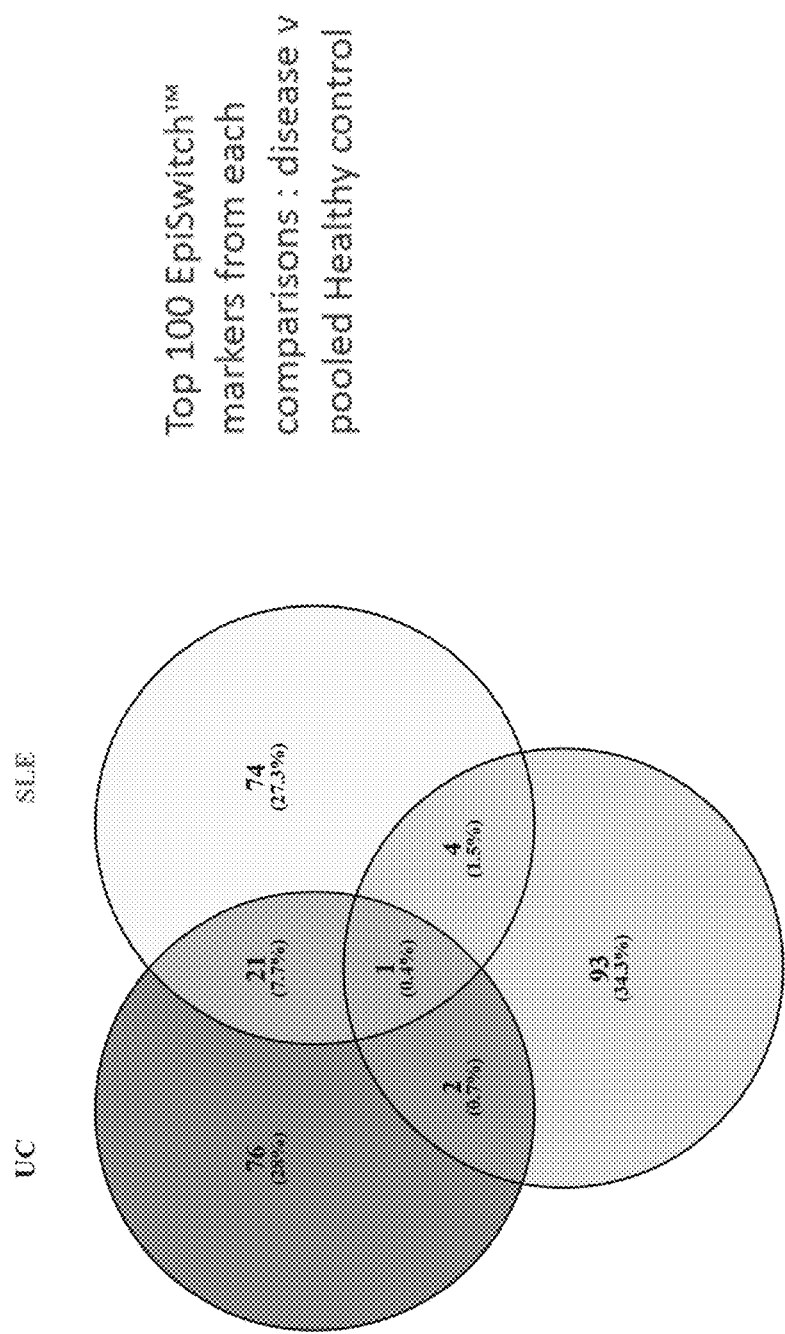
Figure 12:
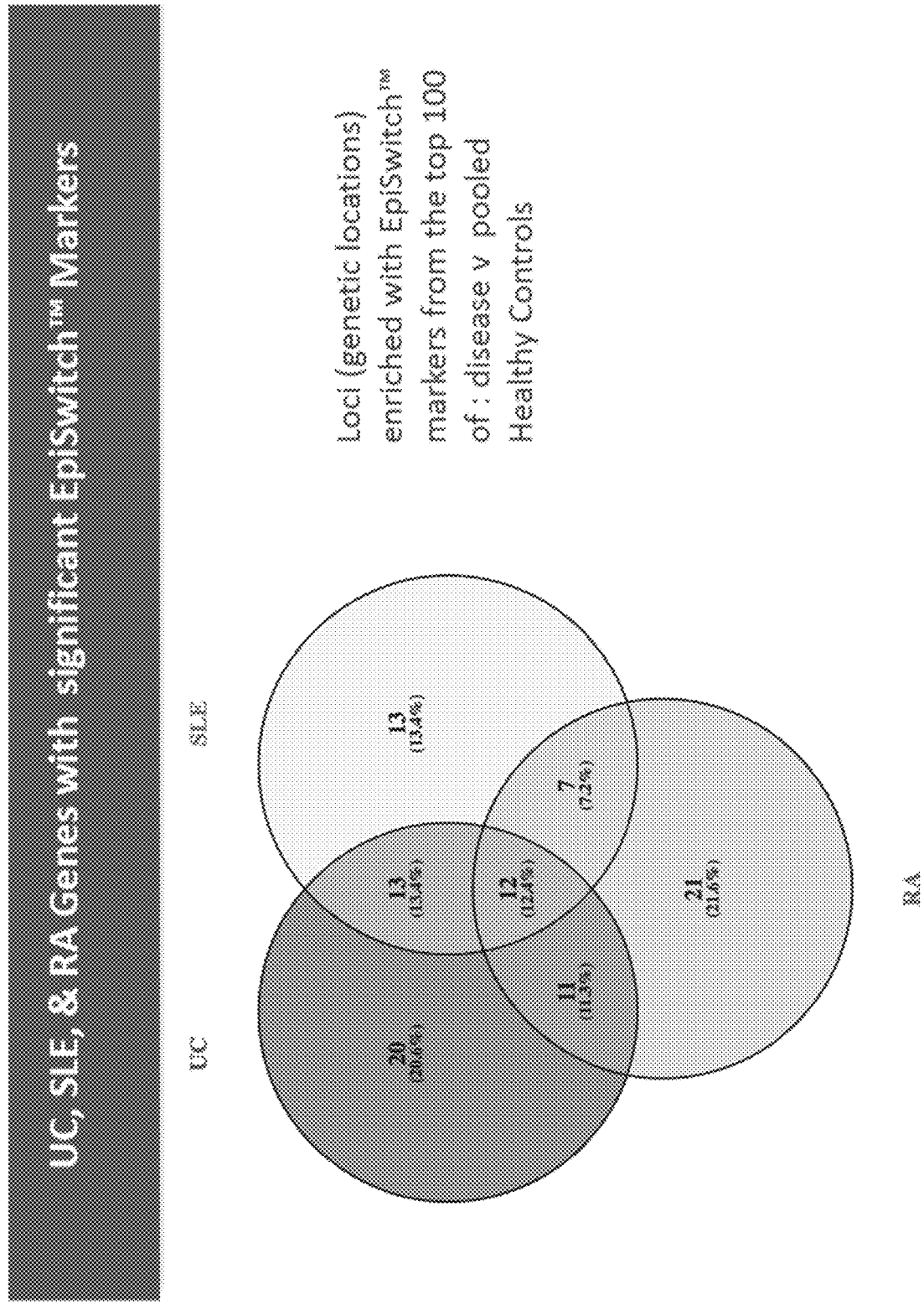
Figure 13:
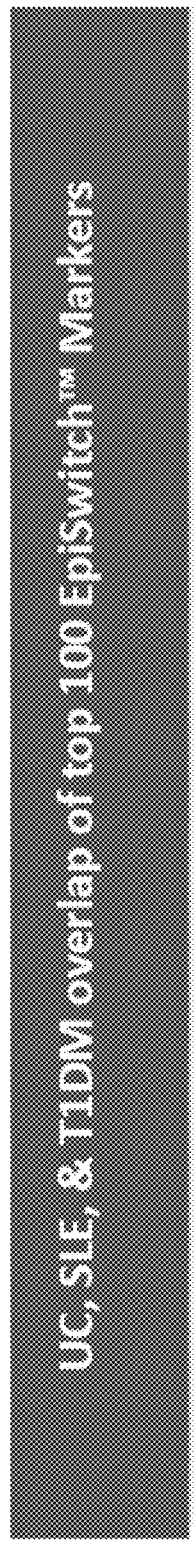
Figure 14:
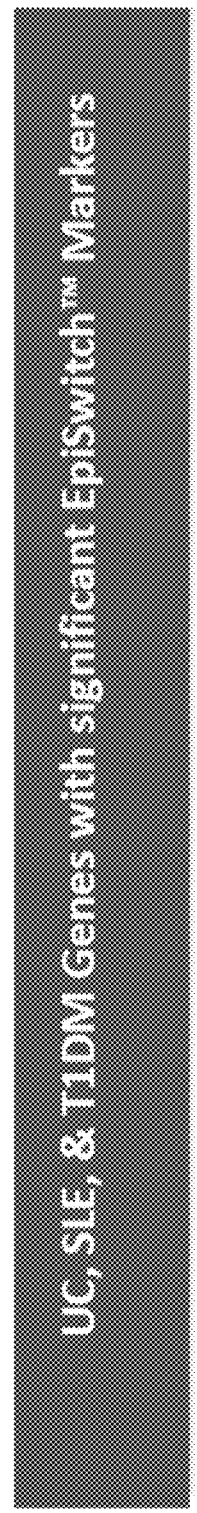
Figure 14:
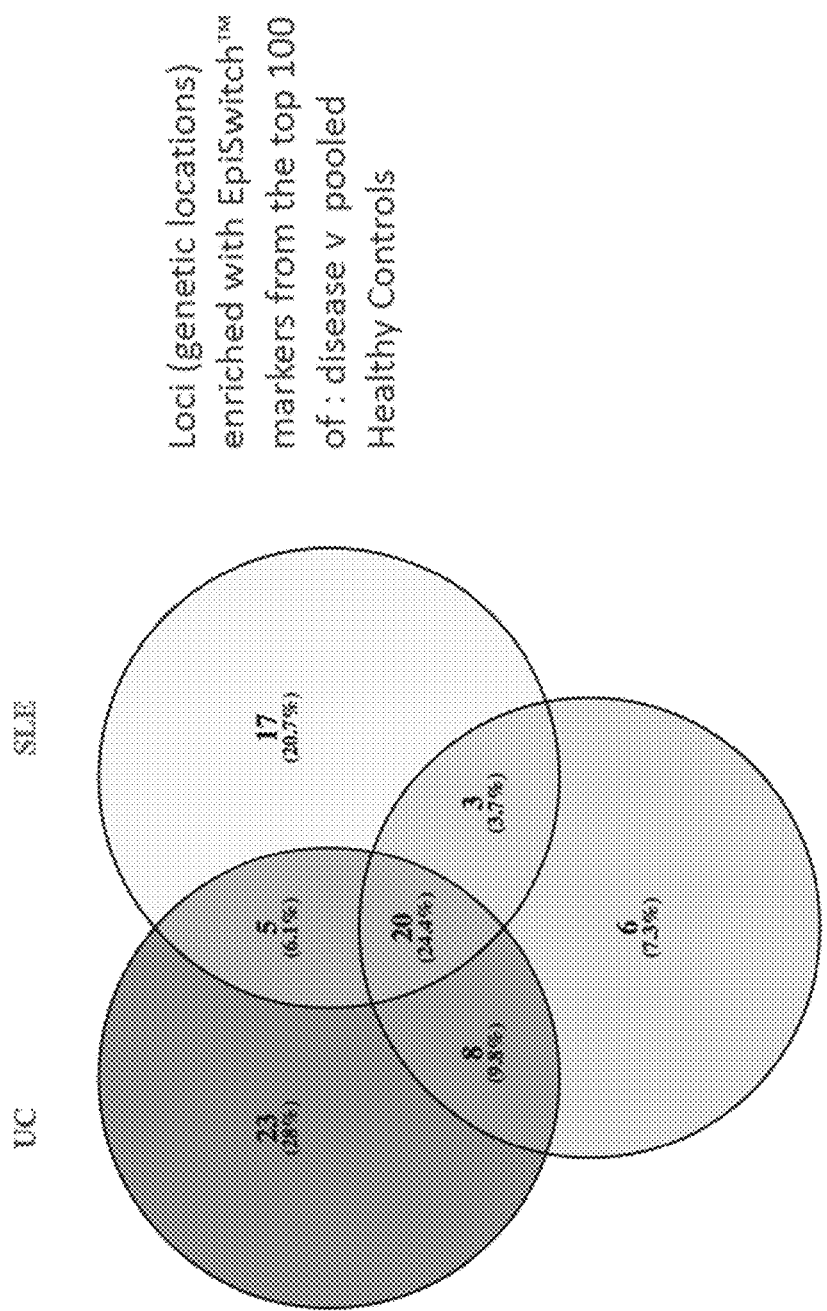
Figure 15:
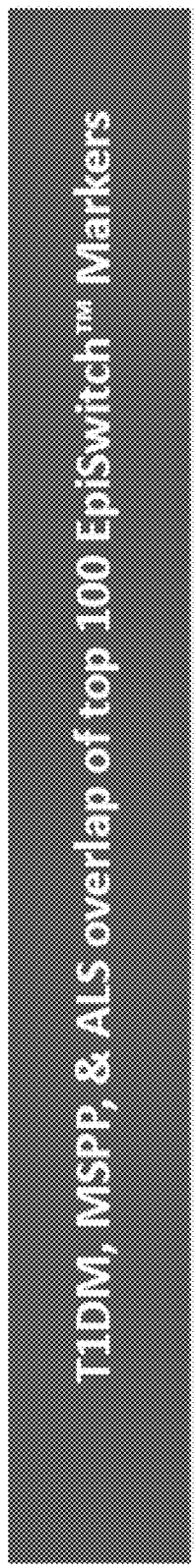
Figure 16:
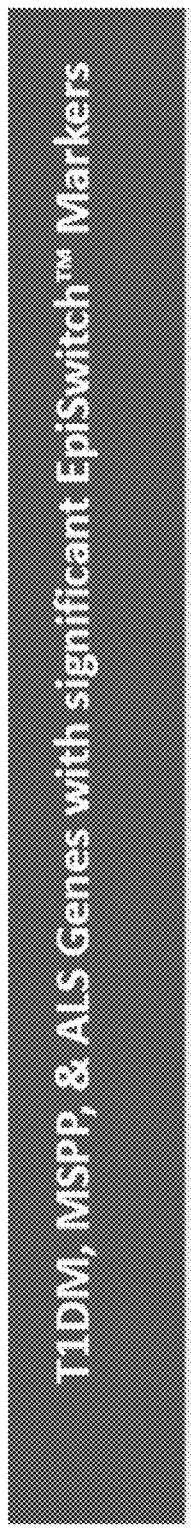
Figure 16:
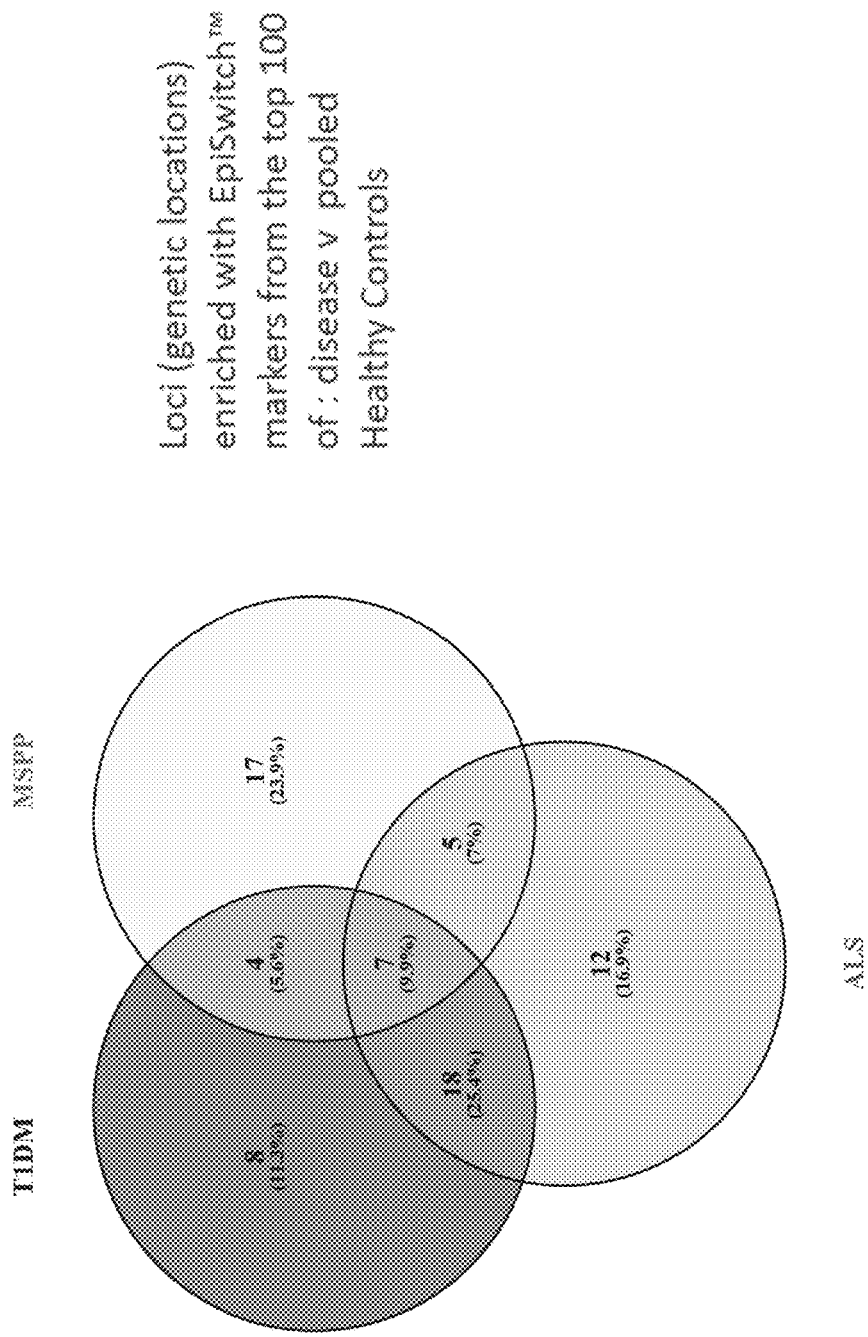
Figure 17:
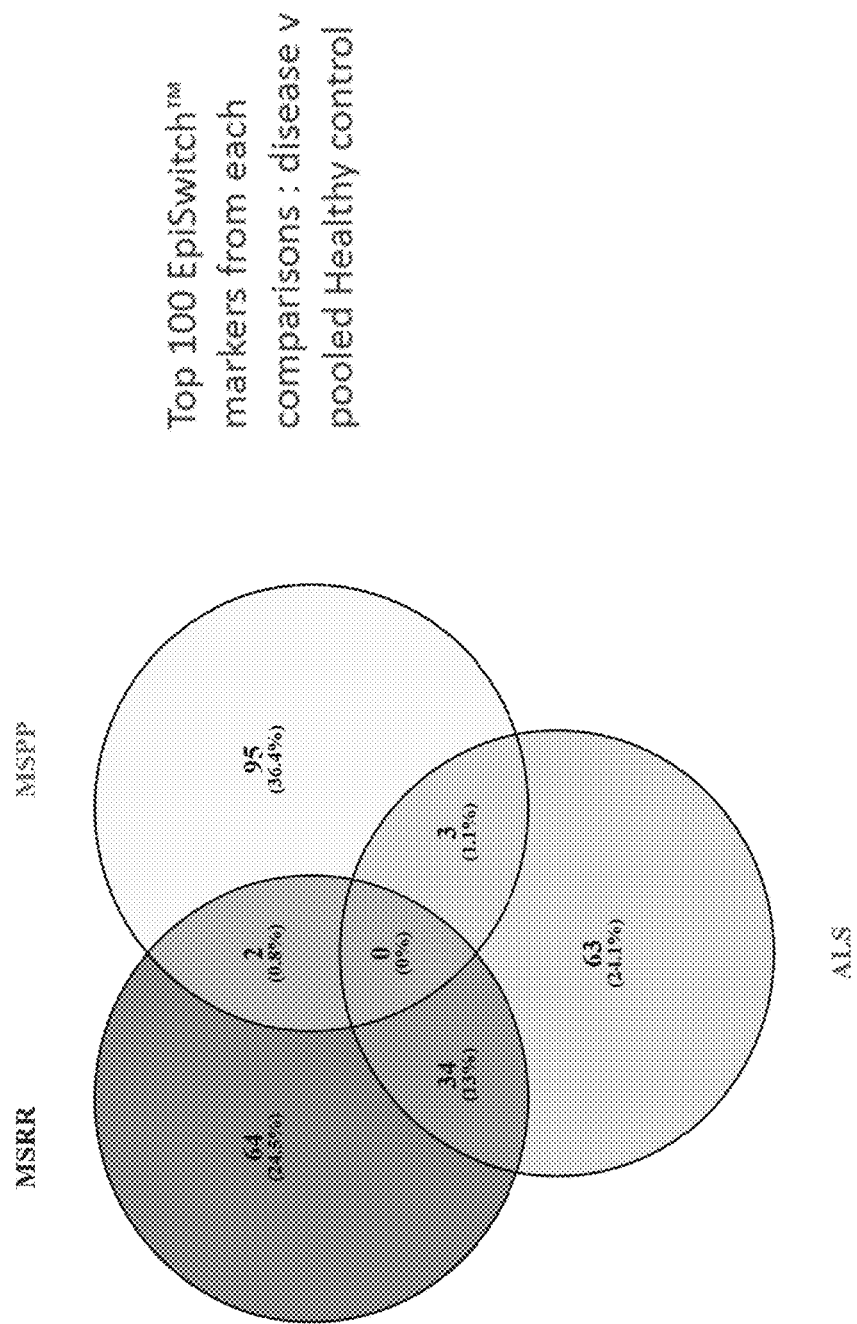
Figure 18:
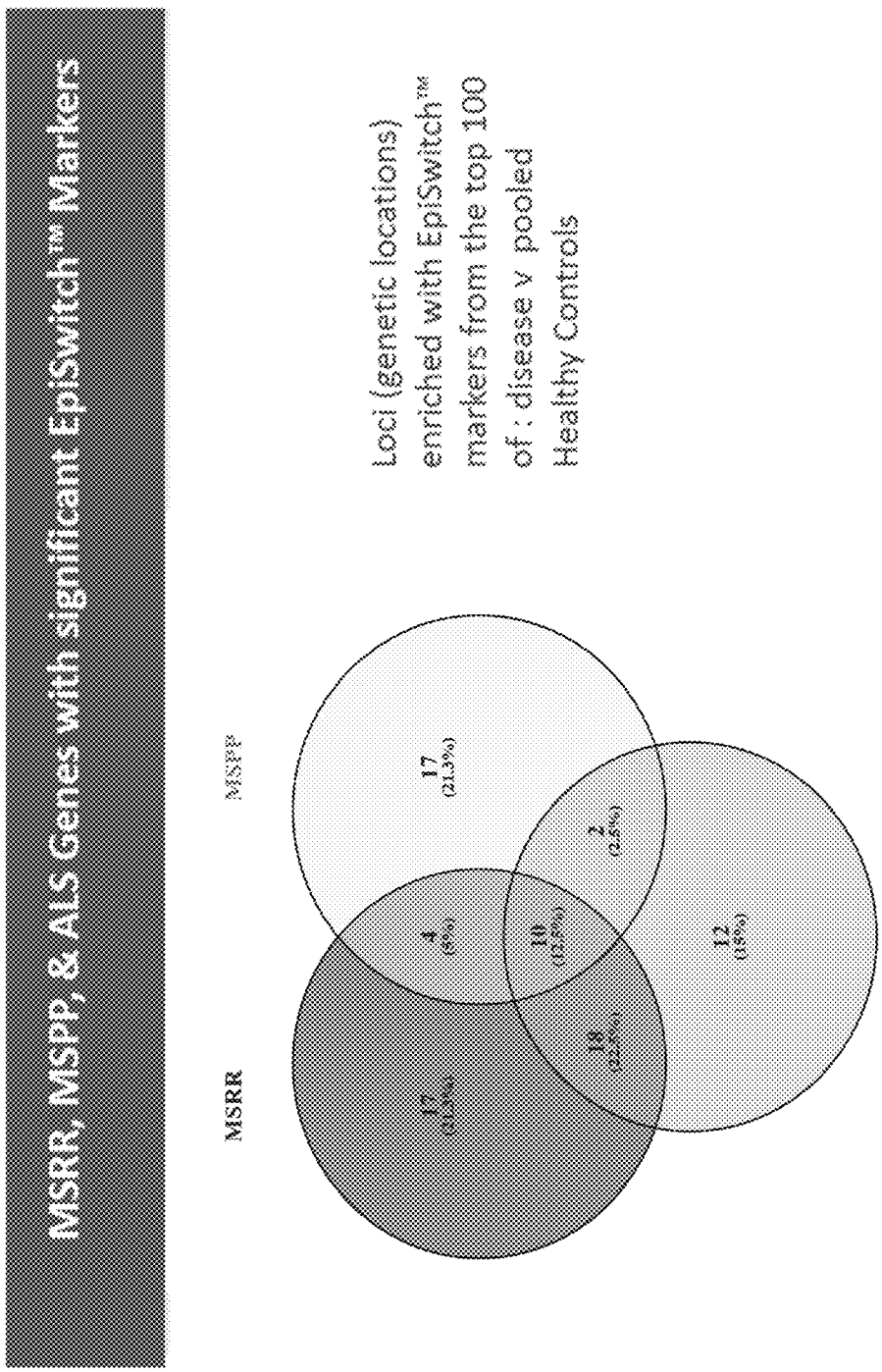

MSRR. MSPP. & ALS Overlap of Top 100 EPiSwitch™ Markers
Analysis was performed of markers present in more than one condition. The results are provided in FIGS. 3 to 18 and below.
2 common elements in "MSRR" and "MSPP":
1_243635945_243637780_243655019_243656128_RR
1_243655019_243656128_243727939_243733240_RF
34 common elements in "MSRR" and "ALS":
14_24795078_24798615_24825321_24828950_RR
14_24795078_24798615_24843066_24844509_RR
1_112077842_112081310_112249361_112251554_RF
11_93843526_93849067_93862654_93867672_RR
3_3117964_3119702_3187910_3199411_RF
1_112077842_112081310_112220594_112223184_RF
1_112077842_112081310_112243250_112249361_RF
1_112077842_112081310_112109631_112115280_RF
1_207229804_207242832_207319008_207321855_RF
1_112077842_112081310_112232549_112240074_RF
1_171811918_171813464_172083100_172087823_RF
1_161590754_161594100_161627152_161631654_RR
1_171887726_171889817_172083100_172087823_RF
11_36588999_36590845_36605543_36609927_FR
11_36583119_36588432_36605543_36609927_RR
1_172083100_172087823_172151185_172154127_FF
6_149520737_149523801_149659887_149661590_FF
6_149520737_149523801_149635378_149637900_FR
1_172061602_172067357_172083100_172087823_RF
11_36531355_36534043_36605543_36609927_FR
11_36524913_36530925_36605543_36609927_FR
1_171936106_171939290_172083100_172087823_RF
1_172083100_172087823_172212232_172223166_FF
5_149542467_149546111_149560865_149574338_FF
11_923549_925733_976127_979142_FR
7_55116799_55120169_55294211_55302386_RF
11_36531355_36534043_36605543_36609927_RR
10_98397707_98399014_98464393_98468588_FF
1_198588217_198596491_198704585_198718385_FF
5_7375991_7381724_7629788_7640118_RR
1_25106841_25109990_25142389_25144224_RF
13_37349477_37354449_37379735_37382280_RF
1_207768357_207776157_207825662_207833535_FF
X_19737340_19741050_19842803_19849464_FR
0 common elements in "MSRR", "MSPP" and "ALS":
3 common elements in "MSPP" and "ALS":
X_19753406_19760963_19778202_19779729_RF
7_55087969_55089963_55146890_55151406_RF
9_93524010_93529835_93546315_93549104_FF
MSRR, MSPP, & ALS overlap of Genes with significant EpiSwitch™ Markers 4 common elements in "MSRR" and "MSPP":
DNM2, IL1RAP, CD200, LCK
18 common elements in "MSRR" and "ALS":
ADCY4
RAP1A
PANX1
IL5RA
C4BPA
CLIC4
RAG2;RAG1
TAB2
RAG1
PDGFRB
AP2A2
PIK3AP1
PRKCQ
B2M
RFXAP
CR1
ADCY8
ARHGEF7
10 common elements in "MSRR", "MSPP" and "ALS":
DNM3
FCGR2B;FCGR3A
SH3KBP1
EGFR
PTPRC
CD36
ADCY2
PLD1
AKT3
CD96
2 common elements in "MSPP" and "ALS":
SYK
PIK3CD
MSRR, RA, & ALS overlap of top 100 EpiSwitch™ Markers
6 common elements in "MSRR" and "RA":
1_25103555_25106841_25157633_25161851_RR
5_7375991_7381724_7459585_7461017_RF
3_112025276_112034935_112084448_112086795_RR
19_10341612_10343024_10406169_10407761_RF
19_55265127_55271536_55301130_55304400_FR
1_32680186_32682814_32702745_32706740_RF
33 common elements in "MSRR" and "ALS":
14_24795078_24798615_24825321_24828950_RR
14_24795078_24798615_24843066_24844509_RR
1_112077842_112081310_112249361_112251554_RF
11_93843526_93849067_93862654_93867672_RR
3_3117964_3119702_3187910_3199411_RF
1_112077842_112081310_112220594_112223184_RF
1_112077842_112081310_112243250_112249361_RF
1_112077842_112081310_112109631_112115280_RF
1_207229804_207242832_207319008_207321855_RF
1_112077842_112081310_112232549_112240074_RF
1_171811918_171813464_172083100_172087823_RF
1_161590754_161594100_161627152_161631654_RR
1_171887726_171889817_172083100_172087823_RF
11_36588999_36590845_36605543_36609927_FR
11_36583119_36588432_36605543_36609927_RR
1_172083100_172087823_172151185_172154127_FF
6_149520737_149523801_149659887_149661590_FF
6_149520737_149523801_149635378_149637900_FR
1_172061602_172067357_172083100_172087823_RF
11_36531355_36534043_36605543_36609927_FR
11_36524913_36530925_36605543_36609927_FR
1_171936106_171939290_172083100_172087823_RF 1_172083100_172087823_172212232_172223166_FF
5_149542467_149546111_149560865_149574338_FF
11_923549_925733_976127_979142_FR
7_55116799_55120169_55294211_55302386_RF
11_36531355_36534043_36605543_36609927_RR
1_198588217_198596491_198704585_198718385_FF
5_7375991_7381724_7629788_7640118_RR
1_25106841_25109990_25142389_25144224_RF
13_37349477_37354449_37379735_37382280_RF
1_207768357_207776157_207825662_207833535_FF
X_19737340_19741050_19842803_19849464_FR
1 common element in "MSRR", "RA" and "ALS":
10_98397707_98399014_98464393_98468588_FF
1 common element in "RA" and "ALS":
16_68779378_68783974_68794947_68799115_RF
MSRR, RA, & ALS Genes with significant EpiSwitch™ Markers
11 common elements in "MSRR" and "RA":
IL6R
DNM2
LY86
CD200
ICAM1
PPAPDC1A
KIR2DL1;KIR2DL4;KIR3DL1;KIR2DL3
C1QBP
FGFR2
LCK
FYN
15 common elements in "MSRR" and "ALS":
ADCY4
IL5RA
FCGR2B;FCGR3A
RAG2;RAG1
TAB2
RAG1
AP2A2
PRKCQ
PTPRC
B2M
RFXAP
CD96
CR1
ADCY8
ARHGEF7
13 common elements in "MSRR", "RA" and "ALS":
RAP1A
PANX1
C4BPA
CLIC4
DNM3
SH3KBP1
PDGFRB
PIK3AP1
EGFR
CD36
ADCY2
PLD1
AKT3
5 common elements in "RA" and "ALS":
CLTA
GRB2
PIK3CD
CDH1
GHR
MSRR, UC, & ALS overlap of top 100 EpiSwitch™ Markers 5 common elements in "MSRR" and "UC":
17_33876495_33878833_34051920_34057525_RF
17_33935188_33940329_34051920_34057525_RF
7_80058024_80060926_80168823_80173631_RF
3_112025276_112034935_112084448_112086795_RR
4_103425294_103430395_103544491_103547903_RR
28 common elements in "MSRR" and "ALS":
1_112077842_112081310_112249361_112251554_RF
1_112077842_112081310_112220594_112223184_RF
1_112077842_112081310_112243250_112249361_RF
1_112077842_112081310_112109631_112115280_RF
1_207229804_207242832_207319008_207321855_RF
1_112077842_112081310_112232549_112240074_RF
1_171811918_171813464_172083100_172087823_RF
1_161590754_161594100_161627152_161631654_RR
1_171887726_171889817_172083100_172087823_RF
11_36588999_36590845_36605543_36609927_FR
11_36583119_36588432_36605543_36609927_RR
1_172083100_172087823_172151185_172154127_FF
6_149520737_149523801_149659887_149661590_FF
6_149520737_149523801_149635378_149637900_FR
1_172061602_172067357_172083100_172087823_RF
11_36531355_36534043_36605543_36609927_FR
11_36524913_36530925_36605543_36609927_FR
1_171936106_171939290_172083100_172087823_RF
1_172083100_172087823_172212232_172223166_FF
11_923549_925733_976127_979142_FR
7_55116799_55120169_55294211_55302386_RF
11_36531355_36534043_36605543_36609927_RR
10_98397707_98399014_98464393_98468588_FF
1_198588217_198596491_198704585_198718385_FF
1_25106841_25109990_25142389_25144224_RF
13_37349477_37354449_37379735_37382280_RF
1_207768357_207776157_207825662_207833535_FF
X_19737340_19741050_19842803_19849464_FR
6 common elements in "MSRR", "UC" and "ALS":
14_24795078_24798615_24825321_24828950_RR
14_24795078_24798615_24843066_24844509_RR
11_93843526_93849067_93862654_93867672_RR
3_3117964_3119702_3187910_3199411_RF
5_149542467_149546111_149560865_149574338_FF
5_7375991_7381724_7629788_7640118_RR
13 common elements in "UC" and "ALS":
5_140023383_140027012_140050153_140052313_RF
X_30936113_30946116_31021869_31025150_RR
X_30990956_30994976_31021869_31025150_FR
7_55087969_55089963_55247129_55257611_RR
7_55087969_55089963_55146890_55151406_RF
1_9667841_9669456_9703942_9711781_RF
15_44994405_44997599_45023742_45026509_RR
5_7555754_7558020_7718590_7724759_RF
1_243774056_243776138_243987880_243989231_RR
20_39721652_39724494_39822701_39824051_FR
1_171770367_171771990_171988822_171992948_FR
X_19753406_19760963_19778202_19779729_RF
10_6593817_6595662_6632086_6637212_RR
MSRR, UC, & ALS Genes with significant EpiSwitch™ Markers
10 common elements in "MSRR" and "UC":
AP2B1
DNM2
IL1RAP
CD200
ICAM1
NFKB1
DLEU2
PPAPDC1A FGFR2
FYN
9 common elements in "MSRR" and "ALS":
RAP1A
C4BPA
RAG2;RAG1
RAG1
AP2A2
PIK3AP1
PTPRC
RFXAP
CR1
19 common elements in "MSRR", "UC" and "ALS":
ADCY4
PANX1
IL5RA
CLIC4
DNM3
FCGR2B;FCGR3A
TAB2
SH3KBP1
PDGFRB
EGFR
PRKCQ
B2M
CD36
ADCY2
PLD1
AKT3
CD96
ADCY8
ARHGEF7
6 common elements in "UC" and "ALS":
TAB3
CD14
PIK3CD
GRB2
PLCG1
GHR
MSRR, SLE, & ALS overlap of top 100 EpiSwitch™ Markers
6 common elements in "MSRR" and "SLE":
1_25103555_25106841_25157633_25161851_RR
1_25103555_25106841_25142389_25144224_RR
6_149520737_149523801_149702218_149703624_FR
1_243635945_243637780_243655019_243656128_RR
19_55265127_55271536_55301130_55304400_FR
1_243655019_243656128_243727939_243733240_RF
21 common elements in "MSRR", "SLE" and "ALS":
14_24795078_24798615_24825321_24828950_RR
14_24795078_24798615_24843066_24844509_RR
1_112077842_112081310_112249361_112251554_RF
11_93843526_93849067_93862654_93867672_RR
3_3117964_3119702_3187910_3199411_RF
1_112077842_112081310_112220594_112223184_RF
1_112077842_112081310_112243250_112249361_RF
1_112077842_112081310_112109631_112115280_RF
1_112077842_112081310_112232549_112240074_RF
1_171811918_171813464_172083100_172087823_RF
1_161590754_161594100_161627152_161631654_RR
1_171887726_171889817_172083100_172087823_RF
11_36588999_36590845_36605543_36609927_FR
11_36583119_36588432_36605543_36609927_RR
1_172083100_172087823_172151185_172154127_FF
1_172061602_172067357_172083100_172087823_RF
11_36524913_36530925_36605543_36609927_FR
1_171936106_171939290_172083100_172087823_RF
1_172083100_172087823_172212232_172223166_FF
11_923549_925733_976127_979142_FR
11_36531355_36534043_36605543_36609927_RR
13 common elements in "MSRR" and "ALS":
1_207229804_207242832_207319008_207321855_RF
6_149520737_149523801_149659887_149661590_FF
6_149520737_149523801_149635378_149637900_FR
11_36531355_36534043_36605543_36609927_FR
5_149542467_149546111_149560865_149574338_FF
7_55116799_55120169_55294211_55302386_RF
10_98397707_98399014_98464393_98468588_FF
1_198588217_198596491_198704585_198718385_FF
5_7375991_7381724_7629788_7640118_RR
1_25106841_25109990_25142389_25144224_RF
13_37349477_37354449_37379735_37382280_RF
1_207768357_207776157_207825662_207833535_FF
X_19737340_19741050_19842803_19849464_FR
14 common elements in "SLE" and "ALS":
1_243637780_243640834_243655019_243656128_RR
1_9667841_9669456_9703942_9711781_RF
13_111748012_111752622_111942125_111944243_RR
1_243774056_243776138_243987880_243989231_RR
20_39721652_39724494_39822701_39824051_FR
7_80060926_80068170_80299255_80301429_RF
13_111770092_111771830_111951910_111954429_RF
1_171770367_171771990_171988822_171992948_FR
15_44994405_44997599_45023742_45026509_RR
7_80060926_80068170_80168823_80173631_RF
7_80060926_80068170_80078955_80088693_RF
1_149704484_149706971_149741040_149747801_RR
1_25106841_25109990_25121474_25132059_RR
13_111770092_111771830_111933217_111937273_RF
MSRR, SLE, & ALS Genes with significant EpiSwitch™ Markers
5 common elements in "MSRR" and "SLE":
AP2B1
DLEU2
PPAPDC1A
KIR2DL1;KIR2DL4;KIR3DL1;KIR2DL3
CD8A;CD8B
20 common elements in "MSRR", "SLE" and "ALS":
ADCY4
RAP1A
PANX1
IL5RA
CLIC4
DNM3
FCGR2B;FCGR3A
RAG2;RAG1
TAB2
RAG1
AP2A2
PTPRC
B2M
CD36
ADCY2
PLD1
AKT3
CD96
ADCY8
ARHGEF7
8 common elements in "MSRR" and "ALS":
C4BPA
SH3KBP1
PDGFRB
PIK3AP1

EGFR
PRKCQ
RFXAP
CR1
Common elements in "SLE" and "ALS":
PIK3CD
CLTA
PLCG1
CDH1
GHR
FCGR1A
UC, SLE, & RA overlap of top 100 EpiSwitch™ Markers
21 common elements in "UC" and "SLE":
7_45584884_45588878_45736475_45743273_RF
1_9667841_9669456_9703942_9711781_RF
14_24795078_24798615_24843066_24844509_RR
11_93843526_93849067_93862654_93867672_RR
16_31228760_31230406_31342509_31344379_FR
3_3117964_3119702_3187910_3199411_RF
14_24795078_24798615_24825321_24828950_RR
15_44994405_44997599_45023742_45026509_RR
1_243774056_243776138_243987880_243989231_RR
20_39721652_39724494_39822701_39824051_FR
3_111054275_111073125_111172267_111189165_FR
1_172106365_172109446_172385900_172393629_RR
3_111125030_111133059_111172267_111189165_RR
10_122178140_122183869_122230047_122236854_RR
5_42686714_42692033_42731106_42735319_RR
17_33876495_33878833_34051920_34057525_FF
8_132007896_132011208_132073037_132077970_RF
1_171770367_171771990_171988822_171992948_FR
3_171302954_171312114_171346086_171352212_RR
13_50630337_50635930_50729702_50737025_RF
3_171346086_171352212_171415103_171427395_RF
1 common element in "UC", "SLE" and "RA":
1_171887726_171889817_171999901_172010156_RR
2 common elements in "UC" and "RA":
10_123310247_123312749_123354723_123356448_RF
3_112025276_112034935_112084448_112086795_RR
4 common elements in "SLE" and "RA":
1_25103555_25106841_25157633_25161851_RR
19_55265127_55271536_55301130_55304400_FR
1_161153513_161156186_161177309_161180481_RR
3_136542667_136549480_136588981_136590172_FR
UC, SLE, & RA Genes with significant EpiSwitch™ Markers
13 common elements in "UC" and "SLE":
ADCY1
FCGR2B;FCGR3A
ADCY4
ITGAM
IL5RA
B2M
AP2B1
PLCG1
CD96
ARHGEF7
ADCY8
TAB2
DLEU2
12 common elements in "UC", "SLE" and "RA":
PIK3CD
PANX1
DNM3
ADCY2
NCK1
RAPGEF4
AKT3
CD36
CLIC4
PPAPDC1A
GHR
PLD1
11 common elements in "UC" and "RA":
PDGFRB
EGFR
KIR2DL4;KIR3DL1
FGFR2
ICAM1
FYN
DNM2
CD200
GRB2
SH3KBP1
KLRG1
7 common elements in "SLE" and "RA":
RAP1A
CLTA
KIR2DL1;KIR2DL4;KIR3DL1;KIR2DL3
CDH1
FCER1G
IGKV2-30
MKL1
UC, SLE, & T1DM overlap of top 100 EpiSwitch™ Markers
10 common elements in "UC", "SLE" and "T1DM":
7_45584884_45588878_45736475_45743273_RF
1_9667841_9669456_9703942_9711781_RF
14_24795078_24798615_24843066_24844509_RR
16_31228760_31230406_31342509_31344379_FR
3_3117964_3119702_3187910_3199411_RF
14_24795078_24798615_24825321_24828950_RR
20_39721652_39724494_39822701_39824051_FR
5_42686714_42692033_42731106_42735319_RR
8_132007896_132011208_132073037_132077970_RF
1_171770367_171771990_171988822_171992948_FR
8 common elements in "UC" and "T1DM":
5_149542467_149546111_149560865_149574338_FF
1_28562883_28566942_28578174_28579330_RR
19_10341612_10343024_10406169_10407761_FF
6_32135728_32138270_32149729_32154447_FF
19_10794793_10797168_10959326_10960538_RF
4_103425294_103430395_103544491_103547903_RR
7_80058024_80060926_80168823_80173631_RF
10_6593817_6595662_6632086_6637212_RR
12 common elements in "UC" and "SLE":
11_93843526_93849067_93862654_93867672_RR
15_44994405_44997599_45023742_45026509_RR
1_243774056_243776138_243987880_243989231_RR
3_111054275_111073125_111172267_111189165_FR
1_172106365_172109446_172385900_172393629_RR
3_111125030_111133059_111172267_111189165_RR
1_171887726_171889817_171999901_172010156_RR
10_122178140_122183869_122230047_122236854_RR
17_33876495_33878833_34051920_34057525_FF
3_171302954_171312114_171346086_171352212_RR
13_50630337_50635930_50729702_50737025_RF
3_171346086_171352212_171415103_171427395_RF
20 common elements in "SLE" and "T1DM":
1_112077842_112081310_112220594_112223184_RF
1_112077842_112081310_112109631_112115280_RF
11_923549_925733_976127_979142_FR
1_112077842_112081310_112249361_112251554_RF 1_172083100_172087823_172151185_172154127_FF
1_112077842_112081310_112232549_112240074_RF
1_112077842_112081310_112243250_112249361_RF
1_171811918_171813464_172083100_172087823_RF
1_161590754_161594100_161627152_161631654_RR
1_172061602_172067357_172083100_172087823_RF
1_243637780_243640834_243655019_243656128_RR
1_171936106_171939290_172083100_172087823_RF
1_171887726_171889817_172083100_172087823_RF
1_172083100_172087823_172212232_172223166_FF
5_7602410_7603529_7797003_7800572_FR
11_36524913_36530925_36605543_36609927_FR
11_36531355_36534043_36605543_36609927_RR
16_31342509_31344379_31355595_31363682_RF
13_111748012_111752622_111942125_111944243_RR
6_149520737_149523801_149702218_149703624_FR 62 elements included exclusively in "T1DM":
16_4065887_4067896_4109379_4115518_FR
11_1010876_1013083_964245_969445_FF
16_4065887_4067896_4204978_4209511_FF
16_4004273_4006715_4065887_4067896_RF
16_4065887_4067896_4209511_4211354_FF
6_149520737_149523801_149659887_149661590_FF
3_111054275_111073152_111238151_111244343_FF
3_111125030_111133059_111238151_111244343_FF
1_243635945_243637780_243680126_243690814_FF
16_4044767_4047085_4065887_4067896_RF
16_4065887_4067896_4145870_4149370_FF
6_149520737_149523801_149635378_149637900_FR
16_4065887_4067896_4169801_4171577_FF
16_4065887_4067896_4209511_4211354_FR
1_172053648_172060321_172083100_172087823_RR
16_23897953_23899994_24163000_24165736_FR
19_50479474_50480574_50495462_50498507_FF
16_23897953_23899994_24036714_24038516_FF
16_23897953_23899994_24182552_24187666_FR
1_25106841_25109990_25142389_25144224_RF
1_25142389_25144224_25157633_25161851_FR
1_172279226_172284712_172385900_172393629_FR
1_172279226_172284712_172334213_172345064_FR
1_172106365_172109446_172279226_172284712_RF
1_25081210_25084028_25142389_25144224_RF
1_172151185_172154127_172279226_172284712_RF
5_7375991_7381724_7459585_7461017_RF
1_171988822_171992948_172279226_172284712_RF
1_171986876_171988822_172279226_172284712_RF
1_172078294_172080108_172279226_172284712_RF
1_172175295_172181349_172279226_172284712_RF
1_172122358_172130474_172279226_172284712_RF
1_172094882_172096647_172279226_172284712_RF
1_101147311_101152350_101179717_101183607_RR
1_172279226_172284712_172326854_172331636_FR
1_172279226_172284712_172307593_172312694_FF
1_25142389_25144224_25175737_25178274_FF
1_172279226_172284712_172396442_172399665_FF
1_171999901_172010156_172279226_172284712_FF
1_172151185_172154127_172279226_172284712_FF
1_172061602_172067357_172279226_172284712_RF
1_25103555_25106841_25142389_25144224_RF
1_101147311_101152350_101179717_101183607_RF
1_172097062_172100084_172279226_172284712_FF
1_101147311_101152350_101214083_101221298_RF
1_172279226_172284712_172334213_172345064_FF
1_25121474_25132059_25142389_25144224_RF
3_136606377_136608617_136635007_136640450_FF
1_25042248_25044726_25142389_25144224_RF
8_131926196_131933918_131968323_131971882_RR 1_154344343_154345343_154368833_154370339_RR
1_25022588_25025940_25142389_25144224_RF
10_6593817_6595662_6639985_6645189_RR
11_93832833_93843526_93903690_93907969_RR
15_44986846_44994405_45005395_45007515_RF
1_207768357_207776157_207825662_207833535_FF
16_23839413_23844788_23965581_23969845_FR
5_7348279_7353422_7459585_7461017_RF
1_207643324_207649644_207825662_207833535_FF
1_154368833_154370339_154387111_154393080_FF
1_172122358_172130474_172279226_172284712_FF
17_73355519_73357935_73428595_73430537_RF UC, SLE, & T1DM Genes with significant EpiSwitch™ Markers 5 common elements in "UC" and "SLE":
RAPGEF4
AP2B1
PPAPDC1A
PLD1
DLEU2

20 common elements in "UC", "SLE" and "T1DM":
ADCY1
FCGR2B;FCGR3A
PIK3CD
ADCY4
PANX1
DNM3
ADCY2
ITGAM
NCK1
IL5RA
B2M
AKT3
PLCG1
CD36
CD96
CLIC4
ARHGEF7
GHR
ADCY8
TAB2

8 common elements in "UC" and "T1DM":
PDGFRB
ATPIF1
ICAM1
AGER
DNM2
GRB2
NFKB1
PRKCQ 3 common elements in "SLE" and "T1DM":
RAP1A
AP2A2
RAG1

T1DM, MSPP, & ALS overlap of top 100 EpiSwitch™ Markers 1 common element in "T1DM" and "MSPP":
1_28562883_28566942_28578174_28579330_RR 43 common elements in "T1DM" and "ALS":
11_923549_925733_976127_979142_FR
1_9667841_9669456_9703942_9711781_RF
3_3117964_3119702_3187910_3199411_RF
1_112077842_112081310_112109631_112115280_RF
1_112077842_112081310_112243250_112249361_RF
16_4065887_4067896_4109379_4115518_FR
1_112077842_112081310_112249361_112251554_RF 1_112077842_112081310_112220594_112223184_RF
1_243637780_243640834_243655019_243656128_RR
1_112077842_112081310_112232549_112240074_RF
1_172083100_172087823_172151185_172154127_FF
5_149542467_149546111_149560865_149574338_FF
1_171936106_171939290_172083100_172087823_RF
1_172061602_172067357_172083100_172087823_RF
14_24795078_24798615_24843066_24844509_RR
1_171811918_171813464_172083100_172087823_RF
11_36531355_36534043_36605543_36609927_RR
14_24795078_24798615_24825321_24828950_RR
1_171887726_171889817_172083100_172087823_RF
1_172083100_172087823_172212232_172223166_FF
16_4065887_4067896_4204978_4209511_FF
1_161590754_161594100_161627152_161631654_RR
16_4004273_4006715_4065887_4067896_RF
16_4065887_4067896_4209511_4211354_FF
6_149520737_149523801_149659887_149661590_FF
3_111054275_111073125_111238151_111244343_FF
13_111748012_111752622_111942125_111944243_RR
3_111125030_111133059_111238151_111244343_FF
16_4044767_4047085_4065887_4067896_RF
16_4065887_4067896_4145870_4149370_FF
6_149520737_149523801_149635378_149637900_FR
16_4065887_4067896_4169801_4171577_RF
16_4065887_4067896_4209511_4211354_FR
11_36524913_36530925_36605543_36609927_FR
1_25106841_25109990_25142389_25144224_RF
1_171770367_171771990_171988822_171992948_FR
1_172061602_172067357_172279226_172284712_FF
1_25121474_25132059_25142389_25144224_RF
10_6593817_6595662_6632086_6637212_RR
10_6593817_6595662_6639985_6645189_RR
1_207768357_207776157_207825662_207833535_FF
20_39721652_39724494_39822701_39824051_FR
1_207643324_207649644_207825662_207833535_FF
3 common elements in "MSPP" and "ALS":
X_19753406_19760963_19778202_19779729_RF
7_55087969_55089963_55146890_55151406_RF
9_93524010_93529835_93546315_93549104_FF
T1DM, MSPP, & ALS Genes with significant EpiSwitch™ Markers
4 common elements in "T1DM" and "MSPP":
ATPIF1
ITGAM
DNM2
NCK1
7 common elements in "T1DM", "MSPP" and "ALS":
PIK3CD
ADCY2
AKT3
DNM3
FCGR2B;FCGR3A
CD96
CD36
18 common elements in "T1DM" and "ALS":
AP2A2
IL5RA
RAP1A
ADCY9
PDGFRB
ADCY4
RAG1
TAB2
ARHGEF7
CLIC4
PRKCQ
GHR
ADCY8
PANX1
B2M
CR1
PLCG1
GRB2
5 common elements in "MSPP" and "ALS":
SH3KBP1
EGFR
SYK
PLD1
PTPRC
MSRR, MSPP, & ALS overlap of top 100 EpiSwitch™ Markers
2 common elements in "MSRR" and "MSPP":
1_243635945_243637780_243655019_243656128_RR
1_243655019_243656128_243727939_243733240_RF
34 common elements in "MSRR" and "ALS":
14_24795078_24798615_24825321_24828950_RR
14_24795078_24798615_24843066_24844509_RR
1_112077842_112081310_112249361_112251554_RF
11_93843526_93849067_93862654_93867672_RR
3_3117964_3119702_3187910_3199411_RF
1_112077842_112081310_112220594_112223184_RF
1_112077842_112081310_112243250_112249361_RF
1_112077842_112081310_112109631_112115280_RF
1_207229804_207242832_207319008_207321855_RF
1_112077842_112081310_112232549_112240074_RF
1_171811918_171813464_172083100_172087823_RF
1_161590754_161594100_161627152_161631654_RR
1_171887726_171889817_172083100_172087823_RF
11_36588999_36590845_36605543_36609927_FR
11_36583119_36588432_36605543_36609927_RR
1_172083100_172087823_172151185_172154127_FF
6_149520737_149523801_149659887_149661590_FF
6_149520737_149523801_149635378_149637900_FR
1_172061602_172067357_172083100_172087823_RF
11_36531355_36534043_36605543_36609927_FR
11_36524913_36530925_36605543_36609927_FR
1_171936106_171939290_172083100_172087823_RF
1_172083100_172087823_172212232_172223166_FF
5_149542467_149546111_149560865_149574338_FF
11_923549_925733_976127_979142_FR
7_55116799_55120169_55294211_55302386_RF
11_36531355_36534043_36605543_36609927_RR
10_98397707_98399014_98464393_98468588_FF
1_198588217_198596491_198704585_198718385_FF
5_7375991_7381724_7629788_7640118_RR
1_25106841_25109990_25142389_25144224_RF
13_37349477_37354449_37379735_37382280_RF
1_207768357_207776157_207825662_207833535_FF
X_19737340_19741050_19842803_19849464_FR
3 common elements in "MSPP" and "ALS":
X_19753406_19760963_19778202_19779729_RF
7_55087969_55089963_55146890_55151406_RF
9_93524010_93529835_93546315_93549104_FF
MSRR, MSPP, & ALS Genes with significant EpiSwitch™ Markers
4 common elements in "MSRR" and "MSPP":
DNM2
IL1RAP
CD200
LCK 10 common elements in "MSRR", "MSPP" and "ALS"1:
DNM3
FCGR2B;FCGR3A
SH3KBP1
EGFR
PTPRC
CD36
ADCY2
PLD1
AKT3
CD96
18 common elements in "MSRR" and "ALS":
ADCY4
RAP1A
PANX1
IL5RA
C4BPA
CLIC4
RAG2;RAG1
TAB2
RAG1
PDGFRB
AP2A2
PIK3AP1
PRKCQ
B2M
RFXAP
CR1
ADCY8
ARHGEF7
2 common elements in "MSPP" and "ALS":
SYK
PIK3CD Lengthy table referenced here
US11802305-20231031-T00001
Please refer to the end of the specification for access instructions.

Lengthy table referenced here
US11802305-20231031-T00002
Please refer to the end of the specification for access instructions.

Lengthy table referenced here
US11802305-20231031-T00003
Please refer to the end of the specification for access instructions.

Lengthy table referenced here
US11802305-20231031-T00004
Please refer to the end of the specification for access instructions.

Lengthy table referenced here
US11802305-20231031-T00005
Please refer to the end of the specification for access instructions.

Lengthy table referenced here
US11802305-20231031-T00006
Please refer to the end of the specification for access instructions.

Lengthy table referenced here
US11802305-20231031-T00007
Please refer to the end of the specification for access instructions.

Lengthy table referenced here
US11802305-20231031-T00008
Please refer to the end of the specification for access instructions.

Lengthy table referenced here
US11802305-20231031-T00009
Please refer to the end of the specification for access instructions.

Lengthy table referenced here
US11802305-20231031-T00010
Please refer to the end of the specification for access instructions.

Lengthy table referenced here
US11802305-20231031-T00011
Please refer to the end of the specification for access instructions.

Lengthy table referenced here
US11802305-20231031-T00012
Please refer to the end of the specification for access instructions.

Lengthy table referenced here
US11802305-20231031-T00013
Please refer to the end of the specification for access instructions.

Lengthy table referenced here
US11802305-20231031-T00014
Please refer to the end of the specification for access instructions.

Lengthy table referenced here
US11802305-20231031-T00015
Please refer to the end of the specification for access instructions.

Lengthy table referenced here
US11802305-20231031-T00016
Please refer to the end of the specification for access instructions.

Lengthy table referenced here
US11802305-20231031-T00017
Please refer to the end of the specification for access instructions.

Lengthy table referenced here
US11802305-20231031-T00018
Please refer to the end of the specification for access instructions.

Lengthy table referenced here
US11802305-20231031-T00019
Please refer to the end of the specification for access instructions.

Lengthy table referenced here
US11802305-20231031-T00020
Please refer to the end of the specification for access instructions.

Lengthy table referenced here
US11802305-20231031-T00021
Please refer to the end of the specification for access instructions.

Lengthy table referenced here
US11802305-20231031-T00022
Please refer to the end of the specification for access instructions.

Lengthy table referenced here
US11802305-20231031-T00023
Please refer to the end of the specification for access instructions.

Lengthy table referenced here
US11802305-20231031-T00024
Please refer to the end of the specification for access instructions.

Lengthy table referenced here
US11802305-20231031-T00025
Please refer to the end of the specification for access instructions.

Lengthy table referenced here
US11802305-20231031-T00026
Please refer to the end of the specification for access instructions.

Lengthy table referenced here
US11802305-20231031-T00027
Please refer to the end of the specification for access instructions.

Lengthy table referenced here
US11802305-20231031-T00028
Please refer to the end of the specification for access instructions.

Lengthy table referenced here
US11802305-20231031-T00029
Please refer to the end of the specification for access instructions.

Lengthy table referenced here
US11802305-20231031-T00030
Please refer to the end of the specification for access instructions.

Lengthy table referenced here
US11802305-20231031-T00031
Please refer to the end of the specification for access instructions.

Lengthy table referenced here
US11802305-20231031-T00032
Please refer to the end of the specification for access instructions.

Lengthy table referenced here
US11802305-20231031-T00033
Please refer to the end of the specification for access instructions.

Lengthy table referenced here
US11802305-20231031-T00034
Please refer to the end of the specification for access instructions.

Lengthy table referenced here
US11802305-20231031-T00035
Please refer to the end of the specification for access instructions.

Lengthy table referenced here
US11802305-20231031-T00036
Please refer to the end of the specification for access instructions.

Lengthy table referenced here
US11802305-20231031-T00037
Please refer to the end of the specification for access instructions.

Lengthy table referenced here
US11802305-20231031-T00038
Please refer to the end of the specification for access instructions.

Lengthy table referenced here
US11802305-20231031-T00039
Please refer to the end of the specification for access instructions.

Lengthy table referenced here
US11802305-20231031-T00040
Please refer to the end of the specification for access instructions.

Lengthy table referenced here
US11802305-20231031-T00041
Please refer to the end of the specification for access instructions.

Lengthy table referenced here
US11802305-20231031-T00042
Please refer to the end of the specification for access instructions.

Lengthy table referenced here
US11802305-20231031-T00043
Please refer to the end of the specification for access instructions.

Lengthy table referenced here
US11802305-20231031-T00044
Please refer to the end of the specification for access instructions.

Lengthy table referenced here
US11802305-20231031-T00045
Please refer to the end of the specification for access instructions.

Lengthy table referenced here
US11802305-20231031-T00046
Please refer to the end of the specification for access instructions.

Lengthy table referenced here
US11802305-20231031-T00047
Please refer to the end of the specification for access instructions.

Lengthy table referenced here
US11802305-20231031-T00048
Please refer to the end of the specification for access instructions.

Lengthy table referenced here
US11802305-20231031-T00049
Please refer to the end of the specification for access instructions.

Lengthy table referenced here
US11802305-20231031-T00050
Please refer to the end of the specification for access instructions.

Lengthy table referenced here
US11802305-20231031-T00051
Please refer to the end of the specification for access instructions.

Lengthy table referenced here
US11802305-20231031-T00052
Please refer to the end of the specification for access instructions.

Lengthy table referenced here
US11802305-20231031-T00053
Please refer to the end of the specification for access instructions.

Lengthy table referenced here
US11802305-20231031-T00054
Please refer to the end of the specification for access instructions.

Lengthy table referenced here
US11802305-20231031-T00055
Please refer to the end of the specification for access instructions.

Lengthy table referenced here
US11802305-20231031-T00056
Please refer to the end of the specification for access instructions.

Lengthy table referenced here
US11802305-20231031-T00057
Please refer to the end of the specification for access instructions.

Lengthy table referenced here
US11802305-20231031-T00058
Please refer to the end of the specification for access instructions.

Lengthy table referenced here
US11802305-20231031-T00059
Please refer to the end of the specification for access instructions.

Lengthy table referenced here
US11802305-20231031-T00060
Please refer to the end of the specification for access instructions.

Lengthy table referenced here
US11802305-20231031-T00061
Please refer to the end of the specification for access instructions.

Lengthy table referenced here
US11802305-20231031-T00062
Please refer to the end of the specification for access instructions.

Lengthy table referenced here
US11802305-20231031-T00063
Please refer to the end of the specification for access instructions.

Lengthy table referenced here
US11802305-20231031-T00064
Please refer to the end of the specification for access instructions.

Lengthy table referenced here
US11802305-20231031-T00065
Please refer to the end of the specification for access instructions.

Lengthy table referenced here
US11802305-20231031-T00066
Please refer to the end of the specification for access instructions.

Lengthy table referenced here
US11802305-20231031-T00067
Please refer to the end of the specification for access instructions.

Lengthy table referenced here
US11802305-20231031-T00068
Please refer to the end of the specification for access instructions.

Lengthy table referenced here
US11802305-20231031-T00069
Please refer to the end of the specification for access instructions.

Lengthy table referenced here
US11802305-20231031-T00070
Please refer to the end of the specification for access instructions.

Lengthy table referenced here
US11802305-20231031-T00071
Please refer to the end of the specification for access instructions.

Lengthy table referenced here
US11802305-20231031-T00072
Please refer to the end of the specification for access instructions.

Lengthy table referenced here
US11802305-20231031-T00073
Please refer to the end of the specification for access instructions.

Lengthy table referenced here
US11802305-20231031-T00074
Please refer to the end of the specification for access instructions.

Lengthy table referenced here
US11802305-20231031-T00075
Please refer to the end of the specification for access instructions.

Lengthy table referenced here
US11802305-20231031-T00076
Please refer to the end of the specification for access instructions.

Lengthy table referenced here
US11802305-20231031-T00077
Please refer to the end of the specification for access instructions.

Lengthy table referenced here
US11802305-20231031-T00078
Please refer to the end of the specification for access instructions.

Lengthy table referenced here
US11802305-20231031-T00079
Please refer to the end of the specification for access instructions.

Lengthy table referenced here
US11802305-20231031-T00080
Please refer to the end of the specification for access instructions.

Lengthy table referenced here
US11802305-20231031-T00081
Please refer to the end of the specification for access instructions.

Lengthy table referenced here
US11802305-20231031-T00082
Please refer to the end of the specification for access instructions.

Lengthy table referenced here
US11802305-20231031-T00083
Please refer to the end of the specification for access instructions.

Lengthy table referenced here
US11802305-20231031-T00084
Please refer to the end of the specification for access instructions.

Lengthy table referenced here
US11802305-20231031-T00085
Please refer to the end of the specification for access instructions.

| Lengthy table referenced here |
| --- |
| US11802305-20231031-T00086 |
| Please refer to the end of the specification for access instructions. |

| Lengthy table referenced here |
| --- |
| US11802305-20231031-T00087 |
| Please refer to the end of the specification for access instructions. |

| Lengthy table referenced here |
| --- |
| US11802305-20231031-T00088 |
| Please refer to the end of the specification for access instructions. |

| Lengthy table referenced here |
| --- |
| US11802305-20231031-T00089 |
| Please refer to the end of the specification for access instructions. |

| Lengthy table referenced here |
| --- |
| US11802305-20231031-T00090 |
| Please refer to the end of the specification for access instructions. |

| Lengthy table referenced here |
| --- |
| US11802305-20231031-T00091 |
| Please refer to the end of the specification for access instructions. |

| Lengthy table referenced here |
| --- |
| US11802305-20231031-T00092 |
| Please refer to the end of the specification for access instructions. |

| Lengthy table referenced here |
| --- |
| US11802305-20231031-T00093 |
| Please refer to the end of the specification for access instructions. |

LENGTHY TABLES

The patent contains a lengthy table section. A copy of the table is available in electronic form from the USPTO web site (https://seqdata.uspto.gov/?pageRequest=docDetail&DocID=US11802305B2). An electronic copy of the table will also be available from the USPTO upon request and payment of the fee set forth in 37 CFR 1.19(b)(3).

The invention claimed is:
1. A method for selecting a human individual who is responsive to anti-PD-1, anti-PD-L1 or anti-PD1-1/anti-PD-L1 combined therapy for melanoma and treating the selected human individual, the method comprising selecting the human individual by determining in a sample from the individual the presence or absence of a first, second, third, fourth, fifth, sixth, seventh, and eighth chromosome interaction,
  wherein selecting of the human individual as responsive to anti-PD-1, anti-PD-L1 or anti-PD1-1/anti-PD-L1 combined therapy for melanoma is based on detection of:
    presence of the first chromosome interaction,
    absence of the second chromosome interaction,
    presence of the third chromosome interaction,
    presence of the fourth chromosome interaction,
    absence of the fifth chromosome interaction,
    absence of the sixth chromosome interaction,
    presence of the seventh chromosome interaction,
    absence of the eighth chromosome interaction, and treating the selected human individual for melanoma by administering to the selected human individual anti-PD-1, anti-PD-L1 or anti-PD1-1/anti-PD-L1 combined therapy,
  wherein said determining the presence or absence of the chromosome interactions is carried out by
  (a) cross-linking of chromosome regions in the sample which have come together in a chromosome interaction;
  (b) subjecting said cross-linked regions to cleavage;
  (c) ligating said cross-linked cleaved DNA ends to form ligated nucleic acids; and
  (d) detecting the presence or absence of the ligated nucleic acids to thereby detect whether regions have been brought together in a chromosome interaction;
  wherein:
  the ligated nucleic acid corresponding to the first chromosome interaction is detected by the probe sequence: TGTAAACTGTAATATCAAAAATT-CAAAATCGAAGAGTTGATTTACTTATTAA-CATTA GAA (SEQ ID NO: 734);
  the ligated nucleic acid corresponding to the second chromosome interaction is detected by the probe sequence: ACTT-TATAGTGAAAAGTGCCATTT-GAGTCGACTGTGATTGAATGTAAAAGGTTTTA AAT (SEQ ID NO: 735);
  the ligated nucleic acid corresponding to the third chromosome interaction is detected by the probe sequence: TACTGTAGTAAGTTCTCTGAGGAGGA-TATCGAAGTCTTGGATTAAGGTTCATTCAAC AAA (SEQ ID NO: 736);
  the ligated nucleic acid corresponding to the fourth chromosome interaction is detected by the probe sequence: TTCCATAGATTACTTTTCAAAT-CATCCTTCGAAGCTGGCGGCT-GAGGGCCCGGCGCC AAG (SEQ ID NO: 741);
  the ligated nucleic acid corresponding to the fifth chromosome interaction is detected by the probe sequence: TCCATTTGAAGGATGAGAAAACT-GAGGCTCGAGGCTTAGAAAGTTTCAT-TTGGTTGC TCA (SEQ ID NO: 737);
  the ligated nucleic acid corresponding to the sixth chromosome interaction is detected by the probe sequence: TTT-TAAACCCAGGTGCACACACAAGAGCTCGAAG CAGGAATCCTGGTTCTGTTCCCA GGC (SEQ ID NO: 738);
  the ligated nucleic acid corresponding to the seventh chromosome interaction is detected by the probe sequence: CCACTCCCCCAGGCTTACCTGCGAGC-CATCGAGGTGGGCCTGGGTTCTCGTGGAGGG AGA (SEQ ID NO: 739);
  the ligated nucleic acid corresponding to the eighth chromosome interaction is detected by the probe sequence: TCACTCATTCTA-GATCCCTCTGTAAAGTTCGAACTCTGGACCTT GTGATCCACCCACC TT (SEQ ID NO: 740);
  and wherein said human individual has melanoma.

* * * * *

UNITED STATES PATENT AND TRADEMARK OFFICE
CERTIFICATE OF CORRECTION

PATENT NO. : 11,802,305 B2
APPLICATION NO. : 15/738469
DATED : October 31, 2023
INVENTOR(S) : Alexandre Akoulitchev, Ewan Hunter and Aroul Ramadass Page 1 of 1

It is certified that error appears in the above-identified patent and that said Letters Patent is hereby corrected as shown below:

In the Claims

Column 256, Line 4: please replace "ACTT-TATAGTGAAAAGTGCCATTT-" with --ACTTTTATAGTGAAAAGTGCCATTT--

Signed and Sealed this
Twenty-sixth Day of December, 2023

Katherine Kelly Vidal
*Director of the United States Patent and Trademark Office*

```
                            SEQUENCE LISTING

<160> NUMBER OF SEQ ID NOS: 744

<210> SEQ ID NO 1
<211> LENGTH: 14
<212> TYPE: DNA
<213> ORGANISM: Homo sapiens
<220> FEATURE:
<221> NAME/KEY: misc_feature
<222> LOCATION: (6)..(6)
<223> OTHER INFORMATION: 'n' can be any base
<220> FEATURE:
<221> NAME/KEY: misc_feature
<222> LOCATION: (9)..(9)
<223> OTHER INFORMATION: 'n' can be any base

<400> SEQUENCE: 1
ccgcgnggng gcag                                                      14

<210> SEQ ID NO 2
<211> LENGTH: 60
<212> TYPE: DNA
<213> ORGANISM: Homo sapiens

<400> SEQUENCE: 2
```
gcctgcaggg ggcgccccccg cgcctgcctc gaccacacat ccacatggac gcatggcagg    60

<210> SEQ ID NO 3
<211> LENGTH: 60
<212> TYPE: DNA
<213> ORGANISM: Homo sapiens

<400> SEQUENCE: 3
ttatcaaccc ggcgtctgga acaatcgctc gatccacacc acaccagcag tggggcacaa    60

<210> SEQ ID NO 4
<211> LENGTH: 60
<212> TYPE: DNA
<213> ORGANISM: Homo sapiens

<400> SEQUENCE: 4
aggacagaga ccctaattc caccaccatc gacccttctg ctttctctcc agggatggc    60

<210> SEQ ID NO 5
<211> LENGTH: 60
<212> TYPE: DNA
<213> ORGANISM: Homo sapiens

<400> SEQUENCE: 5
ccgcccctgt cctctcgctt cccgctggtc gatccacacc acaccagcag tggggcacaa    60

<210> SEQ ID NO 6
<211> LENGTH: 60
<212> TYPE: DNA
<213> ORGANISM: Homo sapiens

<400> SEQUENCE: 6
agttctttct tgaattcttt cctgatactc gatccacacc acaccagcag tggggcacaa    60

<210> SEQ ID NO 7
<211> LENGTH: 60
<212> TYPE: DNA
<213> ORGANISM: Homo sapiens

<400> SEQUENCE: 7
cctgtagctc tgatgtcaga tggcaatgtc gatccacacc acaccagcag tggggcacaa    60

<210> SEQ ID NO 8
<211> LENGTH: 60
<212> TYPE: DNA
<213> ORGANISM: Homo sapiens

<400> SEQUENCE: 8
ccacctcata ggggagggct ttactcagtc gatccacacc acaccagcag tggggcacaa    60

<210> SEQ ID NO 9
<211> LENGTH: 60
<212> TYPE: DNA
<213> ORGANISM: Homo sapiens

<400> SEQUENCE: 9
tcacctctgt cacccacccg ttccactctc gataaagcac ttagaacatg gcatatactc    60

<210> SEQ ID NO 10
<211> LENGTH: 60
<212> TYPE: DNA
<213> ORGANISM: Homo sapiens

<400> SEQUENCE: 10
tcacctctgt cacccacccg ttccactctc gaatagctcc tattgttatg gagtgtagca    60

<210> SEQ ID NO 11
<211> LENGTH: 60
<212> TYPE: DNA
<213> ORGANISM: Homo sapiens

<400> SEQUENCE: 11
tcacctctgt cacccacccg ttccactctc gaattaggaa tcagcatttc ttccactgag    60

<210> SEQ ID NO 12
<211> LENGTH: 60
<212> TYPE: DNA
<213> ORGANISM: Homo sapiens

<400> SEQUENCE: 12
tcacctctgt cacccacccg ttccactctc gatgctctct tagtgttcca attctcagct    60

<210> SEQ ID NO 13
<211> LENGTH: 60
<212> TYPE: DNA
<213> ORGANISM: Homo sapiens

<400> SEQUENCE: 13
tcacctctgt cacccacccg ttccactctc gaaatagtaa aatttgatta tcaaaatttt    60

<210> SEQ ID NO 14
<211> LENGTH: 60
<212> TYPE: DNA
<213> ORGANISM: Homo sapiens

<400> SEQUENCE: 14
tccgtgaccc ccacagccgg tcgccacatc gattatccag aagcttcttt tttttttaacc   60

<210> SEQ ID NO 15
<211> LENGTH: 60
<212> TYPE: DNA
<213> ORGANISM: Homo sapiens

<400> SEQUENCE: 15
tcacctctgt cacccacccg ttccactctc gaggctgcag tgaatcataa tcatagcact    60

<210> SEQ ID NO 16
<211> LENGTH: 60
<212> TYPE: DNA
<213> ORGANISM: Homo sapiens

<400> SEQUENCE: 16
agtgttggtg agatattgtc tctcagtttc gatccacacc acaccagcag tggggcacaa    60

<210> SEQ ID NO 17
<211> LENGTH: 60
<212> TYPE: DNA
<213> ORGANISM: Homo sapiens

<400> SEQUENCE: 17
ggtggcatcc ccatcacttc tccatgcctc gaggtcccca accccctgcc gctcatcgtg    60

<210> SEQ ID NO 18
<211> LENGTH: 60
<212> TYPE: DNA
<213> ORGANISM: Homo sapiens

<400> SEQUENCE: 18
tcctgcccac agccccccgct ttagcctctc gagaatgcta acagcacagg atacagtact    60

<210> SEQ ID NO 19
<211> LENGTH: 60
<212> TYPE: DNA
<213> ORGANISM: Homo sapiens

<400> SEQUENCE: 19
tccgtgaccc ccacagccgg tcgccacatc gagtagctga gattacaggc atgtaccacc    60

<210> SEQ ID NO 20
<211> LENGTH: 60
<212> TYPE: DNA
<213> ORGANISM: Homo sapiens

<400> SEQUENCE: 20
ctccacgtca ccccatgtca attccaagtc gatgccagac actcttctgg gggtggggtg    60

<210> SEQ ID NO 21
<211> LENGTH: 60
<212> TYPE: DNA
<213> ORGANISM: Homo sapiens

<400> SEQUENCE: 21
cctctgtcca caccattatt ttaaagagtc gacatgcctt gctttaccat tgtttaattt    60

<210> SEQ ID NO 22
<211> LENGTH: 60
<212> TYPE: DNA
<213> ORGANISM: Homo sapiens

<400> SEQUENCE: 22
agtggtacaa tcatgaatca ctacagcctc gaccacacat ccacatggac gcatggcagg    60

<210> SEQ ID NO 23
<211> LENGTH: 60
<212> TYPE: DNA
<213> ORGANISM: Homo sapiens

<400> SEQUENCE: 23
ctcccaaggt aaactcattg ccgaaacctc gagttgttgc cacccccaccc tcctcaaacc    60

<210> SEQ ID NO 24
<211> LENGTH: 60
<212> TYPE: DNA
<213> ORGANISM: Homo sapiens

<400> SEQUENCE: 24 tgtttttat tgtttgatgt ccaatgtatc gagccgccct tgacataaca ccatcttta    60

<210> SEQ ID NO 25
<211> LENGTH: 60
<212> TYPE: DNA
<213> ORGANISM: Homo sapiens

<400> SEQUENCE: 25
ttgaacccaa gaggtcacac cactgcactc gacgcccagc aagtaggcac agttcccaat    60

<210> SEQ ID NO 26
<211> LENGTH: 60
<212> TYPE: DNA
<213> ORGANISM: Homo sapiens

<400> SEQUENCE: 26
ttggagcccc ctgcctgca cacacagctc gagatttgtc tttctgttcc tggcttattt    60

<210> SEQ ID NO 27
<211> LENGTH: 60
<212> TYPE: DNA
<213> ORGANISM: Homo sapiens

<400> SEQUENCE: 27
aggacagaga ccctaattc caccaccatc gaacaactgc aaactccact caacatcttt    60

<210> SEQ ID NO 28
<211> LENGTH: 60
<212> TYPE: DNA
<213> ORGANISM: Homo sapiens

<400> SEQUENCE: 28
aaccacacaa ctgctactca caattctttc gaaaccagaa gacccaatat aatatctagt    60

<210> SEQ ID NO 29
<211> LENGTH: 60
<212> TYPE: DNA
<213> ORGANISM: Homo sapiens

<400> SEQUENCE: 29
acccaggata aaacgcagtg ttgaccgatc gagggcgtgg acttctacac gtccatcact    60

<210> SEQ ID NO 30
<211> LENGTH: 60
<212> TYPE: DNA
<213> ORGANISM: Homo sapiens

<400> SEQUENCE: 30
ggcttatcca tgcttaaatt gattaacgtc gagttgttgc caccccaccc tcctcaaacc    60

<210> SEQ ID NO 31
<211> LENGTH: 60
<212> TYPE: DNA
<213> ORGANISM: Homo sapiens

<400> SEQUENCE: 31
agtggtctca ccatggcttt cttccaattc gaggtcccca accccctgcc gctcatcgtg    60

<210> SEQ ID NO 32
<211> LENGTH: 60
<212> TYPE: DNA
<213> ORGANISM: Homo sapiens

<400> SEQUENCE: 32
ggaactgcat ccatacttgt tacacatctc gaaccggagt ggacgtgtgt ccacatgtaa    60

<210> SEQ ID NO 33
<211> LENGTH: 60
<212> TYPE: DNA
<213> ORGANISM: Homo sapiens

<400> SEQUENCE: 33
atctaaacac agtccatgct aaaagcttc gagttgttgc caccccaccc tcctcaaacc    60

<210> SEQ ID NO 34
<211> LENGTH: 60
<212> TYPE: DNA

<213> ORGANISM: Homo sapiens

<400> SEQUENCE: 34
ggaactgcat ccatacttgt tacacatctc gagttgttgc caccccaccc tcctcaaacc    60

<210> SEQ ID NO 35
<211> LENGTH: 60
<212> TYPE: DNA
<213> ORGANISM: Homo sapiens

<400> SEQUENCE: 35
ctcaggaaga agtggatccc tgtttctttc gagttgttgc caccccaccc tcctcaaacc    60

<210> SEQ ID NO 36
<211> LENGTH: 60
<212> TYPE: DNA
<213> ORGANISM: Homo sapiens

<400> SEQUENCE: 36
agtgtatttt tcactacact agtggttttc gagttgttgc caccccaccc tcctcaaacc    60

<210> SEQ ID NO 37
<211> LENGTH: 60
<212> TYPE: DNA
<213> ORGANISM: Homo sapiens

<400> SEQUENCE: 37
taaatacaga tgaaaccaac taatagactc gagttgttgc caccccaccc tcctcaaacc    60

<210> SEQ ID NO 38
<211> LENGTH: 60
<212> TYPE: DNA
<213> ORGANISM: Homo sapiens

<400> SEQUENCE: 38
agctgggccc caaaggttaa aaaggacttc gagttgttgc caccccaccc tcctcaaacc    60

<210> SEQ ID NO 39
<211> LENGTH: 60
<212> TYPE: DNA
<213> ORGANISM: Homo sapiens

<400> SEQUENCE: 39
ccacgtgtcg cgggcctgag tgtgcccctc gaggctgtag tgattcatga ttgtaccact    60

<210> SEQ ID NO 40
<211> LENGTH: 60
<212> TYPE: DNA
<213> ORGANISM: Homo sapiens

<400> SEQUENCE: 40
acctaggata aaaggcagtg ttgaccgatc gacacccata tgagccccac ccggcttcaa    60

<210> SEQ ID NO 41
<211> LENGTH: 60
<212> TYPE: DNA
<213> ORGANISM: Homo sapiens

<400> SEQUENCE: 41
ttccacctgt aatactgtgc ctgtattctc gagcaggcgc tcaacaaata caacttcctt    60

<210> SEQ ID NO 42
<211> LENGTH: 60

<212> TYPE: DNA
<213> ORGANISM: Homo sapiens

<400> SEQUENCE: 42
gtgccctcct cgcccctgat gggtctggtc gagaccagcc tcaacatgga gaaacaccat    60

<210> SEQ ID NO 43
<211> LENGTH: 60
<212> TYPE: DNA
<213> ORGANISM: Homo sapiens

<400> SEQUENCE: 43 ccaccccgc cccgggggag tcgcccggtc gagggcctgg caagaagaca gaagccgact    60

<210> SEQ ID NO 44
<211> LENGTH: 60
<212> TYPE: DNA
<213> ORGANISM: Homo sapiens

<400> SEQUENCE: 44
aagtcctaag aacactgaaa atctcagatc gagttgttgc caccccaccc tcctcaaacc    60

<210> SEQ ID NO 45
<211> LENGTH: 60
<212> TYPE: DNA
<213> ORGANISM: Homo sapiens

<400> SEQUENCE: 45
ctccacgtca cccatgtca attccaagtc gaatactcaa aacagaattt gatattcaaa    60

<210> SEQ ID NO 46
<211> LENGTH: 60
<212> TYPE: DNA
<213> ORGANISM: Homo sapiens

<400> SEQUENCE: 46
ccaaatccga acctcctctg tgaagcattc gagttgttgc caccccaccc tcctcaaacc    60

<210> SEQ ID NO 47
<211> LENGTH: 60
<212> TYPE: DNA
<213> ORGANISM: Homo sapiens

<400> SEQUENCE: 47
gttaacagta atacgatgtt aaaaggactc gagttgttgc caccccaccc tcctcaaacc    60

<210> SEQ ID NO 48
<211> LENGTH: 60
<212> TYPE: DNA
<213> ORGANISM: Homo sapiens

<400> SEQUENCE: 48
ggctggcgga ttacttgaag ccaggagttc gatccacacc acaccagcag tggggcacaa    60

<210> SEQ ID NO 49
<211> LENGTH: 60
<212> TYPE: DNA
<213> ORGANISM: Homo sapiens

<400> SEQUENCE: 49
ttgaacccaa gaggtcacac cactgcactc gagccgccct tgacataaca ccatcttta    60

<210> SEQ ID NO 50

```
<211> LENGTH: 60
<212> TYPE: DNA
<213> ORGANISM: Homo sapiens

<400> SEQUENCE: 50
cccctaattt agcaagcaga aagagaactc gatgcttcat ttgactcaca ctcacattta      60

<210> SEQ ID NO 51
<211> LENGTH: 60
<212> TYPE: DNA
<213> ORGANISM: Homo sapiens

<400> SEQUENCE: 51
ctccacgtca ccccatgtca attccaagtc gaaaataagt cgctagagcc acatcaagca      60

<210> SEQ ID NO 52
<211> LENGTH: 60
<212> TYPE: DNA
<213> ORGANISM: Homo sapiens

<400> SEQUENCE: 52
aggacagaga cccctaattc caccaccatc gacccttctg ctttctctcc aggggatggc      60

<210> SEQ ID NO 53
<211> LENGTH: 60
<212> TYPE: DNA
<213> ORGANISM: Homo sapiens

<400> SEQUENCE: 53
ttccacctgt aatactgtgc ctgtattctc gagcaggcgc tcaacaaata caacttcctt      60

<210> SEQ ID NO 54
<211> LENGTH: 60
<212> TYPE: DNA
<213> ORGANISM: Homo sapiens

<400> SEQUENCE: 54
accaaaccca aggtccgctg ctcgctgctc gaattcccaa ctgagggagc tttgtggaaa      60

<210> SEQ ID NO 55
<211> LENGTH: 60
<212> TYPE: DNA
<213> ORGANISM: Homo sapiens

<400> SEQUENCE: 55
ctcctcaaaa aaaagaggag gcccaggctc gagactccag aaaaatagat tacaggtttg      60

<210> SEQ ID NO 56
<211> LENGTH: 60
<212> TYPE: DNA
<213> ORGANISM: Homo sapiens

<400> SEQUENCE: 56
tttagccaaa aagaaaaaaa ggttcatttc gagaaccaga gtcaaactta gaccccagga      60

<210> SEQ ID NO 57
<211> LENGTH: 60
<212> TYPE: DNA
<213> ORGANISM: Homo sapiens

<400> SEQUENCE: 57
tcctttcttt ttattttttt aagctgtttc gattcaacat taattcattt tagacttctc      60
```

```
<210> SEQ ID NO 58
<211> LENGTH: 60
<212> TYPE: DNA
<213> ORGANISM: Homo sapiens

<400> SEQUENCE: 58
accagccctg ggttcttaag gatgggtgtc gacccctggc tctgcctggg gtctgggctt      60

<210> SEQ ID NO 59
<211> LENGTH: 60
<212> TYPE: DNA
<213> ORGANISM: Homo sapiens

<400> SEQUENCE: 59
acatctcaga catgactttt gtgttcctc gagccttttc gggcaggcgt ccagcacggg      60

<210> SEQ ID NO 60
<211> LENGTH: 60
<212> TYPE: DNA
<213> ORGANISM: Homo sapiens

<400> SEQUENCE: 60
ctcagactgt atattctctt agcttcagtc gagctgtttc tttatatggt ctctgctatc      60

<210> SEQ ID NO 61
<211> LENGTH: 60
<212> TYPE: DNA
<213> ORGANISM: Homo sapiens

<400> SEQUENCE: 61
attataacat ttatatatca tcttttcctc gaggttgcag taagctgatc atgccactac      60

<210> SEQ ID NO 62
<211> LENGTH: 60
<212> TYPE: DNA
<213> ORGANISM: Homo sapiens

<400> SEQUENCE: 62
gaccaaacag ctgtggtttg gccatcactc gagagagagc ctgtgtgagg agtgcagtca      60

<210> SEQ ID NO 63
<211> LENGTH: 60
<212> TYPE: DNA
<213> ORGANISM: Homo sapiens

<400> SEQUENCE: 63
cttttagctt ttacttagca taattttctc gagagggtgg ggcaggagaa tctcttgaac      60

<210> SEQ ID NO 64
<211> LENGTH: 60
<212> TYPE: DNA
<213> ORGANISM: Homo sapiens

<400> SEQUENCE: 64
ggaaggccga ggcggccaga tcacgaggtc gaacctcctg ataacttcag cattaacagc      60

<210> SEQ ID NO 65
<211> LENGTH: 60
<212> TYPE: DNA
<213> ORGANISM: Homo sapiens

<400> SEQUENCE: 65
gaccaaacag ctgtggtttg gccatcactc gagagagagc ctgtgtgagg agtgcagtca      60
```

<210> SEQ ID NO 66
<211> LENGTH: 60
<212> TYPE: DNA
<213> ORGANISM: Homo sapiens

<400> SEQUENCE: 66
gagtaggtaa acaaagcagt caggaagctc gagtctttgg ttttccctag ataattaata    60

<210> SEQ ID NO 67
<211> LENGTH: 60
<212> TYPE: DNA
<213> ORGANISM: Homo sapiens

<400> SEQUENCE: 67
cttagagcaa aggctaggct cagtaatgtc gagagagagc ctgtgtgagg agtgcagtca    60

<210> SEQ ID NO 68
<211> LENGTH: 60
<212> TYPE: DNA
<213> ORGANISM: Homo sapiens

<400> SEQUENCE: 68
agatcaaatc cagtttaagg ctactccttc gattcataca ccattcaggg tatacaatag    60

<210> SEQ ID NO 69
<211> LENGTH: 60
<212> TYPE: DNA
<213> ORGANISM: Homo sapiens

<400> SEQUENCE: 69
ttgcgagcct cgcagcctcc ggaagctgtc gattttaagt ctattttgtt agatctaaag    60

<210> SEQ ID NO 70
<211> LENGTH: 60
<212> TYPE: DNA
<213> ORGANISM: Homo sapiens

<400> SEQUENCE: 70
actgacagtt tcttgggatt ctccagactc gagagaggct ggtgcgcacc tacccagcgg    60

<210> SEQ ID NO 71
<211> LENGTH: 60
<212> TYPE: DNA
<213> ORGANISM: Homo sapiens

<400> SEQUENCE: 71
ccactccccc aggcttacct gcgagccatc gaggtgggcc tgggttctcg tggagggaga    60

<210> SEQ ID NO 72
<211> LENGTH: 60
<212> TYPE: DNA
<213> ORGANISM: Homo sapiens

<400> SEQUENCE: 72
ccatcctgga cgcagaatgt agtcccgttc gaacagagct gggagctggg gcctaggcta    60

<210> SEQ ID NO 73
<211> LENGTH: 60
<212> TYPE: DNA
<213> ORGANISM: Homo sapiens

<400> SEQUENCE: 73 tgcttttaa aaaatcaaag gtgtaacttc gacagcttcc ggaggctgcg aggctcgcaa    60

<210> SEQ ID NO 74
<211> LENGTH: 60
<212> TYPE: DNA
<213> ORGANISM: Homo sapiens

<400> SEQUENCE: 74
tatgaggccc ggttccagca gaagcttctc gaacagagct gggagctggg gcctaggcta    60

<210> SEQ ID NO 75
<211> LENGTH: 60
<212> TYPE: DNA
<213> ORGANISM: Homo sapiens

<400> SEQUENCE: 75
ggaaggccga ggcggccaga tcacgaggtc gaaagcgctc ggattcagcc ttctccccgg    60

<210> SEQ ID NO 76
<211> LENGTH: 60
<212> TYPE: DNA
<213> ORGANISM: Homo sapiens

<400> SEQUENCE: 76
atggacagta ggcaggatga ataagtgctc gagccttttc gggcaggcgt ccagcacggg    60

<210> SEQ ID NO 77
<211> LENGTH: 60
<212> TYPE: DNA
<213> ORGANISM: Homo sapiens

<400> SEQUENCE: 77
taacgtccaa gaaaattatt gtgacccgtc gagaagtcag ggagcgtcta gggcttctgg    60

<210> SEQ ID NO 78
<211> LENGTH: 60
<212> TYPE: DNA
<213> ORGANISM: Homo sapiens

<400> SEQUENCE: 78
tatgaggccc ggttccagca gaagcttctc gaacagagct gggagctggg gcctaggcta    60

<210> SEQ ID NO 79
<211> LENGTH: 60
<212> TYPE: DNA
<213> ORGANISM: Homo sapiens

<400> SEQUENCE: 79
actgacagtt tcttgggatt ctccagactc gaggcctgga gaagcccagg aggaggcgtg    60

<210> SEQ ID NO 80
<211> LENGTH: 60
<212> TYPE: DNA
<213> ORGANISM: Homo sapiens

<400> SEQUENCE: 80
ctcctcaaaa aaaagaggag gcccaggctc gatcccagag ccgtcccagg cctggacaga    60

<210> SEQ ID NO 81
<211> LENGTH: 60
<212> TYPE: DNA
<213> ORGANISM: Homo sapiens

<400> SEQUENCE: 81
aggctgaact tcaaatgtga taataacctc gacttaattt tattacagca ctaatataat        60

<210> SEQ ID NO 82
<211> LENGTH: 60
<212> TYPE: DNA
<213> ORGANISM: Homo sapiens

<400> SEQUENCE: 82
gacttcaact cactatgaat aaataaaatc gagagggtgg ggcaggagaa tctcttgaac        60

<210> SEQ ID NO 83
<211> LENGTH: 60
<212> TYPE: DNA
<213> ORGANISM: Homo sapiens

<400> SEQUENCE: 83 tgcttttaa aaaatcaaag gtgtaacttc gaattaggtg ggtgggggtg ggaaattggg         60

<210> SEQ ID NO 84
<211> LENGTH: 60
<212> TYPE: DNA
<213> ORGANISM: Homo sapiens

<400> SEQUENCE: 84
ataagaaact gaatttaaat gctctctttc gattcataca ccattcaggg tatacaatag        60

<210> SEQ ID NO 85
<211> LENGTH: 60
<212> TYPE: DNA
<213> ORGANISM: Homo sapiens

<400> SEQUENCE: 85
aaggtcttca gcttcactcc tgaagccatc gagttctgta cttaagcaaa cattatcctt        60

<210> SEQ ID NO 86
<211> LENGTH: 60
<212> TYPE: DNA
<213> ORGANISM: Homo sapiens

<400> SEQUENCE: 86
ccatgttgta atattggatt tttatcattc gatatagtgg tttctaggta tcatggtaaa        60

<210> SEQ ID NO 87
<211> LENGTH: 60
<212> TYPE: DNA
<213> ORGANISM: Homo sapiens

<400> SEQUENCE: 87
gagtaggtaa acaaagcagt caggaagctc gatccagtgt gcttttcact tcagaccttg       60

<210> SEQ ID NO 88
<211> LENGTH: 60
<212> TYPE: DNA
<213> ORGANISM: Homo sapiens

<400> SEQUENCE: 88
aatatctttt cattttttgg tgaagtcttc gatggcttca ggagtgaagc tgaagacctt       60

<210> SEQ ID NO 89
<211> LENGTH: 60
<212> TYPE: DNA
<213> ORGANISM: Homo sapiens

<400> SEQUENCE: 89
tgttcaatca aaggaaggga taacactatc gaggttgcag taagctgatc atgccactac    60

<210> SEQ ID NO 90
<211> LENGTH: 60
<212> TYPE: DNA
<213> ORGANISM: Homo sapiens

<400> SEQUENCE: 90
gatgtttata caagattcat tctttccatc gattcaacat taattcattt tagacttctc    60

<210> SEQ ID NO 91
<211> LENGTH: 60
<212> TYPE: DNA
<213> ORGANISM: Homo sapiens

<400> SEQUENCE: 91
ttccttgagg aatcagtgat caggactctc gaacagagct gggagctggg gcctaggcta    60

<210> SEQ ID NO 92
<211> LENGTH: 60
<212> TYPE: DNA
<213> ORGANISM: Homo sapiens

<400> SEQUENCE: 92
taacgtccaa gaaaattatt gtgacccgtc gagaagtcag ggagcgtcta gggcttctgg    60

<210> SEQ ID NO 93
<211> LENGTH: 60
<212> TYPE: DNA
<213> ORGANISM: Homo sapiens

<400> SEQUENCE: 93
tagtactacc actggaaagc tagaatattc gatgcattaa aatgttctcg gaaagagata    60

<210> SEQ ID NO 94
<211> LENGTH: 60
<212> TYPE: DNA
<213> ORGANISM: Homo sapiens

<400> SEQUENCE: 94
caaacctgta atctattttt ctggagtctc gatcccagag ccgtcccagg cctggacaga    60

<210> SEQ ID NO 95
<211> LENGTH: 60
<212> TYPE: DNA
<213> ORGANISM: Homo sapiens

<400> SEQUENCE: 95
gttgaggctg caataaaccg tgatcaagtc gacacccatc cttaagaacc cagggctggt    60

<210> SEQ ID NO 96
<211> LENGTH: 60
<212> TYPE: DNA
<213> ORGANISM: Homo sapiens

<400> SEQUENCE: 96
ctcagactgt atattctctt agcttcagtc gagttctgta cttaagcaaa cattatcctt    60

<210> SEQ ID NO 97
<211> LENGTH: 60
<212> TYPE: DNA
<213> ORGANISM: Homo sapiens

<400> SEQUENCE: 97
ggaaatgagt ctcatgtcta attaaatgtc gaagttaagg tttcttggtt caagtggtgt    60

<210> SEQ ID NO 98
<211> LENGTH: 60
<212> TYPE: DNA
<213> ORGANISM: Homo sapiens

<400> SEQUENCE: 98
tgaggtaggc agatcacagg tcaggagatc gacctccatt acggagagtt tcctatgttt    60

<210> SEQ ID NO 99
<211> LENGTH: 60
<212> TYPE: DNA
<213> ORGANISM: Homo sapiens

<400> SEQUENCE: 99
aaggtcttca gcttcactcc tgaagccatc gagctgtttc tttatatggt ctctgctatc    60

<210> SEQ ID NO 100
<211> LENGTH: 60
<212> TYPE: DNA
<213> ORGANISM: Homo sapiens

<400> SEQUENCE: 100
tgggctcctt cagccccaca tgcctggttc gaacagagct gggagctggg gcctaggcta    60

<210> SEQ ID NO 101
<211> LENGTH: 60
<212> TYPE: DNA
<213> ORGANISM: Homo sapiens

<400> SEQUENCE: 101
tttagccaaa aagaaaaaaa ggttcatttc gaggaatgtt tccaagcaat tctctctgct    60

<210> SEQ ID NO 102
<211> LENGTH: 60
<212> TYPE: DNA
<213> ORGANISM: Homo sapiens

<400> SEQUENCE: 102
ctcctcaaaa aaaagaggag gcccaggctc gatcccagag ccgtcccagg cctggacaga    60

<210> SEQ ID NO 103
<211> LENGTH: 60
<212> TYPE: DNA
<213> ORGANISM: Homo sapiens

<400> SEQUENCE: 103
ccctttaccc cagtccgtgt gagcctcttc gagccttttc gggcaggcgt ccagcacggg    60

<210> SEQ ID NO 104
<211> LENGTH: 60
<212> TYPE: DNA
<213> ORGANISM: Homo sapiens

<400> SEQUENCE: 104
ggattacttc catgagaagc aattaaaatc gaacagagct gggagctggg gcctaggcta    60

<210> SEQ ID NO 105
<211> LENGTH: 60
<212> TYPE: DNA
<213> ORGANISM: Homo sapiens

<400> SEQUENCE: 105
ggaaggccga ggcggccaga tcacgaggtc gaacctcctg ataacttcag cattaacagc    60

<210> SEQ ID NO 106
<211> LENGTH: 60
<212> TYPE: DNA
<213> ORGANISM: Homo sapiens

<400> SEQUENCE: 106
acatctcaga catgactttt gtgtttcctc gagccttttc gggcaggcgt ccagcacggg    60

<210> SEQ ID NO 107
<211> LENGTH: 60
<212> TYPE: DNA
<213> ORGANISM: Homo sapiens

<400> SEQUENCE: 107
cgtggttctt caagttgtag tttaattctc gagagcagtg ttttaagtgg tctgacggga    60

<210> SEQ ID NO 108
<211> LENGTH: 60
<212> TYPE: DNA
<213> ORGANISM: Homo sapiens

<400> SEQUENCE: 108
ttggctgttt tcactcagtg aaattccttc gagcccagga ggcaaaggtt gcagtgagct    60

<210> SEQ ID NO 109
<211> LENGTH: 60
<212> TYPE: DNA
<213> ORGANISM: Homo sapiens

<400> SEQUENCE: 109
ggaaggccga ggcggccaga tcacgaggtc gaaagcgctc ggattcagcc ttctccccgg    60

<210> SEQ ID NO 110
<211> LENGTH: 60
<212> TYPE: DNA
<213> ORGANISM: Homo sapiens

<400> SEQUENCE: 110
atggacagta ggcaggatga ataagtgctc gagccttttc gggcaggcgt ccagcacggg    60

<210> SEQ ID NO 111
<211> LENGTH: 60
<212> TYPE: DNA
<213> ORGANISM: Homo sapiens

<400> SEQUENCE: 111
gggtttcacc atgttggcct ggctgggctc gagaccagcc tggccaacat ggtgaaacca    60

<210> SEQ ID NO 112
<211> LENGTH: 60
<212> TYPE: DNA
<213> ORGANISM: Homo sapiens

<400> SEQUENCE: 112
actgacagtt tcttgggatt ctccagactc gagagaggct ggtgcgcacc tacccagcgg    60

<210> SEQ ID NO 113
<211> LENGTH: 60
<212> TYPE: DNA

<213> ORGANISM: Homo sapiens

<400> SEQUENCE: 113
cttagagcaa aggctaggct cagtaatgtc gagagagagc ctgtgtgagg agtgcagtca    60

<210> SEQ ID NO 114
<211> LENGTH: 60
<212> TYPE: DNA
<213> ORGANISM: Homo sapiens

<400> SEQUENCE: 114
acatctcaga catgactttt gtgtttcctc gagtctcacc aggtcggtcc tgagccacac    60

<210> SEQ ID NO 115
<211> LENGTH: 60
<212> TYPE: DNA
<213> ORGANISM: Homo sapiens

<400> SEQUENCE: 115
actgacagtt tcttgggatt ctccagactc gaggcctgga aagcccagg aggaggcgtg    60

<210> SEQ ID NO 116
<211> LENGTH: 60
<212> TYPE: DNA
<213> ORGANISM: Homo sapiens

<400> SEQUENCE: 116
attataacat ttatatatca tcttttcctc gaggttgcag taagctgatc atgccactac    60

<210> SEQ ID NO 117
<211> LENGTH: 60
<212> TYPE: DNA
<213> ORGANISM: Homo sapiens

<400> SEQUENCE: 117
ggaaaacagg attaaaaaag aaatggattc gagcccagga ggcaaaggtt gcagtgagct    60

<210> SEQ ID NO 118
<211> LENGTH: 60
<212> TYPE: DNA
<213> ORGANISM: Homo sapiens

<400> SEQUENCE: 118
cttagagcaa aggctaggct cagtaatgtc gagcaagcct tgaggctgac acaggacctg    60

<210> SEQ ID NO 119
<211> LENGTH: 60
<212> TYPE: DNA
<213> ORGANISM: Homo sapiens

<400> SEQUENCE: 119
cgtggttctt caagttgtag tttaattctc gagcttgtta ttttctcttt cttacctagt    60

<210> SEQ ID NO 120
<211> LENGTH: 60
<212> TYPE: DNA
<213> ORGANISM: Homo sapiens

<400> SEQUENCE: 120
gaccaaacag ctgtggtttg gccatcactc gagagagagc ctgtgtgagg agtgcagtca    60

<210> SEQ ID NO 121
<211> LENGTH: 60

```
<212> TYPE: DNA
<213> ORGANISM: Homo sapiens

<400> SEQUENCE: 121
cgtggttctt caagttgtag tttaattctc gagcttgaat cagaatggtc aagatacctg    60

<210> SEQ ID NO 122
<211> LENGTH: 60
<212> TYPE: DNA
<213> ORGANISM: Homo sapiens

<400> SEQUENCE: 122
tgtgttaggg taccattctt cttaagtatc gaatctgtac atcaactttg gaaaaactaa    60

<210> SEQ ID NO 123
<211> LENGTH: 60
<212> TYPE: DNA
<213> ORGANISM: Homo sapiens

<400> SEQUENCE: 123
tcctacagaa gttaaaatag agctagggtc gaattggccc gggtccctgc tgggctggag    60

<210> SEQ ID NO 124
<211> LENGTH: 60
<212> TYPE: DNA
<213> ORGANISM: Homo sapiens

<400> SEQUENCE: 124
tttagccaaa aagaaaaaaa ggttcatttc gagaaccaga gtcaaactta gaccccagga    60

<210> SEQ ID NO 125
<211> LENGTH: 60
<212> TYPE: DNA
<213> ORGANISM: Homo sapiens

<400> SEQUENCE: 125
ttagtttttc caaagttgat gtacagattc gagagcagtg ttttaagtgg tctgacggga    60

<210> SEQ ID NO 126
<211> LENGTH: 60
<212> TYPE: DNA
<213> ORGANISM: Homo sapiens

<400> SEQUENCE: 126
tggtgagcag aaggctccag ctgtacgctc gacggcccag ggaaactcaa acccatactc    60

<210> SEQ ID NO 127
<211> LENGTH: 60
<212> TYPE: DNA
<213> ORGANISM: Homo sapiens

<400> SEQUENCE: 127
gagtaggtaa acaaagcagt caggaagctc gagtctttgg ttttccctag ataattaata    60

<210> SEQ ID NO 128
<211> LENGTH: 60
<212> TYPE: DNA
<213> ORGANISM: Homo sapiens

<400> SEQUENCE: 128
acaccacttg aaccaagaaa ccttaacttc gaaggagtgg cataaggtcc cacttgggtg    60

<210> SEQ ID NO 129
```

<211> LENGTH: 60
<212> TYPE: DNA
<213> ORGANISM: Homo sapiens

<400> SEQUENCE: 129
ccctttaccc cagtccgtgt gagcctcttc gagccttttc gggcaggcgt ccagcacggg      60

<210> SEQ ID NO 130
<211> LENGTH: 60
<212> TYPE: DNA
<213> ORGANISM: Homo sapiens

<400> SEQUENCE: 130
actgacagtt tcttgggatt ctccagactc gaggcaggag gacagcttga gcccgggagt      60

<210> SEQ ID NO 131
<211> LENGTH: 60
<212> TYPE: DNA
<213> ORGANISM: Homo sapiens

<400> SEQUENCE: 131
cctaggcaga tcacttgagt tcaggagttc gaaacacttg atcaaaacag aataacaggt      60

<210> SEQ ID NO 132
<211> LENGTH: 60
<212> TYPE: DNA
<213> ORGANISM: Homo sapiens

<400> SEQUENCE: 132 atcttttta aaaatatat ttatttattc gagcccagcc aggccaacat ggtgaaaccc      60

<210> SEQ ID NO 133
<211> LENGTH: 60
<212> TYPE: DNA
<213> ORGANISM: Homo sapiens

<400> SEQUENCE: 133
tcctttcttt tttatttttt aagctgtttc gattcaacat taattcattt tagacttctc      60

<210> SEQ ID NO 134
<211> LENGTH: 60
<212> TYPE: DNA
<213> ORGANISM: Homo sapiens

<400> SEQUENCE: 134
ccaggatgta ctacactgaa tatctaagtc gaggcccagg ggctccagga ggccacgcac      60

<210> SEQ ID NO 135
<211> LENGTH: 60
<212> TYPE: DNA
<213> ORGANISM: Homo sapiens

<400> SEQUENCE: 135
tcccgatcac agctgaagat tggaaaggtc gaggttgcag taagctgatc atgccactac      60

<210> SEQ ID NO 136
<211> LENGTH: 60
<212> TYPE: DNA
<213> ORGANISM: Homo sapiens

<400> SEQUENCE: 136
agaagcaatt gagaaaaacc tcaggtgttc gactactatg ttgttgattt ctatcaaagc      60

```
<210> SEQ ID NO 137
<211> LENGTH: 60
<212> TYPE: DNA
<213> ORGANISM: Homo sapiens

<400> SEQUENCE: 137
tgttcaatca aggaaggga taacactatc gaggttgcag taagctgatc atgccactac      60

<210> SEQ ID NO 138
<211> LENGTH: 60
<212> TYPE: DNA
<213> ORGANISM: Homo sapiens

<400> SEQUENCE: 138
atggacagta ggcaggatga ataagtgctc gagtctcacc aggtcggtcc tgagccacac      60

<210> SEQ ID NO 139
<211> LENGTH: 60
<212> TYPE: DNA
<213> ORGANISM: Homo sapiens

<400> SEQUENCE: 139
ttgcttctgt gagagaagca atttcttttc gattgtctag tgcagaagca agtcctccga      60

<210> SEQ ID NO 140
<211> LENGTH: 60
<212> TYPE: DNA
<213> ORGANISM: Homo sapiens

<400> SEQUENCE: 140
ctccccgtat caagaaattt gccatctatc gaggcccagg ggctccagga ggccacgcac      60

<210> SEQ ID NO 141
<211> LENGTH: 60
<212> TYPE: DNA
<213> ORGANISM: Homo sapiens

<400> SEQUENCE: 141
tttagccaaa aagaaaaaaa ggttcatttc gaggaatgtt ccaagcaat tctctctgct      60

<210> SEQ ID NO 142
<211> LENGTH: 60
<212> TYPE: DNA
<213> ORGANISM: Homo sapiens

<400> SEQUENCE: 142
actgacagtt tcttgggatt ctccagactc gaaggcattg ttctggaggt ggaggaaggg      60

<210> SEQ ID NO 143
<211> LENGTH: 60
<212> TYPE: DNA
<213> ORGANISM: Homo sapiens

<400> SEQUENCE: 143
tcctgaccaa ggatcctgat ccttgatatc gaagttaagg tttcttggtt caagtggtgt      60

<210> SEQ ID NO 144
<211> LENGTH: 60
<212> TYPE: DNA
<213> ORGANISM: Homo sapiens

<400> SEQUENCE: 144
tgaggtaggc agatcacagg tcaggagatc gatccagtgt gcttttcact tcagaccttg      60
```

```
<210> SEQ ID NO 145
<211> LENGTH: 60
<212> TYPE: DNA
<213> ORGANISM: Homo sapiens

<400> SEQUENCE: 145
catggttata tacacatgtt aaaattcatc gattgaaccc tggaggagga ggttgcagtg    60

<210> SEQ ID NO 146
<211> LENGTH: 60
<212> TYPE: DNA
<213> ORGANISM: Homo sapiens

<400> SEQUENCE: 146
aggcgagctg atcacttaag tcaggagttc gaatctgtac atcaactttg gaaaaactaa    60

<210> SEQ ID NO 147
<211> LENGTH: 60
<212> TYPE: DNA
<213> ORGANISM: Homo sapiens

<400> SEQUENCE: 147
cccttgtttt ctggagattc actcttcatc gagatcagcc cgggcaacac agcaagaccc    60

<210> SEQ ID NO 148
<211> LENGTH: 60
<212> TYPE: DNA
<213> ORGANISM: Homo sapiens

<400> SEQUENCE: 148
gagtaggtaa acaaagcagt caggaagctc gatccagtgt gcttttcact tcagaccttg    60

<210> SEQ ID NO 149
<211> LENGTH: 60
<212> TYPE: DNA
<213> ORGANISM: Homo sapiens

<400> SEQUENCE: 149
ccggggagaa ggctgaatcc gagcgctttc gaacctcctg ataacttcag cattaacagc    60

<210> SEQ ID NO 150
<211> LENGTH: 60
<212> TYPE: DNA
<213> ORGANISM: Homo sapiens

<400> SEQUENCE: 150
agcagcagcg agaagcagag ggatcccgtc gatgtccatg cctcggccaa ataggttggt    60

<210> SEQ ID NO 151
<211> LENGTH: 60
<212> TYPE: DNA
<213> ORGANISM: Homo sapiens

<400> SEQUENCE: 151
agcaggatcg tttcacaacc atgtgtgctc gagatattcc gtagtacata tttatttta    60

<210> SEQ ID NO 152
<211> LENGTH: 60
<212> TYPE: DNA
<213> ORGANISM: Homo sapiens

<400> SEQUENCE: 152
cgtggttctt caagttgtag tttaattctc gaatatttaa tctctctaca ccacttaatc    60
```

<210> SEQ ID NO 153
<211> LENGTH: 60
<212> TYPE: DNA
<213> ORGANISM: Homo sapiens

<400> SEQUENCE: 153 atttttgac aattatagta gtatggattc gaccgcatca agcgcaagga cttccgctgg      60

<210> SEQ ID NO 154
<211> LENGTH: 60
<212> TYPE: DNA
<213> ORGANISM: Homo sapiens

<400> SEQUENCE: 154
gggttttatc acgttggcca ggctggtctc gagaccagcc tgggcaaccc agtgaaaccc      60

<210> SEQ ID NO 155
<211> LENGTH: 60
<212> TYPE: DNA
<213> ORGANISM: Homo sapiens

<400> SEQUENCE: 155
gcctgcaggg ggcgcccccg cgcctgcctc gaccacacat ccacatggac gcatggcagg      60

<210> SEQ ID NO 156
<211> LENGTH: 60
<212> TYPE: DNA
<213> ORGANISM: Homo sapiens

<400> SEQUENCE: 156
tgtacaatgt gctacaccac tcacaccctc gacaacttca ggtaggagtg agtgatagct      60

<210> SEQ ID NO 157
<211> LENGTH: 60
<212> TYPE: DNA
<213> ORGANISM: Homo sapiens

<400> SEQUENCE: 157
cgccgggccg acacccacat tgtcttcttc gaaaaaaaaa aaaaagaaa aaaaagaaa      60

<210> SEQ ID NO 158
<211> LENGTH: 60
<212> TYPE: DNA
<213> ORGANISM: Homo sapiens

<400> SEQUENCE: 158
tcacctctgt cacccacccg ttccactctc gatgctctct tagtgttcca attctcagct      60

<210> SEQ ID NO 159
<211> LENGTH: 60
<212> TYPE: DNA
<213> ORGANISM: Homo sapiens

<400> SEQUENCE: 159
ggtggcatcc ccatcacttc tccatgcctc gaggtcccca accccctgcc gctcatcgtg      60

<210> SEQ ID NO 160
<211> LENGTH: 60
<212> TYPE: DNA
<213> ORGANISM: Homo sapiens

<400> SEQUENCE: 160
tcacctctgt cacccacccg ttccactctc gaatagctcc tattgttatg gagtgtagca    60

<210> SEQ ID NO 161
<211> LENGTH: 60
<212> TYPE: DNA
<213> ORGANISM: Homo sapiens

<400> SEQUENCE: 161
tcacctctgt cacccacccg ttccactctc gataaagcac ttagaacatg gcatatactc    60

<210> SEQ ID NO 162
<211> LENGTH: 60
<212> TYPE: DNA
<213> ORGANISM: Homo sapiens

<400> SEQUENCE: 162
tcacctctgt cacccacccg ttccactctc gaattaggaa tcagcatttc ttccactgag    60

<210> SEQ ID NO 163
<211> LENGTH: 60
<212> TYPE: DNA
<213> ORGANISM: Homo sapiens

<400> SEQUENCE: 163
ccgcccctgt cctctcgctt cccgctggtc gatccacacc acaccagcag tggggcacaa    60

<210> SEQ ID NO 164
<211> LENGTH: 60
<212> TYPE: DNA
<213> ORGANISM: Homo sapiens

<400> SEQUENCE: 164
tcacctctgt cacccacccg ttccactctc gaaatagtaa aatttgatta tcaaaatttt    60

<210> SEQ ID NO 165
<211> LENGTH: 60
<212> TYPE: DNA
<213> ORGANISM: Homo sapiens

<400> SEQUENCE: 165
gtgccctcct cgcccctgat gggtctggtc gagaccagcc tcaacatgga gaaacaccat    60

<210> SEQ ID NO 166
<211> LENGTH: 60
<212> TYPE: DNA
<213> ORGANISM: Homo sapiens

<400> SEQUENCE: 166
tcacctctgt cacccacccg ttccactctc gaggctgcag tgaatcataa tcatagcact    60

<210> SEQ ID NO 167
<211> LENGTH: 60
<212> TYPE: DNA
<213> ORGANISM: Homo sapiens

<400> SEQUENCE: 167
actgatggca tccccgtgc gcttccggtc gatggggcca ggggctatg gggataacct    60

<210> SEQ ID NO 168
<211> LENGTH: 60
<212> TYPE: DNA
<213> ORGANISM: Homo sapiens

<400> SEQUENCE: 168
cgccgggccg acacccacat tgtcttcttc gatccctggg ctacaaggtg ggcgattctg    60

<210> SEQ ID NO 169
<211> LENGTH: 60
<212> TYPE: DNA
<213> ORGANISM: Homo sapiens

<400> SEQUENCE: 169
agtggtctca ccatggcttt cttccaattc gaggtcccca accccctgcc gctcatcgtg    60

<210> SEQ ID NO 170
<211> LENGTH: 60
<212> TYPE: DNA
<213> ORGANISM: Homo sapiens

<400> SEQUENCE: 170
aggacagaga cccctaattc caccaccatc gacccttctg ctttctctcc aggggatggc    60

<210> SEQ ID NO 171
<211> LENGTH: 60
<212> TYPE: DNA
<213> ORGANISM: Homo sapiens

<400> SEQUENCE: 171
cgccgggccg acacccacat tgtcttcttc gacatccact cttctgggca ttcccagcct    60

<210> SEQ ID NO 172
<211> LENGTH: 60
<212> TYPE: DNA
<213> ORGANISM: Homo sapiens

<400> SEQUENCE: 172
cgccgggccg acacccacat tgtcttcttc gatttgcatt tccctaatga tcggtgatgt    60

<210> SEQ ID NO 173
<211> LENGTH: 60
<212> TYPE: DNA
<213> ORGANISM: Homo sapiens

<400> SEQUENCE: 173
tccgtgaccc ccacagccgg tcgccacatc gattatccag aagcttcttt ttttttaacc    60

<210> SEQ ID NO 174
<211> LENGTH: 60
<212> TYPE: DNA
<213> ORGANISM: Homo sapiens

<400> SEQUENCE: 174
tgcggaaatg atggacacta caccttcatc gacctcgtga tctggccgcc tcggccttcc    60

<210> SEQ ID NO 175
<211> LENGTH: 60
<212> TYPE: DNA
<213> ORGANISM: Homo sapiens

<400> SEQUENCE: 175
cgccgggccg acacccacat tgtcttcttc gattttatag tatgtgaatt atatctcaac    60

<210> SEQ ID NO 176
<211> LENGTH: 60
<212> TYPE: DNA
<213> ORGANISM: Homo sapiens

```
<400> SEQUENCE: 176
cgccgggccg acacccacat tgtcttcttc gagttccttg aaagctttaa tttgcattcc    60

<210> SEQ ID NO 177
<211> LENGTH: 60
<212> TYPE: DNA
<213> ORGANISM: Homo sapiens

<400> SEQUENCE: 177
cgccgggccg acacccacat tgtcttcttc gaatctccca tctgctcttt caaccaagct    60

<210> SEQ ID NO 178
<211> LENGTH: 60
<212> TYPE: DNA
<213> ORGANISM: Homo sapiens

<400> SEQUENCE: 178
cgccgggccg acacccacat tgtcttcttc gaaccccttt aaaccactga ccttgtccct    60

<210> SEQ ID NO 179
<211> LENGTH: 60
<212> TYPE: DNA
<213> ORGANISM: Homo sapiens

<400> SEQUENCE: 179
ttatcaaccc ggcgtctgga acaatcgctc gatccacacc acaccagcag tggggcacaa    60

<210> SEQ ID NO 180
<211> LENGTH: 60
<212> TYPE: DNA
<213> ORGANISM: Homo sapiens

<400> SEQUENCE: 180
ctccacgtca ccccatgtca attccaagtc gatgccagac actcttctgg gggtggggtg    60

<210> SEQ ID NO 181
<211> LENGTH: 60
<212> TYPE: DNA
<213> ORGANISM: Homo sapiens

<400> SEQUENCE: 181
catcccatcc cccaggctga aatgtgagtc gactgtggcc gccacacagt ggtcactgct    60

<210> SEQ ID NO 182
<211> LENGTH: 60
<212> TYPE: DNA
<213> ORGANISM: Homo sapiens

<400> SEQUENCE: 182
ctcccctctc ccccgggcat gtgggccctc gaactgcaaa aaaaaaaaaa acagaactaa    60

<210> SEQ ID NO 183
<211> LENGTH: 60
<212> TYPE: DNA
<213> ORGANISM: Homo sapiens

<400> SEQUENCE: 183
ttgaacccaa gaggtcacac cactgcactc gacgcccagc aagtaggcac agttcccaat    60

<210> SEQ ID NO 184
<211> LENGTH: 60
<212> TYPE: DNA
<213> ORGANISM: Homo sapiens
```

-continued

<400> SEQUENCE: 184
agttctttct tgaattcttt cctgatactc gatccacacc acaccagcag tggggcacaa    60

<210> SEQ ID NO 185
<211> LENGTH: 60
<212> TYPE: DNA
<213> ORGANISM: Homo sapiens

<400> SEQUENCE: 185
tctttagcac ccgggcccca caattgtctc gaagcttctc ttctgaacct ggtgaagcag    60

<210> SEQ ID NO 186
<211> LENGTH: 60
<212> TYPE: DNA
<213> ORGANISM: Homo sapiens

<400> SEQUENCE: 186
tctttagcac ccgggcccca caattgtctc gatgctttca tgggacactt tgaaaataaa    60

<210> SEQ ID NO 187
<211> LENGTH: 60
<212> TYPE: DNA
<213> ORGANISM: Homo sapiens

<400> SEQUENCE: 187
tctttagcac ccgggcccca caattgtctc gaccatatgg tctttgttgt gacactcaac    60

<210> SEQ ID NO 188
<211> LENGTH: 60
<212> TYPE: DNA
<213> ORGANISM: Homo sapiens

<400> SEQUENCE: 188
agaaacagct aactgatccc taaactcctc gagttgagat ctggcggcct gaatgctggt    60

<210> SEQ ID NO 189
<211> LENGTH: 60
<212> TYPE: DNA
<213> ORGANISM: Homo sapiens

<400> SEQUENCE: 189
tctttagcac ccgggcccca caattgtctc gataaaatgt taataacgtt gtcaagatta    60

<210> SEQ ID NO 190
<211> LENGTH: 60
<212> TYPE: DNA
<213> ORGANISM: Homo sapiens

<400> SEQUENCE: 190
tctttagcac ccgggcccca caattgtctc gatctgctgc ggtgggtcca tagactggca    60

<210> SEQ ID NO 191
<211> LENGTH: 60
<212> TYPE: DNA
<213> ORGANISM: Homo sapiens

<400> SEQUENCE: 191
ggccagagcg ccggcaagag ctcggtgctc gaaaagaaaa aaaaaatact aggggggtagg    60

<210> SEQ ID NO 192
<211> LENGTH: 60
<212> TYPE: DNA

<213> ORGANISM: Homo sapiens

<400> SEQUENCE: 192
acccaggata aaacgcagtg ttgaccgatc gacccttctg ctttctctcc aggggatggc    60

<210> SEQ ID NO 193
<211> LENGTH: 60
<212> TYPE: DNA
<213> ORGANISM: Homo sapiens

<400> SEQUENCE: 193
ttcattcatt cattcattca ttcatacatc gaaaggccag taggtgtgat ctgaggaagg    60

<210> SEQ ID NO 194
<211> LENGTH: 60
<212> TYPE: DNA
<213> ORGANISM: Homo sapiens

<400> SEQUENCE: 194
caagataaag gaagagtgaa atcctgtctc gaccgggcga ctcccccggg gcggggtgg    60

<210> SEQ ID NO 195
<211> LENGTH: 60
<212> TYPE: DNA
<213> ORGANISM: Homo sapiens

<400> SEQUENCE: 195
gcggcactcg gcctctccgc agcagttctc gaggaaagac ttactaggtc ctgcagtatt    60

<210> SEQ ID NO 196
<211> LENGTH: 60
<212> TYPE: DNA
<213> ORGANISM: Homo sapiens

<400> SEQUENCE: 196
tccccagcct gctctctggt agacctcttc gagggcccac atgcccgggg gagaggggag    60

<210> SEQ ID NO 197
<211> LENGTH: 60
<212> TYPE: DNA
<213> ORGANISM: Homo sapiens

<400> SEQUENCE: 197
tctttagcac ccgggcccca caattgtctc gaatctagga tagacgcatg cagcccctgg    60

<210> SEQ ID NO 198
<211> LENGTH: 60
<212> TYPE: DNA
<213> ORGANISM: Homo sapiens

<400> SEQUENCE: 198
gcggcactcg gcctctccgc agcagttctc gaataccaag aaaaagtcac atgactaaca    60

<210> SEQ ID NO 199
<211> LENGTH: 60
<212> TYPE: DNA
<213> ORGANISM: Homo sapiens

<400> SEQUENCE: 199
cactgcacca ccctgtacat aagtcccctc gacttcagct ccagtgaaga agacactact    60

<210> SEQ ID NO 200
<211> LENGTH: 60

<212> TYPE: DNA
<213> ORGANISM: Homo sapiens

<400> SEQUENCE: 200
gcggcactcg gcctctccgc agcagttctc gagagccagg aggctcttgt ggtctaatct    60

<210> SEQ ID NO 201
<211> LENGTH: 60
<212> TYPE: DNA
<213> ORGANISM: Homo sapiens

<400> SEQUENCE: 201
tctttagcac ccgggcccca caattgtctc gagcttcagt tccggcatct acagaatgct    60

<210> SEQ ID NO 202
<211> LENGTH: 60
<212> TYPE: DNA
<213> ORGANISM: Homo sapiens

<400> SEQUENCE: 202
gcggcactcg gcctctccgc agcagttctc gattgagcct gaaaaatgag gtgaaaaaat    60

<210> SEQ ID NO 203
<211> LENGTH: 60
<212> TYPE: DNA
<213> ORGANISM: Homo sapiens

<400> SEQUENCE: 203
cagaatcgcc caccttgtag cccagggatc gacggcaagc cactcaccct cagccctatc    60

<210> SEQ ID NO 204
<211> LENGTH: 60
<212> TYPE: DNA
<213> ORGANISM: Homo sapiens

<400> SEQUENCE: 204
catcccatcc cccaggctga aatgtgagtc gagacttcct ttttcatctg tggatcattt    60

<210> SEQ ID NO 205
<211> LENGTH: 60
<212> TYPE: DNA
<213> ORGANISM: Homo sapiens

<400> SEQUENCE: 205
tccatcccca acttcaatga cttctacatc gacatagtac tgaaagtctt tgctagagta    60

<210> SEQ ID NO 206
<211> LENGTH: 60
<212> TYPE: DNA
<213> ORGANISM: Homo sapiens

<400> SEQUENCE: 206
acccaggata aaacgcagtg ttgaccgatc gattcttggg ccttccacct tcacattcta    60

<210> SEQ ID NO 207
<211> LENGTH: 60
<212> TYPE: DNA
<213> ORGANISM: Homo sapiens

<400> SEQUENCE: 207
agacccggac gtctccgcga ggcggccatc gaggaaggct cctctgagaa agagtctgct    60

<210> SEQ ID NO 208

```
<211> LENGTH: 60
<212> TYPE: DNA
<213> ORGANISM: Homo sapiens

<400> SEQUENCE: 208
ctccagaaag gacctttaaa cactcaggtc gatggccgcc tcgcggagac gtccgggtct      60

<210> SEQ ID NO 209
<211> LENGTH: 60
<212> TYPE: DNA
<213> ORGANISM: Homo sapiens

<400> SEQUENCE: 209
ttcctgaaaa aaaatggcta cttattagtc gatggccgcc tcgcggagac gtccgggtct      60

<210> SEQ ID NO 210
<211> LENGTH: 60
<212> TYPE: DNA
<213> ORGANISM: Homo sapiens

<400> SEQUENCE: 210
agacccggac gtctccgcga ggcggccatc gagtgtcaac atgatggcac ctaaagctgt      60

<210> SEQ ID NO 211
<211> LENGTH: 60
<212> TYPE: DNA
<213> ORGANISM: Homo sapiens

<400> SEQUENCE: 211
acccaggata aaacgcagtg ttgaccgatc gagggcgtgg acttctacac gtccatcact      60

<210> SEQ ID NO 212
<211> LENGTH: 60
<212> TYPE: DNA
<213> ORGANISM: Homo sapiens

<400> SEQUENCE: 212
cactttttat agaagagaaa gtgaagattc gatggccgcc tcgcggagac gtccgggtct      60

<210> SEQ ID NO 213
<211> LENGTH: 60
<212> TYPE: DNA
<213> ORGANISM: Homo sapiens

<400> SEQUENCE: 213
ccttggcgaa ggcgcgtcct gggttggatc gaagtgtatg atcgcatggc attttgtaca      60

<210> SEQ ID NO 214
<211> LENGTH: 60
<212> TYPE: DNA
<213> ORGANISM: Homo sapiens

<400> SEQUENCE: 214
ccttccctcg tattcagtga gattcatttc gaactcctga cctcaggtga ggtgatccac      60

<210> SEQ ID NO 215
<211> LENGTH: 60
<212> TYPE: DNA
<213> ORGANISM: Homo sapiens

<400> SEQUENCE: 215
ggtggcatcc ccatcacttc tccatgcctc gaggtcccca accccctgcc gctcatcgtg      60
```

```
<210> SEQ ID NO 216
<211> LENGTH: 60
<212> TYPE: DNA
<213> ORGANISM: Homo sapiens

<400> SEQUENCE: 216
agacccggac gtctccgcga ggcggccatc gaatgatcag tgatgttgat tttttttct       60

<210> SEQ ID NO 217
<211> LENGTH: 60
<212> TYPE: DNA
<213> ORGANISM: Homo sapiens

<400> SEQUENCE: 217
tgcggaaatg atggacacta caccttcatc gacctcgtga tctggccgcc tcggccttcc      60

<210> SEQ ID NO 218
<211> LENGTH: 60
<212> TYPE: DNA
<213> ORGANISM: Homo sapiens

<400> SEQUENCE: 218
acccaggata aaacgcagtg ttgaccgatc gattcttggg ccttccacct tcacattcta      60

<210> SEQ ID NO 219
<211> LENGTH: 60
<212> TYPE: DNA
<213> ORGANISM: Homo sapiens

<400> SEQUENCE: 219
acccaggata aaacgcagtg ttgaccgatc gacccttctg ctttctctcc aggggatggc      60

<210> SEQ ID NO 220
<211> LENGTH: 60
<212> TYPE: DNA
<213> ORGANISM: Homo sapiens

<400> SEQUENCE: 220
agacccggac gtctccgcga ggcggccatc gacatatttc ctgttccctt ggaataaaaa      60

<210> SEQ ID NO 221
<211> LENGTH: 60
<212> TYPE: DNA
<213> ORGANISM: Homo sapiens

<400> SEQUENCE: 221
actgatggca tcccccgtgc gcttccggtc gatggggcca gggggctatg gggataacct      60

<210> SEQ ID NO 222
<211> LENGTH: 60
<212> TYPE: DNA
<213> ORGANISM: Homo sapiens

<400> SEQUENCE: 222 ccaccccgc cccgggggag tcgcccggtc gagggcctgg caagaagaca gaagccgact      60

<210> SEQ ID NO 223
<211> LENGTH: 60
<212> TYPE: DNA
<213> ORGANISM: Homo sapiens

<400> SEQUENCE: 223
gaattccgac tcccgttttg aaattgtatc gaactcctga cctcgggtga cccgtatgcc      60
```

```
<210> SEQ ID NO 224
<211> LENGTH: 60
<212> TYPE: DNA
<213> ORGANISM: Homo sapiens

<400> SEQUENCE: 224
agaaacagct aactgatccc taaactcctc gagttgagat ctggcggcct gaatgctggt    60

<210> SEQ ID NO 225
<211> LENGTH: 60
<212> TYPE: DNA
<213> ORGANISM: Homo sapiens

<400> SEQUENCE: 225
cagaatcact ctgtggaacc aaagagcttc gattcttggg ccttccacct tcacattcta    60

<210> SEQ ID NO 226
<211> LENGTH: 60
<212> TYPE: DNA
<213> ORGANISM: Homo sapiens

<400> SEQUENCE: 226
agacccggac gtctccgcga ggcggccatc gattttgctg atgcaataca gttttacagg    60

<210> SEQ ID NO 227
<211> LENGTH: 60
<212> TYPE: DNA
<213> ORGANISM: Homo sapiens

<400> SEQUENCE: 227
caagataaag gaagagtgaa atcctgtctc gaccgggcga ctcccccggg gcggggtgg    60

<210> SEQ ID NO 228
<211> LENGTH: 60
<212> TYPE: DNA
<213> ORGANISM: Homo sapiens

<400> SEQUENCE: 228
agtgatggac ttgtagaagt ccacgccctc gattcttggg ccttccacct tcacattcta    60

<210> SEQ ID NO 229
<211> LENGTH: 60
<212> TYPE: DNA
<213> ORGANISM: Homo sapiens

<400> SEQUENCE: 229
cagaatcact ctgtggaacc aaagagcttc gattcttggg ccttccacct tcacattcta    60

<210> SEQ ID NO 230
<211> LENGTH: 60
<212> TYPE: DNA
<213> ORGANISM: Homo sapiens

<400> SEQUENCE: 230
ggcgggtgga tcacctgagg tcaggagctc gatctcctga cctcgtgatc cgcccgcctc    60

<210> SEQ ID NO 231
<211> LENGTH: 60
<212> TYPE: DNA
<213> ORGANISM: Homo sapiens

<400> SEQUENCE: 231
gcctgcaggg ggcgccccg cgcctgcctc gaccacacat ccacatggac gcatggcagg    60
```

<210> SEQ ID NO 232
<211> LENGTH: 60
<212> TYPE: DNA
<213> ORGANISM: Homo sapiens

<400> SEQUENCE: 232
catgatagtt aagagatcat atctagaatc gatacagttc ataatttatg aacatgtgga        60

<210> SEQ ID NO 233
<211> LENGTH: 60
<212> TYPE: DNA
<213> ORGANISM: Homo sapiens

<400> SEQUENCE: 233
agaaacagct aactgatccc taaactcctc gagagagtct taaaaaggga acaaaccaaa        60

<210> SEQ ID NO 234
<211> LENGTH: 60
<212> TYPE: DNA
<213> ORGANISM: Homo sapiens

<400> SEQUENCE: 234
accaaaccca aggtccgctg ctcgctgctc gattttgctg atgcaataca gttttacagg        60

<210> SEQ ID NO 235
<211> LENGTH: 60
<212> TYPE: DNA
<213> ORGANISM: Homo sapiens

<400> SEQUENCE: 235
agtgacctaa tcacagctca ccggagcctc gaggccttag ctcctcaagg atacacattt        60

<210> SEQ ID NO 236
<211> LENGTH: 60
<212> TYPE: DNA
<213> ORGANISM: Homo sapiens

<400> SEQUENCE: 236
aattctgttg gaagaataat ttaaaatatc gaggctccgg tgagctgtga ttaggtcact        60

<210> SEQ ID NO 237
<211> LENGTH: 60
<212> TYPE: DNA
<213> ORGANISM: Homo sapiens

<400> SEQUENCE: 237
tactctagca aagactttca gtactatgtc gatggtgatt ttaccttgtg gagcaatggc        60

<210> SEQ ID NO 238
<211> LENGTH: 60
<212> TYPE: DNA
<213> ORGANISM: Homo sapiens

<400> SEQUENCE: 238
agcaagaggc tgagcctaac tctcccttc gatggccgcc tcgcggagac gtccgggtct        60

<210> SEQ ID NO 239
<211> LENGTH: 60
<212> TYPE: DNA
<213> ORGANISM: Homo sapiens

<400> SEQUENCE: 239

```
ccttggcgaa ggcgcgtcct gggttggatc gatctcttga cctcacgatc cacccgcctc    60
```

<210> SEQ ID NO 240
<211> LENGTH: 60
<212> TYPE: DNA
<213> ORGANISM: Homo sapiens

<400> SEQUENCE: 240

```
gcagagggaa ttgagagaag ttaagagttc gaactcctga cctcgggtga cccgtatgcc    60
```

<210> SEQ ID NO 241
<211> LENGTH: 60
<212> TYPE: DNA
<213> ORGANISM: Homo sapiens

<400> SEQUENCE: 241

```
gacacgggcg catcacgagg tcaagagatc gatctcttga cctggtgatc tacccgcctc    60
```

<210> SEQ ID NO 242
<211> LENGTH: 60
<212> TYPE: DNA
<213> ORGANISM: Homo sapiens

<400> SEQUENCE: 242

```
atactgacac actattccac ccacaaagtc gataacatgt ttatagagaa atagccctct    60
```

<210> SEQ ID NO 243
<211> LENGTH: 60
<212> TYPE: DNA
<213> ORGANISM: Homo sapiens

<400> SEQUENCE: 243

```
agaaacagct aactgatccc taaactcctc gattctagat atgatctctt aactatcatg    60
```

<210> SEQ ID NO 244
<211> LENGTH: 60
<212> TYPE: DNA
<213> ORGANISM: Homo sapiens

<400> SEQUENCE: 244

```
tccacatgtt cataaattat gaactgtatc gaaatgtcta ttcatattca ttaactcaag    60
```

<210> SEQ ID NO 245
<211> LENGTH: 60
<212> TYPE: DNA
<213> ORGANISM: Homo sapiens

<400> SEQUENCE: 245

```
accaaaccca aggtccgctg ctcgctgctc gagatgggga aggaaaggtc agaagaggag    60
```

<210> SEQ ID NO 246
<211> LENGTH: 60
<212> TYPE: DNA
<213> ORGANISM: Homo sapiens

<400> SEQUENCE: 246

```
ttcctgaaaa aaaatggcta cttattagtc gacctgagtg tttaaaggtc ctttctggag    60
```

<210> SEQ ID NO 247
<211> LENGTH: 60
<212> TYPE: DNA
<213> ORGANISM: Homo sapiens

<400> SEQUENCE: 247
cactttttat agaagagaaa gtgaagattc gagcagcgag cagcggacct tgggtttggt    60

<210> SEQ ID NO 248
<211> LENGTH: 60
<212> TYPE: DNA
<213> ORGANISM: Homo sapiens

<400> SEQUENCE: 248 ccaccccgc cccggggag tcgcccggtc gaactccgga cctcgtgatc tgcccacctc    60

<210> SEQ ID NO 249
<211> LENGTH: 60
<212> TYPE: DNA
<213> ORGANISM: Homo sapiens

<400> SEQUENCE: 249
gaggtgggcg gatcctaagg tcaggagttc gatctcctga cctcgtgatc cgcccgcctc    60

<210> SEQ ID NO 250
<211> LENGTH: 60
<212> TYPE: DNA
<213> ORGANISM: Homo sapiens

<400> SEQUENCE: 250
ttaacatggt ctatgtgtcc ctgcatgatc gatggccgcc tcgcggagac gtccgggtct    60

<210> SEQ ID NO 251
<211> LENGTH: 60
<212> TYPE: DNA
<213> ORGANISM: Homo sapiens

<400> SEQUENCE: 251
cactttttat agaagagaaa gtgaagattc gacctcctga cctcggaacc acaatcactc    60

<210> SEQ ID NO 252
<211> LENGTH: 60
<212> TYPE: DNA
<213> ORGANISM: Homo sapiens

<400> SEQUENCE: 252
ttttccctgg aaatcctagt tggggtgctc gagccgccaa cgaggatttc taggagaaga    60

<210> SEQ ID NO 253
<211> LENGTH: 60
<212> TYPE: DNA
<213> ORGANISM: Homo sapiens

<400> SEQUENCE: 253
catgatagtt aagagatcat atctagaatc gactgtgcag ctatgctgtt ttatgtgtaa    60

<210> SEQ ID NO 254
<211> LENGTH: 60
<212> TYPE: DNA
<213> ORGANISM: Homo sapiens

<400> SEQUENCE: 254
tctttgttac tggaatatac gaataaaatc gatattttaa attattcttc caacagaatt    60

<210> SEQ ID NO 255
<211> LENGTH: 60
<212> TYPE: DNA
<213> ORGANISM: Homo sapiens

```
<400> SEQUENCE: 255
caaataaatt agaatgtatt ttcattgctc gagcaggtat tttggatgcg gtgccgcctg    60

<210> SEQ ID NO 256
<211> LENGTH: 60
<212> TYPE: DNA
<213> ORGANISM: Homo sapiens

<400> SEQUENCE: 256
tactgaagaa gtctttgaag agatttcttc gagcaggtat tttggatgcg gtgccgcctg    60

<210> SEQ ID NO 257
<211> LENGTH: 60
<212> TYPE: DNA
<213> ORGANISM: Homo sapiens

<400> SEQUENCE: 257
atttattgac tccctagggt ctaggagctc gagcaggtat tttggatgcg gtgccgcctg    60

<210> SEQ ID NO 258
<211> LENGTH: 60
<212> TYPE: DNA
<213> ORGANISM: Homo sapiens

<400> SEQUENCE: 258
tgttttataa tcattataat tttttctttc gagcaggtat tttggatgcg gtgccgcctg    60

<210> SEQ ID NO 259
<211> LENGTH: 60
<212> TYPE: DNA
<213> ORGANISM: Homo sapiens

<400> SEQUENCE: 259
tagaactgaa catgttaaa tgatatcgtc gagcaggtat tttggatgcg gtgccgcctg    60

<210> SEQ ID NO 260
<211> LENGTH: 60
<212> TYPE: DNA
<213> ORGANISM: Homo sapiens

<400> SEQUENCE: 260
ttataccaga tttcaggtgc ctagctgttc gagcaggtat tttggatgcg gtgccgcctg    60

<210> SEQ ID NO 261
<211> LENGTH: 60
<212> TYPE: DNA
<213> ORGANISM: Homo sapiens

<400> SEQUENCE: 261
cccacctccc accagacagt ggaagcagtc gagtgctgtg agcaaagagg ccctgggcca    60

<210> SEQ ID NO 262
<211> LENGTH: 60
<212> TYPE: DNA
<213> ORGANISM: Homo sapiens

<400> SEQUENCE: 262
ttccacttat gtgatgtgtc taaagtagtc gagcaggtat tttggatgcg gtgccgcctg    60

<210> SEQ ID NO 263
<211> LENGTH: 60
<212> TYPE: DNA
<213> ORGANISM: Homo sapiens
```

<400> SEQUENCE: 263
cccacctccc accagacagt ggaagcagtc gaagcaaaac tgtggagatt gggtcggtga    60

<210> SEQ ID NO 264
<211> LENGTH: 60
<212> TYPE: DNA
<213> ORGANISM: Homo sapiens

<400> SEQUENCE: 264
tgaatggacc tcatcctacc attctttttc gagcaggtat tttggatgcg gtgccgcctg    60

<210> SEQ ID NO 265
<211> LENGTH: 60
<212> TYPE: DNA
<213> ORGANISM: Homo sapiens

<400> SEQUENCE: 265
gcctgcaggg ggcgcccccg cgcctgcctc gaccacacat ccacatggac gcatggcagg    60

<210> SEQ ID NO 266
<211> LENGTH: 60
<212> TYPE: DNA
<213> ORGANISM: Homo sapiens

<400> SEQUENCE: 266
catctcatgt ggattcagaa aaggtagtc gagcaggtat tttggatgcg gtgccgcctg    60

<210> SEQ ID NO 267
<211> LENGTH: 60
<212> TYPE: DNA
<213> ORGANISM: Homo sapiens

<400> SEQUENCE: 267
aggacagaga ccctaattc caccaccatc gacccttctg ctttctctcc aggggatggc    60

<210> SEQ ID NO 268
<211> LENGTH: 60
<212> TYPE: DNA
<213> ORGANISM: Homo sapiens

<400> SEQUENCE: 268
tgcccaccca gacctccgg cggctgcttc gagcaggtat tttggatgcg gtgccgcctg    60

<210> SEQ ID NO 269
<211> LENGTH: 60
<212> TYPE: DNA
<213> ORGANISM: Homo sapiens

<400> SEQUENCE: 269
tccatcccca acttcaatga cttctacatc gacatagtac tgaaagtctt tgctagagta    60

<210> SEQ ID NO 270
<211> LENGTH: 60
<212> TYPE: DNA
<213> ORGANISM: Homo sapiens

<400> SEQUENCE: 270
ggtggcatcc ccatcacttc tccatgcctc gaggtcccca accccctgcc gctcatcgtg    60

<210> SEQ ID NO 271
<211> LENGTH: 60
<212> TYPE: DNA

<213> ORGANISM: Homo sapiens

<400> SEQUENCE: 271
cactgcccca cctcttactg gcatctcctc gaccccgtgc caagtccccg ggtggtagag    60

<210> SEQ ID NO 272
<211> LENGTH: 60
<212> TYPE: DNA
<213> ORGANISM: Homo sapiens

<400> SEQUENCE: 272
cggccgagcc cgggcctagt atccagagtc gagcaggtat tttggatgcg gtgccgcctg    60

<210> SEQ ID NO 273
<211> LENGTH: 60
<212> TYPE: DNA
<213> ORGANISM: Homo sapiens

<400> SEQUENCE: 273
ccacctcata ggggagggct ttactcagtc gatccacacc acaccagcag tggggcacaa    60

<210> SEQ ID NO 274
<211> LENGTH: 60
<212> TYPE: DNA
<213> ORGANISM: Homo sapiens

<400> SEQUENCE: 274
gagcagtacc tagcaaataa ttaggtgttc gagcaggtat tttggatgcg gtgccgcctg    60

<210> SEQ ID NO 275
<211> LENGTH: 60
<212> TYPE: DNA
<213> ORGANISM: Homo sapiens

<400> SEQUENCE: 275
caggcggcac cgcatccaaa atacctgctc gagtagaggt gtctaatatg atgcacctat    60

<210> SEQ ID NO 276
<211> LENGTH: 60
<212> TYPE: DNA
<213> ORGANISM: Homo sapiens

<400> SEQUENCE: 276
agtggtctca ccatggcttt cttccaattc gaggtcccca accccctgcc gctcatcgtg    60

<210> SEQ ID NO 277
<211> LENGTH: 60
<212> TYPE: DNA
<213> ORGANISM: Homo sapiens

<400> SEQUENCE: 277
tccgtgaccc ccacagccgg tcgccacatc gattatccag aagcttcttt tttttttaacc    60

<210> SEQ ID NO 278
<211> LENGTH: 60
<212> TYPE: DNA
<213> ORGANISM: Homo sapiens

<400> SEQUENCE: 278
cctgtagctc tgatgtcaga tggcaatgtc gatccacacc acaccagcag tggggcacaa    60

<210> SEQ ID NO 279
<211> LENGTH: 60

```
<212> TYPE: DNA
<213> ORGANISM: Homo sapiens

<400> SEQUENCE: 279
ccaaaggtat tacaaactca gccttggttc gagcaggtat tttggatgcg gtgccgcctg    60

<210> SEQ ID NO 280
<211> LENGTH: 60
<212> TYPE: DNA
<213> ORGANISM: Homo sapiens

<400> SEQUENCE: 280
caggcggcac cgcatccaaa atacctgctc gagtattgtg tttgatactt tgttcttgat    60

<210> SEQ ID NO 281
<211> LENGTH: 60
<212> TYPE: DNA
<213> ORGANISM: Homo sapiens

<400> SEQUENCE: 281
caggcggcac cgcatccaaa atacctgctc gaagggattc tgacttgata caggtccaga    60

<210> SEQ ID NO 282
<211> LENGTH: 60
<212> TYPE: DNA
<213> ORGANISM: Homo sapiens

<400> SEQUENCE: 282
ctgctgaaca gaggtgcctg cagatgcgtc gagcaggtat tttggatgcg gtgccgcctg    60

<210> SEQ ID NO 283
<211> LENGTH: 60
<212> TYPE: DNA
<213> ORGANISM: Homo sapiens

<400> SEQUENCE: 283
caggcggcac cgcatccaaa atacctgctc gatggccaat gatttgatta attatgtcta    60

<210> SEQ ID NO 284
<211> LENGTH: 60
<212> TYPE: DNA
<213> ORGANISM: Homo sapiens

<400> SEQUENCE: 284
caggcggcac cgcatccaaa atacctgctc gacagtagaa tctgctgcct gtgaccatct    60

<210> SEQ ID NO 285
<211> LENGTH: 60
<212> TYPE: DNA
<213> ORGANISM: Homo sapiens

<400> SEQUENCE: 285
ataaaggtgg ggcaaagggt tgaattggtc gacggggcgg gtggacgtgg agccacagtt    60

<210> SEQ ID NO 286
<211> LENGTH: 60
<212> TYPE: DNA
<213> ORGANISM: Homo sapiens

<400> SEQUENCE: 286
caggcggcac cgcatccaaa atacctgctc gatgctataa atgttacgga aattatgtac    60

<210> SEQ ID NO 287
```

```
<211> LENGTH: 60
<212> TYPE: DNA
<213> ORGANISM: Homo sapiens

<400> SEQUENCE: 287
ggtctctggt aatggccaaa taatctaatc gaccgccctg cccctactg tggagttcta      60

<210> SEQ ID NO 288
<211> LENGTH: 60
<212> TYPE: DNA
<213> ORGANISM: Homo sapiens

<400> SEQUENCE: 288
accgcctcac ctcagctctc cagtgagatc gatcctttgc tgcctgatcg gtcttcctct      60

<210> SEQ ID NO 289
<211> LENGTH: 60
<212> TYPE: DNA
<213> ORGANISM: Homo sapiens

<400> SEQUENCE: 289
caggcggcac cgcatccaaa atacctgctc gatgtcctca aacccatata ggaagtacat      60

<210> SEQ ID NO 290
<211> LENGTH: 60
<212> TYPE: DNA
<213> ORGANISM: Homo sapiens

<400> SEQUENCE: 290
caggcggcac cgcatccaaa atacctgctc gatgcaacaa aaagagctaa ctatcctaaa      60

<210> SEQ ID NO 291
<211> LENGTH: 60
<212> TYPE: DNA
<213> ORGANISM: Homo sapiens

<400> SEQUENCE: 291
caggcggcac cgcatccaaa atacctgctc gatcaataga caaacatata tacacatgtt      60

<210> SEQ ID NO 292
<211> LENGTH: 60
<212> TYPE: DNA
<213> ORGANISM: Homo sapiens

<400> SEQUENCE: 292
gcccgaccct gagctccaga acagaccatc gacctcaaca gaggtttctg aaggggtca      60

<210> SEQ ID NO 293
<211> LENGTH: 60
<212> TYPE: DNA
<213> ORGANISM: Homo sapiens

<400> SEQUENCE: 293
ataccaagcc agaggtttct tgacttaatc gaccgccctg cccctactg tggagttcta      60

<210> SEQ ID NO 294
<211> LENGTH: 60
<212> TYPE: DNA
<213> ORGANISM: Homo sapiens

<400> SEQUENCE: 294
tacacaatga cttcattttg tcctcatatc gaccgccctg cccctactg tggagttcta      60
```

```
<210> SEQ ID NO 295
<211> LENGTH: 60
<212> TYPE: DNA
<213> ORGANISM: Homo sapiens

<400> SEQUENCE: 295
cactgcccca cctcttactg gcatctcctc gagctccaga gctttcctct gagcccatgt    60

<210> SEQ ID NO 296
<211> LENGTH: 60
<212> TYPE: DNA
<213> ORGANISM: Homo sapiens

<400> SEQUENCE: 296
tccgtgaccc ccacagccgg tcgccacatc gagtagctga gattacaggc atgtaccacc    60

<210> SEQ ID NO 297
<211> LENGTH: 60
<212> TYPE: DNA
<213> ORGANISM: Homo sapiens

<400> SEQUENCE: 297
tgcagcccac tcccacaaca gggaagactc gaactctctc tgccagcctc tctgggggtg    60

<210> SEQ ID NO 298
<211> LENGTH: 60
<212> TYPE: DNA
<213> ORGANISM: Homo sapiens

<400> SEQUENCE: 298
cactgcccca cctcttactg gcatctcctc gactgcccta ttttgtctat agattatttc    60

<210> SEQ ID NO 299
<211> LENGTH: 60
<212> TYPE: DNA
<213> ORGANISM: Homo sapiens

<400> SEQUENCE: 299
caggcggcac cgcatccaaa atacctgctc gactcaaggt tgccacaaat cttcaatttg    60

<210> SEQ ID NO 300
<211> LENGTH: 60
<212> TYPE: DNA
<213> ORGANISM: Homo sapiens

<400> SEQUENCE: 300
gcccgaccct gagctccaga acagaccatc gactgccgcg ggggtcgcgt cctctccatc    60

<210> SEQ ID NO 301
<211> LENGTH: 60
<212> TYPE: DNA
<213> ORGANISM: Homo sapiens

<400> SEQUENCE: 301
ggaactgcat ccatacttgt tacacatctc gagttgttgc cacccacccc tcctcaaacc    60

<210> SEQ ID NO 302
<211> LENGTH: 60
<212> TYPE: DNA
<213> ORGANISM: Homo sapiens

<400> SEQUENCE: 302
cactgcccca cctcttactg gcatctcctc gagcattaag tcttggatgc tgttgttcta    60
```

<210> SEQ ID NO 303
<211> LENGTH: 60
<212> TYPE: DNA
<213> ORGANISM: Homo sapiens

<400> SEQUENCE: 303
caatacaaca gaatgcagag tccagaaatc gagcaggtat tttggatgcg gtgccgcctg    60

<210> SEQ ID NO 304
<211> LENGTH: 60
<212> TYPE: DNA
<213> ORGANISM: Homo sapiens

<400> SEQUENCE: 304
agtggtacaa tcatgaatca ctacagcctc gaccacacat ccacatggac gcatggcagg    60

<210> SEQ ID NO 305
<211> LENGTH: 60
<212> TYPE: DNA
<213> ORGANISM: Homo sapiens

<400> SEQUENCE: 305
tcacctctgt cacccacccg ttccactctc gaattaggaa tcagcatttc ttccactgag    60

<210> SEQ ID NO 306
<211> LENGTH: 60
<212> TYPE: DNA
<213> ORGANISM: Homo sapiens

<400> SEQUENCE: 306
tcacctctgt cacccacccg ttccactctc gaaatagtaa aatttgatta tcaaaatttt    60

<210> SEQ ID NO 307
<211> LENGTH: 60
<212> TYPE: DNA
<213> ORGANISM: Homo sapiens

<400> SEQUENCE: 307
cctgtagctc tgatgtcaga tggcaatgtc gatccacacc acaccagcag tggggcacaa    60

<210> SEQ ID NO 308
<211> LENGTH: 60
<212> TYPE: DNA
<213> ORGANISM: Homo sapiens

<400> SEQUENCE: 308
ccacctcata ggggagggct ttactcagtc gatccacacc acaccagcag tggggcacaa    60

<210> SEQ ID NO 309
<211> LENGTH: 60
<212> TYPE: DNA
<213> ORGANISM: Homo sapiens

<400> SEQUENCE: 309
tcacctctgt cacccacccg ttccactctc gatgctctct tagtgttcca attctcagct    60

<210> SEQ ID NO 310
<211> LENGTH: 60
<212> TYPE: DNA
<213> ORGANISM: Homo sapiens

<400> SEQUENCE: 310
tcacctctgt cacccacccg ttccactctc gataaagcac ttagaacatg gcatatactc    60

```
<210> SEQ ID NO 311
<211> LENGTH: 60
<212> TYPE: DNA
<213> ORGANISM: Homo sapiens

<400> SEQUENCE: 311
agttctttct tgaattcttt cctgatactc gatccacacc acaccagcag tggggcacaa      60

<210> SEQ ID NO 312
<211> LENGTH: 60
<212> TYPE: DNA
<213> ORGANISM: Homo sapiens

<400> SEQUENCE: 312
ttatcaaccc ggcgtctgga acaatcgctc gatccacacc acaccagcag tggggcacaa      60

<210> SEQ ID NO 313
<211> LENGTH: 60
<212> TYPE: DNA
<213> ORGANISM: Homo sapiens

<400> SEQUENCE: 313
ttcattcatt cattcattca ttcatacatc gattctctat ttcatttatt tccactgtaa      60

<210> SEQ ID NO 314
<211> LENGTH: 60
<212> TYPE: DNA
<213> ORGANISM: Homo sapiens

<400> SEQUENCE: 314
ttcattcatt cattcattca ttcatacatc gaaatgtcta ttcatattca ttaactcaag      60

<210> SEQ ID NO 315
<211> LENGTH: 60
<212> TYPE: DNA
<213> ORGANISM: Homo sapiens

<400> SEQUENCE: 315
tcacctctgt cacccacccg ttccactctc gaatagctcc tattgttatg gagtgtagca      60

<210> SEQ ID NO 316
<211> LENGTH: 60
<212> TYPE: DNA
<213> ORGANISM: Homo sapiens

<400> SEQUENCE: 316
tcacctctgt cacccacccg ttccactctc gaggctgcag tgaatcataa tcatagcact      60

<210> SEQ ID NO 317
<211> LENGTH: 60
<212> TYPE: DNA
<213> ORGANISM: Homo sapiens

<400> SEQUENCE: 317
gcctgcaggg ggcgcccccg cgcctgcctc gaccacacat ccacatggac gcatggcagg      60

<210> SEQ ID NO 318
<211> LENGTH: 60
<212> TYPE: DNA
<213> ORGANISM: Homo sapiens

<400> SEQUENCE: 318
```

-continued gggtgggatg ggacagacac aagaactctc gaggttgtag acctcatggc tggcacaagt    60

<210> SEQ ID NO 319
<211> LENGTH: 60
<212> TYPE: DNA
<213> ORGANISM: Homo sapiens

<400> SEQUENCE: 319
ttcattcatt cattcattca ttcatacatc gaaaggccag taggtgtgat ctgaggaagg    60

<210> SEQ ID NO 320
<211> LENGTH: 60
<212> TYPE: DNA
<213> ORGANISM: Homo sapiens

<400> SEQUENCE: 320
agtgttggtg agatattgtc tctcagtttc gatccacacc acaccagcag tggggcacaa    60

<210> SEQ ID NO 321
<211> LENGTH: 60
<212> TYPE: DNA
<213> ORGANISM: Homo sapiens

<400> SEQUENCE: 321
ccaaccccac tccccaagta ccccactctc gagtcaggta cagcgcttga gtccattgtg    60

<210> SEQ ID NO 322
<211> LENGTH: 60
<212> TYPE: DNA
<213> ORGANISM: Homo sapiens

<400> SEQUENCE: 322
ccgcccctgt cctctcgctt cccgctggtc gatccacacc acaccagcag tggggcacaa    60

<210> SEQ ID NO 323
<211> LENGTH: 60
<212> TYPE: DNA
<213> ORGANISM: Homo sapiens

<400> SEQUENCE: 323
agagagctgg agaagagggc gagaagagtc gaaagaattg tgagtagcag ttgtgtggtt    60

<210> SEQ ID NO 324
<211> LENGTH: 60
<212> TYPE: DNA
<213> ORGANISM: Homo sapiens

<400> SEQUENCE: 324
agagagctgg agaagagggc gagaagagtc gataaaggaa aaagttcagt aaagtgtgaa    60

<210> SEQ ID NO 325
<211> LENGTH: 60
<212> TYPE: DNA
<213> ORGANISM: Homo sapiens

<400> SEQUENCE: 325
agtggtacaa tcatgaatca ctacagcctc gaccacacat ccacatggac gcatggcagg    60

<210> SEQ ID NO 326
<211> LENGTH: 60
<212> TYPE: DNA
<213> ORGANISM: Homo sapiens

<400> SEQUENCE: 326
tggcatccca taggctttat agagcaggtc gacctcctga cctcgtgatc cacctgcctc    60

<210> SEQ ID NO 327
<211> LENGTH: 60
<212> TYPE: DNA
<213> ORGANISM: Homo sapiens

<400> SEQUENCE: 327
agagagctgg agaagagggc gagaagagtc gaggtatctt ttttctccga aggctagtaa    60

<210> SEQ ID NO 328
<211> LENGTH: 60
<212> TYPE: DNA
<213> ORGANISM: Homo sapiens

<400> SEQUENCE: 328
atccacttac atgaggtacc tagaggagtc gagttgttgc caccccaccc tcctcaaacc    60

<210> SEQ ID NO 329
<211> LENGTH: 60
<212> TYPE: DNA
<213> ORGANISM: Homo sapiens

<400> SEQUENCE: 329
gttaacagta atacgatgtt aaaaggactc gagttgttgc caccccaccc tcctcaaacc    60

<210> SEQ ID NO 330
<211> LENGTH: 60
<212> TYPE: DNA
<213> ORGANISM: Homo sapiens

<400> SEQUENCE: 330
tggggaagag gagcaagtgt caggaagatc gactcattta atccccaaaa ccattccatg    60

<210> SEQ ID NO 331
<211> LENGTH: 60
<212> TYPE: DNA
<213> ORGANISM: Homo sapiens

<400> SEQUENCE: 331
ggaactgcat ccatacttgt tacacatctc gagttgttgc caccccaccc tcctcaaacc    60

<210> SEQ ID NO 332
<211> LENGTH: 60
<212> TYPE: DNA
<213> ORGANISM: Homo sapiens

<400> SEQUENCE: 332
ccacctcata ggggagggct ttactcagtc gagcatttgt gtgtgtatgt gtgaagtata    60

<210> SEQ ID NO 333
<211> LENGTH: 60
<212> TYPE: DNA
<213> ORGANISM: Homo sapiens

<400> SEQUENCE: 333
tttaaagatg aggggaggga agcaggagtc gataaaggaa aaagttcagt aaagtgtgaa    60

<210> SEQ ID NO 334
<211> LENGTH: 60
<212> TYPE: DNA
<213> ORGANISM: Homo sapiens

<400> SEQUENCE: 334
tgtaatctgt tttgctatcc aatcaagatc gaggtccccc cacccccaca tgtctctacc    60

<210> SEQ ID NO 335
<211> LENGTH: 60
<212> TYPE: DNA
<213> ORGANISM: Homo sapiens

<400> SEQUENCE: 335
gggtgggatg ggacagacac aagaactctc gaacactcag ctatcagttt tgttgagttc    60

<210> SEQ ID NO 336
<211> LENGTH: 60
<212> TYPE: DNA
<213> ORGANISM: Homo sapiens

<400> SEQUENCE: 336
agagagctgg agaagagggc gagaagagtc gactgaatat cttcactctt gagccaaagt    60

<210> SEQ ID NO 337
<211> LENGTH: 60
<212> TYPE: DNA
<213> ORGANISM: Homo sapiens

<400> SEQUENCE: 337
cactgcacca ccctgtacat aagtcccctc gacttcagct ccagtgaaga agacactact    60

<210> SEQ ID NO 338
<211> LENGTH: 60
<212> TYPE: DNA
<213> ORGANISM: Homo sapiens

<400> SEQUENCE: 338
aagcagtttt tatcatttca ttaatccttc gaggtccccc cacccccaca tgtctctacc    60

<210> SEQ ID NO 339
<211> LENGTH: 60
<212> TYPE: DNA
<213> ORGANISM: Homo sapiens

<400> SEQUENCE: 339
ctccacgtca ccccatgtca attccaagtc gatgccagac actcttctgg gggtggggtg    60

<210> SEQ ID NO 340
<211> LENGTH: 60
<212> TYPE: DNA
<213> ORGANISM: Homo sapiens

<400> SEQUENCE: 340
ggctggcgga ttacttgaag ccaggagttc gatccacacc acaccagcag tggggcacaa    60

<210> SEQ ID NO 341
<211> LENGTH: 60
<212> TYPE: DNA
<213> ORGANISM: Homo sapiens

<400> SEQUENCE: 341
taaatacaga tgaaaccaac taatagactc gagttgttgc cacccaccc tcctcaaacc    60

<210> SEQ ID NO 342
<211> LENGTH: 60
<212> TYPE: DNA
<213> ORGANISM: Homo sapiens

```
<400> SEQUENCE: 342
aagtcctaag aacactgaaa atctcagatc gagttgttgc caccccaccc tcctcaaacc      60

<210> SEQ ID NO 343
<211> LENGTH: 60
<212> TYPE: DNA
<213> ORGANISM: Homo sapiens

<400> SEQUENCE: 343
tgcggaaatg atggacacta caccttcatc gacctcgtga tctggccgcc tcggccttcc      60

<210> SEQ ID NO 344
<211> LENGTH: 60
<212> TYPE: DNA
<213> ORGANISM: Homo sapiens

<400> SEQUENCE: 344
ctcaggaaga agtggatccc tgtttctttc gagttgttgc caccccaccc tcctcaaacc      60

<210> SEQ ID NO 345
<211> LENGTH: 60
<212> TYPE: DNA
<213> ORGANISM: Homo sapiens

<400> SEQUENCE: 345
agagagctgg agaagagggc gagaagagtc gaagatgtca aaaggaaaaa tggaaatagt      60

<210> SEQ ID NO 346
<211> LENGTH: 60
<212> TYPE: DNA
<213> ORGANISM: Homo sapiens

<400> SEQUENCE: 346
tttggtttgt tcccttttta agactctctc gactcactca catctgcctc atgatggtta      60

<210> SEQ ID NO 347
<211> LENGTH: 60
<212> TYPE: DNA
<213> ORGANISM: Homo sapiens

<400> SEQUENCE: 347
tttaaagatg agggagggga agcaggagtc gaaaccagaa gacccaatat aatatctagt      60

<210> SEQ ID NO 348
<211> LENGTH: 60
<212> TYPE: DNA
<213> ORGANISM: Homo sapiens

<400> SEQUENCE: 348
tttaaagatg agggagggga agcaggagtc gaaagaattg tgagtagcag ttgtgtggtt      60

<210> SEQ ID NO 349
<211> LENGTH: 60
<212> TYPE: DNA
<213> ORGANISM: Homo sapiens

<400> SEQUENCE: 349
atctaaacac agtccatgct aaaaagcttc gagttgttgc caccccaccc tcctcaaacc      60

<210> SEQ ID NO 350
<211> LENGTH: 60
<212> TYPE: DNA
```

<213> ORGANISM: Homo sapiens

<400> SEQUENCE: 350
catgatagtt aagagatcat atctagaatc gactcactca catctgcctc atgatggtta    60

<210> SEQ ID NO 351
<211> LENGTH: 60
<212> TYPE: DNA
<213> ORGANISM: Homo sapiens

<400> SEQUENCE: 351
cttcaccaga cattttaaat aaaatctatc gaggtccccc caccccaca tgtctctacc    60

<210> SEQ ID NO 352
<211> LENGTH: 60
<212> TYPE: DNA
<213> ORGANISM: Homo sapiens

<400> SEQUENCE: 352
cactgcccca cctcttactg gcatctcctc gagacaattc attgaacctg actcatttct    60

<210> SEQ ID NO 353
<211> LENGTH: 60
<212> TYPE: DNA
<213> ORGANISM: Homo sapiens

<400> SEQUENCE: 353
ccaaatccga acctcctctg tgaagcattc gagttgttgc caccccaccc tcctcaaacc    60

<210> SEQ ID NO 354
<211> LENGTH: 60
<212> TYPE: DNA
<213> ORGANISM: Homo sapiens

<400> SEQUENCE: 354
agagagctgg agaagagggc gagaagagtc gaattgtgct ccattgttac cttttgtgt    60

<210> SEQ ID NO 355
<211> LENGTH: 60
<212> TYPE: DNA
<213> ORGANISM: Homo sapiens

<400> SEQUENCE: 355
cccacctccc accagacagt ggaagcagtc gagtgctgtg agcaaagagg ccctgggcca    60

<210> SEQ ID NO 356
<211> LENGTH: 60
<212> TYPE: DNA
<213> ORGANISM: Homo sapiens

<400> SEQUENCE: 356
cccacctccc accagacagt ggaagcagtc gaagcaaaac tgtggagatt gggtcggtga    60

<210> SEQ ID NO 357
<211> LENGTH: 60
<212> TYPE: DNA
<213> ORGANISM: Homo sapiens

<400> SEQUENCE: 357
gcctgcaggg ggcgcccccg cgcctgcctc gaccacacat ccacatggac gcatggcagg    60

<210> SEQ ID NO 358
<211> LENGTH: 60

<212> TYPE: DNA
<213> ORGANISM: Homo sapiens

<400> SEQUENCE: 358
cgccgggccg acacccacat tgtcttcttc gaaccccttt aaaccactga ccttgtccct    60

<210> SEQ ID NO 359
<211> LENGTH: 60
<212> TYPE: DNA
<213> ORGANISM: Homo sapiens

<400> SEQUENCE: 359
cgccgggccg acacccacat tgtcttcttc gagttccttg gaagctttaa tttgcattcc    60

<210> SEQ ID NO 360
<211> LENGTH: 60
<212> TYPE: DNA
<213> ORGANISM: Homo sapiens

<400> SEQUENCE: 360
agacccggac gtctccgcga ggcggccatc gattttgctg atgcaataca gttttacagg    60

<210> SEQ ID NO 361
<211> LENGTH: 60
<212> TYPE: DNA
<213> ORGANISM: Homo sapiens

<400> SEQUENCE: 361
cgccgggccg acacccacat tgtcttcttc gaatctccca tctgctcttt caaccaagct    60

<210> SEQ ID NO 362
<211> LENGTH: 60
<212> TYPE: DNA
<213> ORGANISM: Homo sapiens

<400> SEQUENCE: 362
cgccgggccg acacccacat tgtcttcttc gacatccact cttctgggca ttcccagcct    60

<210> SEQ ID NO 363
<211> LENGTH: 60
<212> TYPE: DNA
<213> ORGANISM: Homo sapiens

<400> SEQUENCE: 363
actgatggca tcccccgtgc gcttccggtc gatggggcca gggggctatg gggataacct    60

<210> SEQ ID NO 364
<211> LENGTH: 60
<212> TYPE: DNA
<213> ORGANISM: Homo sapiens

<400> SEQUENCE: 364
cgccgggccg acacccacat tgtcttcttc gattttatag tatgtgaatt atatctcaac    60

<210> SEQ ID NO 365
<211> LENGTH: 60
<212> TYPE: DNA
<213> ORGANISM: Homo sapiens

<400> SEQUENCE: 365
acagctgcat cttatgtcag aagagtgttc gactccagtg aagattattt tgtgtcagtc    60

<210> SEQ ID NO 366

<211> LENGTH: 60
<212> TYPE: DNA
<213> ORGANISM: Homo sapiens

<400> SEQUENCE: 366
cagaatcgcc caccttgtag cccagggatc gacggcaagc cactcaccct cagccctatc    60

<210> SEQ ID NO 367
<211> LENGTH: 60
<212> TYPE: DNA
<213> ORGANISM: Homo sapiens

<400> SEQUENCE: 367
caaatcccgg ctatctctta gaattgcatc gagtttatct tgagtttata tattttaatg    60

<210> SEQ ID NO 368
<211> LENGTH: 60
<212> TYPE: DNA
<213> ORGANISM: Homo sapiens

<400> SEQUENCE: 368
tccatcccca acttcaatga cttctacatc gacatagtac tgaaagtctt tgctagagta    60

<210> SEQ ID NO 369
<211> LENGTH: 60
<212> TYPE: DNA
<213> ORGANISM: Homo sapiens

<400> SEQUENCE: 369
agacccggac gtctccgcga ggcggccatc gacatatttc ctgttccctt ggaataaaaa    60

<210> SEQ ID NO 370
<211> LENGTH: 60
<212> TYPE: DNA
<213> ORGANISM: Homo sapiens

<400> SEQUENCE: 370
cgccgggccg acacccacat tgtcttcttc gatttgcatt tccctaatga tcggtgatgt    60

<210> SEQ ID NO 371
<211> LENGTH: 60
<212> TYPE: DNA
<213> ORGANISM: Homo sapiens

<400> SEQUENCE: 371
aggacagaga ccctaattc caccaccatc gacccttctg ctttctctcc aggggatggc    60

<210> SEQ ID NO 372
<211> LENGTH: 60
<212> TYPE: DNA
<213> ORGANISM: Homo sapiens

<400> SEQUENCE: 372
cgccgggccg acacccacat tgtcttcttc gatccctggg ctacaaggtg ggcgattctg    60

<210> SEQ ID NO 373
<211> LENGTH: 60
<212> TYPE: DNA
<213> ORGANISM: Homo sapiens

<400> SEQUENCE: 373
ttcctgaaaa aaaatggcta cttattagtc gatggccgcc tcgcggagac gtccgggtct    60

-continued

<210> SEQ ID NO 374
<211> LENGTH: 60
<212> TYPE: DNA
<213> ORGANISM: Homo sapiens

<400> SEQUENCE: 374
agcacaggca agatgacctt caaggtgctc gacccactg ctggccatcc ctacctgcat    60

<210> SEQ ID NO 375
<211> LENGTH: 60
<212> TYPE: DNA
<213> ORGANISM: Homo sapiens

<400> SEQUENCE: 375
cactttttat agaagagaaa gtgaagattc gatggccgcc tcgcggagac gtccgggtct    60

<210> SEQ ID NO 376
<211> LENGTH: 60
<212> TYPE: DNA
<213> ORGANISM: Homo sapiens

<400> SEQUENCE: 376
ccacgtgtcg cgggcctgag tgtgcccctc gaggctgtag tgattcatga ttgtaccact    60

<210> SEQ ID NO 377
<211> LENGTH: 60
<212> TYPE: DNA
<213> ORGANISM: Homo sapiens

<400> SEQUENCE: 377
cgccgggccg acacccacat tgtcttcttc gaaaaaaaaa aaaaagaaa aaaaagaaa     60

<210> SEQ ID NO 378
<211> LENGTH: 60
<212> TYPE: DNA
<213> ORGANISM: Homo sapiens

<400> SEQUENCE: 378
gtgcccacac tcctcagccc tccggtggtc daccgcctgg gctcaaccaa tcctcccatc    60

<210> SEQ ID NO 379
<211> LENGTH: 60
<212> TYPE: DNA
<213> ORGANISM: Homo sapiens

<400> SEQUENCE: 379
gtgccctcct cgcccctgat gggtctggtc gagaccagcc tcaacatgga gaaacaccat    60

<210> SEQ ID NO 380
<211> LENGTH: 60
<212> TYPE: DNA
<213> ORGANISM: Homo sapiens

<400> SEQUENCE: 380
ataggcaccg aatagataaa tagatagatc gatagataat agatagaaat atgcagaaag    60

<210> SEQ ID NO 381
<211> LENGTH: 60
<212> TYPE: DNA
<213> ORGANISM: Homo sapiens

<400> SEQUENCE: 381
gccagagtgg aaatggaatt gggagaaatc gaagagtttt aatatctgct gtaaaccttg    60

<210> SEQ ID NO 382
<211> LENGTH: 60
<212> TYPE: DNA
<213> ORGANISM: Homo sapiens

<400> SEQUENCE: 382
ataggcaccg aatagataaa tagatagatc gaagattctg acaataacta agagcagagg    60

<210> SEQ ID NO 383
<211> LENGTH: 60
<212> TYPE: DNA
<213> ORGANISM: Homo sapiens

<400> SEQUENCE: 383
gccagagtgg aaatggaatt gggagaaatc gaaatgagtc aaggaaactt acaagctttt    60

<210> SEQ ID NO 384
<211> LENGTH: 60
<212> TYPE: DNA
<213> ORGANISM: Homo sapiens

<400> SEQUENCE: 384
gccagagtgg aaatggaatt gggagaaatc gattcggacc actgcatgag aagagaggca    60

<210> SEQ ID NO 385
<211> LENGTH: 60
<212> TYPE: DNA
<213> ORGANISM: Homo sapiens

<400> SEQUENCE: 385
atcttgggta actagggagt ggagttgttc gacttcgcca gctgaagtga tcctcccact    60

<210> SEQ ID NO 386
<211> LENGTH: 60
<212> TYPE: DNA
<213> ORGANISM: Homo sapiens

<400> SEQUENCE: 386
attcctagac acatacaacc tgccaagatc gaagagtttt aatatctgct gtaaaccttg    60

<210> SEQ ID NO 387
<211> LENGTH: 60
<212> TYPE: DNA
<213> ORGANISM: Homo sapiens

<400> SEQUENCE: 387
tacagatttt ggtatctgag tggagatctc gaagattctg acaataacta agagcagagg    60

<210> SEQ ID NO 388
<211> LENGTH: 60
<212> TYPE: DNA
<213> ORGANISM: Homo sapiens

<400> SEQUENCE: 388
ctgttctggt tttggatttc ttcaaggttc gatttctccc aattccattt ccactctggc    60

<210> SEQ ID NO 389
<211> LENGTH: 60
<212> TYPE: DNA
<213> ORGANISM: Homo sapiens

<400> SEQUENCE: 389
cgaggcgagt ggatcatgag tcaggagatc gatttaaaaa tagtttattt taataatgtt    60

```
<210> SEQ ID NO 390
<211> LENGTH: 60
<212> TYPE: DNA
<213> ORGANISM: Homo sapiens

<400> SEQUENCE: 390
ataaagaaaa tgcagtacac atacacaatc gagaccagcc tggtcaatac ggcaaaaccc    60

<210> SEQ ID NO 391
<211> LENGTH: 60
<212> TYPE: DNA
<213> ORGANISM: Homo sapiens

<400> SEQUENCE: 391
ggcaggtgga tcacctgagg tcaggagttc gaactcttaa cctcaggtga tccacccgca    60

<210> SEQ ID NO 392
<211> LENGTH: 60
<212> TYPE: DNA
<213> ORGANISM: Homo sapiens

<400> SEQUENCE: 392
gtagtaggga ttcattcaaa agcaccactc gaggatttac gatgcagtgc gacaaccctg    60

<210> SEQ ID NO 393
<211> LENGTH: 60
<212> TYPE: DNA
<213> ORGANISM: Homo sapiens

<400> SEQUENCE: 393
tatatttata tcccagattc aatcatcatc gagaccagcc tagctaacat ggtgaaaccc    60

<210> SEQ ID NO 394
<211> LENGTH: 60
<212> TYPE: DNA
<213> ORGANISM: Homo sapiens

<400> SEQUENCE: 394
tgataaacat cttaacagga aacagggttc gattgtcatc ctctaggact tacagtttct    60

<210> SEQ ID NO 395
<211> LENGTH: 60
<212> TYPE: DNA
<213> ORGANISM: Homo sapiens

<400> SEQUENCE: 395
ggcaggcaga tcacttgagg tcaggagttc gaacacctga cctcaggtga tctgcccacc    60

<210> SEQ ID NO 396
<211> LENGTH: 60
<212> TYPE: DNA
<213> ORGANISM: Homo sapiens

<400> SEQUENCE: 396
ggcaggtgga tcacctgagg tcaggagttc gaactcctga cctcagggga tccacccacc    60

<210> SEQ ID NO 397
<211> LENGTH: 60
<212> TYPE: DNA
<213> ORGANISM: Homo sapiens

<400> SEQUENCE: 397
```

```
ctgttctggt tttggatttc ttcaaggttc gaaagcagaa tgttttgatc atgagaaaat    60

<210> SEQ ID NO 398
<211> LENGTH: 60
<212> TYPE: DNA
<213> ORGANISM: Homo sapiens

<400> SEQUENCE: 398
aacaaatgtt taccaagtac ctactatgtc gaaaatcaga tggttatagg tgtgtggcct    60

<210> SEQ ID NO 399
<211> LENGTH: 60
<212> TYPE: DNA
<213> ORGANISM: Homo sapiens

<400> SEQUENCE: 399
cgaggcgagt ggatcatgag tcaggagatc gaaaggtatc tgtcttggaa aaaccttgat    60

<210> SEQ ID NO 400
<211> LENGTH: 60
<212> TYPE: DNA
<213> ORGANISM: Homo sapiens

<400> SEQUENCE: 400
aaagatgttg agtggagttt gcagttgttc gaaccctgtt tcctgttaag atgtttatca    60

<210> SEQ ID NO 401
<211> LENGTH: 60
<212> TYPE: DNA
<213> ORGANISM: Homo sapiens

<400> SEQUENCE: 401
cgaggcgagt ggatcatgag tcaggagatc gacaataaac tgaagagaca gcattaatgt    60

<210> SEQ ID NO 402
<211> LENGTH: 60
<212> TYPE: DNA
<213> ORGANISM: Homo sapiens

<400> SEQUENCE: 402
aaggtgggtg gatcatgagg tcaggagttc gaacccctga cctcaaatga tccacctagg    60

<210> SEQ ID NO 403
<211> LENGTH: 60
<212> TYPE: DNA
<213> ORGANISM: Homo sapiens

<400> SEQUENCE: 403
aaggaaggaa tcaaacactt ctgaaaagtc gagaccagcc tggtcaatac ggcaaaaccc    60

<210> SEQ ID NO 404
<211> LENGTH: 60
<212> TYPE: DNA
<213> ORGANISM: Homo sapiens

<400> SEQUENCE: 404
tatatttata tcccagattc aatcatcatc gagaccagta tgggcaacac ggcaagattc    60

<210> SEQ ID NO 405
<211> LENGTH: 60
<212> TYPE: DNA
<213> ORGANISM: Homo sapiens

<400> SEQUENCE: 405
```

```
aagctcaata aatcccaagc acacacactc gaccttcatc acaacagtgc tcataggttt    60

<210> SEQ ID NO 406
<211> LENGTH: 60
<212> TYPE: DNA
<213> ORGANISM: Homo sapiens

<400> SEQUENCE: 406
aagctcaata aatcccaagc acacacactc gaggacccct tccacccaaa aaaagcaagg    60

<210> SEQ ID NO 407
<211> LENGTH: 60
<212> TYPE: DNA
<213> ORGANISM: Homo sapiens

<400> SEQUENCE: 407
aagctcaata aatcccaagc acacacactc gaagtcagct gggatgaagg aagggaaaga    60

<210> SEQ ID NO 408
<211> LENGTH: 60
<212> TYPE: DNA
<213> ORGANISM: Homo sapiens

<400> SEQUENCE: 408
aagctcaata aatcccaagc acacacactc gaaagcagcc acaggcagtc agtatatgtc    60

<210> SEQ ID NO 409
<211> LENGTH: 60
<212> TYPE: DNA
<213> ORGANISM: Homo sapiens

<400> SEQUENCE: 409
aagctcaata aatcccaagc acacacactc gaataaatag tatctttgcc caataatatg    60

<210> SEQ ID NO 410
<211> LENGTH: 60
<212> TYPE: DNA
<213> ORGANISM: Homo sapiens

<400> SEQUENCE: 410
aagctcaata aatcccaagc acacacactc gaatgtaaaa tgagagacct gatgcacagt    60

<210> SEQ ID NO 411
<211> LENGTH: 60
<212> TYPE: DNA
<213> ORGANISM: Homo sapiens

<400> SEQUENCE: 411
aagctcaata aatcccaagc acacacactc gaggcaaagt gggcattttc cagcaccctg    60

<210> SEQ ID NO 412
<211> LENGTH: 60
<212> TYPE: DNA
<213> ORGANISM: Homo sapiens

<400> SEQUENCE: 412
aagctcaata aatcccaagc acacacactc gaaatggctc cagattcctg gccgagtagg    60

<210> SEQ ID NO 413
<211> LENGTH: 60
<212> TYPE: DNA
<213> ORGANISM: Homo sapiens
```

```
<400> SEQUENCE: 413
acctgaatac attgagatta ttttgcaatc gagatctgag tgtgagggtg gggggctgag    60

<210> SEQ ID NO 414
<211> LENGTH: 60
<212> TYPE: DNA
<213> ORGANISM: Homo sapiens

<400> SEQUENCE: 414
aaggttgtga aaattttatc ttacgtgatc gatgacacaa agtgtgttta aatacagggt   60

<210> SEQ ID NO 415
<211> LENGTH: 60
<212> TYPE: DNA
<213> ORGANISM: Homo sapiens

<400> SEQUENCE: 415
gtatgtcagg ggtcagaggg ggcagaggtc gaggagacta cttaggaata atacaacaaa   60

<210> SEQ ID NO 416
<211> LENGTH: 60
<212> TYPE: DNA
<213> ORGANISM: Homo sapiens

<400> SEQUENCE: 416
gtatgtcagg ggtcagaggg ggcagaggtc gaggacctag ctacccggca aacatcaaat   60

<210> SEQ ID NO 417
<211> LENGTH: 60
<212> TYPE: DNA
<213> ORGANISM: Homo sapiens

<400> SEQUENCE: 417
gtatgtcagg ggtcagaggg ggcagaggtc gactttaaca taatttatta aaattatact   60

<210> SEQ ID NO 418
<211> LENGTH: 60
<212> TYPE: DNA
<213> ORGANISM: Homo sapiens

<400> SEQUENCE: 418
gtatgtcagg ggtcagaggg ggcagaggtc gaacttttac catgagtctt ttactgaaaa   60

<210> SEQ ID NO 419
<211> LENGTH: 60
<212> TYPE: DNA
<213> ORGANISM: Homo sapiens

<400> SEQUENCE: 419
gtatgtcagg ggtcagaggg ggcagaggtc gactttgatg aacaaaaatg gatatctaac   60

<210> SEQ ID NO 420
<211> LENGTH: 60
<212> TYPE: DNA
<213> ORGANISM: Homo sapiens

<400> SEQUENCE: 420
ggtgggtgga ttggttgaag tcagcagttc gaacttttac catgagtctt ttactgaaaa   60

<210> SEQ ID NO 421
<211> LENGTH: 60
<212> TYPE: DNA
<213> ORGANISM: Homo sapiens
```

<400> SEQUENCE: 421
ggtgggtgga ttggttgaag tcagcagttc gaactgccac cttgtccctc ttctatcact    60

<210> SEQ ID NO 422
<211> LENGTH: 60
<212> TYPE: DNA
<213> ORGANISM: Homo sapiens

<400> SEQUENCE: 422
agggagagag aggagtctaa agtttatctc gaggggtgg gagggcatgt ctatttgctc    60

<210> SEQ ID NO 423
<211> LENGTH: 60
<212> TYPE: DNA
<213> ORGANISM: Homo sapiens

<400> SEQUENCE: 423
tttacaatat ccctttttaa gtgcaaagtc gatggttgat gttgtgtgtg ggtgtgtacg    60

<210> SEQ ID NO 424
<211> LENGTH: 60
<212> TYPE: DNA
<213> ORGANISM: Homo sapiens

<400> SEQUENCE: 424
tggtgaggag ggcagtgtcc aaggcaagtc gatgcaagag tcccaggaca gtcaaagaat    60

<210> SEQ ID NO 425
<211> LENGTH: 60
<212> TYPE: DNA
<213> ORGANISM: Homo sapiens

<400> SEQUENCE: 425
atgggtaagt gatgaatggg tggatagttc gatgtttaga ttttcccaac tgggttctat    60

<210> SEQ ID NO 426
<211> LENGTH: 60
<212> TYPE: DNA
<213> ORGANISM: Homo sapiens

<400> SEQUENCE: 426
atgggtaagt gatgaatggg tggatagttc gacgtgccgg aggtgcgtgg ggaactgttc    60

<210> SEQ ID NO 427
<211> LENGTH: 60
<212> TYPE: DNA
<213> ORGANISM: Homo sapiens

<400> SEQUENCE: 427
tttttttttt tttttttagat atagggtttc gaggctaatc tggctgagag aggagggtct    60

<210> SEQ ID NO 428
<211> LENGTH: 60
<212> TYPE: DNA
<213> ORGANISM: Homo sapiens

<400> SEQUENCE: 428
ccctggacag caactaagct gtcctgggtc gagactactc aaatattttt atttatttct    60

<210> SEQ ID NO 429
<211> LENGTH: 60
<212> TYPE: DNA

<213> ORGANISM: Homo sapiens

<400> SEQUENCE: 429
agacacacac tgagacagct caatctgctc gaggatcaaa ggatgttgtg tgaggcttgc    60

<210> SEQ ID NO 430
<211> LENGTH: 60
<212> TYPE: DNA
<213> ORGANISM: Homo sapiens

<400> SEQUENCE: 430
gaccaggctg gagtgcagtg gcacaatctc gagccactgc actccatcct gggcagcaga    60

<210> SEQ ID NO 431
<211> LENGTH: 60
<212> TYPE: DNA
<213> ORGANISM: Homo sapiens

<400> SEQUENCE: 431
gattccttat agtttaaaat taaattattc gagtctctta atgacctgcg agattgtac    60

<210> SEQ ID NO 432
<211> LENGTH: 60
<212> TYPE: DNA
<213> ORGANISM: Homo sapiens

<400> SEQUENCE: 432
cagtcaggtg gatcacgagg tcaggagatc gatctcctga cctcgtgatc cgcccgcctc    60

<210> SEQ ID NO 433
<211> LENGTH: 60
<212> TYPE: DNA
<213> ORGANISM: Homo sapiens

<400> SEQUENCE: 433
gaggcgggcg gatcacgagg tcaggagatc gatctcctga cctcgtgatc cgcccgcctc    60

<210> SEQ ID NO 434
<211> LENGTH: 60
<212> TYPE: DNA
<213> ORGANISM: Homo sapiens

<400> SEQUENCE: 434
gggtttcacc ttgttagcca ggatggtctc gagaccatcc tggctaacac ggtgaaaccc    60

<210> SEQ ID NO 435
<211> LENGTH: 60
<212> TYPE: DNA
<213> ORGANISM: Homo sapiens

<400> SEQUENCE: 435
acactgatta aatcttaatt attccatttc gatccctcaa ggatcaggac tgtgttgcat    60

<210> SEQ ID NO 436
<211> LENGTH: 60
<212> TYPE: DNA
<213> ORGANISM: Homo sapiens

<400> SEQUENCE: 436
acactgatta aatcttaatt attccatttc gagggaataa tctcctaaac atttctggtg    60

<210> SEQ ID NO 437
<211> LENGTH: 60

```
<212> TYPE: DNA
<213> ORGANISM: Homo sapiens

<400> SEQUENCE: 437
cttgggccct atcttatgta tggagctgtc gagtttatgt tcttacccct gtttctcttt    60

<210> SEQ ID NO 438
<211> LENGTH: 60
<212> TYPE: DNA
<213> ORGANISM: Homo sapiens

<400> SEQUENCE: 438
atgctaaatt atgtaaaatg aatatgttc gagttcatag atactcaagg gcccctcagt    60

<210> SEQ ID NO 439
<211> LENGTH: 60
<212> TYPE: DNA
<213> ORGANISM: Homo sapiens

<400> SEQUENCE: 439
caacaatttt attaattttc aactttcatc gattttataa aattatcagt aataaccttt    60

<210> SEQ ID NO 440
<211> LENGTH: 60
<212> TYPE: DNA
<213> ORGANISM: Homo sapiens

<400> SEQUENCE: 440
gaggtgggca gatcacgagg tcaggagatc gatctcctga cctcgtgatc cgcccgcctc    60

<210> SEQ ID NO 441
<211> LENGTH: 60
<212> TYPE: DNA
<213> ORGANISM: Homo sapiens

<400> SEQUENCE: 441
gaggcgggcg gatcacgagg tcaggagatc gatctcccga cctcgtgatc cgcccgcctc    60

<210> SEQ ID NO 442
<211> LENGTH: 60
<212> TYPE: DNA
<213> ORGANISM: Homo sapiens

<400> SEQUENCE: 442
tgacaccata cattttattt ctcccttctc gagattttgt tattaagctt ccgtctcgtt    60

<210> SEQ ID NO 443
<211> LENGTH: 60
<212> TYPE: DNA
<213> ORGANISM: Homo sapiens

<400> SEQUENCE: 443
agtcctttat ttctgttaca atcttaaatc gagattttgt tattaagctt ccgtctcgtt    60

<210> SEQ ID NO 444
<211> LENGTH: 60
<212> TYPE: DNA
<213> ORGANISM: Homo sapiens

<400> SEQUENCE: 444 tacctttta gagctatgtc atgtatgttc gaacagagtt taccacagct ttgcagcgcg    60

<210> SEQ ID NO 445
```

```
<210> SEQ ID NO 445
<211> LENGTH: 60
<212> TYPE: DNA
<213> ORGANISM: Homo sapiens

<400> SEQUENCE: 445
tgtattctgt atcacttaga ctcttctttc gaagaaggaa tcttaaacaa gagaagcaag    60

<210> SEQ ID NO 446
<211> LENGTH: 60
<212> TYPE: DNA
<213> ORGANISM: Homo sapiens

<400> SEQUENCE: 446
agttgttttt ccttgaaaag ggtttacctc gacggttaca atttcagtat gcacgggact    60

<210> SEQ ID NO 447
<211> LENGTH: 60
<212> TYPE: DNA
<213> ORGANISM: Homo sapiens

<400> SEQUENCE: 447
ttaacctagc agatctggtt cttctggttc gaggtattta tatcaccttg agtattattt    60

<210> SEQ ID NO 448
<211> LENGTH: 60
<212> TYPE: DNA
<213> ORGANISM: Homo sapiens

<400> SEQUENCE: 448
cctaataaag aaaaaaaaat gagtcccttc gaagcacaaa gttacaggac atggcatcca    60

<210> SEQ ID NO 449
<211> LENGTH: 60
<212> TYPE: DNA
<213> ORGANISM: Homo sapiens

<400> SEQUENCE: 449
tcctttggcc tggtaatctt ttcaatattc gaagcacaaa gttacaggac atggcatcca    60

<210> SEQ ID NO 450
<211> LENGTH: 60
<212> TYPE: DNA
<213> ORGANISM: Homo sapiens

<400> SEQUENCE: 450
ctgctccatg tctgtattcc tactttattc gaaagcatct ttgtgtcatt gtccatgctc    60

<210> SEQ ID NO 451
<211> LENGTH: 60
<212> TYPE: DNA
<213> ORGANISM: Homo sapiens

<400> SEQUENCE: 451
cctaaactaa gcttgggctt aagatccatc gaaaggatac ttttatagga accaggctag    60

<210> SEQ ID NO 452
<211> LENGTH: 60
<212> TYPE: DNA
<213> ORGANISM: Homo sapiens

<400> SEQUENCE: 452
atatatatat atcacaatgc ctaagggatc gaatagcttt ttaagaacag tgtataaaat    60
```

```
<210> SEQ ID NO 453
<211> LENGTH: 60
<212> TYPE: DNA
<213> ORGANISM: Homo sapiens

<400> SEQUENCE: 453
ctctctgatt tgccacataa agtaggcatc gattccaaat aaattagttg gtgatgtgga      60

<210> SEQ ID NO 454
<211> LENGTH: 60
<212> TYPE: DNA
<213> ORGANISM: Homo sapiens

<400> SEQUENCE: 454
acttcatgca caagttaggt atttactctc gagattataa acattttcat ttggattttg      60

<210> SEQ ID NO 455
<211> LENGTH: 60
<212> TYPE: DNA
<213> ORGANISM: Homo sapiens

<400> SEQUENCE: 455
tgttttttgg ctgcataaat gtcttctttc gaaataatca tcaaaatatt tttcattgac      60

<210> SEQ ID NO 456
<211> LENGTH: 60
<212> TYPE: DNA
<213> ORGANISM: Homo sapiens

<400> SEQUENCE: 456 caccccatc tccctttgct gactctcttc gatgaatcca ttttttttgga aatagatgat      60

<210> SEQ ID NO 457
<211> LENGTH: 60
<212> TYPE: DNA
<213> ORGANISM: Homo sapiens

<400> SEQUENCE: 457 caccccatc tccctttgct gactctcttc gaactgtggc aattttaact tttcaaattg      60

<210> SEQ ID NO 458
<211> LENGTH: 60
<212> TYPE: DNA
<213> ORGANISM: Homo sapiens

<400> SEQUENCE: 458 caccccatc tccctttgct gactctcttc gaggcatgat ttgagtcttg acagaagttc      60

<210> SEQ ID NO 459
<211> LENGTH: 60
<212> TYPE: DNA
<213> ORGANISM: Homo sapiens

<400> SEQUENCE: 459
tgccagtatt ttattgagga ttttgcatc gagattgggt tgcatcatgt tggccaggct      60

<210> SEQ ID NO 460
<211> LENGTH: 60
<212> TYPE: DNA
<213> ORGANISM: Homo sapiens

<400> SEQUENCE: 460
tgttttttgg ctgcataaat gtcttctttc gaactcatgg gcacaagcaa tcctcccacc      60
```

<210> SEQ ID NO 461
<211> LENGTH: 60
<212> TYPE: DNA
<213> ORGANISM: Homo sapiens

<400> SEQUENCE: 461
tgccagtatt ttattgagga tttttgcatc gaacagatgg agggaagagg ggatagctcc    60

<210> SEQ ID NO 462
<211> LENGTH: 60
<212> TYPE: DNA
<213> ORGANISM: Homo sapiens

<400> SEQUENCE: 462
tgccctagag atctgtggaa ctttgaactc gagtcaaaga gatatcaaga gcttctatca    60

<210> SEQ ID NO 463
<211> LENGTH: 60
<212> TYPE: DNA
<213> ORGANISM: Homo sapiens

<400> SEQUENCE: 463 caccccatc tccctttgct gactctcttc gagggcagaa tgagcctcag acatctccag    60

<210> SEQ ID NO 464
<211> LENGTH: 60
<212> TYPE: DNA
<213> ORGANISM: Homo sapiens

<400> SEQUENCE: 464
tctcctgcct gattgccctg ccagaacttc gatttgggct atagtgttgt tccagtctaa    60

<210> SEQ ID NO 465
<211> LENGTH: 60
<212> TYPE: DNA
<213> ORGANISM: Homo sapiens

<400> SEQUENCE: 465 caccccatc tccctttgct gactctcttc gatcttgaag agatctcttc ttagcaaagc    60

<210> SEQ ID NO 466
<211> LENGTH: 60
<212> TYPE: DNA
<213> ORGANISM: Homo sapiens

<400> SEQUENCE: 466 caccccatc tccctttgct gactctcttc gaaatatttt tgcttgagct cctgtctcat    60

<210> SEQ ID NO 467
<211> LENGTH: 60
<212> TYPE: DNA
<213> ORGANISM: Homo sapiens

<400> SEQUENCE: 467
taggcgcaca tgcacacagc tcgcctcttc gacccaggaa gatccaaagg aggaactgag    60

<210> SEQ ID NO 468
<211> LENGTH: 60
<212> TYPE: DNA
<213> ORGANISM: Homo sapiens

<400> SEQUENCE: 468
cccccacccc catcccagga aattggtttc gatgagagaa ggcaagagaa catgggtct    60

<210> SEQ ID NO 469
<211> LENGTH: 60
<212> TYPE: DNA
<213> ORGANISM: Homo sapiens

<400> SEQUENCE: 469
tgccagtatt ttattgagga tttttgcatc gagttcaaag ttccacagat ctctagggca    60

<210> SEQ ID NO 470
<211> LENGTH: 60
<212> TYPE: DNA
<213> ORGANISM: Homo sapiens

<400> SEQUENCE: 470
ctaaaaatta catccaggaa atgagatatc gaaagaagac atttatgcag ccaaaaaaca    60

<210> SEQ ID NO 471
<211> LENGTH: 60
<212> TYPE: DNA
<213> ORGANISM: Homo sapiens

<400> SEQUENCE: 471
taggcgcaca tgcacacagc tcgcctcttc gatgtacaag ctgcctattg atagactttc    60

<210> SEQ ID NO 472
<211> LENGTH: 60
<212> TYPE: DNA
<213> ORGANISM: Homo sapiens

<400> SEQUENCE: 472
aaagttgtgc aatcaggcaa gtcaagattc gaaagaagac atttatgcag ccaaaaaaca    60

<210> SEQ ID NO 473
<211> LENGTH: 60
<212> TYPE: DNA
<213> ORGANISM: Homo sapiens

<400> SEQUENCE: 473 caccccatc tccctttgct gactctcttc gagtggtgag cagccaaacc agggttcact    60

<210> SEQ ID NO 474
<211> LENGTH: 60
<212> TYPE: DNA
<213> ORGANISM: Homo sapiens

<400> SEQUENCE: 474
gggtcttgct atgttgccca ggctggcctc gagatcagcc tgggcaacac ggtgaaaacc    60

<210> SEQ ID NO 475
<211> LENGTH: 60
<212> TYPE: DNA
<213> ORGANISM: Homo sapiens

<400> SEQUENCE: 475
ctggtttagt cttgggagag tgtatgtgtc gagttaagcc atctgcaaat agcaagagag    60

<210> SEQ ID NO 476
<211> LENGTH: 60
<212> TYPE: DNA
<213> ORGANISM: Homo sapiens

<400> SEQUENCE: 476
agccttgcat cccagggatg aagcccactc gagatataga ttgagcccca gttttggag    60

<210> SEQ ID NO 477
<211> LENGTH: 60
<212> TYPE: DNA
<213> ORGANISM: Homo sapiens

<400> SEQUENCE: 477
atcgtgtggg ctgtgtgtgg cagactgttc gaaatcggaa gcctctctga aggtccaagg    60

<210> SEQ ID NO 478
<211> LENGTH: 60
<212> TYPE: DNA
<213> ORGANISM: Homo sapiens

<400> SEQUENCE: 478
tgccagtatt ttattgagga tttttgcatc gaattcctgg gtttatatcc caatcattgt    60

<210> SEQ ID NO 479
<211> LENGTH: 60
<212> TYPE: DNA
<213> ORGANISM: Homo sapiens

<400> SEQUENCE: 479 caccccatc tccctttgct gactctcttc gatattggtg tatattcaaa gggtacttga    60

<210> SEQ ID NO 480
<211> LENGTH: 60
<212> TYPE: DNA
<213> ORGANISM: Homo sapiens

<400> SEQUENCE: 480
tgatcactgt ttcctatgag gatacagctc gaggggcagg gggcggtcct gggccaggcg    60

<210> SEQ ID NO 481
<211> LENGTH: 60
<212> TYPE: DNA
<213> ORGANISM: Homo sapiens

<400> SEQUENCE: 481
aacttatgat tctaatcttg aatgtctgtc gatctatgag gaaatgcccc cagcctccca    60

<210> SEQ ID NO 482
<211> LENGTH: 60
<212> TYPE: DNA
<213> ORGANISM: Homo sapiens

<400> SEQUENCE: 482
cataatgcat gtgcatgaaa actaatcttc gatctatgag gaaatgcccc cagcctccca    60

<210> SEQ ID NO 483
<211> LENGTH: 60
<212> TYPE: DNA
<213> ORGANISM: Homo sapiens

<400> SEQUENCE: 483
atcagtaagc tggtcagcta cccatgaatc gatctatgag gaaatgcccc cagcctccca    60

<210> SEQ ID NO 484
<211> LENGTH: 60
<212> TYPE: DNA
<213> ORGANISM: Homo sapiens

<400> SEQUENCE: 484

```
gtgtcccaat ttctagtgca ctgtgaactc gacctcgcgg gaggggtgcc aggccgcatc    60
```

<210> SEQ ID NO 485
<211> LENGTH: 60
<212> TYPE: DNA
<213> ORGANISM: Homo sapiens

<400> SEQUENCE: 485

```
ccggggcttc tcgtttaaga attctttgtc gatctatgag gaaatgcccc cagcctccca    60
```

<210> SEQ ID NO 486
<211> LENGTH: 60
<212> TYPE: DNA
<213> ORGANISM: Homo sapiens

<400> SEQUENCE: 486

```
gtctttgaag aaggactaat gcttagtatc gagtgcagcg ccggtgggcc agcactgctg    60
```

<210> SEQ ID NO 487
<211> LENGTH: 60
<212> TYPE: DNA
<213> ORGANISM: Homo sapiens

<400> SEQUENCE: 487

```
gttcatttaa acattttatt atgtatattc gaggggccag gcttttatac ccccatctga    60
```

<210> SEQ ID NO 488
<211> LENGTH: 60
<212> TYPE: DNA
<213> ORGANISM: Homo sapiens

<400> SEQUENCE: 488

```
ttctccacag ccggccggtc cttggcagtc gaggggcagg gggcggtcct gggccaggcg    60
```

<210> SEQ ID NO 489
<211> LENGTH: 60
<212> TYPE: DNA
<213> ORGANISM: Homo sapiens

<400> SEQUENCE: 489

```
gcaacacata caacgactaa tcttcttttc gacgccgagg agctctgcag tgggggcgta    60
```

<210> SEQ ID NO 490
<211> LENGTH: 60
<212> TYPE: DNA
<213> ORGANISM: Homo sapiens

<400> SEQUENCE: 490

```
gtaggtgctg agtaagtgag cacttgcctc gaggggcagg gggcggtcct gggccaggcg    60
```

<210> SEQ ID NO 491
<211> LENGTH: 60
<212> TYPE: DNA
<213> ORGANISM: Homo sapiens

<400> SEQUENCE: 491

```
cagaaagacc ttgcaatcat acggtgcttc gacgccgagg agctctgcag tgggggcgta    60
```

<210> SEQ ID NO 492
<211> LENGTH: 60
<212> TYPE: DNA
<213> ORGANISM: Homo sapiens

```
<400> SEQUENCE: 492
tactgtgctg tgctcgtcaa agagtatgtc gatctatgag gaaatgcccc cagcctccca    60

<210> SEQ ID NO 493
<211> LENGTH: 60
<212> TYPE: DNA
<213> ORGANISM: Homo sapiens

<400> SEQUENCE: 493
cagaaattaa tcaaatgcaa gtgcaccctc gaccacccaa gggctgagga gtgcgggcac    60

<210> SEQ ID NO 494
<211> LENGTH: 60
<212> TYPE: DNA
<213> ORGANISM: Homo sapiens

<400> SEQUENCE: 494
aagggaccta gtcccctatt aagatttctc gaggggccag gcttttatac ccccatctga    60

<210> SEQ ID NO 495
<211> LENGTH: 60
<212> TYPE: DNA
<213> ORGANISM: Homo sapiens

<400> SEQUENCE: 495
cctgccgaga cacgggacgt gggattgctc gatctatgag gaaatgcccc cagcctccca    60

<210> SEQ ID NO 496
<211> LENGTH: 60
<212> TYPE: DNA
<213> ORGANISM: Homo sapiens

<400> SEQUENCE: 496
ccaaagctcg ctttcttaac cactatgctc gaggggccag gcttttatac ccccatctga    60

<210> SEQ ID NO 497
<211> LENGTH: 60
<212> TYPE: DNA
<213> ORGANISM: Homo sapiens

<400> SEQUENCE: 497
tgaattgtgt agcgtaagaa tttatatctc gaagtttgtg aactggcagg tggacgggga    60

<210> SEQ ID NO 498
<211> LENGTH: 60
<212> TYPE: DNA
<213> ORGANISM: Homo sapiens

<400> SEQUENCE: 498
acctgatctg gggaagatta ggaattgttc gaaaccaatt tcctgggatg ggggtggggg    60

<210> SEQ ID NO 499
<211> LENGTH: 60
<212> TYPE: DNA
<213> ORGANISM: Homo sapiens

<400> SEQUENCE: 499
gcaagaggat ctcttgaggc ccaggagttc gaggggccag gcttttatac ccccatctga    60

<210> SEQ ID NO 500
<211> LENGTH: 60
<212> TYPE: DNA
<213> ORGANISM: Homo sapiens
```

<400> SEQUENCE: 500
tatcaagtga tccaaaaggc tgccagtgtc gaggggcagg gggcggtcct gggccaggcg    60

<210> SEQ ID NO 501
<211> LENGTH: 60
<212> TYPE: DNA
<213> ORGANISM: Homo sapiens

<400> SEQUENCE: 501
aagggaccta gtcccctatt aagatttctc gaaaccaatt tcctgggatg ggggtggggg    60

<210> SEQ ID NO 502
<211> LENGTH: 60
<212> TYPE: DNA
<213> ORGANISM: Homo sapiens

<400> SEQUENCE: 502
tatggacttt gtagtctcat atcaaagctc gaaaccaatt tcctgggatg ggggtggggg    60

<210> SEQ ID NO 503
<211> LENGTH: 60
<212> TYPE: DNA
<213> ORGANISM: Homo sapiens

<400> SEQUENCE: 503
aaaaataatc tggctctaca cttaggattc gaaaccaatt tcctgggatg ggggtggggg    60

<210> SEQ ID NO 504
<211> LENGTH: 60
<212> TYPE: DNA
<213> ORGANISM: Homo sapiens

<400> SEQUENCE: 504
tgatcactgt ttcctatgag gatacagctc gaggggcagg gggcggtcct gggccaggcg    60

<210> SEQ ID NO 505
<211> LENGTH: 60
<212> TYPE: DNA
<213> ORGANISM: Homo sapiens

<400> SEQUENCE: 505
aacctggaga acgccaagcg cttcgccatc gaggggcagg gggcggtcct gggccaggcg    60

<210> SEQ ID NO 506
<211> LENGTH: 60
<212> TYPE: DNA
<213> ORGANISM: Homo sapiens

<400> SEQUENCE: 506
ctacctttgt ggcacttggt acagcaaatc gacgggcccc gtgaggcggg ggcgggaccc    60

<210> SEQ ID NO 507
<211> LENGTH: 60
<212> TYPE: DNA
<213> ORGANISM: Homo sapiens

<400> SEQUENCE: 507
catcaattat aactcacctt acagatcatc gacgggcccc gtgaggcggg ggcgggaccc    60

<210> SEQ ID NO 508
<211> LENGTH: 60
<212> TYPE: DNA

<213> ORGANISM: Homo sapiens

<400> SEQUENCE: 508
tgatcactgt tcctatgag atacagctc gaagattagg taaaggtggg gacgcggaga    60

<210> SEQ ID NO 509
<211> LENGTH: 60
<212> TYPE: DNA
<213> ORGANISM: Homo sapiens

<400> SEQUENCE: 509
gaaaggtaat tgcccccaat atttattttc gaaacagatc gggcggctcg ggttacacac    60

<210> SEQ ID NO 510
<211> LENGTH: 60
<212> TYPE: DNA
<213> ORGANISM: Homo sapiens

<400> SEQUENCE: 510
ttctccacag ccggccggtc cttggcagtc gaggggcagg gggcggtcct gggccaggcg    60

<210> SEQ ID NO 511
<211> LENGTH: 60
<212> TYPE: DNA
<213> ORGANISM: Homo sapiens

<400> SEQUENCE: 511
cgtgtcccaa tttctagtgc actgtgaact cgacctcgcg ggaggggtgc caggccgcat    60

<210> SEQ ID NO 512
<211> LENGTH: 60
<212> TYPE: DNA
<213> ORGANISM: Homo sapiens

<400> SEQUENCE: 512
cctctcttct aaaaggtctc aacatcactc gactggagag cccggggcct cgcgccgctt    60

<210> SEQ ID NO 513
<211> LENGTH: 60
<212> TYPE: DNA
<213> ORGANISM: Homo sapiens

<400> SEQUENCE: 513
gtttcccctt gatgctcaga gaaaggcctc gaaacagatc gggcggctcg ggttacacac    60

<210> SEQ ID NO 514
<211> LENGTH: 60
<212> TYPE: DNA
<213> ORGANISM: Homo sapiens

<400> SEQUENCE: 514
cataatgcat gtgcatgaaa actaatcttc gatctatgag gaaatgcccc cagcctccca    60

<210> SEQ ID NO 515
<211> LENGTH: 60
<212> TYPE: DNA
<213> ORGANISM: Homo sapiens

<400> SEQUENCE: 515
agatgtgtaa gtcaccaggg agtgcattcg cgacctcgcg ggaggggtgc caggccgcat    60

<210> SEQ ID NO 516
<211> LENGTH: 60

<212> TYPE: DNA
<213> ORGANISM: Homo sapiens

<400> SEQUENCE: 516
gtaatggtgc catcatagct caagctcctc gatctatgag gaaatgcccc cagcctccca     60

<210> SEQ ID NO 517
<211> LENGTH: 60
<212> TYPE: DNA
<213> ORGANISM: Homo sapiens

<400> SEQUENCE: 517
aatacaaagg atggtatatt ttgcatattc gatctatgag gaaatgcccc cagcctccca     60

<210> SEQ ID NO 518
<211> LENGTH: 60
<212> TYPE: DNA
<213> ORGANISM: Homo sapiens

<400> SEQUENCE: 518
cctctcttct aaaaggtctc aacatcactc gatggtgcgg gaggtggccg gcagggttgg     60

<210> SEQ ID NO 519
<211> LENGTH: 60
<212> TYPE: DNA
<213> ORGANISM: Homo sapiens

<400> SEQUENCE: 519
ataattcttc ctggcacata ataagtattc gaatcgggcg ggttccggcg tgggtttcag     60

<210> SEQ ID NO 520
<211> LENGTH: 60
<212> TYPE: DNA
<213> ORGANISM: Homo sapiens

<400> SEQUENCE: 520
tctaaaggga tttccactat atgtagattc gagggggcgtg tgcgcgcgtg gcggggcccg     60

<210> SEQ ID NO 521
<211> LENGTH: 60
<212> TYPE: DNA
<213> ORGANISM: Homo sapiens

<400> SEQUENCE: 521
aacttatgat tctaatcttg aatgtctgtc gatctatgag gaaatgcccc cagcctccca     60

<210> SEQ ID NO 522
<211> LENGTH: 60
<212> TYPE: DNA
<213> ORGANISM: Homo sapiens

<400> SEQUENCE: 522
gaggtgggca gatcacgggg tcagggtatc gaggcccatc actggcgggg agacgggagg     60

<210> SEQ ID NO 523
<211> LENGTH: 60
<212> TYPE: DNA
<213> ORGANISM: Homo sapiens

<400> SEQUENCE: 523
actgaatatg aaaaaaaatg taaaaattat cgacctcgcg ggagggtgc caggccgcat      60

<210> SEQ ID NO 524

```
<211> LENGTH: 60
<212> TYPE: DNA
<213> ORGANISM: Homo sapiens

<400> SEQUENCE: 524
gattttatag caaatttaca aaaatgagtc gatctatgag gaaatgcccc cagcctccca      60

<210> SEQ ID NO 525
<211> LENGTH: 60
<212> TYPE: DNA
<213> ORGANISM: Homo sapiens

<400> SEQUENCE: 525
accaagagtt ggacccccctt tttgatgttc gatggtgcgg gaggtggccg gcagggttgg      60

<210> SEQ ID NO 526
<211> LENGTH: 60
<212> TYPE: DNA
<213> ORGANISM: Homo sapiens

<400> SEQUENCE: 526
tatattgcta tctactagca aaggataatc gaagaggttc agggcggtgc ccgcggcgct      60

<210> SEQ ID NO 527
<211> LENGTH: 60
<212> TYPE: DNA
<213> ORGANISM: Homo sapiens

<400> SEQUENCE: 527
atcagtaagc tggtcagcta cccatgaatc gatctatgag gaaatgcccc cagcctccca      60

<210> SEQ ID NO 528
<211> LENGTH: 60
<212> TYPE: DNA
<213> ORGANISM: Homo sapiens

<400> SEQUENCE: 528
tgaaaacagt tcatcctgag tttcagtctc gaagattagg taaaggtggg gacgcggaga      60

<210> SEQ ID NO 529
<211> LENGTH: 60
<212> TYPE: DNA
<213> ORGANISM: Homo sapiens

<400> SEQUENCE: 529
gtgcagagcg agagcggggc agaggcggtc gaaactggga gaattcatct gaaatgatta      60

<210> SEQ ID NO 530
<211> LENGTH: 60
<212> TYPE: DNA
<213> ORGANISM: Homo sapiens

<400> SEQUENCE: 530
gaggcaggca gatcatgagg tcaggagttc gagccctgga ccccaggcca gctaatgagg      60

<210> SEQ ID NO 531
<211> LENGTH: 60
<212> TYPE: DNA
<213> ORGANISM: Homo sapiens

<400> SEQUENCE: 531
gctcactgca acctccacct cccaggttcg cgaacctcct gataacttca gcattaacag      60
```

```
<210> SEQ ID NO 532
<211> LENGTH: 60
<212> TYPE: DNA
<213> ORGANISM: Homo sapiens

<400> SEQUENCE: 532
agggtcttgc tatgttgccc aggctggcct cgagatcagc ctgggcaaca cggtgaaaac    60

<210> SEQ ID NO 533
<211> LENGTH: 60
<212> TYPE: DNA
<213> ORGANISM: Homo sapiens

<400> SEQUENCE: 533
tgtaatataa gcatagctca ctgcagcctc gaagcatttg tacgacattc tcatcttctt    60

<210> SEQ ID NO 534
<211> LENGTH: 60
<212> TYPE: DNA
<213> ORGANISM: Homo sapiens

<400> SEQUENCE: 534
acagaggagc gaggcccgat ccttactttc gaactcctga cctcgtgatc tgcccacctc    60

<210> SEQ ID NO 535
<211> LENGTH: 60
<212> TYPE: DNA
<213> ORGANISM: Homo sapiens

<400> SEQUENCE: 535
gggtttcacc atgttagcca ggatggtctc gatctcctga cctcatgatc cgcctgcctc    60

<210> SEQ ID NO 536
<211> LENGTH: 60
<212> TYPE: DNA
<213> ORGANISM: Homo sapiens

<400> SEQUENCE: 536
gcatttcacc atgttggtga ggctggtctc gaagagttca cacgtgtcca aatttggtgg    60

<210> SEQ ID NO 537
<211> LENGTH: 60
<212> TYPE: DNA
<213> ORGANISM: Homo sapiens

<400> SEQUENCE: 537
ctgggatcac aggcatgtgc caccatgctc gacaagaata gtctccttgt ttctgaacat    60

<210> SEQ ID NO 538
<211> LENGTH: 60
<212> TYPE: DNA
<213> ORGANISM: Homo sapiens

<400> SEQUENCE: 538
cgaggcgggc ggatcacgag gtcaggagat cgaccccac gttctcacca cctgtttctt     60

<210> SEQ ID NO 539
<211> LENGTH: 60
<212> TYPE: DNA
<213> ORGANISM: Homo sapiens

<400> SEQUENCE: 539
gtatttctgg ttctagatcc ttgaggaatc gacctcctgg gctcaaccta tcctcccacc    60
```

<210> SEQ ID NO 540
<211> LENGTH: 60
<212> TYPE: DNA
<213> ORGANISM: Homo sapiens

<400> SEQUENCE: 540
gggtttcact gtgttagcca ggatggtctc gacctccctg gctcaagtga tcttcccacc     60

<210> SEQ ID NO 541
<211> LENGTH: 60
<212> TYPE: DNA
<213> ORGANISM: Homo sapiens

<400> SEQUENCE: 541
tgccctagag atctgtggaa ctttgaactc gatatatgaa aatagttttt taattataaa     60

<210> SEQ ID NO 542
<211> LENGTH: 60
<212> TYPE: DNA
<213> ORGANISM: Homo sapiens

<400> SEQUENCE: 542
ggtgggggaa tcacttgagg tcagaagttc gagaccatcc tgggcaacat ggtaaaaccc     60

<210> SEQ ID NO 543
<211> LENGTH: 60
<212> TYPE: DNA
<213> ORGANISM: Homo sapiens

<400> SEQUENCE: 543
aatggcacga tcacggctca ctgcagcctc gaatgttact gacagtggac acagtaagaa     60

<210> SEQ ID NO 544
<211> LENGTH: 60
<212> TYPE: DNA
<213> ORGANISM: Homo sapiens

<400> SEQUENCE: 544
gagttttgcc atgttgccca ggctggtctc gagaacagcc tggccaacat ggtgaaaccc     60

<210> SEQ ID NO 545
<211> LENGTH: 60
<212> TYPE: DNA
<213> ORGANISM: Homo sapiens

<400> SEQUENCE: 545
aggtctcact atgttgcccg ggctggtctc gacgccgagg agctctgcag tgggggcgta     60

<210> SEQ ID NO 546
<211> LENGTH: 60
<212> TYPE: DNA
<213> ORGANISM: Homo sapiens

<400> SEQUENCE: 546
gggtttcacc atgttggcga ggctggtctc gaactcctga cctcaggtga tccgcctgcc     60

<210> SEQ ID NO 547
<211> LENGTH: 60
<212> TYPE: DNA
<213> ORGANISM: Homo sapiens

<400> SEQUENCE: 547
ggtgggtgga tcacctgagg tcaggagttc gacctaaggg tggtcataat tctgctgctg     60

```
<210> SEQ ID NO 548
<211> LENGTH: 60
<212> TYPE: DNA
<213> ORGANISM: Homo sapiens

<400> SEQUENCE: 548
gggtctcaca gccttcagag ctgagagcct aggcttcagt gagccataat cacgccacta    60

<210> SEQ ID NO 549
<211> LENGTH: 60
<212> TYPE: DNA
<213> ORGANISM: Homo sapiens

<400> SEQUENCE: 549
ctttgggagg ccaaggtgag tggattgctc gacatctcat ttgataggat taagtcaacg    60

<210> SEQ ID NO 550
<211> LENGTH: 60
<212> TYPE: DNA
<213> ORGANISM: Homo sapiens

<400> SEQUENCE: 550
aggtctcact atgttgcccg ggctggtctc gaacagcagc gtgtgcgccg acagcgcgcc    60

<210> SEQ ID NO 551
<211> LENGTH: 60
<212> TYPE: DNA
<213> ORGANISM: Homo sapiens

<400> SEQUENCE: 551
tctgtcgccc aggttggagt acagtggctc gaggatgtcc tattttgcca ccttatctaa    60

<210> SEQ ID NO 552
<211> LENGTH: 60
<212> TYPE: DNA
<213> ORGANISM: Homo sapiens

<400> SEQUENCE: 552
ttatatctcc tacctccaag cctggcagtc gattccaaag tgaagcaaaa aaaaaacttc    60

<210> SEQ ID NO 553
<211> LENGTH: 60
<212> TYPE: DNA
<213> ORGANISM: Homo sapiens

<400> SEQUENCE: 553
aaagaccctg tctctaaata aatagaacat cgagatcatg ccactgcact ccagcctggg    60

<210> SEQ ID NO 554
<211> LENGTH: 60
<212> TYPE: DNA
<213> ORGANISM: Homo sapiens

<400> SEQUENCE: 554
ggggtttttc catgttagtc aggctggtct aatggctccc ttaccttgct ggctgtgggc    60

<210> SEQ ID NO 555
<211> LENGTH: 60
<212> TYPE: DNA
<213> ORGANISM: Homo sapiens

<400> SEQUENCE: 555
```
agtggcatga tcacagctca ctgccacctc gaaaccaaac cctgtgactt caacacccaa        60

<210> SEQ ID NO 556
<211> LENGTH: 60
<212> TYPE: DNA
<213> ORGANISM: Homo sapiens

<400> SEQUENCE: 556
ccctccctca acatgcaggg attacaattc gaagatggtc tgaaggaagc aattgggaaa        60

<210> SEQ ID NO 557
<211> LENGTH: 60
<212> TYPE: DNA
<213> ORGANISM: Homo sapiens

<400> SEQUENCE: 557
agaaaatata gtattgattg ctttcaagtc gatgcgcgcc cgccggggcc cggtcggagc        60

<210> SEQ ID NO 558
<211> LENGTH: 60
<212> TYPE: DNA
<213> ORGANISM: Homo sapiens

<400> SEQUENCE: 558
tactgtagta agttctctga ggaggatatc gatttttat tgtatcctat attttttcta         60

<210> SEQ ID NO 559
<211> LENGTH: 60
<212> TYPE: DNA
<213> ORGANISM: Homo sapiens

<400> SEQUENCE: 559
tactgtagta agttctctga ggaggatatc gaagtcttgg attaaggttc attcaacaaa        60

<210> SEQ ID NO 560
<211> LENGTH: 60
<212> TYPE: DNA
<213> ORGANISM: Homo sapiens

<400> SEQUENCE: 560
cacttcccca acataagcct cggtctcttc gagggcgggc ccggcggccc cggagcaaac        60

<210> SEQ ID NO 561
<211> LENGTH: 60
<212> TYPE: DNA
<213> ORGANISM: Homo sapiens

<400> SEQUENCE: 561
gagttcagcg tgccgccggg cgtgaaagtc gaggcatatt tgagtttagg gaggtgttgc        60

<210> SEQ ID NO 562
<211> LENGTH: 60
<212> TYPE: DNA
<213> ORGANISM: Homo sapiens

<400> SEQUENCE: 562
gagttcagcg tgccgccggg cgtgaaagtc gactctgggc ccagaccaca gaaggagggg        60

<210> SEQ ID NO 563
<211> LENGTH: 60
<212> TYPE: DNA
<213> ORGANISM: Homo sapiens

<400> SEQUENCE: 563
gagttcagcg tgccgccggg cgtgaaagtc gatttgttta tggttttatc cccagtgcct    60

<210> SEQ ID NO 564
<211> LENGTH: 60
<212> TYPE: DNA
<213> ORGANISM: Homo sapiens

<400> SEQUENCE: 564
tttgttgaat gaaccttaat ccaagacttc gatttttat tgtatcctat atttttcta    60

<210> SEQ ID NO 565
<211> LENGTH: 60
<212> TYPE: DNA
<213> ORGANISM: Homo sapiens

<400> SEQUENCE: 565
ttccatagat tacttttcaa atcatccttc gaagctggcg gctgagggcc cggcgccaag    60

<210> SEQ ID NO 566
<211> LENGTH: 60
<212> TYPE: DNA
<213> ORGANISM: Homo sapiens

<400> SEQUENCE: 566
gtttgctccg gggccgccgg gcccgccctc gattttaaca ccaccatggt ttgaatgaat    60

<210> SEQ ID NO 567
<211> LENGTH: 60
<212> TYPE: DNA
<213> ORGANISM: Homo sapiens

<400> SEQUENCE: 567
tccattgtct tattccagtc taggcttgtc gagttgcagg ccgccctggt ggctagacat    60

<210> SEQ ID NO 568
<211> LENGTH: 60
<212> TYPE: DNA
<213> ORGANISM: Homo sapiens

<400> SEQUENCE: 568
aaaaaacaat tatgtaattg aaaacccatc gaggggctta ctaatgcctt ttagctccct    60

<210> SEQ ID NO 569
<211> LENGTH: 60
<212> TYPE: DNA
<213> ORGANISM: Homo sapiens

<400> SEQUENCE: 569
gacccccggg aattggctcc agcacatctc gagggcgggc ccggcggccc cggagcaaac    60

<210> SEQ ID NO 570
<211> LENGTH: 60
<212> TYPE: DNA
<213> ORGANISM: Homo sapiens

<400> SEQUENCE: 570
aaaaaacaat tatgtaattg aaaacccatc gaagctcttt ggttccacag agtgattctg    60

<210> SEQ ID NO 571
<211> LENGTH: 60
<212> TYPE: DNA
<213> ORGANISM: Homo sapiens

```
<400> SEQUENCE: 571
aggcattcgt tcttcagctc ttctataatc gattttttat tgtatcctat attttttcta    60

<210> SEQ ID NO 572
<211> LENGTH: 60
<212> TYPE: DNA
<213> ORGANISM: Homo sapiens

<400> SEQUENCE: 572
gctcttataa attatgtatt caaagaaatc gagttgcagg ccgccctggt ggctagacat    60

<210> SEQ ID NO 573
<211> LENGTH: 60
<212> TYPE: DNA
<213> ORGANISM: Homo sapiens

<400> SEQUENCE: 573
cccgcggcgg agctgctact gtttactttc gaagcttctt cctttcggcc cccaggccta    60

<210> SEQ ID NO 574
<211> LENGTH: 60
<212> TYPE: DNA
<213> ORGANISM: Homo sapiens

<400> SEQUENCE: 574
gctcttataa attatgtatt caaagaaatc gaactggcgg caaccgctgc agcgcctgct    60

<210> SEQ ID NO 575
<211> LENGTH: 60
<212> TYPE: DNA
<213> ORGANISM: Homo sapiens

<400> SEQUENCE: 575
aaaaaacaat tatgtaattg aaaacccatc gagggggctta ctaatgcctt ttagctccct    60

<210> SEQ ID NO 576
<211> LENGTH: 60
<212> TYPE: DNA
<213> ORGANISM: Homo sapiens

<400> SEQUENCE: 576
tctcctgcct accacactgt gagaaagctc gagggcgggc ccggcggccc cggagcaaac    60

<210> SEQ ID NO 577
<211> LENGTH: 60
<212> TYPE: DNA
<213> ORGANISM: Homo sapiens

<400> SEQUENCE: 577
gagttcagcg tgccgccggg cgtgaaagtc gaattctccc aggagccact gtcagaaccc    60

<210> SEQ ID NO 578
<211> LENGTH: 60
<212> TYPE: DNA
<213> ORGANISM: Homo sapiens

<400> SEQUENCE: 578
ccgcgcccgc agggcccgcc ccgcgccgtc gacaatgtta ttctttgttt ctcttaccaa    60

<210> SEQ ID NO 579
<211> LENGTH: 60
<212> TYPE: DNA
<213> ORGANISM: Homo sapiens
```

```
<400> SEQUENCE: 579
gaaggcccgg tgcgcccagc tgtgctcctc gagaacagcc aggctaacac ggagaaaccc    60

<210> SEQ ID NO 580
<211> LENGTH: 60
<212> TYPE: DNA
<213> ORGANISM: Homo sapiens

<400> SEQUENCE: 580
tccattgtct tattccagtc taggcttgtc gaactggcgg caaccgctgc agcgcctgct    60

<210> SEQ ID NO 581
<211> LENGTH: 60
<212> TYPE: DNA
<213> ORGANISM: Homo sapiens

<400> SEQUENCE: 581
ccgcgcccgc agggcccgcc ccgcgccgtc gatgtgttgg aagtcagggc ggcggtgccc    60

<210> SEQ ID NO 582
<211> LENGTH: 60
<212> TYPE: DNA
<213> ORGANISM: Homo sapiens

<400> SEQUENCE: 582
ccgcgcccgc agggcccgcc ccgcgccgtc gaggctttca agggatccag ggtggggtgc    60

<210> SEQ ID NO 583
<211> LENGTH: 60
<212> TYPE: DNA
<213> ORGANISM: Homo sapiens

<400> SEQUENCE: 583
ccgcgcccgc agggcccgcc ccgcgccgtc gacaatgtta ttctttgttt ctcttaccaa    60

<210> SEQ ID NO 584
<211> LENGTH: 60
<212> TYPE: DNA
<213> ORGANISM: Homo sapiens

<400> SEQUENCE: 584
ccgcgcccgc agggcccgcc ccgcgccgtc gatgtgttgg aagtcagggc ggcggtgccc    60

<210> SEQ ID NO 585
<211> LENGTH: 60
<212> TYPE: DNA
<213> ORGANISM: Homo sapiens

<400> SEQUENCE: 585
cacttcccca acataagcct cggtctcttc gagggcgggc ccggcggccc cggagcaaac    60

<210> SEQ ID NO 586
<211> LENGTH: 60
<212> TYPE: DNA
<213> ORGANISM: Homo sapiens

<400> SEQUENCE: 586
ccgcgcccgc agggcccgcc ccgcgccgtc gagaagcata aagcagggac aggtatggag    60

<210> SEQ ID NO 587
<211> LENGTH: 60
<212> TYPE: DNA
```

```
<213> ORGANISM: Homo sapiens

<400> SEQUENCE: 587
gaccccnggg aattggctcc agcacatctc gagggcgggc ccggcggccc cggagcaaac      60

<210> SEQ ID NO 588
<211> LENGTH: 60
<212> TYPE: DNA
<213> ORGANISM: Homo sapiens

<400> SEQUENCE: 588
gtttgctccg gggccgccgg gcccgccctc gattttaaca ccaccatggt ttgaatgaat      60

<210> SEQ ID NO 589
<211> LENGTH: 60
<212> TYPE: DNA
<213> ORGANISM: Homo sapiens

<400> SEQUENCE: 589
gtgtctcggc ccctggggc cccacccttc gatttccctg ttgccgccgc gtttgcaaga      60

<210> SEQ ID NO 590
<211> LENGTH: 60
<212> TYPE: DNA
<213> ORGANISM: Homo sapiens

<400> SEQUENCE: 590
tctcctgcct accacactgt gagaaagctc gagggcgggc ccggcggccc cggagcaaac      60

<210> SEQ ID NO 591
<211> LENGTH: 60
<212> TYPE: DNA
<213> ORGANISM: Homo sapiens

<400> SEQUENCE: 591
gagttcagcg tgccgccggg cgtgaaagtc gaggcatatt tgagtttagg gaggtgttgc      60

<210> SEQ ID NO 592
<211> LENGTH: 60
<212> TYPE: DNA
<213> ORGANISM: Homo sapiens

<400> SEQUENCE: 592
gggcaccgcc gccctgactt ccaacacatc gatctctgcc tcgcgcagcc ccagcgtgcg      60

<210> SEQ ID NO 593
<211> LENGTH: 60
<212> TYPE: DNA
<213> ORGANISM: Homo sapiens

<400> SEQUENCE: 593 ccaccccgc cccggggag tcgcccggtc gatttccaaa agctcacaca tgggtgcaca      60

<210> SEQ ID NO 594
<211> LENGTH: 60
<212> TYPE: DNA
<213> ORGANISM: Homo sapiens

<400> SEQUENCE: 594
gggcaccgcc gccctgactt ccaacacatc gaagaatggg tggggccttg cacctcatac      60

<210> SEQ ID NO 595
<211> LENGTH: 60
```

<212> TYPE: DNA
<213> ORGANISM: Homo sapiens

<400> SEQUENCE: 595
ccacccccgc cccgggggag tcgcccggtc gaccccctga catggggctg cctggagcag     60

<210> SEQ ID NO 596
<211> LENGTH: 60
<212> TYPE: DNA
<213> ORGANISM: Homo sapiens

<400> SEQUENCE: 596
gggcaccgcc gccctgactt ccaacacatc gagaagcata aagcagggac aggtatggag     60

<210> SEQ ID NO 597
<211> LENGTH: 60
<212> TYPE: DNA
<213> ORGANISM: Homo sapiens

<400> SEQUENCE: 597
gagttcagcg tgccgccggg cgtgaaagtc gactctgggc ccagaccaca gaaggagggg     60

<210> SEQ ID NO 598
<211> LENGTH: 60
<212> TYPE: DNA
<213> ORGANISM: Homo sapiens

<400> SEQUENCE: 598
aattctgttg gaagaataat ttaaaatatc gatgtggcga ccggctgtgg gggtcacgga     60

<210> SEQ ID NO 599
<211> LENGTH: 60
<212> TYPE: DNA
<213> ORGANISM: Homo sapiens

<400> SEQUENCE: 599
ttccatagat tacttttcaa atcatccttc gaagctggcg gctgagggcc cggcgccaag     60

<210> SEQ ID NO 600
<211> LENGTH: 60
<212> TYPE: DNA
<213> ORGANISM: Homo sapiens

<400> SEQUENCE: 600
gagttcagcg tgccgccggg cgtgaaagtc gatttgttta tggttttatc cccagtgcct     60

<210> SEQ ID NO 601
<211> LENGTH: 60
<212> TYPE: DNA
<213> ORGANISM: Homo sapiens

<400> SEQUENCE: 601
caccctccct tcttcctggg ccctcagatc gaccccccccc accccaccg ggctggctgc     60

<210> SEQ ID NO 602
<211> LENGTH: 60
<212> TYPE: DNA
<213> ORGANISM: Homo sapiens

<400> SEQUENCE: 602
ccacccccgc cccgggggag tcgcccggtc gagggcctgg caagaagaca gaagccgact     60

<210> SEQ ID NO 603

```
<211> LENGTH: 60
<212> TYPE: DNA
<213> ORGANISM: Homo sapiens

<400> SEQUENCE: 603
tatgagtaat aattacaatt tccccctttc gacctccagg tccccgcca cttccacggc    60

<210> SEQ ID NO 604
<211> LENGTH: 60
<212> TYPE: DNA
<213> ORGANISM: Homo sapiens

<400> SEQUENCE: 604
cagaaactgc tggttgggct catacttttc gagggccagc tccccgcacc cccaccaagc    60

<210> SEQ ID NO 605
<211> LENGTH: 60
<212> TYPE: DNA
<213> ORGANISM: Homo sapiens

<400> SEQUENCE: 605
ttcccctgta agattcattt cctgtgattc gagtcacagc tgtagtgggg tgggggtga    60

<210> SEQ ID NO 606
<211> LENGTH: 60
<212> TYPE: DNA
<213> ORGANISM: Homo sapiens

<400> SEQUENCE: 606
tctttgttac tggaatatac gaataaaatc gatgtggcga ccggctgtgg gggtcacgga    60

<210> SEQ ID NO 607
<211> LENGTH: 60
<212> TYPE: DNA
<213> ORGANISM: Homo sapiens

<400> SEQUENCE: 607
ccgcgcccgc agggcccgcc ccgcgccgtc gaggctttca agggatccag ggtggggtgc    60

<210> SEQ ID NO 608
<211> LENGTH: 60
<212> TYPE: DNA
<213> ORGANISM: Homo sapiens

<400> SEQUENCE: 608
ccgcgcccgc agggcccgcc ccgcgccgtc gacaatgtta ttctttgttt ctcttaccaa    60

<210> SEQ ID NO 609
<211> LENGTH: 60
<212> TYPE: DNA
<213> ORGANISM: Homo sapiens

<400> SEQUENCE: 609
ccgcgcccgc agggcccgcc ccgcgccgtc gatgtgttgg aagtcagggc ggcggtgccc    60

<210> SEQ ID NO 610
<211> LENGTH: 60
<212> TYPE: DNA
<213> ORGANISM: Homo sapiens

<400> SEQUENCE: 610
cacttcccca acataagcct cggtctcttc gagggcgggc ccggcggccc cggagcaaac    60
```

```
<210> SEQ ID NO 611
<211> LENGTH: 60
<212> TYPE: DNA
<213> ORGANISM: Homo sapiens

<400> SEQUENCE: 611
ccgcgcccgc agggcccgcc ccgcgccgtc gagaagcata aagcagggac aggtatggag      60

<210> SEQ ID NO 612
<211> LENGTH: 60
<212> TYPE: DNA
<213> ORGANISM: Homo sapiens

<400> SEQUENCE: 612
gaccccaggg aattggctcc agcacatctc gagggcgggc ccggcggccc cggagcaaac      60

<210> SEQ ID NO 613
<211> LENGTH: 60
<212> TYPE: DNA
<213> ORGANISM: Homo sapiens

<400> SEQUENCE: 613
gtttgctccg gggccgccgg gcccgccctc gattttaaca ccaccatggt ttgaatgaat      60

<210> SEQ ID NO 614
<211> LENGTH: 60
<212> TYPE: DNA
<213> ORGANISM: Homo sapiens

<400> SEQUENCE: 614
gtgtctcggc ccctggggc cccacccttc gatttccctg ttgccgccgc gtttgcaaga      60

<210> SEQ ID NO 615
<211> LENGTH: 60
<212> TYPE: DNA
<213> ORGANISM: Homo sapiens

<400> SEQUENCE: 615
tctcctgcct accacactgt gagaaagctc gagggcgggc ccggcggccc cggagcaaac      60

<210> SEQ ID NO 616
<211> LENGTH: 60
<212> TYPE: DNA
<213> ORGANISM: Homo sapiens

<400> SEQUENCE: 616
gagttcagcg tgccgccggg cgtgaaagtc gaggcatatt tgagtttagg gaggtgttgc      60

<210> SEQ ID NO 617
<211> LENGTH: 60
<212> TYPE: DNA
<213> ORGANISM: Homo sapiens

<400> SEQUENCE: 617
gggcaccgcc gccctgactt ccaacacatc gatctctgcc tcgcgcagcc ccagcgtgcg      60

<210> SEQ ID NO 618
<211> LENGTH: 60
<212> TYPE: DNA
<213> ORGANISM: Homo sapiens

<400> SEQUENCE: 618 ccaccccgc cccgggggag tcgcccggtc gatttccaaa agctcacaca tgggtgcaca      60
```

```
<210> SEQ ID NO 619
<211> LENGTH: 60
<212> TYPE: DNA
<213> ORGANISM: Homo sapiens

<400> SEQUENCE: 619
gggcaccgcc gccctgactt ccaacacatc gaagaatggg tggggccttg cacctcatac      60

<210> SEQ ID NO 620
<211> LENGTH: 60
<212> TYPE: DNA
<213> ORGANISM: Homo sapiens

<400> SEQUENCE: 620 ccaccccgc cccgggggag tcgcccggtc gaccccctga catggggctg cctggagcag       60

<210> SEQ ID NO 621
<211> LENGTH: 60
<212> TYPE: DNA
<213> ORGANISM: Homo sapiens

<400> SEQUENCE: 621
gggcaccgcc gccctgactt ccaacacatc gagaagcata aagcagggac aggtatggag      60

<210> SEQ ID NO 622
<211> LENGTH: 60
<212> TYPE: DNA
<213> ORGANISM: Homo sapiens

<400> SEQUENCE: 622
gagttcagcg tgccgccggg cgtgaaagtc gactctgggc ccagaccaca aaggagggg       60

<210> SEQ ID NO 623
<211> LENGTH: 60
<212> TYPE: DNA
<213> ORGANISM: Homo sapiens

<400> SEQUENCE: 623
aattctgttg gaagaataat ttaaaatatc gatgtggcga ccggctgtgg gggtcacgga      60

<210> SEQ ID NO 624
<211> LENGTH: 60
<212> TYPE: DNA
<213> ORGANISM: Homo sapiens

<400> SEQUENCE: 624
ttccatagat tacttttcaa atcatccttc gaagctggcg gctgagggcc cggcgccaag     60

<210> SEQ ID NO 625
<211> LENGTH: 60
<212> TYPE: DNA
<213> ORGANISM: Homo sapiens

<400> SEQUENCE: 625
gagttcagcg tgccgccggg cgtgaaagtc gatttgttta tggttttatc cccagtgcct     60

<210> SEQ ID NO 626
<211> LENGTH: 60
<212> TYPE: DNA
<213> ORGANISM: Homo sapiens

<400> SEQUENCE: 626
caccctccct tcttcctggg ccctcagatc gacccccccc accccaccg ggctggctgc      60
```

<210> SEQ ID NO 627
<211> LENGTH: 60
<212> TYPE: DNA
<213> ORGANISM: Homo sapiens

<400> SEQUENCE: 627
ccacccccgc cccggggag tcgcccggtc gagggcctgg caagaagaca gaagccgact    60

<210> SEQ ID NO 628
<211> LENGTH: 60
<212> TYPE: DNA
<213> ORGANISM: Homo sapiens

<400> SEQUENCE: 628
tatgagtaat aattacaatt tcccccttc gacctccagg tcccccgcca cttccacggc    60

<210> SEQ ID NO 629
<211> LENGTH: 60
<212> TYPE: DNA
<213> ORGANISM: Homo sapiens

<400> SEQUENCE: 629
cagaaactgc tggttgggct catactttc gagggccagc tccccgcacc cccaccaagc    60

<210> SEQ ID NO 630
<211> LENGTH: 60
<212> TYPE: DNA
<213> ORGANISM: Homo sapiens

<400> SEQUENCE: 630
ttcccctgta agattcattt cctgtgattc gagtcacagc tgtagtgggg tgggggtga    60

<210> SEQ ID NO 631
<211> LENGTH: 60
<212> TYPE: DNA
<213> ORGANISM: Homo sapiens

<400> SEQUENCE: 631
tctttgttac tggaatatac gaataaaatc gatgtggcga ccggctgtgg gggtcacgga    60

<210> SEQ ID NO 632
<211> LENGTH: 60
<212> TYPE: DNA
<213> ORGANISM: Homo sapiens

<400> SEQUENCE: 632
aaggcaggca gatcaggagc tcaagagatc gaaagaaaaa aaaaaaagca taaaaatcca    60

<210> SEQ ID NO 633
<211> LENGTH: 60
<212> TYPE: DNA
<213> ORGANISM: Homo sapiens

<400> SEQUENCE: 633
aaggcaggca gatcaggagc tcaagagatc gaacgctaag tgtagtttaa cacctactag    60

<210> SEQ ID NO 634
<211> LENGTH: 60
<212> TYPE: DNA
<213> ORGANISM: Homo sapiens

<400> SEQUENCE: 634

```
atagtaaaat gtgaaaatgt tacagttatc gaagttcagc gagtatattt ttactgatac    60

<210> SEQ ID NO 635
<211> LENGTH: 60
<212> TYPE: DNA
<213> ORGANISM: Homo sapiens

<400> SEQUENCE: 635
aaggcccaag aaccaggaat ctaggtattc gaaaagccct aaagttggct taataaactt    60

<210> SEQ ID NO 636
<211> LENGTH: 60
<212> TYPE: DNA
<213> ORGANISM: Homo sapiens

<400> SEQUENCE: 636
ggtgggcaga tcacttaagg ccaggaattc gaatgcaaaa ctcactaccc actggtaaga    60

<210> SEQ ID NO 637
<211> LENGTH: 60
<212> TYPE: DNA
<213> ORGANISM: Homo sapiens

<400> SEQUENCE: 637
ggtgggcaga tcacttaagg ccaggaattc gattctatca actctagaat ttttttaaat    60

<210> SEQ ID NO 638
<211> LENGTH: 60
<212> TYPE: DNA
<213> ORGANISM: Homo sapiens

<400> SEQUENCE: 638
aaggcaggca gatcaggagc tcaagagatc gaggtaaatg tgggggttct agaacccagt    60

<210> SEQ ID NO 639
<211> LENGTH: 60
<212> TYPE: DNA
<213> ORGANISM: Homo sapiens

<400> SEQUENCE: 639
ggtgggcaga tcacttaagg ccaggaattc gaaattcttt cctaatgcca agtgtgttat    60

<210> SEQ ID NO 640
<211> LENGTH: 60
<212> TYPE: DNA
<213> ORGANISM: Homo sapiens

<400> SEQUENCE: 640
ggtcccctga tttccatcct agtgcttctc gaaacatgtg ctctggagat aaagcgccaa    60

<210> SEQ ID NO 641
<211> LENGTH: 60
<212> TYPE: DNA
<213> ORGANISM: Homo sapiens

<400> SEQUENCE: 641
ggtgggcaga tcacttaagg ccaggaattc gatattcaat aaaagaccgg atgtgcaaag    60

<210> SEQ ID NO 642
<211> LENGTH: 60
<212> TYPE: DNA
<213> ORGANISM: Homo sapiens

<400> SEQUENCE: 642
```

```
ggtgggcaga tcacttaagg ccaggaattc gagaaatggt ttatccaatt catccaaaat    60
```

<210> SEQ ID NO 643
<211> LENGTH: 60
<212> TYPE: DNA
<213> ORGANISM: Homo sapiens

<400> SEQUENCE: 643

```
ggtgggcaga tcacttaagg ccaggaattc gagagactgt aaagacatgt gtctgcctct    60
```

<210> SEQ ID NO 644
<211> LENGTH: 60
<212> TYPE: DNA
<213> ORGANISM: Homo sapiens

<400> SEQUENCE: 644

```
ggtgggcaga tcacttaagg ccaggaattc gatcacttct taaaggccct acctcttaat    60
```

<210> SEQ ID NO 645
<211> LENGTH: 60
<212> TYPE: DNA
<213> ORGANISM: Homo sapiens

<400> SEQUENCE: 645

```
gttgggttga agatgaaatc ataggaagtc gagctgtaac ctctgcttgg tattctccct    60
```

<210> SEQ ID NO 646
<211> LENGTH: 60
<212> TYPE: DNA
<213> ORGANISM: Homo sapiens

<400> SEQUENCE: 646

```
ggtgggcaga tcacttaagg ccaggaattc gaaacaccag ctctcttaaa tcctgtgcct    60
```

<210> SEQ ID NO 647
<211> LENGTH: 60
<212> TYPE: DNA
<213> ORGANISM: Homo sapiens

<400> SEQUENCE: 647

```
ggtgggcaga tcacttaagg ccaggaattc gaggaaaacc tcggggcaaa atagggaaag    60
```

<210> SEQ ID NO 648
<211> LENGTH: 60
<212> TYPE: DNA
<213> ORGANISM: Homo sapiens

<400> SEQUENCE: 648

```
tgagaatgga atagatcaaa gggagggttc gagacaaggt ctcactttat cacccaacct    60
```

<210> SEQ ID NO 649
<211> LENGTH: 60
<212> TYPE: DNA
<213> ORGANISM: Homo sapiens

<400> SEQUENCE: 649

```
ggtgggcaga tcacttaagg ccaggaattc gactgtgtgc ccatgaagaa agaagatggg    60
```

<210> SEQ ID NO 650
<211> LENGTH: 60
<212> TYPE: DNA
<213> ORGANISM: Homo sapiens

```
<400> SEQUENCE: 650
agtgatagaa gagggacaag gtggcagttc gattttaaaa cacgctcttc aataaaaaga      60

<210> SEQ ID NO 651
<211> LENGTH: 60
<212> TYPE: DNA
<213> ORGANISM: Homo sapiens

<400> SEQUENCE: 651
agcaggggga tcacataagg ccaggagttc gataaaataa attagagaag atataaataa      60

<210> SEQ ID NO 652
<211> LENGTH: 60
<212> TYPE: DNA
<213> ORGANISM: Homo sapiens

<400> SEQUENCE: 652
ggtgggcaga tcacttaagg ccaggaattc gatttctctg cttctctcac agcccacatc      60

<210> SEQ ID NO 653
<211> LENGTH: 60
<212> TYPE: DNA
<213> ORGANISM: Homo sapiens

<400> SEQUENCE: 653
tctttgcaga tgttgtaaga taaggatgtc gaaaagccct aaagttggct taataaactt      60

<210> SEQ ID NO 654
<211> LENGTH: 60
<212> TYPE: DNA
<213> ORGANISM: Homo sapiens

<400> SEQUENCE: 654
ggtcccctga tttccatcct agtgcttctc gatgatataa tactctgctg actacatttt      60

<210> SEQ ID NO 655
<211> LENGTH: 60
<212> TYPE: DNA
<213> ORGANISM: Homo sapiens

<400> SEQUENCE: 655
aaggcccaag aaccaggaat ctaggtattc gaccaccttt aaagaaaaat ctcttggaac      60

<210> SEQ ID NO 656
<211> LENGTH: 60
<212> TYPE: DNA
<213> ORGANISM: Homo sapiens

<400> SEQUENCE: 656
agcaggggga tcacataagg ccaggagttc gatgaacgtt tacccaatta tttctaaaca      60

<210> SEQ ID NO 657
<211> LENGTH: 60
<212> TYPE: DNA
<213> ORGANISM: Homo sapiens

<400> SEQUENCE: 657
gatgcggact gtttcctgct ttgatttatc gacttcttat ttctattttg tgacttagga      60

<210> SEQ ID NO 658
<211> LENGTH: 60
<212> TYPE: DNA
<213> ORGANISM: Homo sapiens
```

<400> SEQUENCE: 658
gatgcggact gtttcctgct ttgatttatc gacacagtgt gtctgaagtt tggggtggta    60

<210> SEQ ID NO 659
<211> LENGTH: 60
<212> TYPE: DNA
<213> ORGANISM: Homo sapiens

<400> SEQUENCE: 659
gatgcggact gtttcctgct ttgatttatc gatatctccc tcctttcgct tcttcctttc    60

<210> SEQ ID NO 660
<211> LENGTH: 60
<212> TYPE: DNA
<213> ORGANISM: Homo sapiens

<400> SEQUENCE: 660
gatgcggact gtttcctgct ttgatttatc gagtcattaa gagactctcc gcctgggtgg    60

<210> SEQ ID NO 661
<211> LENGTH: 60
<212> TYPE: DNA
<213> ORGANISM: Homo sapiens

<400> SEQUENCE: 661
ttccacctgt aatactgtgc ctgtattctc gactcttctc gccctcttct ccagctctct    60

<210> SEQ ID NO 662
<211> LENGTH: 60
<212> TYPE: DNA
<213> ORGANISM: Homo sapiens

<400> SEQUENCE: 662
taaagtactg tgtcccacat ataagtactc gaccaagaaa ttcattctta cctcctaaga    60

<210> SEQ ID NO 663
<211> LENGTH: 60
<212> TYPE: DNA
<213> ORGANISM: Homo sapiens

<400> SEQUENCE: 663
accccaccaa tctataataa gattgatttc gacacaaggg tttgtaacaa aaaacaaaaa    60

<210> SEQ ID NO 664
<211> LENGTH: 60
<212> TYPE: DNA
<213> ORGANISM: Homo sapiens

<400> SEQUENCE: 664
agcgctttat ttgtcaggac gatagacctc gacaatgtcc tattcttcca gaaactcatt    60

<210> SEQ ID NO 665
<211> LENGTH: 60
<212> TYPE: DNA
<213> ORGANISM: Homo sapiens

<400> SEQUENCE: 665
ttattacttt attctgactg aatatcattc gaaagaaacc aaaaacacaa gtatacatca    60

<210> SEQ ID NO 666
<211> LENGTH: 60
<212> TYPE: DNA

<213> ORGANISM: Homo sapiens

<400> SEQUENCE: 666
tatcctttgg tttagaagta tttcttattc gacaaaattt taacatgtta tgcagttaca    60

<210> SEQ ID NO 667
<211> LENGTH: 60
<212> TYPE: DNA
<213> ORGANISM: Homo sapiens

<400> SEQUENCE: 667
ttcagctatt cactggtttt tcttcagatc gactcctgct tccctcccct catctttaaa    60

<210> SEQ ID NO 668
<211> LENGTH: 60
<212> TYPE: DNA
<213> ORGANISM: Homo sapiens

<400> SEQUENCE: 668
tccagtacaa taaacaatgt accaaagatc gacaaaattt taacatgtta tgcagttaca    60

<210> SEQ ID NO 669
<211> LENGTH: 60
<212> TYPE: DNA
<213> ORGANISM: Homo sapiens

<400> SEQUENCE: 669
taaactctga cattgcctat tagcattctc gaatgcatgg ctcactgtaa cctccaactc    60

<210> SEQ ID NO 670
<211> LENGTH: 60
<212> TYPE: DNA
<213> ORGANISM: Homo sapiens

<400> SEQUENCE: 670
tatcctttgg tttagaagta tttcttattc gacaactact ggcttaaaaa aggcaaaaca    60

<210> SEQ ID NO 671
<211> LENGTH: 60
<212> TYPE: DNA
<213> ORGANISM: Homo sapiens

<400> SEQUENCE: 671
tacctccttg ggaacatatt tgagagtttc gactcctgct tccctcccct catctttaaa    60

<210> SEQ ID NO 672
<211> LENGTH: 60
<212> TYPE: DNA
<213> ORGANISM: Homo sapiens

<400> SEQUENCE: 672
acacttgatt tttgctttcc aagctgactc gagacatcta agaaggtcca gccagatgtt    60

<210> SEQ ID NO 673
<211> LENGTH: 60
<212> TYPE: DNA
<213> ORGANISM: Homo sapiens

<400> SEQUENCE: 673
gcgccctatt tccaccttgt gccttctgtc gacacaccaa gatgtcacgg aggagtctgt    60

<210> SEQ ID NO 674
<211> LENGTH: 60

<212> TYPE: DNA
<213> ORGANISM: Homo sapiens

<400> SEQUENCE: 674
ccagctgaag tttcgcaggt cccctgcttc gagtaggcca atcccatttt tggcgaaaac    60

<210> SEQ ID NO 675
<211> LENGTH: 60
<212> TYPE: DNA
<213> ORGANISM: Homo sapiens

<400> SEQUENCE: 675
tacctccttg ggaacatatt tgagagtttc gactcctgct tccctcccct catctttaaa    60

<210> SEQ ID NO 676
<211> LENGTH: 60
<212> TYPE: DNA
<213> ORGANISM: Homo sapiens

<400> SEQUENCE: 676
acacttgatt tttgctttcc aagctgactc gagacatcta agaaggtcca gccagatgtt    60

<210> SEQ ID NO 677
<211> LENGTH: 60
<212> TYPE: DNA
<213> ORGANISM: Homo sapiens

<400> SEQUENCE: 677
gcgccctatt tccaccttgt gccttctgtc gacacaccaa gatgtcacgg aggagtctgt    60

<210> SEQ ID NO 678
<211> LENGTH: 60
<212> TYPE: DNA
<213> ORGANISM: Homo sapiens

<400> SEQUENCE: 678
ccagctgaag tttcgcaggt cccctgcttc gagtaggcca atcccatttt tggcgaaaac    60

<210> SEQ ID NO 679
<211> LENGTH: 60
<212> TYPE: DNA
<213> ORGANISM: Homo sapiens

<400> SEQUENCE: 679
actttggctc aagagtgaag atattcagtc gactcctgct tccctcccct catctttaaa    60

<210> SEQ ID NO 680
<211> LENGTH: 60
<212> TYPE: DNA
<213> ORGANISM: Homo sapiens

<400> SEQUENCE: 680
ttccttaggc aagtcatcca attccatgtc gacacaaggg tttgtaacaa aaaacaaaaa    60

<210> SEQ ID NO 681
<211> LENGTH: 60
<212> TYPE: DNA
<213> ORGANISM: Homo sapiens

<400> SEQUENCE: 681
tcttaggagg taagaatgaa tttcttggtc gaactcctga ccaggaggct gggagggggt    60

<210> SEQ ID NO 682

```
<211> LENGTH: 60
<212> TYPE: DNA
<213> ORGANISM: Homo sapiens

<400> SEQUENCE: 682 catcattta ataggtgcaa gagttccgtc gaacgcccat acctgtggga atcaagcaat      60

<210> SEQ ID NO 683
<211> LENGTH: 60
<212> TYPE: DNA
<213> ORGANISM: Homo sapiens

<400> SEQUENCE: 683
aaaaacaaaa aagccaattc tgtacccctc gaaccagccc tggctctgtc cccagacctt      60

<210> SEQ ID NO 684
<211> LENGTH: 60
<212> TYPE: DNA
<213> ORGANISM: Homo sapiens

<400> SEQUENCE: 684
gcgccctatt tccaccttgt gccttctgtc gagacatcta agaaggtcca gccagatgtt      60

<210> SEQ ID NO 685
<211> LENGTH: 60
<212> TYPE: DNA
<213> ORGANISM: Homo sapiens

<400> SEQUENCE: 685
ttgattattt caggttgaca gctgtaaatc gactcctgct tccctcccct catctttaaa      60

<210> SEQ ID NO 686
<211> LENGTH: 21
<212> TYPE: DNA
<213> ORGANISM: Homo sapiens

<400> SEQUENCE: 686
ggaacctcgc tgtccataaa c                                               21

<210> SEQ ID NO 687
<211> LENGTH: 24
<212> TYPE: DNA
<213> ORGANISM: Homo sapiens

<400> SEQUENCE: 687
tctgtatgca agtcctgatg tttc                                            24

<210> SEQ ID NO 688
<211> LENGTH: 22
<212> TYPE: DNA
<213> ORGANISM: Homo sapiens

<400> SEQUENCE: 688
ggtaggagtg tgccttatta ac                                              22

<210> SEQ ID NO 689
<211> LENGTH: 21
<212> TYPE: DNA
<213> ORGANISM: Homo sapiens

<400> SEQUENCE: 689
gaggctgtta ggcattctaa g                                               21
```

-continued

```
<210> SEQ ID NO 690
<211> LENGTH: 22
<212> TYPE: DNA
<213> ORGANISM: Homo sapiens

<400> SEQUENCE: 690
gaaaccaacc ctatctgtaa ac                                              22

<210> SEQ ID NO 691
<211> LENGTH: 18
<212> TYPE: DNA
<213> ORGANISM: Homo sapiens

<400> SEQUENCE: 691
aaagaaagga ggctgtgg                                                   18

<210> SEQ ID NO 692
<211> LENGTH: 19
<212> TYPE: DNA
<213> ORGANISM: Homo sapiens

<400> SEQUENCE: 692
gctctggact gcctttaac                                                  19

<210> SEQ ID NO 693
<211> LENGTH: 22
<212> TYPE: DNA
<213> ORGANISM: Homo sapiens

<400> SEQUENCE: 693
aagtcagact cctcttctct ac                                              22

<210> SEQ ID NO 694
<211> LENGTH: 20
<212> TYPE: DNA
<213> ORGANISM: Homo sapiens

<400> SEQUENCE: 694
gtgaaactaa gccctcaacc                                                 20

<210> SEQ ID NO 695
<211> LENGTH: 20
<212> TYPE: DNA
<213> ORGANISM: Homo sapiens

<400> SEQUENCE: 695
taccctcctt ccattcagac                                                 20

<210> SEQ ID NO 696
<211> LENGTH: 21
<212> TYPE: DNA
<213> ORGANISM: Homo sapiens

<400> SEQUENCE: 696
gctacagagg tgaaggagat c                                               21

<210> SEQ ID NO 697
<211> LENGTH: 20
<212> TYPE: DNA
<213> ORGANISM: Homo sapiens

<400> SEQUENCE: 697
aagtctggag ctgggcaaag                                                 20
```

<210> SEQ ID NO 698
<211> LENGTH: 20
<212> TYPE: DNA
<213> ORGANISM: Homo sapiens

<400> SEQUENCE: 698
gaaacagcat tcttgccaac 20

<210> SEQ ID NO 699
<211> LENGTH: 21
<212> TYPE: DNA
<213> ORGANISM: Homo sapiens

<400> SEQUENCE: 699
gcttcatgag agagtgagaa c 21

<210> SEQ ID NO 700
<211> LENGTH: 20
<212> TYPE: DNA
<213> ORGANISM: Homo sapiens

<400> SEQUENCE: 700
aaagagaaca gggtgtaacg 20

<210> SEQ ID NO 701
<211> LENGTH: 18
<212> TYPE: DNA
<213> ORGANISM: Homo sapiens

<400> SEQUENCE: 701
gagccgggaa taaacgac 18

<210> SEQ ID NO 702
<211> LENGTH: 20
<212> TYPE: DNA
<213> ORGANISM: Homo sapiens

<400> SEQUENCE: 702
aggtctaggg ttcagggctc 20

<210> SEQ ID NO 703
<211> LENGTH: 21
<212> TYPE: DNA
<213> ORGANISM: Homo sapiens

<400> SEQUENCE: 703
gggttcattt gactggactg g 21

<210> SEQ ID NO 704
<211> LENGTH: 20
<212> TYPE: DNA
<213> ORGANISM: Homo sapiens

<400> SEQUENCE: 704
gccagtgtga caagattgcc 20

<210> SEQ ID NO 705
<211> LENGTH: 21
<212> TYPE: DNA
<213> ORGANISM: Homo sapiens

<400> SEQUENCE: 705
gacatcagtg gagggaggaa c 21

```
<210> SEQ ID NO 706
<211> LENGTH: 19
<212> TYPE: DNA
<213> ORGANISM: Homo sapiens

<400> SEQUENCE: 706
atgcctgcaa cttaaggac                                               19

<210> SEQ ID NO 707
<211> LENGTH: 23
<212> TYPE: DNA
<213> ORGANISM: Homo sapiens

<400> SEQUENCE: 707
gaggacaaag agatagctta ctg                                          23

<210> SEQ ID NO 708
<211> LENGTH: 22
<212> TYPE: DNA
<213> ORGANISM: Homo sapiens

<400> SEQUENCE: 708
ctgtctagag tccagatctt tc                                           22

<210> SEQ ID NO 709
<211> LENGTH: 19
<212> TYPE: DNA
<213> ORGANISM: Homo sapiens

<400> SEQUENCE: 709
aaactacagg tgagggttg                                               19

<210> SEQ ID NO 710
<211> LENGTH: 20
<212> TYPE: DNA
<213> ORGANISM: Homo sapiens

<400> SEQUENCE: 710
tgacttgtcc accttcaccc                                              20

<210> SEQ ID NO 711
<211> LENGTH: 20
<212> TYPE: DNA
<213> ORGANISM: Homo sapiens

<400> SEQUENCE: 711
tacggcagtg tgggtctaac                                              20

<210> SEQ ID NO 712
<211> LENGTH: 60
<212> TYPE: DNA
<213> ORGANISM: Homo sapiens

<400> SEQUENCE: 712
aaatacaatt gaaataaaaa taatcttgtc gaagcaaggg cttccaggtc ataggtggat   60

<210> SEQ ID NO 713
<211> LENGTH: 60
<212> TYPE: DNA
<213> ORGANISM: Homo sapiens

<400> SEQUENCE: 713
```

```
tgttactggg ctcaccacaa gcttaaaatc gaacgctgcc agcattagaa cctatttgtt    60
```

<210> SEQ ID NO 714
<211> LENGTH: 60
<212> TYPE: DNA
<213> ORGANISM: Homo sapiens

<400> SEQUENCE: 714

```
aaaaaggcac tatgaaaaaa caacatgctc gaactcctga cctcagatga tccacacacc    60
```

<210> SEQ ID NO 715
<211> LENGTH: 60
<212> TYPE: DNA
<213> ORGANISM: Homo sapiens

<400> SEQUENCE: 715

```
caaacaagaa taaagagtag agggtgtttc gagaatcttc aacttttgt atcttctatt    60
```

<210> SEQ ID NO 716
<211> LENGTH: 60
<212> TYPE: DNA
<213> ORGANISM: Homo sapiens

<400> SEQUENCE: 716

```
tctctttgga atgtcagtta ttcaaatatc gaatagctcc tattgttatg gagtgtagca    60
```

<210> SEQ ID NO 717
<211> LENGTH: 60
<212> TYPE: DNA
<213> ORGANISM: Homo sapiens

<400> SEQUENCE: 717

```
tatctcagct tttggcctgt ctcagctttc gacatagtag gtacttggta aacatttgtt    60
```

<210> SEQ ID NO 718
<211> LENGTH: 20
<212> TYPE: DNA
<213> ORGANISM: Homo sapiens

<400> SEQUENCE: 718

```
tgagtaacac aaagcatctg                                                20
```

<210> SEQ ID NO 719
<211> LENGTH: 18
<212> TYPE: DNA
<213> ORGANISM: Homo sapiens

<400> SEQUENCE: 719

```
agtgactggc tatgttcc                                                  18
```

<210> SEQ ID NO 720
<211> LENGTH: 21
<212> TYPE: DNA
<213> ORGANISM: Homo sapiens

<400> SEQUENCE: 720

```
ctggtgattt gtgtgacttt g                                              21
```

<210> SEQ ID NO 721
<211> LENGTH: 18
<212> TYPE: DNA
<213> ORGANISM: Homo sapiens

<400> SEQUENCE: 721

```
agggaagatg tggaggag                                                18

<210> SEQ ID NO 722
<211> LENGTH: 19
<212> TYPE: DNA
<213> ORGANISM: Homo sapiens

<400> SEQUENCE: 722
gtacgactcc agccaaatg                                               19

<210> SEQ ID NO 723
<211> LENGTH: 22
<212> TYPE: DNA
<213> ORGANISM: Homo sapiens

<400> SEQUENCE: 723
gctgtctgtt actagattgc ac                                           22

<210> SEQ ID NO 724
<211> LENGTH: 18
<212> TYPE: DNA
<213> ORGANISM: Homo sapiens

<400> SEQUENCE: 724
accttgcaag aagcacag                                                18

<210> SEQ ID NO 725
<211> LENGTH: 21
<212> TYPE: DNA
<213> ORGANISM: Homo sapiens

<400> SEQUENCE: 725
atgatacttc ccaactgaca c                                            21

<210> SEQ ID NO 726
<211> LENGTH: 20
<212> TYPE: DNA
<213> ORGANISM: Homo sapiens

<400> SEQUENCE: 726
aggagcatcc atatcaagtg                                              20

<210> SEQ ID NO 727
<211> LENGTH: 19
<212> TYPE: DNA
<213> ORGANISM: Homo sapiens

<400> SEQUENCE: 727
ctgccatgtc tgactatcc                                               19

<210> SEQ ID NO 728
<211> LENGTH: 20
<212> TYPE: DNA
<213> ORGANISM: Homo sapiens

<400> SEQUENCE: 728
cagtgaagaa gccatcatcg                                              20

<210> SEQ ID NO 729
<211> LENGTH: 22
<212> TYPE: DNA
<213> ORGANISM: Homo sapiens
```

```
<400> SEQUENCE: 729
gcttagagaa ataccaccagc ag                                              22

<210> SEQ ID NO 730
<211> LENGTH: 18
<212> TYPE: DNA
<213> ORGANISM: Homo sapiens

<400> SEQUENCE: 730
atgggcagca tttctcac                                                    18

<210> SEQ ID NO 731
<211> LENGTH: 22
<212> TYPE: DNA
<213> ORGANISM: Homo sapiens

<400> SEQUENCE: 731
agggacgatt tatatgactt gc                                               22

<210> SEQ ID NO 732
<211> LENGTH: 22
<212> TYPE: DNA
<213> ORGANISM: Homo sapiens

<400> SEQUENCE: 732
gtgctggtat gtacctgtaa tc                                               22

<210> SEQ ID NO 733
<211> LENGTH: 20
<212> TYPE: DNA
<213> ORGANISM: Homo sapiens

<400> SEQUENCE: 733
gagggttgag aagcatcttg                                                  20

<210> SEQ ID NO 734
<211> LENGTH: 60
<212> TYPE: DNA
<213> ORGANISM: Homo sapiens

<400> SEQUENCE: 734
tgtaaactgt aatatcaaaa attcaaaatc gaagagttga tttacttatt aacattagaa      60

<210> SEQ ID NO 735
<211> LENGTH: 60
<212> TYPE: DNA
<213> ORGANISM: Homo sapiens

<400> SEQUENCE: 735
acttttatag tgaaaagtgc catttgagtc gactgtgatt gaatgtaaaa ggttttaaat      60

<210> SEQ ID NO 736
<211> LENGTH: 60
<212> TYPE: DNA
<213> ORGANISM: Homo sapiens

<400> SEQUENCE: 736
tactgtagta agttctctga ggaggatatc gaagtcttgg attaaggttc attcaacaaa      60

<210> SEQ ID NO 737
<211> LENGTH: 60
<212> TYPE: DNA
<213> ORGANISM: Homo sapiens
```

<400> SEQUENCE: 737
tccatttgaa ggatgagaaa actgaggctc gaggcttaga aagtttcatt tggttgctca    60

<210> SEQ ID NO 738
<211> LENGTH: 60
<212> TYPE: DNA
<213> ORGANISM: Homo sapiens

<400> SEQUENCE: 738
ttttaaaccc aggtgcacac acaagagctc gaagcaggaa tcctggttct gttcccaggc    60

<210> SEQ ID NO 739
<211> LENGTH: 60
<212> TYPE: DNA
<213> ORGANISM: Homo sapiens

<400> SEQUENCE: 739
ccactccccc aggcttacct gcgagccatc gaggtgggcc tgggttctcg tggagggaga    60

<210> SEQ ID NO 740
<211> LENGTH: 60
<212> TYPE: DNA
<213> ORGANISM: Homo sapiens

<400> SEQUENCE: 740
tcactcattc tagatccctc tgtaaagttc gaactctgga ccttgtgatc cacccacctt    60

<210> SEQ ID NO 741
<211> LENGTH: 60
<212> TYPE: DNA
<213> ORGANISM: Homo sapiens

<400> SEQUENCE: 741
ttccatagat tactttcaa atcatcctc gaagctggcg gctgagggcc cggcgccaag    60

<210> SEQ ID NO 742
<211> LENGTH: 60
<212> TYPE: DNA
<213> ORGANISM: Homo sapiens

<400> SEQUENCE: 742
tacagtcttt gtagatgcag agtagcgttc gaagctggcg gctgagggcc cggcgccaag    60

<210> SEQ ID NO 743
<211> LENGTH: 21
<212> TYPE: DNA
<213> ORGANISM: Homo sapiens

<400> SEQUENCE: 743
ctgcccgtaa ataagcagaa g                                              21

<210> SEQ ID NO 744
<211> LENGTH: 20
<212> TYPE: DNA
<213> ORGANISM: Homo sapiens

<400> SEQUENCE: 744
gagggttgag aagcatcttg                                                20